US012521446B2

(12) United States Patent
Vincent Jordan et al.

(10) Patent No.: US 12,521,446 B2
(45) Date of Patent: Jan. 13, 2026

(54) ANTI-CEACAM5 ANTIBODY DRUG CONJUGATES

(71) Applicant: Bristol-Myers Squibb Company, Princeton, NJ (US)

(72) Inventors: Nicole Vincent Jordan, Needham, MA (US); Ruchira Dasgupta, Auburndale, MA (US); Lore Florin, Redwood City, CA (US); Derek Giuliana, Ashland, MA (US); Raphael Levy, Belmont, CA (US); Carrie J. Marshall, Walpole, MA (US); Thomas McDonagh, Charlestown, MA (US); Akbar Nayeem, Newtown, PA (US); Sayumi Yamazoe, Mountain View, CA (US); Hong Zhang, Belmont, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 19/064,273

(22) Filed: Feb. 26, 2025

(65) Prior Publication Data

US 2025/0269052 A1 Aug. 28, 2025

Related U.S. Application Data

(60) Provisional application No. 63/678,883, filed on Aug. 2, 2024, provisional application No. 63/558,431, filed on Feb. 27, 2024.

(51) Int. Cl.
*A61K 47/68* (2017.01)
*A61P 35/00* (2006.01)

(52) U.S. Cl.
CPC .... *A61K 47/6853* (2017.08); *A61K 47/68037* (2023.08); *A61K 47/6889* (2017.08); *A61P 35/00* (2018.01)

(58) Field of Classification Search
None
See application file for complete search history.

(56) References Cited

U.S. PATENT DOCUMENTS 5,624,821 A 4/1997 Winter et al.
6,096,871 A 8/2000 Presta et al.
(Continued)

FOREIGN PATENT DOCUMENTS

CA 3241254 A1 6/2023
EP 0865492 B1 9/1998
(Continued)

OTHER PUBLICATIONS

Arnon, et al., "Monoclonal Antibodies for Immunotargeting of Drugs in Cancer Therapy," in Monoclonal Antibodies And Cancer Therapy, pp. 243-256, Reisfeld et al., eds., Alan R. Liss, Inc., United States (1985).

(Continued)

*Primary Examiner* — Karl J Puttlitz
(74) *Attorney, Agent, or Firm* — Sterne, Kessler, Goldstein & Fox P.L.L.C.

(57) ABSTRACT

Provided herein are antibody drug conjugates of the formula (I) comprising an anti-CEACAM5 antibodies, antigen binding portions thereof that is conjugated with a linker and exatecan. The disclosure also provides a method of treating cancer in a subject in need thereof comprising administering to the subject an antibody drug conjugate disclosed herein.

23 Claims, 48 Drawing Sheets

Specification includes a Sequence Listing.

| | Ab# | Control 3 | Bin 6<br>MBA001 | Bin 7<br>MBN005 | Bin 1<br>MBN001 | Bin 3<br>MBN004 | Bin 2<br>MBN002 | Bin 5<br>MBV002 | PBST |
|---|---|---|---|---|---|---|---|---|---|
| | Control 3 | -0.2098 | 0.9789 | 0.7824 | 0.8244 | -0.0582 | 0.8321 | 0.7855 | -0.3099 |
| Bin 6 | MBA001 | 0.852 | -0.3265 | 0.5705 | 0.6645 | 1.0393 | 1.4165 | 0.6581 | -0.4274 |
| Bin 7 | MBN005 | 0.9697 | 1.0029 | -0.3881 | 0.8364 | 1.1846 | 1.6827 | 0.7306 | -0.4427 |
| Bin 1 | MBN001 | 1.0304 | 1.0149 | 0.7758 | -0.2185 | 1.1801 | 1.3824 | 0.7127 | -0.2724 |
| Bin 3 | MBN004 | -0.1677 | 0.9315 | 0.8456 | 0.7465 | -0.0564 | 0.8324 | 0.7526 | -0.2672 |
| Bin 2 | MBN002 | 0.1891 | 0.6704 | 0.609 | 0.5325 | 0.2701 | 0.1461 | 0.5274 | -0.053 |
| Bin 5 | MBV002 | 1.1007 | 1.0253 | 0.8381 | 0.9074 | 1.2824 | 1.6045 | 0.0042 | -0.0717 |

| | CEACAM5 | CEACAM1 | CEACAM6 |
|---|---|---|---|
| Bin1 | + | - | - |
| Bin2 | + | - | - |
| Bin3 | + | - | - |
| Bin4 | + | + | - |
| Bin5 | + | - | - |
| Bin6 | + | - | + |
| Bin7 | + | + | - |
| Bin8 | + | + | - |

(56) References Cited

U.S. PATENT DOCUMENTS

| | | | |
|---|---|---|---|
| 6,180,377 | B1 | 1/2001 | Morgan et al. |
| 6,194,551 | B1 | 2/2001 | Idusogie et al. |
| 6,737,056 | B1 | 5/2004 | Presta |
| 7,662,378 | B2 | 2/2010 | Goldenberg et al. |
| 7,919,090 | B2 | 4/2011 | Goldenberg et al. |
| 7,943,743 | B2 | 5/2011 | Korman et al. |
| 8,008,449 | B2 | 8/2011 | Korman et al. |
| 8,062,636 | B2 | 11/2011 | Goldenberg et al. |
| 8,216,572 | B2 | 7/2012 | Goldenberg et al. |
| 8,354,509 | B2 | 1/2013 | Carven et al. |
| 8,535,676 | B2 | 9/2013 | Goldenberg et al. |
| 8,900,587 | B2 | 12/2014 | Carven et al. |
| 9,580,507 | B2 | 2/2017 | Korman et al. |
| 9,987,500 | B2 | 6/2018 | Papadopoulos et al. |
| 10,077,306 | B2 | 9/2018 | Schebye et al. |
| 2009/0280114 | A1 | 11/2009 | Solomon |
| 2011/0142858 | A1 | 6/2011 | Solomon et al. |
| 2011/0150892 | A1 | 6/2011 | Thudium et al. |
| 2014/0093511 | A1 | 4/2014 | Lonberg et al. |
| 2017/0340733 | A1 | 11/2017 | Cao |
| 2017/0368169 | A1 | 12/2017 | Loew et al. |
| 2019/0359945 | A1 | 11/2019 | Gorr et al. |
| 2020/0055938 | A1 | 2/2020 | Desai et al. |
| 2020/0172617 | A1 | 6/2020 | Stein et al. |
| 2022/0080053 | A1 | 3/2022 | Allard et al. |
| 2022/0106400 | A1 | 4/2022 | Yamniuk |
| 2023/0158154 | A1* | 5/2023 | Kasper ................. A61K 47/545 424/181.1 |
| 2023/0330258 | A1 | 10/2023 | Hackenberger et al. |

FOREIGN PATENT DOCUMENTS

| | | | |
|---|---|---|---|
| EP | 2922875 | B1 | 9/2015 |
| WO | WO-9734631 | A1 | 9/1997 |
| WO | WO-2005117973 | A2 | 12/2005 |
| WO | WO-2006091209 | A2 | 8/2006 |
| WO | WO-2008156712 | A1 | 12/2008 |
| WO | WO-2012145493 | A1 | 10/2012 |
| WO | WO-2013173223 | A1 | 11/2013 |
| WO | WO-2014079886 | A1 | 5/2014 |
| WO | WO-2014089113 | A1 | 6/2014 |
| WO | WO-2015042246 | A1 | 3/2015 |
| WO | WO-2015112900 | A1 | 7/2015 |
| WO | WO-2016028672 | A1 | 2/2016 |
| WO | WO-2017019894 | A1 | 2/2017 |
| WO | WO-2018041985 | A1 | 3/2018 |
| WO | WO-2018085555 | A1 | 5/2018 |
| WO | WO-2018160536 | A1 | 9/2018 |
| WO | WO-2019170710 | A2 | 9/2019 |
| WO | WO-2022048883 | A1 | 3/2022 |
| WO | WO-2022223783 | A1 | 10/2022 |
| WO | WO-2023034555 | A1 | 3/2023 |
| WO | WO-2023083900 | A1 | 5/2023 |
| WO | WO-2023083919 | A1 | 5/2023 |
| WO | WO-2023105087 | A1 | 6/2023 |
| WO | WO-2025046090 | A1 | 3/2025 |

OTHER PUBLICATIONS

Baldwin, et al., "Analysis Results, and Future Prospective of the Therapeutic Use of the Radiolabeled Antibody in Cancer Therapy," in Monoclonal Antibodies for Cancer Detection and Therapy, pp. 303-316, eds. Academic Press, United States (1985).

Bischoff, R., and Kolbe, H.V., "Deamidation of Asparagine and Glutamine Residues in Proteins and Peptides: Structural Determinants and Analytical Methodology," Journal of Chromatography B, Biomedical Applications 662(2):261-278, Elsevier, Netherlands (Dec. 1994).

Boehm, M.K., and Perkins, S.J., "Structural Models for Carcinoembryonic Antigen and Its Complex With the Single-chain Fv Antibody Molecule MFE23," FEBS Letters 475(1):11-16, John Wiley & Sons Ltd, United Kingdom (Jun. 2000).

Brummell, D.A., et al., "Probing the Combining Site of an Anti-Carbohydrate Antibody by Saturation-Mutagenesis: Role of the Heavy-Chain CDR3 Residues," Biochemistry 32(4):1180-1187, American Chemical Society, United States (Feb. 1993).

Burks, E.A., et al., "In vitro Scanning Saturation Mutagenesis of an Antibody Binding Pocket," Proceedings of die National Academy of Sciences of the United States of America 94(2):412-417, National Academy of Sciences, United States (Jan. 1997).

Ceska, T., et al., "Cryo-EM in Drug Discovery," Biochemical Society Transactions 47(1):281-293, Portland Press On The Behalf Of The Biochemical Society, United Kingdom (Feb. 2019).

Chen, X., et al., "Induction of Myelodysplasia by Myeloid-derived Suppressor Cells," The Journal of Clinical Investigation 123(11):4595-4611, American Society for Clinical Investigation, United States (Nov. 2013).

Connolly, M.L., "Analytical Molecular Surface Calculation," Journal of Crystallography 16:548-558, Wiley, United States (1983).

Dranoff, G., et al., "Vaccination With Irradiated Tumor Cells Engineered to Secrete Murine Granulocyte-macrophage Colony-stimulating Factor Stimulates Potent, Specific, and Long-lasting Anti-tumor Immunity," Proceedings of the National Academy of Sciences of the United States of America 90(8):3539-3543, National Academy of Sciences, United States (Apr. 1993).

Gala, F.A., and Morrison, S.L., "V Region Carbohydrate and Antibody Expression," The Journal of Immunology 172(9):5489-5494, Williams & Wilkins, United States (May 2004).

Gazzah, A., et al., "Safety, Pharmacokinetics, and Antitumor Activity of the Anti-CEACAM5-DM4 Antibody-drug Conjugate Tusamitamab Ravtansine (SAR408701) in Patients With Advanced Solid Tumors: First-in-human Dose-escalation Study," Annals of Oncology 33(4):416-425, Elsevier, United Kingdom (Apr. 2022).

Geyh, S., et al., "Transforming Growth Factor B1-mediated Functional Inhibition of Mesenchymal Stromal Cells in Myelodysplastic Syndromes and Acute Myeloid Leukemia," Haematologica 103(9):1462-1471, Ferrata Storti Foundation, Italy (Sep. 2018).

Hellstrom, et al., "Antibodies for Drug Delivery" in Controlled Drug Delivery, pp. 623-653, 2nd edition, Robinson et al., eds., Marcel Dekker, Inc., United States (1987).

Hodi, F.S., et al., "Improved Survival with Ipilimumab in Patients with Metastatic Melanoma," The New England Journal of Medicine 363(8):711-723, Massachusetts Medical Society, United States (Aug. 2010).

Kobayashi, H., et al., "Tryptophan H33 Plays an Important Role in Pyrimidine (6-4) Pyrimidone Photoproduct Binding by a High-Affinity Antibody," Protein Engineering 12(10):879-884, Oxford University Press, United Kingdom (Oct. 1999).

Kohrt, H.E., et al., "CD137 Stimulation Enhances the Antilymphoma Activity of Anti-CD20 Antibodies," Blood 117(8):2423-2432, Elsevier, United States (Feb. 2011).

Kovtun, Y.V., et al., "Antibody-drug Conjugates Designed to Eradicate Tumors with Homogeneous and Heterogeneous Expression of the Target Antigen," Cancer Research 66(6):3214-3221, American Association for Cancer Research, United States (2006).

Marshall, R.D., "Glycoproteins," Annual Review of Biochemistry 41:673-702, Annual Reviews, United States (1972).

Mies, A., et al., "Activin Receptor II Ligand Traps and Their Therapeutic Potential in Myelodysplastic Syndromes with Ring Sideroblasts," Current Hematologic Malignancy Reports 11(6):416-424, Current Science, United States (Dec. 2016).

Nallamsetty, S., et al., "Efficient Site-specific Processing of Fusion Proteins by Tobacco Vein Mottling Virus Protease in Vivo and in Vitro," Protein Expression and Purification 38(1):108-115, Academic Press, United States (Nov. 2004).

NCT03110107, "First-In-Human Study of Monoclonal Antibody BMS-986218 by Itself and in Combination With Nivolumab in Participants With Advanced Solid Tumors," ClinicalTrials.gov, Accessed at :[https://clinicaltrials.gov/study/NCT03110107?term=NCT03110107&rank=1], (May 2024), 16 Pages.

NCT03369223, "A Study of BMS-986249 Alone and in Combination With Nivolumab in Advanced Solid Tumors," ClinicalTrials.gov, Accessed at :[https://clinicaltrials.gov/study/NCT03369223?term=NCT03369223&rank=1], (Dec. 2024), 19 Pages.

(56) References Cited

OTHER PUBLICATIONS

Papadopoulos, K., et al., "172P Phase I Study of JTX-8064, a LILRB2 (ILT4) Inhibitor, as Monotherapy and Combination with Pimivalimab (pimi), a PD-1 Inhibitor (PD-li), in Patients (pts) with Advanced Solid Tumors," Immuno Oncology and Technology, 16(Suppl 1):100284, Elsevier, Netherlands (Dec. 2022).
Perets, R., et al., "Safety and Efficacy of Quavonlimab, a Novel Anti-CTLA-4 Antibody (MK-1308), in Combination With Pembrolizumab in First-line Advanced Non-small-cell Lung Cancer," Annals of oncology 32(3):395-403, Elsevier, United Kingdom (Mar. 2021).
Renaud, J-P., et al., "Cryo-em in Drug Discovery: Achievements, Limitations and Prospects," Nature Reviews Drug Discovery 17(7):471-492, Nature Pub. Group, United Kingdom (Jul. 2018).
Roberts, R. W. and Szostak, J.W., "RNA-Peptide Fusions for the in Vitro Selection of Peptides and Proteins," Proceedings of the National Academy of Sciences of the USA 94(23):12297-12302, National Academy of Sciences, United States (1997).
Scapin, G., et al., "Cryo-EM for Small Molecules Discovery, Design, Understanding, and Application," Cell Chemical Biology 25(11):1318-1325, Cell Press, United States (Nov. 2018).
Sheriff, S., et al., "Structure of Myohemerythrin in the Azidomet State at 1.7/1.3 A Resolution," Journal of Molecular Biology 197(2):273-296, Elsevier, Netherlands (Sep. 1987).
Steven, S., "Some Methods for Examining the Interactions between Two Molecules," ImmunoMethods 3(3):191-196, Elsevier, United States (Dec. 1993).
Strohl, W.R., "Optimization of Fc-mediated Effector Functions of Monoclonal Antibodies," Current Opinion in Biotechnology 20(6):685-691, Elsevier, United Kingdom (Dec. 2009).
Thorpe, P.E. and Ross, W.C., "The Preparation and Cytotoxic Properties of Antibody-toxin Conjugates," Immunological Reviews 62:119-158, Blackwell, United Kingdom (1982).
Thorpe, P.E., "Antibody Carriers of Cytotoxic Agents in Cencer Therapy: A Review," in Monoclonal Antibodies 84: Biological and Clinical Applications, pp. 475-506, Pinchera et al., eds., Kurtis, United States (1985).
UniProtKB, "RecName: Full-Cell adhesion molecule CEACAM5; AltName: Full=Carcinoembryonic antigen; Short=CEA; AltName: Full=Carcinoembryonic antigen-related cell adhesion molecule 5; Short=CEA cell adhesion molecule 5; AltName: Full=Meconium antigen 100; AltName: CD_antige . . . ," Acession No. P06731, Retrieved from Internet:[https://www.ncbi.nlm.nih.gov/protein/P06731/], [Feb. 25, 2025]. 13 Pages.
Xu, L., et al., "Directed Evolution of High-affinity Antibody Mimics Using mRNA Display," Chemistry & Biology 9: 933-942, Elsevier Science Ltd., The Netherlands (Aug. 2002).
Decary, S., et al., "Preclinical Activity of SAR408701: A Novel Anti-CEACAM5-maytansinoid Antibody-drug Conjugate for the Treatment of CEACAM5-positive Epithelial Tumors," Clinical Cancer Research 26(24):6589-6599, American Association for Cancer Research, United States (Dec. 2020).
Hefta, L.J., et al., "Kinetic and Affinity Constants of Epitope Specific Anti-carcinoembryonic Antigen (CEA) Monoclonal Antibodies for CEA and Engineered CEA Domain Constructs," Immunotechnology 4(1):49-57, Elsevier, Netherlands (Jun. 1998).
International Search Report and Written Opinion for Application No. PCT/US2025/017392, European Patent Office, Netherlands, mailed on Jun. 10, 2025, 17 pages.
International Search Report and Written Opinion for International Application No. PCT/US2025/017395, European Patent Office, Netherlands, mailed on May 14, 2025, 14 pages.
Shinmi, D., et al., "Novel Anticarcinoembryonic Antigen Antibody-drug Conjugate Has Antitumor Activity in the Existence of Soluble Antigen," Cancer Medicine 6(4):798-808, John Wiley & Sons Ltd., United States (Apr. 2017).

* cited by examiner

| | | | Bin 6 | Bin 7 | Bin 1 | Bin 3 | Bin 2 | Bin 5 | |
|---|---|---|---|---|---|---|---|---|---|
| | Ab# | Control 3 | MBA001 | MBN005 | MBN001 | MBN004 | MBN002 | MBV002 | PBST |
| | Control 3 | -0.2098 | 0.9789 | 0.7824 | 0.8244 | -0.0582 | 0.8321 | 0.7855 | -0.3099 |
| Bin 6 | MBA001 | 0.852 | -0.3265 | 0.5705 | 0.6645 | 1.0393 | 1.4165 | 0.6581 | -0.4274 |
| Bin 7 | MBN005 | 0.9697 | 1.0029 | -0.3881 | 0.8364 | 1.1846 | 1.6827 | 0.7306 | -0.4427 |
| Bin 1 | MBN001 | 1.0304 | 1.0149 | 0.7758 | -0.2185 | 1.1801 | 1.3824 | 0.7127 | -0.2724 |
| Bin 3 | MBN004 | -0.1677 | 0.9315 | 0.8456 | 0.7465 | -0.0564 | 0.8324 | 0.7526 | -0.2672 |
| Bin 2 | MBN002 | 0.1891 | 0.6704 | 0.609 | 0.5325 | 0.2701 | 0.1461 | 0.5274 | -0.053 |
| Bin 5 | MBV002 | 1.1007 | 1.0253 | 0.8381 | 0.9074 | 1.2824 | 1.6045 | 0.0042 | -0.0717 |

FIG. 1A

| | CEACAM5 | CEACAM1 | CEACAM6 |
|---|---|---|---|
| Bin1 | + | - | - |
| Bin2 | + | - | - |
| Bin3 | + | - | - |
| Bin4 | + | + | - |
| Bin5 | + | - | - |
| Bin6 | + | - | + |
| Bin7 | + | + | - |
| Bin8 | + | + | - |

FIG. 1B

| | | |
|---|---|---|
| **Heavy Chain** | | |
| HCDR1 | 26 27 28 29 30 31 32<br>G I T F S S H | SEQ ID NO: 61 |
| HCDR2 | 49 50 51 52 52a 53 54 55 56 57 58 59 60 61 62 63 64 65<br>T F I S Y D G S Y K S Y V D S V K G | SEQ ID NO: 62 |
| HCDR3 | 94 95 96 97 98 99 100 100a 100b 101 102<br>T G L T G T G A F D I | SEQ ID NO: 63 |
| **Light Chain** | | |
| LCDR1 | 24 25 26 27 27a 28 29 30 31 32 33 34<br>R A S Q S V S S S Y L A | SEQ ID NO: 64 |
| LCDR2 | 50 51 52 53 54 55 56<br>G A S S R A T | SEQ ID NO: 65 |
| LCDR3 | 89 90 91 92 93 94 95 96<br>Q Q Y G S S P Y | SEQ ID NO: 66 |

Mutations to germline VH: T7S, S40A, A68T, P84A

FIG. 5B

MBN001 HCDR1
Human CEACAM5

Legend

| Legend | |
|---|---|
| **Favorable** | >2 |
| Neutral | 0.5 to 2 |
| Unfavorable | <0.5 |

SEQ ID NO: 61

| Germline | _ | F | _ | _ | _ | _ | Y |
|---|---|---|---|---|---|---|---|
| Parental | G | I | T | F | S | S | H |
| | 26 | 27 | 28 | 29 | 30 | 31 | 32 |
| Normalized Enrichment Ratio | | | | | | | |
| * | 0.00 | 0.00 | 0.00 | 0.00 | 0.00 | 0.51 | 0.00 |
| P | 0.06 | 0.07 | 0.28 | 0.00 | 0.33 | 0.07 | 0.45 |
| G | 1.00 | 0.04 | 1.32 | 0.03 | 0.53 | 0.16 | 0.02 |
| A | 0.46 | 0.08 | 0.92 | 0.00 | 0.24 | 0.38 | 0.00 |
| C | 0.35 | 0.00 | 1.45 | 0.16 | 0.36 | 0.76 | 0.00 |
| S | 0.26 | 0.00 | 1.11 | 0.03 | 1.00 | 1.00 | 0.09 |
| T | 0.67 | 0.05 | 1.00 | 0.00 | 0.43 | 0.22 | 0.09 |
| V | 0.49 | 0.28 | 0.79 | 0.12 | 0.24 | 0.29 | 0.12 |
| L | 0.18 | 1.25 | **3.86** | 0.02 | 0.25 | 0.75 | 0.50 |
| I | 0.17 | 1.00 | **3.29** | 0.07 | 0.45 | **2.68** | 0.17 |
| M | 0.09 | 0.27 | **3.97** | 0.00 | 0.42 | 1.67 | 0.08 |
| K | 0.62 | 0.15 | 0.32 | 0.20 | 0.00 | 0.42 | 0.05 |
| R | 0.44 | 0.09 | **3.55** | 0.03 | 0.18 | 0.35 | 0.10 |
| H | 0.34 | 0.00 | **2.55** | 0.00 | 0.00 | **5.51** | 1.00 |
| F | 0.09 | 0.09 | **4.12** | 1.00 | 0.00 | **8.08** | 0.16 |
| Y | 0.40 | 0.00 | **8.19** | 1.24 | 0.52 | **15.50** | 0.59 |
| W | 0.20 | 0.09 | 0.00 | 0.25 | 0.42 | **14.41** | 0.00 |
| N | 0.51 | 0.08 | 1.91 | 0.00 | 1.24 | 0.94 | 0.68 |
| D | 0.44 | 0.00 | **3.73** | 0.00 | **4.06** | **2.70** | 0.17 |
| E | 0.67 | 0.00 | 1.64 | 0.13 | 0.86 | **8.62** | 0.08 |
| Q | 0.54 | 0.00 | 1.10 | 0.00 | 0.40 | 1.52 | 0.25 |

FIG. 5C

MBN001 HCDR1
Cynomolgus CEACAM5

SEQ ID NO: 61

| Germline | — | F | — | — | — | — | Y |
|---|---|---|---|---|---|---|---|
| Parental | G | I | T | F | S | S | H |
| | 26 | 27 | 28 | 29 | 30 | 31 | 32 |
| Normalized Enrichment Ratio | | | | | | | |
| * | 0.19 | 0.00 | 0.00 | 0.00 | 0.00 | 0.76 | 0.00 |
| P | 0.00 | 0.16 | 0.44 | 0.00 | 0.00 | 0.26 | 0.66 |
| G | 1.00 | 0.10 | 0.97 | 0.19 | 0.72 | 0.35 | 0.22 |
| A | 0.43 | 0.17 | 0.52 | 0.31 | 0.00 | 0.29 | 0.06 |
| C | 0.23 | 0.17 | **2.44** | 0.19 | **2.14** | 0.43 | 0.17 |
| S | 0.70 | 0.10 | 1.88 | 0.10 | 1.00 | 1.00 | 0.08 |
| T | 0.53 | 0.00 | 1.00 | 0.44 | 0.74 | 1.27 | 0.08 |
| V | 0.40 | 0.21 | 1.74 | 0.30 | 0.58 | 0.89 | 0.12 |
| L | 0.33 | 1.19 | **3.59** | 0.22 | 0.56 | 0.58 | 0.52 |
| I | 0.35 | 1.00 | **8.73** | 0.29 | 0.19 | 1.86 | 0.38 |
| M | 0.48 | 0.27 | **3.30** | 0.28 | 0.35 | 0.67 | 0.29 |
| K | 0.57 | 0.14 | 0.41 | 0.00 | 0.35 | 0.66 | 0.11 |
| R | 0.44 | 0.16 | 1.63 | 0.06 | 0.57 | 0.52 | 0.19 |
| H | 0.50 | 0.13 | **4.28** | 0.00 | 0.27 | **3.48** | 1.00 |
| F | 0.14 | 0.19 | **32.19** | 1.00 | 0.00 | **4.46** | 0.29 |
| Y | 0.58 | 0.00 | **48.51** | 0.85 | 0.00 | **7.19** | 0.69 |
| W | 0.28 | 0.11 | 1.29 | 0.38 | **2.71** | **17.45** | 0.15 |
| N | 0.71 | 0.13 | **6.49** | 0.00 | 0.00 | 0.91 | 0.66 |
| D | 0.33 | 0.00 | 1.51 | 0.00 | 1.27 | 1.07 | 0.26 |
| E | 0.57 | 0.11 | 0.69 | 0.00 | 0.50 | **3.23** | 0.31 |
| Q | 0.36 | 0.30 | 1.51 | 0.00 | 0.00 | 0.63 | 0.46 |

Legend

| | |
|---|---|
| **Favorable** | >2 |
| Neutral | 0.5 to 2 |
| Unfavorable | <0.5 |

FIG. 5D

MBN001 HCDR2
Human CEACAM5

SEQ ID NO: 62

| Germline | A | V | – | – | – | – | – | – | N | – | Y | – | A | – | – | – | – | – |
|---|---|---|---|---|---|---|---|---|---|---|---|---|---|---|---|---|---|---|
| Parental | T | F | I | S | Y | D | G | S | Y | K | S | Y | V | D | S | V | K | G |
| | 49 | 50 | 51 | 52 | 52a | 53 | 54 | 55 | 56 | 57 | 58 | 59 | 60 | 61 | 62 | 63 | 64 | 65 |
| Normalized Enrichment Ratio | | | | | | | | | | | | | | | | | | |
| * | 0.00 | 0.00 | 0.00 | 0.00 | 0.24 | 0.40 | 0.00 | 0.00 | 0.23 | 0.20 | 0.60 | 0.52 | 0.18 | 0.15 | 0.00 | 0.00 | 0.35 | 0.00 |
| P | 0.27 | 0.06 | 0.06 | 0.40 | 0.07 | 0.16 | 0.00 | 0.13 | 0.00 | **2.15** | 0.39 | 0.25 | 0.49 | 1.59 | 0.92 | 0.19 | 0.43 | 0.88 |
| G | 0.55 | 0.27 | 0.69 | 0.08 | 0.00 | 0.12 | 1.00 | 0.06 | 0.08 | 0.44 | 1.21 | 0.81 | 0.35 | 0.86 | 1.06 | 0.67 | 0.43 | 1.00 |
| A | 0.97 | 0.19 | **3.85** | 0.24 | 0.00 | 0.08 | 1.80 | 0.08 | 0.05 | 0.90 | 0.57 | 1.10 | 0.50 | 0.76 | 0.71 | 0.76 | 0.32 | 0.78 |
| C | 0.70 | 0.53 | 0.44 | 0.07 | 0.13 | 0.09 | 1.31 | 0.05 | 0.09 | 1.28 | 1.27 | 0.90 | 0.67 | 1.05 | 1.06 | 1.33 | 0.24 | 1.16 |
| S | 0.84 | 0.16 | **3.59** | 1.00 | 0.06 | 0.10 | 1.90 | 1.00 | 0.17 | 0.73 | 1.00 | 1.14 | 0.76 | 0.91 | 1.00 | 0.59 | 0.39 | 1.41 |
| T | 1.00 | 0.14 | **1.94** | **2.58** | 0.00 | 0.11 | 0.59 | 0.56 | 0.07 | 1.54 | **4.02** | 1.12 | 0.74 | 0.68 | 1.34 | **2.29** | 0.24 | 1.14 |
| V | 1.19 | 0.35 | 1.75 | 1.39 | 0.05 | 0.09 | 0.15 | 0.06 | 0.43 | **2.41** | 1.21 | 0.94 | 1.00 | 1.03 | 1.06 | 1.00 | 0.20 | 1.00 |
| L | 1.26 | 0.33 | 0.85 | 0.09 | 0.05 | 0.14 | 0.26 | 0.07 | 1.27 | **3.34** | **7.72** | 1.57 | 1.41 | 0.88 | 0.85 | 0.62 | 0.30 | 0.80 |
| I | 1.39 | 0.24 | 1.00 | 0.11 | 0.13 | 0.20 | 0.07 | 0.05 | **3.76** | **3.85** | **4.67** | 1.34 | 1.47 | 0.66 | 0.79 | 1.03 | 0.41 | 0.68 |
| M | 0.87 | 1.40 | 0.69 | 0.00 | 0.11 | 0.17 | 0.58 | 0.08 | **3.55** | 1.99 | **5.92** | 1.62 | 1.25 | 0.62 | 1.14 | 0.54 | 0.45 | 0.79 |
| K | 0.34 | 0.00 | 0.19 | 0.00 | 0.00 | 0.11 | 0.24 | 0.00 | 0.00 | 1.00 | **4.57** | 0.52 | 0.37 | 0.79 | 0.66 | 0.60 | 1.00 | 1.05 |
| R | 0.35 | 0.06 | 0.05 | 0.03 | 0.00 | 0.06 | 0.41 | 0.10 | 0.00 | 1.13 | 1.15 | 1.40 | 0.38 | 0.75 | 0.96 | 0.42 | 0.94 | 0.86 |
| H | 0.33 | 0.00 | 0.00 | 0.37 | 0.31 | 0.11 | 0.32 | 0.00 | 0.31 | 1.59 | 0.60 | 1.75 | 0.48 | 0.48 | 1.41 | 0.66 | 0.56 | 1.30 |
| F | 0.99 | 1.00 | 0.19 | 0.15 | 0.41 | 0.09 | 0.19 | 0.07 | 0.39 | 1.22 | 0.96 | 1.42 | 0.68 | 0.89 | 0.79 | 0.62 | 0.18 | 1.78 |
| Y | 1.02 | 0.87 | 0.25 | 0.10 | 1.00 | 0.25 | 0.39 | 0.17 | 1.00 | 1.81 | 0.12 | 1.00 | 0.69 | 0.84 | 0.91 | 0.70 | 0.51 | 1.59 |
| W | 0.35 | 0.39 | 0.06 | 0.06 | 0.18 | 0.09 | 0.35 | 0.11 | 0.79 | 1.39 | 1.22 | 1.07 | 0.76 | 1.37 | 0.81 | 0.51 | 0.38 | **2.74** |
| N | **2.00** | 0.06 | 0.16 | 0.00 | 0.09 | 0.14 | 0.24 | 0.11 | 0.09 | 0.97 | 0.68 | 0.61 | 0.36 | 0.88 | 0.62 | 0.16 | 0.33 | 1.50 |
| D | 1.02 | 0.17 | 1.09 | 0.00 | 0.14 | 1.00 | 0.32 | 0.06 | 0.00 | 0.70 | 0.05 | 0.61 | 0.57 | 1.00 | 1.00 | 0.46 | 0.20 | 1.09 |
| E | 0.96 | 0.57 | 0.93 | 0.00 | 0.00 | 0.15 | 1.06 | 0.00 | 0.00 | 1.45 | 0.00 | 0.70 | 0.83 | 1.33 | 0.66 | 0.45 | 0.28 | 0.60 |
| Q | 0.48 | 0.21 | 0.11 | 0.00 | 0.00 | 0.21 | 1.97 | 0.00 | 0.57 | 0.21 | **9.58** | 1.91 | 0.46 | 0.72 | 0.76 | 0.34 | 0.46 | 0.62 |

Legend

| Legend | |
|---|---|
| **Favorable** | >2 |
| Neutral | 0.5 to 2 |
| Unfavorable | <0.5 |

FIG. 5E

MBN001 HCDR2
Cynomolgus CEACAM5

SEQ ID NO: 62

| Germline | A | V | – | – | – | – | – | – | N | – | Y | – | A | – | – | – | – | – |
|---|---|---|---|---|---|---|---|---|---|---|---|---|---|---|---|---|---|---|
| Parental | T | F | I | S | Y | D | G | S | Y | K | S | Y | V | D | S | V | K | G |
| | 49 | 50 | 51 | 52 | 52a | 53 | 54 | 55 | 56 | 57 | 58 | 59 | 60 | 61 | 62 | 63 | 64 | 65 |
| Normalized Enrichment Ratio | | | | | | | | | | | | | | | | | | |
| * | 0.00 | 0.00 | 0.00 | 0.00 | 0.23 | 0.00 | 0.00 | 0.00 | 0.59 | 0.54 | 1.38 | 0.49 | 0.00 | 0.15 | 0.00 | 0.00 | 0.51 | 0.00 |
| P | 0.58 | 0.32 | 0.11 | 0.00 | 0.12 | 0.32 | 0.16 | 0.23 | 0.40 | 1.50 | 1.42 | 0.24 | 0.86 | 0.88 | 1.15 | 0.79 | 0.78 | 1.01 |
| G | 0.49 | 0.18 | 1.22 | 0.38 | 0.07 | 0.27 | 1.00 | 0.19 | 0.10 | 0.43 | 1.02 | 0.75 | 0.31 | 1.03 | 0.77 | 0.62 | 0.61 | 1.00 |
| A | 0.93 | 0.22 | **4.51** | 0.26 | 0.00 | 0.18 | 1.75 | 0.19 | 0.06 | 0.66 | 1.27 | 1.29 | 1.05 | 1.65 | 1.04 | 0.95 | 0.60 | 0.96 |
| C | 0.68 | 0.44 | 0.45 | 0.17 | 0.13 | 0.23 | 1.31 | 0.09 | 0.38 | 1.67 | 0.95 | 1.58 | 0.71 | **2.01** | 0.84 | 1.01 | 0.24 | 1.16 |
| S | 0.94 | 0.19 | **6.18** | 1.00 | 0.21 | 0.33 | **2.87** | 1.00 | 0.17 | 0.54 | 1.00 | 0.46 | 0.62 | 0.95 | 1.00 | 0.63 | 0.56 | 1.09 |
| T | 1.00 | 0.22 | 1.59 | **2.34** | 0.35 | 0.37 | 0.48 | 0.73 | 0.43 | 1.05 | **9.46** | 1.18 | 0.57 | 1.07 | 1.10 | **2.71** | 0.62 | 1.44 |
| V | 1.11 | 0.31 | 1.27 | 0.81 | 0.12 | 0.15 | 0.41 | 0.19 | 0.38 | **2.23** | 1.05 | 1.14 | 1.00 | 1.14 | 1.26 | 1.00 | 0.36 | 0.91 |
| L | 1.06 | 0.45 | 1.12 | 0.35 | 0.12 | 0.43 | 0.54 | 0.20 | 1.39 | **3.52** | **20.15** | 1.00 | 1.13 | 1.26 | 0.79 | 0.66 | 0.33 | 0.86 |
| I | 0.98 | 0.77 | 1.00 | 0.21 | 0.00 | 0.28 | 0.30 | 0.19 | **13.42** | **6.98** | **4.97** | 1.27 | 1.64 | 0.77 | 1.19 | 1.25 | 0.23 | 1.02 |
| M | 0.96 | 0.87 | 1.00 | 0.28 | 0.12 | 0.47 | 0.53 | 0.10 | **11.09** | **1.87** | **10.49** | 1.45 | 0.40 | 0.57 | 0.62 | 0.63 | 0.35 | 1.04 |
| K | 0.70 | 0.00 | 0.00 | 0.00 | 0.20 | 0.25 | 1.02 | 0.00 | 0.00 | 1.00 | **3.54** | 0.50 | 0.53 | 0.83 | 0.80 | 0.60 | 1.00 | 0.90 |
| R | 0.47 | 0.20 | 0.36 | 0.25 | 0.11 | 0.14 | 0.37 | 0.18 | 0.13 | 1.19 | 1.13 | 1.07 | 0.25 | 0.85 | 0.67 | 0.35 | 1.00 | 1.15 |
| H | 1.01 | 0.22 | 0.00 | 0.00 | 0.58 | 0.00 | 0.82 | 0.11 | 0.58 | 0.91 | 0.32 | 1.33 | 0.44 | 1.21 | 1.21 | 0.60 | 0.70 | 0.61 |
| F | 1.57 | 1.00 | 0.58 | 0.34 | 0.47 | 0.31 | 0.41 | 0.26 | 0.37 | 0.84 | 0.97 | 1.89 | 0.62 | 0.70 | 0.79 | 0.73 | 0.40 | 1.00 |
| Y | 1.33 | 0.53 | 0.47 | 0.23 | 1.00 | 0.33 | 0.29 | 0.23 | 1.00 | 1.40 | 0.26 | 1.00 | 0.46 | 1.08 | 0.80 | 0.66 | 0.86 | 1.07 |
| W | 0.28 | 0.72 | 0.24 | 0.35 | 0.39 | 0.18 | 0.48 | 0.17 | 1.07 | 1.05 | 1.03 | 0.59 | 0.80 | 1.47 | 0.71 | 0.53 | 0.34 | **2.12** |
| N | 1.39 | 0.22 | 0.38 | 0.11 | 0.07 | 0.34 | 0.46 | 0.27 | 0.18 | 0.89 | 0.54 | 0.76 | 0.35 | 1.40 | 0.36 | 0.78 | 0.60 | 1.09 |
| D | 1.11 | 0.15 | 0.95 | 0.08 | 0.34 | 1.00 | 0.38 | 0.14 | 0.13 | 0.49 | 0.26 | 0.34 | 0.70 | 1.00 | 0.78 | 0.57 | 0.22 | 0.79 |
| E | 0.50 | 0.40 | 0.79 | 0.11 | 0.14 | 0.33 | 0.92 | 0.06 | 0.29 | 1.07 | 0.12 | 0.28 | 0.75 | 1.57 | 0.48 | 0.62 | 0.31 | 0.54 |
| Q | 0.63 | 0.00 | 0.85 | 0.00 | 0.00 | 0.52 | 1.43 | 0.25 | 0.00 | 0.46 | **11.91** | 1.06 | 0.23 | 0.90 | 0.98 | 0.39 | 0.24 | 1.14 |

Legend

| | |
|---|---|
| **Favorable** | >2 |
| Neutral | 0.5 to 2 |
| Unfavorable | <0.5 |

FIG. 5F

MBN001 HCDR3
Human CEACAM5

| Legend | |
|---|---|
| **Favorable** | >2 |
| Neutral | 0.5 to 2 |
| Unfavorable | <0.5 |

SEQ ID NO: 63

| Germline | – | – | – | – | – | – | – | – | – | – | – |
|---|---|---|---|---|---|---|---|---|---|---|---|
| Parental | T | G | L | T | G | T | G | A | F | D | I |
| | 94 | 95 | 96 | 97 | 98 | 99 | 100 | 100a | 100b | 101 | 102 |
| Normalized Enrichment Ratio | | | | | | | | | | | |
| * | 0.00 | ND | ND | 0.00 | 0.00 | ND | 0.00 | 0.00 | 0.00 | 0.00 | 0.00 |
| P | 0.14 | 0.00 | 0.00 | 0.00 | 0.00 | 0.11 | 1.78 | 0.07 | 0.00 | 0.00 | 0.00 |
| G | 0.00 | 1.00 | 0.05 | 0.05 | 1.00 | 0.00 | 1.00 | 0.15 | 0.18 | 0.27 | 0.08 |
| A | 0.14 | 0.07 | 0.13 | 0.00 | 0.00 | 0.29 | 0.19 | 1.00 | 0.63 | 0.05 | 0.00 |
| C | 0.00 | 0.11 | 1.40 | 0.19 | 0.00 | 0.07 | 0.84 | 0.08 | 1.23 | 0.17 | 0.00 |
| S | 0.05 | 0.03 | 0.03 | 0.04 | 0.03 | 0.06 | 0.22 | 0.21 | **2.59** | 0.14 | 0.09 |
| T | 1.00 | 0.06 | 0.00 | 1.00 | 0.00 | 1.00 | 0.10 | 0.04 | 1.64 | 0.00 | 0.00 |
| V | 0.03 | 0.00 | 0.13 | 0.11 | 0.07 | 0.14 | 0.59 | 0.08 | **2.64** | 0.21 | 1.24 |
| L | 0.04 | 0.08 | 1.00 | 0.03 | 0.00 | 0.15 | **2.49** | 0.06 | **3.16** | 0.00 | 0.10 |
| I | 0.09 | 0.00 | 0.00 | 0.22 | 0.08 | 0.26 | 1.16 | 0.13 | 1.28 | 0.00 | 1.00 |
| M | 0.07 | 0.00 | 0.36 | 0.10 | 0.00 | 0.00 | 0.31 | 0.00 | **3.07** | 0.00 | 0.16 |
| K | 0.00 | 0.00 | 0.00 | 0.00 | 0.32 | 0.00 | 0.00 | 0.00 | **3.26** | 0.00 | 0.19 |
| R | 0.00 | 0.04 | 0.00 | 0.00 | 0.00 | 0.00 | 0.12 | 0.09 | 0.00 | 0.00 | 0.00 |
| H | 0.00 | 0.00 | 0.00 | 0.00 | 0.00 | 0.23 | 0.00 | 0.25 | **2.74** | 0.14 | 0.00 |
| F | 0.06 | 0.05 | 0.11 | 0.06 | 0.00 | 0.00 | 0.00 | 0.09 | 1.00 | 0.12 | 0.15 |
| Y | 0.08 | 0.00 | 0.00 | 0.00 | 0.00 | 0.00 | 0.00 | 0.10 | **4.01** | 0.00 | 0.00 |
| W | 0.09 | 0.21 | 0.00 | 0.00 | 0.17 | 0.04 | 0.29 | 0.18 | 0.64 | 0.08 | 0.00 |
| N | 0.24 | 0.13 | 0.25 | 0.14 | 0.00 | 0.14 | **3.68** | 0.00 | **7.04** | 0.12 | 0.00 |
| D | 0.08 | 0.00 | 0.04 | 0.00 | 0.06 | 0.00 | 0.66 | 0.04 | 1.15 | 1.00 | 0.00 |
| E | 0.06 | 0.11 | 0.08 | 0.00 | 0.00 | 0.20 | 0.12 | 0.00 | 0.11 | 0.40 | 0.00 |
| Q | 0.00 | 0.13 | 0.34 | 0.00 | 0.12 | 0.00 | 0.26 | 0.00 | 1.55 | 0.00 | 0.30 |

ND= Enrichment ratios could not be determined because NGS counts in the starting library were too low

FIG. 5G

MBN001 HCDR3
Cynomolgus CEACAM5

Legend

| Legend | |
|---|---|
| **Favorable** | >2 |
| Neutral | 0.5 to 2 |
| Unfavorable | <0.5 |

SEQ ID NO: 63

| Germline | – | – | – | – | – | – | – | – | – | – | – |
|---|---|---|---|---|---|---|---|---|---|---|---|
| Parental | T | G | L | T | G | T | G | A | F | D | I |
| | 94 | 95 | 96 | 97 | 98 | 99 | 100 | 100a | 100b | 101 | 102 |
| Normalized Enrichment Ratio | | | | | | | | | | | |
| * | 0.00 | ND | ND | 0.00 | 0.00 | ND | 0.00 | 0.00 | 0.00 | 0.00 | 0.00 |
| P | 0.16 | 0.15 | 0.15 | 0.00 | 0.19 | 0.11 | 0.62 | 0.00 | 0.00 | 0.00 | 0.00 |
| G | 0.26 | 1.00 | 0.25 | 0.06 | 1.00 | 0.12 | 1.00 | 0.22 | 0.07 | 0.33 | 0.11 |
| A | 0.07 | 0.00 | 0.19 | 0.14 | 0.08 | 0.35 | 0.26 | 1.00 | 1.03 | 0.08 | 0.33 |
| C | 0.16 | 0.20 | **2.58** | 0.00 | 0.11 | 0.00 | 0.40 | 0.27 | 1.94 | 0.43 | 0.33 |
| S | 0.11 | 0.23 | 0.18 | 0.22 | 0.18 | 0.28 | 0.46 | 0.28 | **2.16** | 0.68 | 0.17 |
| T | 1.00 | 0.20 | 0.30 | 1.00 | 0.00 | 1.00 | 0.00 | 0.08 | 0.90 | 0.38 | 0.00 |
| V | 0.04 | 0.14 | 0.25 | 0.04 | 0.09 | 0.23 | 0.48 | 0.15 | **3.11** | 0.27 | 1.10 |
| L | 0.13 | 0.14 | 1.00 | 0.13 | 0.10 | 0.11 | 0.96 | 0.15 | **5.23** | 0.00 | 0.11 |
| I | 0.00 | 0.21 | 0.26 | 0.21 | 0.33 | 0.14 | 0.27 | 0.12 | 1.30 | 0.00 | 1.00 |
| M | 0.14 | 0.16 | 0.44 | 0.19 | 0.00 | 0.00 | 0.24 | 0.11 | **5.08** | 0.00 | 0.00 |
| K | 0.00 | 0.15 | 0.00 | 0.00 | 0.00 | 0.00 | 0.00 | 0.15 | **3.43** | 0.00 | 0.00 |
| R | 0.11 | 0.15 | 0.19 | 0.06 | 0.00 | 0.19 | 0.11 | 0.24 | 0.23 | 0.00 | 0.15 |
| H | 0.00 | 0.00 | 0.00 | 0.23 | 0.00 | 0.36 | 0.00 | 0.67 | **3.10** | 0.00 | 0.00 |
| F | 0.24 | 0.14 | 0.21 | 0.34 | 0.10 | 0.35 | 0.27 | 0.08 | 1.00 | 0.00 | 0.51 |
| Y | 0.22 | 0.14 | 0.17 | 0.17 | 0.21 | 0.32 | 0.38 | 0.28 | **4.49** | 0.18 | 0.19 |
| W | 0.24 | 0.12 | 0.12 | 0.18 | 0.39 | 0.07 | 0.17 | 0.20 | 0.50 | 0.25 | 0.50 |
| N | 0.32 | 0.35 | 0.00 | 0.25 | 0.19 | 0.22 | **19.17** | 0.00 | **22.72** | 0.00 | 0.21 |
| D | 0.26 | 0.38 | 0.00 | 0.00 | 0.00 | 0.00 | 0.92 | 0.28 | 1.64 | 1.00 | 0.00 |
| E | 0.00 | 0.13 | 0.22 | 0.00 | 0.00 | 0.00 | 0.22 | 0.09 | 0.28 | 0.37 | 0.00 |
| Q | 0.25 | 0.39 | 0.98 | 0.00 | 0.00 | 0.00 | 0.14 | 0.00 | 0.78 | 0.00 | 0.00 |

ND= Enrichment ratios could not be determined because NGS counts in the starting library were too low

FIG. 5H

MBN001 LCDR1
Human CEACAM5

SEQ ID NO: 64

| Germline | – | – | – | – | – | – | – | – | – | – | – | – |
|---|---|---|---|---|---|---|---|---|---|---|---|---|
| Parental | R | A | S | Q | S | V | S | S | S | Y | L | A |
| | 24 | 25 | 26 | 27 | 27a | 28 | 29 | 30 | 31 | 32 | 33 | 34 |
| Normalized Enrichment Ratio | | | | | | | | | | | | |
| * | 0.21 | ND | 0.00 | 0.31 | 0.00 | 0.00 | 0.00 | 0.00 | 0.00 | 0.00 | 0.00 | ND |
| P | 0.47 | **2.56** | 0.77 | 1.23 | 0.68 | **2.27** | 0.47 | 1.79 | **2.20** | **2.20** | 0.00 | 0.00 |
| G | 1.19 | 0.70 | 1.25 | 0.54 | 0.97 | 0.35 | 1.61 | 0.40 | 0.90 | **2.68** | **2.01** | 0.39 |
| A | 0.94 | 1.00 | 1.20 | 0.56 | 0.83 | 0.44 | 0.90 | 1.19 | 1.16 | 0.53 | **2.20** | 1.00 |
| C | 1.03 | **3.03** | 0.75 | 0.82 | 1.01 | **2.44** | 1.19 | 0.14 | 1.70 | 0.10 | 0.80 | 0.71 |
| S | 1.04 | 0.86 | 1.00 | 0.59 | 1.00 | 0.75 | 1.00 | 1.00 | 1.00 | 0.61 | 1.82 | 0.72 |
| T | 0.75 | 1.58 | 0.55 | 1.01 | 0.66 | **2.00** | 0.28 | 0.49 | 1.26 | 0.57 | 0.86 | 0.22 |
| V | 0.73 | 1.38 | 0.79 | 1.11 | 0.77 | 1.00 | 0.37 | 0.87 | **2.48** | 0.64 | 1.45 | 0.00 |
| L | 0.82 | 1.98 | 1.12 | 0.65 | 0.61 | 1.62 | 0.72 | 0.30 | 1.81 | 0.09 | 1.00 | 0.00 |
| I | 1.05 | 1.55 | 1.13 | 1.20 | 0.59 | 1.66 | 0.48 | 0.57 | **6.43** | 0.84 | **2.32** | 0.00 |
| M | 0.78 | 1.99 | 1.40 | 0.73 | 0.52 | **2.73** | 0.41 | 0.19 | 1.54 | 0.95 | 1.88 | 0.00 |
| K | 0.94 | 0.29 | 1.12 | 0.90 | 0.85 | 0.55 | 0.19 | 0.22 | 1.15 | 0.08 | 0.57 | 0.00 |
| R | 1.00 | 0.12 | 0.97 | 0.55 | 0.95 | 0.24 | 0.10 | 0.37 | 0.61 | 0.13 | 0.75 | 0.00 |
| H | 0.72 | 0.34 | 1.57 | 0.64 | 1.32 | 0.44 | 0.57 | 0.00 | 0.73 | 0.75 | 0.34 | 0.00 |
| F | 1.31 | 1.42 | 1.04 | 0.56 | 1.39 | **2.23** | 0.39 | 0.11 | 0.75 | 0.91 | 1.67 | 0.00 |
| Y | 1.13 | 0.37 | 1.46 | 0.59 | 1.55 | 0.63 | 0.56 | 0.27 | 1.02 | 1.00 | 1.85 | 0.00 |
| W | 1.10 | 0.31 | 0.87 | 0.43 | 0.82 | 0.49 | 0.46 | 0.08 | **6.16** | 0.89 | 1.96 | 0.30 |
| N | 0.98 | 0.57 | 0.75 | 0.52 | 0.51 | 0.36 | 0.66 | 0.27 | 0.00 | 0.84 | 0.52 | 0.00 |
| D | 0.62 | 0.50 | 1.11 | 0.63 | 0.68 | 0.69 | 1.12 | 0.55 | 0.31 | 0.76 | 1.19 | 0.00 |
| E | 1.05 | 0.28 | 1.48 | 1.14 | 0.64 | 0.26 | 1.53 | 0.26 | 0.88 | 0.37 | 1.74 | 0.00 |
| Q | 0.73 | 0.83 | 1.49 | 1.00 | 0.95 | 0.75 | 0.80 | 0.19 | ND | 0.33 | 0.84 | ND |

ND= Enrichment ratios could not be determined because NGS counts in the starting library were too low Legend

| Legend | |
|---|---|
| **Favorable** | >2 |
| Neutral | 0.5 to 2 |
| Unfavorable | <0.5 |

FIG. 5I

MBN001 LCDR1
Cynomolgus CEACAM5

Legend

| Legend | |
|---|---|
| **Favorable** | >2 |
| Neutral | 0.5 to 2 |
| Unfavorable | <0.5 |

SEQ ID NO: 64

| Germline | – | – | – | – | – | – | – | – | – | – | – | – |
|---|---|---|---|---|---|---|---|---|---|---|---|---|
| Parental | R | A | S | Q | S | V | S | S | S | Y | L | A |
| | 24 | 25 | 26 | 27 | 27a | 28 | 29 | 30 | 31 | 32 | 33 | 34 |
| Normalized Enrichment Ratio | | | | | | | | | | | | |
| * | 0.00 | ND | 0.00 | 0.00 | 0.00 | 0.00 | 0.00 | 0.00 | 0.36 | 0.00 | 0.00 | ND |
| P | 0.89 | **3.13** | 0.61 | 0.98 | 1.03 | 0.77 | 0.59 | **2.12** | 1.78 | 1.84 | 0.00 | 0.00 |
| G | 0.82 | 0.53 | 1.27 | 0.50 | 0.71 | 0.14 | 2.54 | 0.08 | 0.00 | 1.33 | 1.15 | 0.79 |
| A | 0.63 | 1.00 | 0.92 | 0.49 | 1.19 | 0.49 | 0.41 | 1.92 | 1.60 | 0.25 | 1.39 | 1.00 |
| C | 1.23 | **2.85** | 0.85 | 0.54 | 1.20 | 1.22 | 0.86 | 0.26 | 1.52 | 0.73 | 0.24 | 1.01 |
| S | 0.68 | 1.34 | 1.00 | 0.62 | 1.00 | 0.44 | 1.00 | 1.00 | 1.00 | 0.79 | 0.61 | 0.52 |
| T | 0.50 | 1.95 | 0.82 | 0.89 | 0.60 | **2.11** | 0.27 | 0.81 | 1.31 | 0.57 | 0.34 | 0.50 |
| V | 0.63 | 1.38 | 0.87 | 1.23 | 0.60 | 1.00 | 0.13 | 0.99 | **3.15** | 0.91 | 1.81 | 0.25 |
| L | 0.65 | **3.20** | 0.51 | 0.62 | 0.62 | 1.41 | 0.45 | 0.11 | 1.79 | 0.05 | 1.00 | 0.11 |
| I | 0.99 | **2.09** | 1.03 | 1.12 | 0.88 | 1.77 | 0.15 | 0.91 | **10.62** | 1.24 | **3.41** | 0.00 |
| M | 0.66 | **2.77** | 1.52 | 1.08 | 1.24 | **2.69** | 0.00 | 0.25 | 1.56 | 1.05 | **2.86** | 0.53 |
| K | 0.45 | 0.40 | 1.71 | 0.82 | 0.00 | 0.76 | 0.00 | 0.00 | **2.62** | 0.00 | 0.63 | 0.00 |
| R | 1.00 | 0.44 | 0.89 | 0.80 | 0.96 | 0.36 | 0.60 | 0.13 | 0.76 | 0.00 | 0.52 | 0.00 |
| H | 0.38 | 0.62 | 0.46 | 0.64 | 1.17 | 0.29 | 0.36 | 0.00 | 1.13 | 0.48 | 0.26 | 0.00 |
| F | 1.49 | 1.80 | 1.14 | 0.44 | 1.47 | **2.20** | 0.34 | 0.00 | 0.24 | 0.77 | 1.65 | 0.00 |
| Y | 0.59 | 0.70 | 0.98 | 0.78 | **3.51** | 0.53 | 0.11 | 0.21 | 0.71 | 1.00 | **2.11** | 0.58 |
| W | 0.73 | 0.52 | 0.74 | 0.87 | **4.29** | 0.36 | 0.67 | 0.61 | **12.32** | 1.65 | **2.76** | 0.26 |
| N | **1.95** | 0.73 | 0.84 | 0.55 | 0.54 | 0.35 | 0.68 | 0.00 | 0.00 | 0.59 | 0.63 | 0.00 |
| D | 0.63 | 0.24 | 0.80 | 0.41 | 0.35 | 0.00 | 1.18 | 0.00 | 0.18 | 0.74 | 0.00 | 0.00 |
| E | 1.12 | 0.65 | 0.84 | 0.50 | 0.37 | 0.00 | 0.87 | 0.35 | 0.00 | 0.00 | 1.09 | 0.00 |
| Q | 0.62 | 0.45 | 1.70 | 1.00 | 0.73 | 0.00 | 0.00 | 0.39 | ND | 0.68 | 1.06 | ND |

ND= Enrichment ratios could not be determined because NGS counts in the starting library were too low

FIG. 5J

MBN001 LCDR2
Human CEACAM5

Legend

| |
|---|
| **Favorable** >2 |
| Neutral } 0.5 to 2 |
| Unfavorable <0.5 |

SEQ ID NO: 65

| Germline | _ | _ | _ | _ | _ | _ | _ |
|---|---|---|---|---|---|---|---|
| Parental | G | A | S | S | R | A | T |
| | 50 | 51 | 52 | 53 | 54 | 55 | 56 |
| Normalized Enrichment Ratio | | | | | | | |
| * | ND | ND | 0.00 | 0.00 | 0.00 | 0.00 | 0.00 |
| P | ND | **2.98** | 0.16 | 0.59 | 0.53 | 0.62 | 1.52 |
| G | 1.00 | **3.07** | 0.52 | 0.55 | 0.47 | 0.82 | 0.37 |
| A | **4.16** | 1.00 | 0.85 | 1.19 | 0.53 | 1.00 | 0.32 |
| C | 0.91 | **2.36** | 0.86 | 0.64 | 0.50 | 0.19 | 0.50 |
| S | **2.43** | 0.91 | 1.00 | 1.00 | 0.49 | 0.74 | 0.50 |
| T | 0.79 | 1.80 | 0.73 | 1.64 | 0.74 | 0.45 | 1.00 |
| V | 1.92 | 0.24 | 0.96 | 1.50 | 0.79 | 0.48 | 0.76 |
| L | 0.14 | 0.76 | 1.04 | 0.04 | 1.10 | **2.21** | 0.55 |
| I | 0.35 | 0.00 | 0.56 | 0.44 | 0.87 | 0.49 | 0.56 |
| M | **4.11** | 0.67 | 0.38 | 0.60 | 1.22 | 1.67 | 0.59 |
| K | 0.00 | 0.27 | 0.81 | 0.00 | 0.83 | 0.22 | 0.22 |
| R | 0.71 | 0.47 | 0.66 | 0.07 | 1.00 | 0.29 | 0.70 |
| H | 1.58 | 1.20 | 0.43 | 1.71 | 1.32 | **2.25** | 0.44 |
| F | **7.10** | 0.23 | 1.37 | **2.52** | 0.83 | 0.31 | 0.59 |
| Y | **6.97** | 0.25 | **2.35** | **4.04** | 1.10 | 1.57 | 0.51 |
| W | **8.12** | 1.61 | 1.66 | 5.71 | 0.80 | 0.62 | 0.97 |
| N | 0.80 | 1.08 | 0.64 | 1.19 | 0.62 | 1.60 | 1.20 |
| D | 0.00 | 0.42 | 0.65 | 0.09 | 0.32 | **2.76** | 0.66 |
| E | 0.00 | 0.47 | 0.62 | 0.42 | 0.53 | 0.19 | 0.34 |
| Q | 0.91 | 0.53 | **2.41** | 0.88 | 0.79 | 1.13 | 0.66 |

ND= Enrichment ratios could not be determined because NGS counts in the starting library were too low

FIG. 5K

MBN001 LCDR2
Cynomolgus CEACAM5

Legend

| | |
|---|---|
| **Favorable** | >2 |
| Neutral | 0.5 to 2 |
| Unfavorable | <0.5 |

SEQ ID NO: 65

| Germline | – | – | – | – | – | – | – |
|---|---|---|---|---|---|---|---|
| Parental | G | A | S | S | R | A | T |
| | 50 | 51 | 52 | 53 | 54 | 55 | 56 |
| Normalized Enrichment Ratio | | | | | | | |
| * | ND | ND | 1.46 | 0.00 | 0.00 | 0.36 | 0.00 |
| P | ND | **2.92** | 0.49 | 0.52 | 1.19 | 0.79 | **2.79** |
| G | 1.00 | **2.79** | 0.28 | 0.31 | 0.40 | 0.76 | 0.74 |
| A | **2.75** | 1.00 | 1.03 | 1.84 | 0.40 | 1.00 | 0.85 |
| C | **4.63** | **3.14** | 1.16 | 0.20 | 0.53 | 0.43 | **2.08** |
| S | **4.64** | 1.66 | 1.00 | 1.00 | 0.13 | 0.74 | 0.74 |
| T | 0.26 | 1.61 | 0.19 | 1.06 | 1.03 | 0.65 | 1.00 |
| V | **4.74** | 0.00 | 1.01 | 0.32 | 0.44 | 0.42 | 0.45 |
| L | 0.55 | 0.77 | 1.05 | 0.00 | 1.08 | **2.67** | 0.92 |
| I | 0.28 | 0.00 | 1.22 | 0.00 | 0.57 | 0.42 | 0.51 |
| M | **12.30** | 0.67 | 1.06 | 0.22 | 0.79 | **10.37** | 0.21 |
| K | 0.00 | 1.12 | 0.30 | 0.21 | 0.78 | 0.00 | 1.18 |
| R | 0.62 | 0.85 | 0.11 | 0.17 | 1.00 | 0.18 | 1.07 |
| H | 0.59 | **2.45** | 0.00 | 1.13 | 0.44 | 0.92 | 0.90 |
| F | **21.52** | 0.22 | **3.24** | 1.58 | 0.61 | **2.90** | 0.67 |
| Y | **32.14** | 0.00 | **4.09** | 1.85 | 0.19 | **7.46** | 1.48 |
| W | **45.22** | 1.20 | **2.13** | **10.33** | 0.91 | 0.36 | **3.29** |
| N | 0.00 | 0.21 | 0.26 | 0.55 | 0.81 | **8.97** | **2.10** |
| D | 0.16 | 0.00 | 0.00 | 0.10 | 0.49 | **5.65** | 0.16 |
| E | 0.44 | 0.14 | 0.64 | 0.21 | 0.15 | 0.24 | 0.48 |
| Q | 0.35 | 0.51 | **3.50** | 1.37 | 1.05 | 0.49 | 0.00 |

ND= Enrichment ratios could not be determined because NGS counts in the starting library were too low

FIG. 5L

MBN001 LCDR3
Human CEACAM5

Legend

| |
|---|
| **Favorable** >2 |
| Neutral } 0.5 to 2 |
| Unfavorable <0.5 |

SEQ ID NO: 66

| Germline | -- | -- | -- | -- | -- | -- | -- | -- |
|---|---|---|---|---|---|---|---|---|
| Parental | Q | Q | Y | G | S | S | P | Y |
| | 89 | 90 | 91 | 92 | 93 | 94 | 95 | 96 |
| Normalized Enrichment Ratio | | | | | | | | |
| * | 0.00 | 0.49 | 0.44 | 0.53 | ND | ND | 0.00 | 0.00 |
| P | 0.38 | 0.10 | 0.00 | 0.07 | **7.51** | 0.80 | 1.00 | 1.98 |
| G | 1.74 | 0.09 | 1.49 | 1.00 | 0.20 | 0.77 | 0.14 | 1.27 |
| A | 1.04 | 0.00 | 1.42 | **1.97** | 0.91 | 0.85 | 1.02 | 1.10 |
| C | 0.00 | 0.00 | 1.52 | **2.47** | 1.90 | 1.77 | 1.12 | 1.68 |
| S | **2.56** | 0.07 | **3.34** | 1.74 | 1.00 | 1.00 | 0.48 | **3.11** |
| T | 0.35 | 0.00 | **2.76** | 0.98 | 1.85 | 1.19 | 1.44 | **3.02** |
| V | 0.03 | 0.10 | 0.62 | **2.63** | **2.47** | 1.49 | **2.39** | **2.52** |
| L | 0.43 | 0.17 | 0.08 | **4.75** | **4.94** | **3.46** | 1.71 | 0.85 |
| I | 0.00 | 0.12 | 0.11 | **3.43** | **3.51** | **3.58** | 1.75 | **3.12** |
| M | **2.23** | 0.23 | 0.25 | **3.49** | **2.43** | 1.59 | **2.09** | **5.58** |
| K | 0.95 | 0.00 | 0.00 | **4.04** | 0.72 | 0.46 | **3.10** | 0.00 |
| R | 0.22 | 0.10 | 0.15 | **2.66** | **3.39** | 1.32 | **2.13** | 0.08 |
| H | **3.22** | 0.16 | 0.27 | 1.16 | **2.01** | 1.64 | **2.16** | **2.46** |
| F | **4.29** | 0.15 | 0.55 | **3.53** | **3.04** | **3.06** | 1.66 | 0.29 |
| Y | **2.50** | 0.10 | 1.00 | **3.87** | **2.72** | **3.35** | 1.53 | 1.00 |
| W | 0.26 | 0.16 | 0.10 | **3.65** | 1.37 | 1.14 | 1.78 | **2.97** |
| N | **2.68** | 0.00 | **3.24** | 1.35 | 1.53 | 1.69 | 1.22 | **3.56** |
| D | **2.70** | 0.09 | 1.60 | 0.94 | 0.44 | 0.29 | 0.20 | **3.19** |
| E | 1.32 | 0.27 | 0.31 | 1.94 | 0.49 | 0.00 | 1.31 | 1.46 |
| Q | 1.00 | 1.00 | 1.92 | 1.45 | **2.71** | 1.79 | **3.79** | **4.11** |

ND= Enrichment ratios could not be determined because NGS counts in the starting library were too low

FIG. 5M

MBN001 LCDR3
Cynomolgus CEACAM5

Legend

| | |
|---|---|
| **Favorable** | >2 |
| Neutral | 0.5 to 2 |
| Unfavorable | <0.5 |

SEQ ID NO: 66

| Germline | – | – | – | – | – | – | – | – |
|---|---|---|---|---|---|---|---|---|
| Parental | Q | Q | Y | G | S | S | P | Y |
| | 89 | 90 | 91 | 92 | 93 | 94 | 95 | 96 |
| Normalized Enrichment Ratio | | | | | | | | |
| * | 0.00 | 0.00 | 0.51 | 0.68 | ND | ND | 0.00 | 0.00 |
| P | 0.65 | 0.00 | 0.00 | 0.07 | **43.51** | 0.47 | 1.00 | 1.17 |
| G | 1.24 | 0.17 | **4.40** | 1.00 | 0.32 | 0.54 | 0.23 | 0.42 |
| A | 1.46 | 0.07 | 1.07 | 1.09 | 0.59 | 0.79 | 0.77 | 0.73 |
| C | 0.00 | 0.19 | **2.61** | 1.47 | **3.50** | **2.72** | 0.61 | 0.51 |
| S | **2.03** | 0.10 | **3.81** | 1.07 | 1.00 | 1.00 | 0.32 | 0.87 |
| T | 0.00 | 0.00 | **2.68** | 0.63 | **5.66** | 1.01 | 1.05 | 1.42 |
| V | 0.25 | 0.00 | 0.36 | 1.61 | **8.10** | 1.69 | 0.85 | 0.89 |
| L | 0.26 | 0.05 | 0.00 | **6.63** | **16.69** | **8.11** | 1.04 | 0.49 |
| I | 0.00 | 0.25 | 0.00 | **3.92** | **15.44** | **2.52** | **2.19** | 1.67 |
| M | 0.73 | 0.00 | 0.35 | **2.97** | **4.31** | **2.02** | 1.46 | **2.10** |
| K | 0.51 | 0.00 | 0.00 | **29.40** | **3.63** | 0.00 | **3.58** | 0.20 |
| R | 0.08 | 0.05 | 0.35 | **9.73** | **33.98** | 1.08 | 1.36 | 0.10 |
| H | **4.56** | 0.00 | 0.62 | 0.40 | **6.28** | 1.25 | 0.64 | 0.00 |
| F | 1.14 | 0.00 | 0.39 | 1.82 | **3.58** | **5.30** | 1.12 | 0.42 |
| Y | 0.77 | 0.00 | 1.00 | 2.44 | **6.25** | **2.80** | 0.36 | 1.00 |
| W | 0.20 | 0.00 | 0.13 | **3.08** | **2.67** | 1.09 | 1.19 | 1.79 |
| N | 0.80 | 0.00 | **20.59** | **2.10** | **2.75** | 0.47 | 1.19 | **3.42** |
| D | **2.77** | 0.48 | 1.14 | 0.22 | 0.00 | 0.00 | 0.21 | **2.32** |
| E | 1.49 | 0.27 | 0.00 | 0.41 | 0.17 | 0.00 | 0.60 | **2.34** |
| Q | 1.00 | 1.00 | **2.27** | 1.06 | 4.12 | **2.68** | 0.88 | 1.90 |

ND= Enrichment ratios could not be determined because NGS counts in the starting library were too low

FIG. 5N

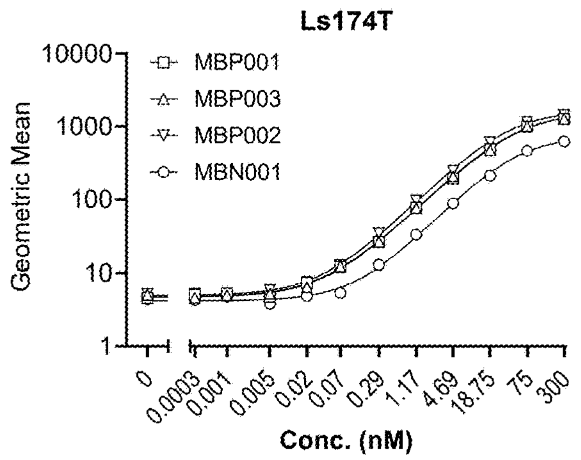
FIG. 9A
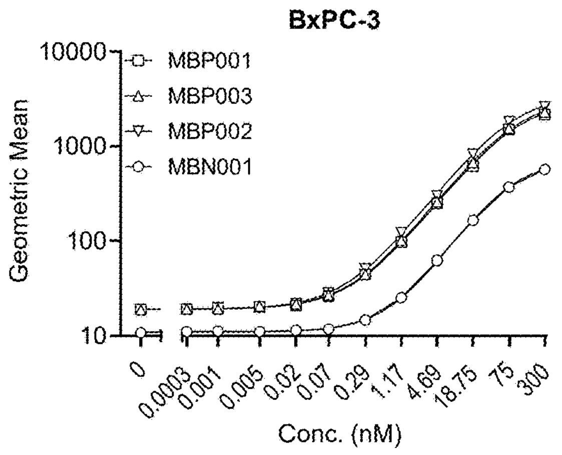
FIG. 9B
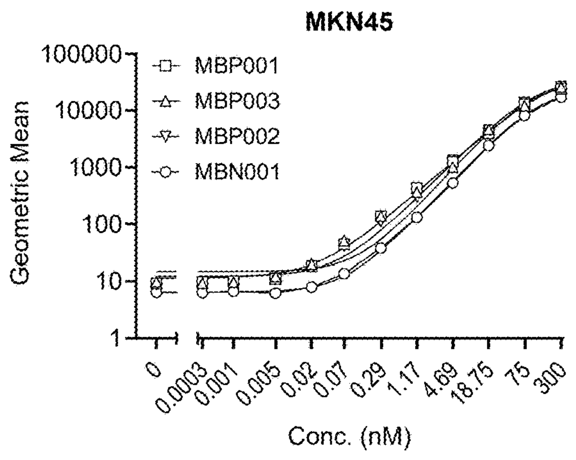
FIG. 9C
| Clone name | LS174T EC50 (nM) | BxPC3 EC50 (nM) | MKN45 EC50 (nM) |
|---|---|---|---|
| MBN001 | 1.7 | 1.8 | 2.2 |
| MBP003 | 1.7 | 1.9 | 2.4 |
| MBP001 | 1.7 | 1.9 | 2.0 |
| MBP002 | 1.5 | 1.9 | 2.1 |
FIG. 9D

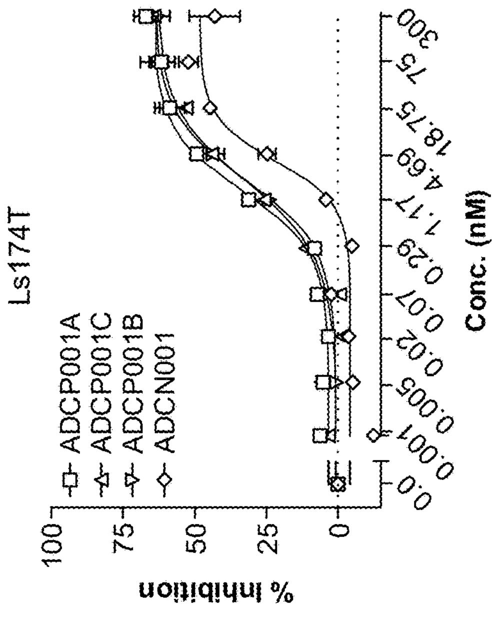
FIG. 10A
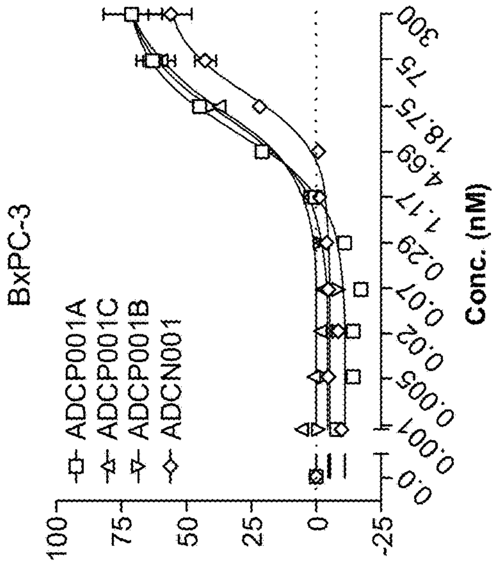
FIG. 10B
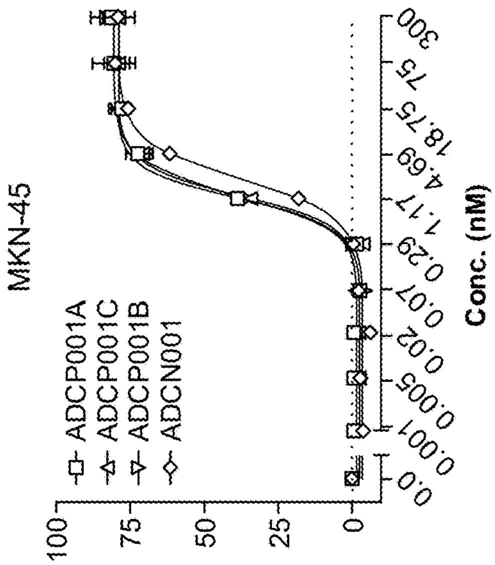
FIG. 10C
| Clone name | LS174T IC50 (nM) | BxPC3 IC50 (nM) | MKN45 IC50 (nM) |
|---|---|---|---|
| ADCN001 | 3.9 | 27.5 | 2.2 |
| ADCP001C | 2.2 | 13.4 | 1.3 |
| ADCP001A | 2.0 | 16.8 | 1.3 |
| ADCP001B | 1.6 | 8.3 | 1.2 |
FIG. 10D

| | ADCP001A | ADCP001B | ADCP001C |
|---|---|---|---|
| IC50 | 0.4133 | 0.3038 | 0.4295 |

| | ADCP001A | ADCP001B | ADCP001C |
|---|---|---|---|
| IC50 | 0.3372 | 0.2716 | 0.3140 |

| | ADCP001A | ADCP001B | ADCP001C |
|---|---|---|---|
| IC50 | 0.4752 | 0.3537 | 0.4980 |

| | ADCP001A | ADCP001B | ADCP001C |
|---|---|---|---|
| IC50 | 0.3265 | 0.2628 | 0.3074 |

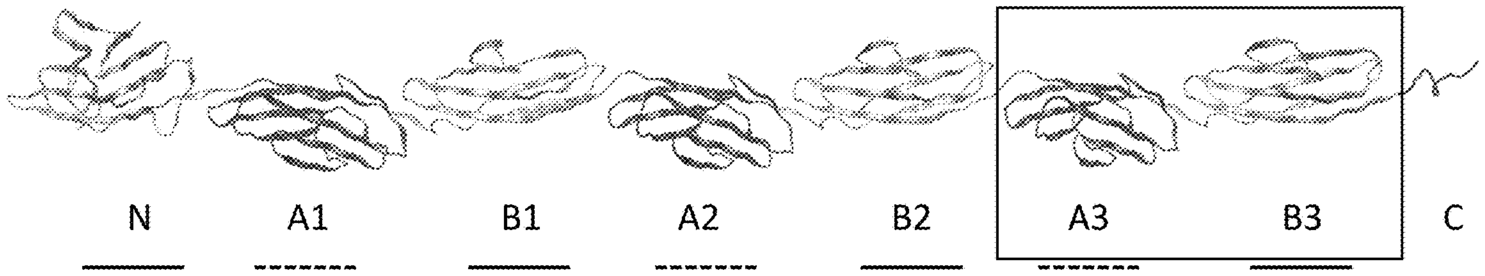

FIG. 13A

>sp|P06731|CEAM5_HUMAN

KLTIESTPFNVAEGKEVLLLVHNLPQHLFGYSWYKGERVDGNRQIIGYVIGTQQATPGPAYSGREIIYPNASLLI N

QNIIQNDTGFYTLHVIKSDLVNEEATGQFRVYPELPKPSISSNNSKPVEDKDAVAFTCEPETQDATYLWWVNNQS A1

LPVSPRLQLSNGNRTLTLFNVTRNDTASYKCETQNPVSARRSDSVILNVLYGPDAPTISPLNTSYRSGENLNLSC B1

HAASNPPAQYSWFVNGTFQQSTQELFIPNITVNNSGSYTCQAHNSDTGLNRTTVTTITVYAEPPKPFITSNNSNP A2

VEDEDAVALTCEPEIQNTTYLWWVNNQSLPVSPRLQLSNDNRTLTLLSVTRNDVGPYECGIQNELSVDHSDPVIL

NVLYGPDDPTISPSYTYYRPGVNLSLSCHAASNPPAQYSWLIDGNIQQHTQELFISNITEKNSGLYTCQANNSAS B2

GHSRTTVKTITVSAELPKPSISSNNSKPVEDKDAVAFTCEPEAQNTTYLWWVNGQSLPVSPRLQLSNGNRTLTLF A3

NVTRNDARAYVCGIQNSVSANRSDPVTLDVLYGPDTPIISPPDSSYLSGANLNLSCHSASNPSPQYSWRINGIPQ B3

QHTQVLFIAKITPNNNGTYACFVSNLATGRNNSIVKSITVSASGTSPGLSAGATVGIMIGVLVGVALI C (SEQ ID NO: 105)

FIG. 13B hCEACAM5 A3-B3-CT:

*HHHHHHETVRFQGPKPSISSNNSKPVEDKDAVA*FTCEPEAQNTTYLWWVNG*QSLPVSPRLQLSNGNRTLTLFNVTRNDA*
*R*AYVCGIQNSVSANRSDPVTL*DV*LYG_P_DT_P_IIS_PP_DSSYLSGANL*NL*SCHSASNPSPQYSWRINGIPQQHTQVLF*IAKITPNN*
*NGTYACFVSNL*ATGRNNSIVKSITVSASGTS_P_GLSA (SEQ ID NO: 24)

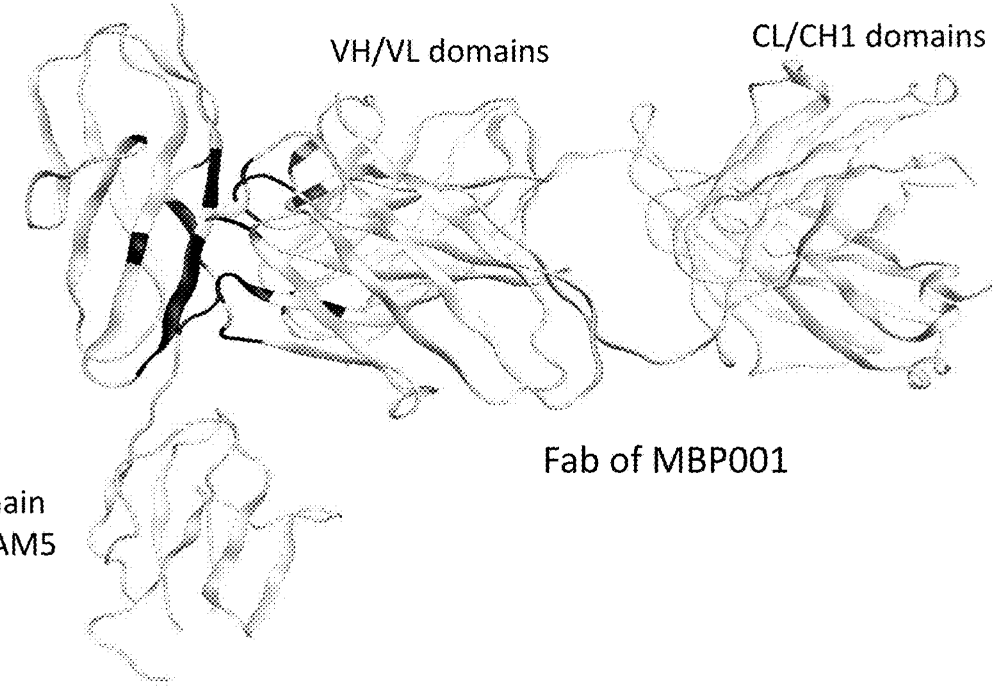

6xHis-A3-B3 huCEACAM5 (MBP001 epitope residues bolded)
HHHHHHETVRFQGPKPSISSNNSKPVEDKDAVAFTCEPEAQNTTYLWWVNGQSLPVSPRLQLSNGNRTLTLFNVTRNDARAYVCGIQNSVSANRSDPVTLDVLYGPDTPIISPPDSSY
LSGANLNLSCHSASNPSPQYSWRINGIPQQHTQVLFIAKITPNNNGTYACFVSNLATGRNNSIVKSITVSASGTSPGLSA (SEQ ID NO: 24)

MBP001 VL (paratope residues bolded; CDRs underlined)
EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPYTFGQGTKLEIKRTVAAPSVFIFPPSD
EQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 46)

MBP001 VH (paratope residues bolded; CDRs underlined)
QVQLVESGGGVVQPGRSLRLSCAASGIYFSSHGMHWVRQAPGKGLEWVTFISYDGSYKSYVDSVKGRFTISRDNSKNTLYLQMNSLRAEDTAVYYCATGLTGTGAFDIWGQGTMV
TVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCGG (SEQ ID NO:
100)

FIG. 14C

SEQUENCE LISTING

```
Sequence total quantity: 117
SEQ ID NO: 1            moltype = AA  length = 702
FEATURE                 Location/Qualifiers
source                  1..702
                        mol_type = protein
                        organism = Homo sapiens
SEQUENCE: 1
MESPSAPPHR WCIPWQRLLL TASLLTFWNP PTTAKLTIES TPFNVAEGKE VLLLVHNLPQ  60
HLFGYSWYKG ERVDGNRQII GYVIGTQQAT PGPAYSGREI IYPNASLLIQ NIIQNDTGFY  120
TLHVIKSDLV NEEATGQFRV YPELPKPSIS SNNSKPVEDK DAVAFTCEPE TQDATYLWWV  180
NNQSLPVSPR LQLSNGNRTL TLFNVTRNDS ASYKCETQNP VSARRSDSVI LNVLYGPDAP  240
TISPLNTSYR SGENLNLSCH AASNPPAQYS WFVNGTFQQS TQELFIPNIT VNNSGSYTCQ  300
AHNSDTGLNR TTVTTITVYA EPPKPFITSN NSNPVEDEDA VALTCEPEIQ NTTYLWWVNN  360
QSLPVSPRLQ LSNDNRTLTL LSVTRNDVGP YECGIQNELS VDHSDPVILN VLYGPDDPTI  420
SPSYTYYRPG VNLSLSCHAA SNPPAQYSWL IDGNIQQHTQ ELFISNITEK NSGLYTCQAN  480
NSASGHSRTT VKTITVSAEL PKPSISSNNS KPVEDKDAVA FTCEPEAQNT TYLWWVNGQS  540
LPVSPRLQLS NGNRTLTLFN VTRNDARAYV CGIQNSVSAN RSDPVTLDVL YGPDTPIISP  600
PDSSYLSGAN LNLSCHSASN PSPQYSWRIN GIPQQHTQVL FIAKITPNNN GTYACFVSNL  660
ATGRNNSIVK SITVSASGTS PGLSAGATVG IMIGVLVGVA LI                    702

SEQ ID NO: 2            moltype = DNA  length = 2888
FEATURE                 Location/Qualifiers
source                  1..2888
                        mol_type = genomic DNA
                        organism = Homo sapiens
SEQUENCE: 2
ggacagcaga ccagacagtc acagcagcct tgacaaaacg ttcctggaac tcaagctctt  60
ctccacagag gaggacagag cagacagcag agaccatgga gtctccctcg gcccctcccc  120
acagatggtg catcccctgg cagaggctcc tgctcacagc ctcacttcta accttctgga  180
acccgcccac cactgccaag ctcactattg aatccacgcc gttcaatgtc gcagagggga  240
aggaggtgct tctacttgtc cacaatctgc cccagcatct tttggctac agctggtaca   300
aaggtgaaag agtggatggc aaccgtcaaa ttataggata tgtaatagga actcaacaag  360
ctaccccagg gcccgcatac agtggtcgag agataatata ccccaatgca tccctgctga  420
tccagaacat catccagaat gacacaggat tctacaccct acacgtcata aagtcagatc  480
ttgtgaatga agaagcaact ggccagttcc gggtataccc ggagctgccc aagccctcca  540
tctccagcaa caactccaaa cccgtggagg acaaggatgc tgtggccttc acctgtgaac  600
ctgagactca ggacgcaacc tacctgtggt gggtaaacaa tcagagcctc ccggtcagtc  660
ccaggctgca gctgtccaat ggcaacagga ccctcactct attcaatgtc acaagaaatg  720
actcagcaag ctacaaatgt gaaacccaga acccagtgag tgccaggcgc agtgattcag  780
```

-continued

```
tcatcctgaa tgtcctctat ggcccggatg cccccaccat ttcccctcta aacacatctt  840
acagatcagg ggaaaatctg aacctctcct gccacgcagc ctctaaccca cctgcacagt  900
actcttggtt tgtcaatggg actttccagc aatccaccca agagctcttt atccccaaca  960
tcactgtgaa taatagtgga tcctatacgt gccaagccca taactcagac actggcctca  1020
ataggaccac agtcacgacg atcacagtct atgcagagcc acccaaaccc ttcatcacca  1080
gcaacaactc caaccccgtg gaggatgagg atgctgtagc cttaacctgt gaacctgaga  1140
ttcagaacac aacctacctg tggtgggtaa ataatcagag cctcccggtc agtcccaggc  1200
tgcagctgtc caatgacaac aggaccctca ctctactcag tgtcacaagg aatgatgtag  1260
gaccctatga gtgtggaatc cagaacgaat taagtgttga ccacagcgac ccagtcatcc  1320
tgaatgtcct ctatggccca gacgacccca ccatttcccc ctcatacacc tattaccgtc  1380
caggggtgaa cctcagcctc tcctgccatg cagcctctaa cccacctgca cagtattctt  1440
ggctgattga tgggaacatc cagcaacaca cacaagagct ctttatctcc aacatcactg  1500
agaagaacag cggactctat acctgccagg ccaataactc agccagtggc cacagcagga  1560
ctacagtcaa gacaatcaca gtctctgcgg agctgcccaa gccctccatc tccagcaaca  1620
actccaaacc cgtggaggac aaggatgctg tggccttcac ctgtgaacct gaggctcaga  1680
acacaaccta cctgtggtgg gtaaatggtc agagcctccc agtcagtccc aggctgcagc  1740
tgtccaatgg caacaggacc ctcactctat tcaatgtcac aagaaatgac gcaagagcct  1800
atgtatgtgg aatccagaac tcagtgagtg caaaccgcag tgacccagtc accctggatg  1860
tcctctatgg gccggacacc cccatcattt cccccccaga ctcgtcttac ctttcgggag  1920
cgaacctcaa cctctcctgc cactcggcct ctaacccatc cccgcagtat tcttggcgta  1980
tcaatgggat accgcagcaa cacacacaag ttctctttat cgccaaaatc acgccaaata  2040
ataacgggac ctatgcctgt tttgtctcta acttggctac tggccgcaat aattccatag  2100
tcaagagcat cacagtctct gcatctggaa cttctcctgg tctctcagct ggggccactg  2160
tcggcatcat gattggagtg ctggttgggg ttgctctgat atagcagccc tggtgtagtt  2220
tcttcatttc aggaagactg acagttgttt tgcttcttcc ttaaagcatt tgcaacagct  2280
acagtctaaa attgcttctt taccaaggat atttacagaa aagactctga ccagagatcg  2340
agaccatcct agccaacatc gtgaaacccc atctctacta aaaatacaaa aatgagctgg  2400
gcttggtggc gcgcacctgt agtcccagtt actcgggagg ctgaggcagg agaatcgctt  2460
gaacccggga ggtggagatt gcagtgagcc cagatcgcac cactgcactc cagtctggca  2520
acagagcaag actccatctc aaaaagaaaa gaaaagaaga ctctgacctg tactcttgaa  2580
tacaagtttc tgataccact gcactgtctg agaatttcca aaactttaat gaactaactg  2640
acagcttcat gaaactgtcc cccaagatca agcagagaaa ataattaatt tcatgggact  2700
aaatgaacta atgaggataa tattttcata atttttttatt tgaaattttg ctgattcttt  2760
aaatgtcttg tttcccagat ttcaggaaac ttttttttctt ttaagctatc cacagcttac  2820
agcaatttga taaaatatac ttttgtgaac aaaaaaaaaa aaaaaaaaaa aaaaaaaaaa  2880
aaaaaaaa                                                          2888

SEQ ID NO: 3           moltype = AA  length = 705
FEATURE                Location/Qualifiers
source                 1..705
                       mol_type = protein
                       organism = Macaca fascicularis
SEQUENCE: 3
MGSPSAPLHR WCIPWQTLLL TASLLTFWNP PTTAQLTIES RPFNVAEGKE VLLLAHNVSQ  60
NLFGYIWYKG ERVDASRRIG SCVIRTQQIT PGPAHSGRET IDFNASLLIH NVTQSDTGSY  120
TIQVIKEDLV NEEATGQFRV YPELPKPYIS SNNSNPVEDK DAVALTCEPE TQDTTYLWWV  180
NNQSLPVSPR LELSSDNRTL TVFNIPRNDT TSYKCETQNP VSVRRSDPVT LNVLYGPDAP  240
TISPLNTPYR AGENLNLSCH AASNPAAQYS WFVNGTFQQS TQELFIPNIT VNNSGSYMCQ  300
AHNSATGLNR TTVTAITVYA ELPKPYITSN NSNPIEDKDA VTLTCEPETQ DTTYLWWVNN  360
QSLSVSSRLE LSNDNRTLTV FNIPRNDTTF YECETQNPVS VRRSDPVTLN VLYGPDAPTI  420
SPLNTPYRAG ENLNLSCHAA SNPAAQYSWF VNGTFQQSTQ ELFIPNITVN NSGSYMCQAH  480
NSATGLNRTT VTAITVYVEL PKPYISSNNS NPIEDKDAVT LTCEPVAENT TYLWWVNNQS  540
LSVSPRLQLS NGNRILTLLS VTRNDTGPYE CGIQNSESAK RSDPVTLNVT YGPDTPIISP  600
PDLSYRSGAN LNLSCHSDSN PSPQYSWLIN GTLRQHTQVL FISKITSNNN GAYACFVSNL  660
ATGRNNSIVK NISVSSGDSA PGSSGLSARA TVGIIIGMLV GVALM                 705

SEQ ID NO: 4           moltype = DNA  length = 3053
FEATURE                Location/Qualifiers
source                 1..3053
                       mol_type = genomic DNA
                       organism = Macaca fascicularis
SEQUENCE: 4
gatgccgaga agtactcctg ctgtaggagg agactcagga cagagggagg aaggacagca  60
gaccaggcag tcacagctgc cctgacaaga gcgttcctag agctcaggat cttctccaca  120
gaagaggaca gagcagacag cagagaccat ggggtctccc tcggcccctc ttcacagatg  180
gtgcatcccc tggcagacgc tcctgctcac agcctcactt ctaaccttct ggaacccgcc  240
caccactgcc cagctcacta ttgaatccag gccgttcaat gttgcagagg ggaaggaggt  300
tcttctactt gcccacaatg tgtcccagaa tctttttggc tacatctggt acaagggaga  360
aagagtggat gccagccgtc gaattggatc atgtgtaata agaactcaac aaattacccc  420
agggcccgca cacagcggtc gagagacaat agacttcaat gcatccctgc tgatccacaa  480
tgtcacccag agtgacacag gatcctacac catacaagtc ataaaggaag atcttgtgaa  540
tgaagaagca actggccagt tccgggtata cccggagctg cccaagccct acatctccag  600
caacaactcc aaccctgtgg aggacaagga tgctgtggcc ttaacctgtg aacctgagac  660
tcaggacaca acctacctgt ggtgggtaaa caatcagagc ctcccggtca gtcccaggct  720
ggagctgtcc agtgacaaca ggaccctcac tgtattcaat attccaagaa atgacacaac  780
atcctacaaa tgtgaaaccc agaacccagt gagtgtcaga cgcagcgacc cagtcaccct  840
gaatgtcctc tatggcccgg atgcgcccac catttcccct ctaaacacac cttacagagc  900
aggggaaaat ctgaacctct cctgccacgc agcctctaac ccagctgcac agtactcttg  960
gtttgtcaat gggacgttcc agcaatccac acaagagctc tttataccca acatcaccgt  1020
```

-continued

```
gaataatagc ggatcctata tgtgccaagc ccataactca gccactggcc tcaataggac  1080
cacagtcacg gcgatcacag tctacgcgga gctgcccaag ccctacatca ccagcaacaa  1140
ctccaacccc atagaggaca aggatgctgt gaccttaacc tgtgaacctg agactcagga  1200
cacaacctac ctgtggtggg taaacaatca gagcctctcg gtcagttcca ggctggagct  1260
gtccaatgac aacaggaccc tcactgtatt caatattcca agaaacgaca caacgttcta  1320
cgaatgtgaa acccagaacc cagtgagtgt cagacgcagc gacccagtca ccctgaatgt  1380
cctctatggc ccggatgcgc ccaccatttc ccctctaaac acaccttaca gagcagggga  1440
aaatctgaac ctctcctgcc acgcagcctc taacccagct gcacagtact cttggtttgt  1500
caatgggacg ttccagcaat ccacacaaga gctctttata cccaacatca ccgtgaataa  1560
tagcggatcc tatatgtgcc aagcccataa ctcagccact ggcctcaata ggaccacagt  1620
cacggcgatc acagtctatg tggagctgcc caagccctac atctccagca acaactccaa  1680
ccccatagag gacaaggatg ctgtgacctt aacctgtgaa cctgtggctg agaacacaac  1740
ctacctgtgg tgggtaaaca atcagagcct ctcggtcagt cccaggctgc agctctccaa  1800
tggcaacagg atcctcactc tactcagtgt cacacggaat gacacaggac cctatgaatg  1860
tggaatccag aactcagaga gtgcaaaacg cagtgaccca gtcaccctga atgtcaccta  1920
tggcccagac acccccatca tatccccccc agacttgtct taccgttcgg gagcaaacct  1980
caacctctcc tgccactcgg actctaaccc atccccgcag tattcttggc ttatcaatgg  2040
gacactgcgg caacacacac aagttctctt tatctccaaa atcacatcaa acaataacgg  2100
ggcctatgcc tgttttgtct ctaacttggc tactggtcgc aataactcca tagtcaagaa  2160
catctcagtc tcctctggcg attcagcacc tggaagttct ggtctctcag ctagggctac  2220
tgtcggcatc ataattggaa tgctggttgg ggttgctctg atgtagcagc cgtggtgtag  2280
tttctgcaat taagaaagac tgacagttgt tttgattctt ccttaaagca tttgcaacag  2340
ctacagtcta aaattgcctc tttaccaagg atatttatag aaaagactct gaccagagat  2400
cgagaccatc ctagccaata tggtgaaacc ccatctctac ggaattagct gggcgtggtg  2460
gtgtgctcct gtagtcccag ctactcggga ggctgaggca ggagaatcgc ttgaacctgg  2520
gaagcagaga ttgcagtgag ccaagatcgc gccactgcac tccagcctgg cgacagagca  2580
agactccata tcaaaaaaaa aaaaaaaaag tatatatata tatgaaagaa aagactctga  2640
cctgtactct tgaatgaaag tttctgatac cactggactg tctgagaatt tccaaaacgt  2700
aatgaacaaa ctgacagctt catgaaactg ccgaccaaga tcaagcaaag aaaataatta  2760
atttcatggg accaaatgaa ctaatgagga taatattttc ataaattttt tttgaaattt  2820
tgctgattct ttaaatgtct tgtttcccag atttcaggaa actttttttc ctttgcgcta  2880
tctacagctt acaacaattt gataaaatat acttttgtga ataaacattg agacatttac  2940
attttctccc tatgtggtcg ctccagactt gggaaactat tcatgaatat ttatattgta  3000
tggtaatatg tttattgtat aagttcaata actctgctct ttgtataaca gaa         3053
```

SEQ ID NO: 5 moltype = length =
SEQUENCE: 5
000

SEQ ID NO: 6 moltype = length =
SEQUENCE: 6
000

SEQ ID NO: 7 moltype = length =
SEQUENCE: 7
000

SEQ ID NO: 8 moltype = length =
SEQUENCE: 8
000

SEQ ID NO: 9 moltype = length =
SEQUENCE: 9
000

SEQ ID NO: 10 moltype = length =
SEQUENCE: 10
000

SEQ ID NO: 11 moltype = length =
SEQUENCE: 11
000

SEQ ID NO: 12 moltype = length =
SEQUENCE: 12
000

SEQ ID NO: 13 moltype = length =
SEQUENCE: 13
000

SEQ ID NO: 14 moltype = AA length = 5
FEATURE Location/Qualifiers
source 1..5
mol_type = protein
organism = synthetic construct
SEQUENCE: 14
SHGMH 5

-continued

```
SEQ ID NO: 15          moltype = AA  length = 17
FEATURE                Location/Qualifiers
source                 1..17
                       mol_type = protein
                       organism = synthetic construct
SEQUENCE: 15
FISYDGSYKS YVDSVKG                                                17

SEQ ID NO: 16          moltype = AA  length = 10
FEATURE                Location/Qualifiers
source                 1..10
                       mol_type = protein
                       organism = synthetic construct
SEQUENCE: 16
GLTGTGAFDI                                                        10

SEQ ID NO: 17          moltype = AA  length = 119
FEATURE                Location/Qualifiers
source                 1..119
                       mol_type = protein
                       organism = synthetic construct
SEQUENCE: 17
QVQLVETGGG VVQPGRSLRL SCAASGITFS SHGMHWVRQS PGKGLEWVTF ISYDGSYKSY  60
VDSVKGRFAI SRDNSKNTLY LQMNSLRPED TAVYYCATGL TGTGAFDIWG QGTMVTVSS   119

SEQ ID NO: 18          moltype = DNA  length = 357
FEATURE                Location/Qualifiers
source                 1..357
                       mol_type = other DNA
                       organism = synthetic construct
SEQUENCE: 18
caggtgcagc tggtggagac tgggggaggc gtggtccagc ctgggaggtc cctgagactc  60
tcctgtgcag cctctggaat caccttcagt agccatggca tgcactgggt ccgccagtct  120
ccaggcaagg ggctggagtg ggtgacattt atatcatatg atggaagtta taaatcctat  180
gtcgactccg tgaagggccg attcgccatc tccagagaca attccaagaa cacgctgtat  240
ctgcaaatga acagcctgag acctgaggac acggctgtgt attactgtgc gaccggatta  300
actggaactg gtgcttttga tatctggggc caagggacaa tggtcaccgt ctcctca     357

SEQ ID NO: 19          moltype = AA  length = 12
FEATURE                Location/Qualifiers
source                 1..12
                       mol_type = protein
                       organism = synthetic construct
SEQUENCE: 19
RASQSVSSSY LA                                                     12

SEQ ID NO: 20          moltype = AA  length = 7
FEATURE                Location/Qualifiers
source                 1..7
                       mol_type = protein
                       organism = synthetic construct
SEQUENCE: 20
GASSRAT                                                           7

SEQ ID NO: 21          moltype = AA  length = 9
FEATURE                Location/Qualifiers
source                 1..9
                       mol_type = protein
                       organism = synthetic construct
SEQUENCE: 21
QQYGSSPYT                                                         9

SEQ ID NO: 22          moltype = AA  length = 108
FEATURE                Location/Qualifiers
source                 1..108
                       mol_type = protein
                       organism = synthetic construct
SEQUENCE: 22
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPYTFG QGTKLEIK              108

SEQ ID NO: 23          moltype = DNA  length = 324
FEATURE                Location/Qualifiers
source                 1..324
                       mol_type = other DNA
                       organism = synthetic construct
SEQUENCE: 23
gaaattgtat tgacgcagtc tccagggacc ctgtctttgt ctccagggga aagagccacc  60
ctctcctgcc gggccagtca gagtgtctcc agctcgtact tagcctggta ccaacagaaa  120
```

-continued

```
cctggccagg ccccccgact cctcatctat ggtgcctcct caagggccac tggaatccca  180
gacagattca gtgggagtgg gtctgggaca gacttcactc tcaccatctc aagactggag  240
cctgaagatt ttgccgtata ttactgtcaa cagtatggga gctcaccgta cacttttggc  300
caggggacca agctggagat caaa                                         324

SEQ ID NO: 24          moltype = AA  length = 198
FEATURE                Location/Qualifiers
source                 1..198
                       mol_type = protein
                       organism = synthetic construct
SEQUENCE: 24
HHHHHHETVR FQGPKPSISS NNSKPVEDKD AVAFTCEPEA QNTTYLWWVN GQSLPVSPRL  60
QLSNGNRTLT LFNVTRNDAR AYVCGIQNSV SANRSDPVTL DVLYGPDTPI ISPPDSSYLS  120
GANLNLSCHS ASNPSPQYSW RINGIPQQHT QVLFIAKITP NNNGTYACFV SNLATGRNNS  180
IVKSITVSAS GTSPGLSA                                                198

SEQ ID NO: 25          moltype = AA  length = 17
FEATURE                Location/Qualifiers
source                 1..17
                       mol_type = protein
                       organism = synthetic construct
SEQUENCE: 25
CGIQNSVSAN RSDPVTL                                                 17

SEQ ID NO: 26          moltype = AA  length = 15
FEATURE                Location/Qualifiers
source                 1..15
                       mol_type = protein
                       organism = synthetic construct
SEQUENCE: 26
SWRINGIPQQ HTQVL                                                   15

SEQ ID NO: 27          moltype = AA  length = 12
FEATURE                Location/Qualifiers
source                 1..12
                       mol_type = protein
                       organism = synthetic construct
SEQUENCE: 27
VSASGTSPGL SA                                                      12

SEQ ID NO: 28          moltype = AA  length = 24
FEATURE                Location/Qualifiers
source                 1..24
                       mol_type = protein
                       organism = synthetic construct
SEQUENCE: 28
ASNPSPQYSW RINGIPQQHT QVLF                                         24

SEQ ID NO: 29          moltype = AA  length = 16
FEATURE                Location/Qualifiers
source                 1..16
                       mol_type = protein
                       organism = synthetic construct
SEQUENCE: 29
LYGPDTPIIS PPDSSY                                                  16

SEQ ID NO: 30          moltype = AA  length = 329
FEATURE                Location/Qualifiers
source                 1..329
                       mol_type = protein
                       organism = synthetic construct
SEQUENCE: 30
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPEAEGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 31          moltype = AA  length = 5
FEATURE                Location/Qualifiers
source                 1..5
                       mol_type = protein
                       organism = synthetic construct
SEQUENCE: 31
PVGVV                                                              5

SEQ ID NO: 32          moltype = AA  length = 8
FEATURE                Location/Qualifiers
```

-continued

```
source                1..8
                      mol_type = protein
                      organism = synthetic construct
SEQUENCE: 32
ASNPSPQY                                                          8

SEQ ID NO: 33         moltype = AA  length = 7
FEATURE               Location/Qualifiers
source                1..7
                      mol_type = protein
                      organism = synthetic construct
SEQUENCE: 33
SGANLNL                                                           7

SEQ ID NO: 34         moltype = AA  length = 13
FEATURE               Location/Qualifiers
source                1..13
                      mol_type = protein
                      organism = synthetic construct
SEQUENCE: 34
INGIPQQHTQ VLF                                                    13

SEQ ID NO: 35         moltype = AA  length = 5
FEATURE               Location/Qualifiers
source                1..5
                      mol_type = protein
                      organism = synthetic construct
SEQUENCE: 35
SHGMH                                                             5

SEQ ID NO: 36         moltype = AA  length = 17
FEATURE               Location/Qualifiers
source                1..17
                      mol_type = protein
                      organism = synthetic construct
SEQUENCE: 36
FISYDGSYKS YVDSVKG                                                17

SEQ ID NO: 37         moltype = AA  length = 10
FEATURE               Location/Qualifiers
source                1..10
                      mol_type = protein
                      organism = synthetic construct
SEQUENCE: 37
GLTGTGAFDI                                                        10

SEQ ID NO: 38         moltype = AA  length = 119
FEATURE               Location/Qualifiers
source                1..119
                      mol_type = protein
                      organism = synthetic construct
SEQUENCE: 38
QVQLVESGGG VVQPGRSLRL SCAASGIYFS SHGMHWVRQA PGKGLEWVTF ISYDGSYKSY  60
VDSVKGRFTI SRDNSKNTLY LQMNSLRAED TAVYYCATGL TGTGAFDIWG QGTMVTVSS   119

SEQ ID NO: 39         moltype = DNA  length = 357
FEATURE               Location/Qualifiers
source                1..357
                      mol_type = other DNA
                      organism = synthetic construct
SEQUENCE: 39
caggtgcagc tggtggagtc tgggggaggc gtggtccagc ctgggaggtc cctgagactc  60
tcctgtgcag cctctggaat ctacttcagt agccatggca tgcactgggt ccgccaggct  120
ccaggcaagg ggctggagtg ggtgacattt atatcatatg atggaagtta taaatcctat  180
gtcgactccg tgaagggccg attcaccatc tccagagaca attccaagaa cacgctgtat  240
ctgcaaatga acagcctgag agctgaggac acggctgtgt attactgtgc gaccggatta  300
actggaactg gtgcttttga tatctggggc caagggacaa tggtcaccgt ctcctca     357

SEQ ID NO: 40         moltype = AA  length = 12
FEATURE               Location/Qualifiers
source                1..12
                      mol_type = protein
                      organism = synthetic construct
SEQUENCE: 40
RASQSVSSSY LA                                                     12

SEQ ID NO: 41         moltype = AA  length = 7
FEATURE               Location/Qualifiers
source                1..7
```

-continued

```
                         mol_type = protein
                         organism = synthetic construct
SEQUENCE: 41
GASSRAT                                                                7

SEQ ID NO: 42            moltype = AA  length = 9
FEATURE                  Location/Qualifiers
source                   1..9
                         mol_type = protein
                         organism = synthetic construct
SEQUENCE: 42
QQYGSSPYT                                                              9

SEQ ID NO: 43            moltype = AA  length = 108
FEATURE                  Location/Qualifiers
source                   1..108
                         mol_type = protein
                         organism = synthetic construct
SEQUENCE: 43
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPYTFG QGTKLEIK               108

SEQ ID NO: 44            moltype = DNA  length = 324
FEATURE                  Location/Qualifiers
source                   1..324
                         mol_type = other DNA
                         organism = synthetic construct
SEQUENCE: 44
gaaattgtat tgacgcagtc tccagggacc ctgtctttgt ctccagggga aagagccacc  60
ctctcctgcc gggccagtca gagtgtctcc agctcgtact tagcctggta ccaacagaaa  120
cctggccagg ccccccgact cctcatctat ggtgcctcct caagggccac tggaatccca  180
gacagattca gtgggagtgg gtctgggaca gacttcactc tcaccatctc aagactggag  240
cctgaagatt ttgccgtata ttactgtcaa cagtatggga gctcaccgta cacttttggc  300
caggggacca agctggagat caaa                                         324

SEQ ID NO: 45            moltype = AA  length = 448
FEATURE                  Location/Qualifiers
source                   1..448
                         mol_type = protein
                         organism = synthetic construct
SEQUENCE: 45
QVQLVESGGG VVQPGRSLRL SCAASGIYFS SHGMHWVRQA PGKGLEWVTF ISYDGSYKSY  60
VDSVKGRFTI SRDNSKNTLY LQMNSLRAED TAVYYCATGL TGTGAFDIWG QGTMVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                     448

SEQ ID NO: 46            moltype = AA  length = 215
FEATURE                  Location/Qualifiers
source                   1..215
                         mol_type = protein
                         organism = synthetic construct
SEQUENCE: 46
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPYTFG QGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                              215

SEQ ID NO: 47            moltype = DNA  length = 1344
FEATURE                  Location/Qualifiers
source                   1..1344
                         mol_type = other DNA
                         organism = synthetic construct
SEQUENCE: 47
caggtccagc tcgtggaatc cggaggcgga gtggtgcagc cgggaagatc actgcgcctg  60
tcatgcgcag cctcggggat ctacttttcg tcccacggaa tgcattgggt ccgccaagct  120
cccggaaagg gtttggaatg ggtcaccttc attagctacg acggctccta caagtcgtac  180
gtggactccg tgaaggggag gttcactatc tcccgggaca acagcaagaa cacgctgtac  240
ctccaaatga actcccttcg ggccgaggat accgccgtgt actattgtgc caccggtctg  300
accggcactg gagcgttcga tatctggggc cagggcacta tggtcaccgt gtccagcgct  360
agcaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagagagt tgagcccaaa  660
tcttgtgaca aaactcacac atgcccaccg tgcccagcac ctgaactcct ggggggaccg  720
```

-continued

```
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctatagc aagctcaccg tggacaagag caggtggcag  1260
caggggaacg tcttctcatg ctccgtgatg catgaggctc tgcacaacca ctacacgcag  1320
aagtcactct ccctgtcccc gggt                                         1344

SEQ ID NO: 48          moltype = DNA  length = 645
FEATURE                Location/Qualifiers
source                 1..645
                       mol_type = other DNA
                       organism = synthetic construct
SEQUENCE: 48
gaaattgtat tgacgcagtc tccagggacc ctgtctttgt ctccagggga aagagccacc  60
ctctcctgcc gggccagtca gagtgtctcc agctcgtact tagcctggta ccaacagaaa  120
cctggccagg ccccccgact cctcatctat ggtgcctcct caagggccac tggaatccca  180
gacagattca gtgggagtgg gtctgggaca gacttcactc tcaccatctc aagactggag  240
cctgaagatt ttgccgtata ttactgtcaa cagtatggga gctcaccgta cacttttggc  300
caggggacca agctggagat caaacgtacg gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgt                  645

SEQ ID NO: 49          moltype = AA  length = 119
FEATURE                Location/Qualifiers
source                 1..119
                       mol_type = protein
                       organism = synthetic construct
SEQUENCE: 49
QVQLVESGGG VVQPGRSLRL SCAASGITFS SHGMHWVRQA PGKGLEWVTF ISYDGSYKSY  60
VDSVKGRFTI SRDNSKNTLY LQMNSLRAED TAVYYCATGL TGTNALDIWG QGTMVTVSS   119

SEQ ID NO: 50          moltype = AA  length = 108
FEATURE                Location/Qualifiers
source                 1..108
                       mol_type = protein
                       organism = synthetic construct
SEQUENCE: 50
EIVLTQSPGT LSLSPGERAT LSCRASQSVS SSYLAWYQQK PGQAPRLLIY YASSRATGIP  60
DRFSGSGSGT DFTLTISRLE PEDFAVYYCQ QYGRSPYTFG QGTKLEIK               108

SEQ ID NO: 51          moltype = AA  length = 119
FEATURE                Location/Qualifiers
source                 1..119
                       mol_type = protein
                       organism = synthetic construct
SEQUENCE: 51
QVQLVESGGG VVQPGRSLRL SCAASGITFS SHGMHWVRQA PGKGLEWVTF ISYDGSYKSY  60
VDSVKGRFTI SRDNSKNTLY LQMNSLRAED TAVYYCATGL TGTGAFDIWG QGTMVTVSS   119

SEQ ID NO: 52          moltype = AA  length = 108
FEATURE                Location/Qualifiers
source                 1..108
                       mol_type = protein
                       organism = synthetic construct
SEQUENCE: 52
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGRSPYTFG QGTKLEIK               108

SEQ ID NO: 53          moltype = DNA  length = 357
FEATURE                Location/Qualifiers
source                 1..357
                       mol_type = other DNA
                       organism = synthetic construct
SEQUENCE: 53
caggtccaac tggtggaaag cggcggtgga gtggtgcagc ctggacggtc cctgagactc  60
tcatgtgccg ccagcggaat caccttttcg tcccatggca tgcactgggt ccgccaagca  120
ccgggaaagg ggctggaatg ggtcaccttc atttcctacg atggctcgta caagtcctac  180
gtggactcag tgaaagggag gttcacgatc tcccgcgaca actcgaagaa caccctgtac  240
ttgcaaatga acagcctgcg ggctgaggat actgccgtgt actattgcgc caccggactt  300
accggaacta atgcgctcga catctggggc cagggtacca tggtcactgt gtcctcc     357
```

-continued

```
SEQ ID NO: 54          moltype = DNA  length = 324
FEATURE                Location/Qualifiers
source                 1..324
                       mol_type = other DNA
                       organism = synthetic construct
SEQUENCE: 54
gaaattgtat tgacgcagtc tccagggacc ctgtctttgt ctccagggga aagagccacc  60
ctctcctgcc gggccagtca gagtgtctcc agctcgtact tagcctggta ccaacagaaa  120
cctggccagg ccccccgact cctcatctat tacgcctcct caagggccac tggaatccca  180
gacagattca gtgggagtgg gtctgggaca gacttcactc tcaccatctc aagactggag  240
cctgaagatt ttgccgtata ttactgtcaa cagtatgggc gttcaccgta cacttttggc  300
caggggacca agctggagat caaa                                        324

SEQ ID NO: 55          moltype = DNA  length = 357
FEATURE                Location/Qualifiers
source                 1..357
                       mol_type = other DNA
                       organism = synthetic construct
SEQUENCE: 55
caagtgcagt tggtggaaag cggaggcgga gtggtgcagc ccggaagaag cctgcgcctt  60
tcttgtgccg ctagcggtat cacgttctcc tcacatggga tgcactgggt ccgccaagca  120
ccgggaaagg gcctggaatg ggtcaccttc atctcgtacg acggttcata taagtcgtac  180
gtggattccg tgaaagggcg gttcactatt tcccgggaca actccaagaa caccctctac  240
ctccaaatga actccctgag ggccgaggat accgccgtgt actactgcgc gaccggactg  300
accggaactg gcgcctttga catctggggc cagggcacta tggtcaccgt gtcgtcc     357

SEQ ID NO: 56          moltype = DNA  length = 324
FEATURE                Location/Qualifiers
source                 1..324
                       mol_type = other DNA
                       organism = synthetic construct
SEQUENCE: 56
gaaattgtat tgacgcagtc tccagggacc ctgtctttgt ctccagggga aagagccacc  60
ctctcctgcc gggccagtca gagtgtctcc agctcgtact tagcctggta ccaacagaaa  120
cctggccagg ccccccgact cctcatctat ggtgcctcct caagggccac tggaatccca  180
gacagattca gtgggagtgg gtctgggaca gacttcactc tcaccatctc aagactggag  240
cctgaagatt ttgccgtata ttactgtcaa cagtatgggc gttcaccgta cacttttggc  300
caggggacca agctggagat caaa                                        324

SEQ ID NO: 57          moltype = AA  length = 19
FEATURE                Location/Qualifiers
source                 1..19
                       mol_type = protein
                       organism = synthetic construct
SEQUENCE: 57
YVCGIQNSVS ANRSDPVTL                                              19

SEQ ID NO: 58          moltype = AA  length = 15
FEATURE                Location/Qualifiers
source                 1..15
                       mol_type = protein
                       organism = synthetic construct
SEQUENCE: 58
SWRINGIPQQ HTQVL                                                  15

SEQ ID NO: 59          moltype = AA  length = 18
FEATURE                Location/Qualifiers
source                 1..18
                       mol_type = protein
                       organism = synthetic construct
SEQUENCE: 59
DVLYGPDTPI ISPPDSSY                                               18

SEQ ID NO: 60          moltype = AA  length = 14
FEATURE                Location/Qualifiers
source                 1..14
                       mol_type = protein
                       organism = synthetic construct
SEQUENCE: 60
ITVSASGTSP GLSA                                                   14

SEQ ID NO: 61          moltype = AA  length = 7
FEATURE                Location/Qualifiers
source                 1..7
                       mol_type = protein
                       organism = synthetic construct
SEQUENCE: 61
GITFSSH                                                           7
```

-continued

```
SEQ ID NO: 62          moltype = AA  length = 18
FEATURE                Location/Qualifiers
source                 1..18
                       mol_type = protein
                       organism = synthetic construct
SEQUENCE: 62
TFISYDGSYK SYVDSVKG                                        18

SEQ ID NO: 63          moltype = AA  length = 11
FEATURE                Location/Qualifiers
source                 1..11
                       mol_type = protein
                       organism = synthetic construct
SEQUENCE: 63
TGLTGTGAFD I                                               11

SEQ ID NO: 64          moltype = AA  length = 12
FEATURE                Location/Qualifiers
source                 1..12
                       mol_type = protein
                       organism = synthetic construct
SEQUENCE: 64
RASQSVSSSY LA                                              12

SEQ ID NO: 65          moltype = AA  length = 7
FEATURE                Location/Qualifiers
source                 1..7
                       mol_type = protein
                       organism = synthetic construct
SEQUENCE: 65
GASSRAT                                                    7

SEQ ID NO: 66          moltype = AA  length = 8
FEATURE                Location/Qualifiers
source                 1..8
                       mol_type = protein
                       organism = synthetic construct
SEQUENCE: 66
QQYGSSPY                                                   8

SEQ ID NO: 67          moltype = AA  length = 119
FEATURE                Location/Qualifiers
source                 1..119
                       mol_type = protein
                       organism = synthetic construct
SEQUENCE: 67
QVQLVESGGG VVQPGRSLRL SCAASGITFS SHGMHWVRQA PGKGLEWVTF ISYDGSYKSY  60
VDSVKGRFTI SRDNSKNTLY LQMNSLRAED TAVYYCATGL TGTGAFDIWG QGTMVTVSS   119

SEQ ID NO: 68          moltype = AA  length = 108
FEATURE                Location/Qualifiers
source                 1..108
                       mol_type = protein
                       organism = synthetic construct
SEQUENCE: 68
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGRSPYTFG QGTKLEIK              108

SEQ ID NO: 69          moltype = AA  length = 119
FEATURE                Location/Qualifiers
source                 1..119
                       mol_type = protein
                       organism = synthetic construct
SEQUENCE: 69
QVQLVESGGG VVQPGRSLRL SCAASGIYFS SHGMHWVRQA PGKGLEWVTF ISYDGSYKSY  60
VDSVKGRFTI SRDNSKNTLY LQMNSLRAED TAVYYCATGL TGTGAFDIWG QGTMVTVSS   119

SEQ ID NO: 70          moltype = AA  length = 108
FEATURE                Location/Qualifiers
source                 1..108
                       mol_type = protein
                       organism = synthetic construct
SEQUENCE: 70
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPYTFG QGTKLEIK              108

SEQ ID NO: 71          moltype = AA  length = 119
FEATURE                Location/Qualifiers
source                 1..119
```

```
                        mol_type = protein
                        organism = synthetic construct
SEQUENCE: 71
QVQLVESGGG VVQPGRSLRL SCAASGITFS SHGMHWVRQA PGKGLEWVTF ISYDGSYISY  60
VDSVKGRFTI SRDNSKNTLY LQMNSLRAED TAVYYCATGL TGTGANDIWG QGTMVTVSS   119

SEQ ID NO: 72           moltype = AA  length = 108
FEATURE                 Location/Qualifiers
source                  1..108
                        mol_type = protein
                        organism = synthetic construct
SEQUENCE: 72
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYKSSPYTFG QGTKLEIK              108

SEQ ID NO: 73           moltype = AA  length = 119
FEATURE                 Location/Qualifiers
source                  1..119
                        mol_type = protein
                        organism = synthetic construct
SEQUENCE: 73
QVQLVESGGG VVQPGRSLRL SCAASGIYFS SHGMHWVRQA PGKGLEWVTF ISYDGSYKSY  60
VDSVKGRFTI SRDNSKNTLY LQMNSLRAED TAVYYCATGL TGTGANDIWG QGTMVTVSS   119

SEQ ID NO: 74           moltype = AA  length = 108
FEATURE                 Location/Qualifiers
source                  1..108
                        mol_type = protein
                        organism = synthetic construct
SEQUENCE: 74
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QNKPSPYTFG QGTKLEIK              108

SEQ ID NO: 75           moltype = AA  length = 119
FEATURE                 Location/Qualifiers
source                  1..119
                        mol_type = protein
                        organism = synthetic construct
SEQUENCE: 75
QVQLVESGGG VVQPGRSLRL SCAASGITFS SHGMHWVRQA PGKGLEWVTF ISYDGSYKSY  60
VDSVKGRFTI SRDNSKNTLY LQMNSLRAED TAVYYCATGL TGTNALDIWG QGTMVTVSS   119

SEQ ID NO: 76           moltype = AA  length = 108
FEATURE                 Location/Qualifiers
source                  1..108
                        mol_type = protein
                        organism = synthetic construct
SEQUENCE: 76
EIVLTQSPGT LSLSPGERAT LSCRASQSVS SSYLAWYQQK PGQAPRLLIY YASSRATGIP  60
DRFSGSGSGT DFTLTISRLE PEDFAVYYCQ QYGRSPYTFG QGTKLEIK              108

SEQ ID NO: 77           moltype = AA  length = 119
FEATURE                 Location/Qualifiers
source                  1..119
                        mol_type = protein
                        organism = synthetic construct
SEQUENCE: 77
QVQLVESGGG VVQPGRSLRL SCAASGIYFS SHGMHWVRQA PGKGLEWVTF ISYDGSYKSY  60
VDSVKGRFTI SRDNSKNTLY LQMNSLRAED TAVYYCATGL TGTGAFDIWG QGTMVTVSS   119

SEQ ID NO: 78           moltype = AA  length = 108
FEATURE                 Location/Qualifiers
source                  1..108
                        mol_type = protein
                        organism = synthetic construct
SEQUENCE: 78
EIVLTQSPGT LSLSPGERAT LSCRASQSVS SIYLAWYQQK PGQAPRLLIY YASSRATGIP  60
DRFSGSGSGT DFTLTISRLE PEDFAVYYCQ QYGSSPYTFG QGTKLEIK              108

SEQ ID NO: 79           moltype = AA  length = 119
FEATURE                 Location/Qualifiers
source                  1..119
                        mol_type = protein
                        organism = synthetic construct
SEQUENCE: 79
QVQLVESGGG VVQPGRSLRL SCAASGITFS SHGMHWVRQA PGKGLEWVTF ISYDSSYKSY  60
VDSVKGRFTI SRDNSKNTLY LQMNSLRAED TAVYYCATGL TGTGAFDIWG QGTMVTVSS   119

SEQ ID NO: 80           moltype = AA  length = 108
```

```
FEATURE                Location/Qualifiers
source                 1..108
                       mol_type = protein
                       organism = synthetic construct
SEQUENCE: 80
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QNKRSPYTFG QGTKLEIK              108

SEQ ID NO: 81          moltype = AA  length = 119
FEATURE                Location/Qualifiers
source                 1..119
                       mol_type = protein
                       organism = synthetic construct
SEQUENCE: 81
QVQLVESGGG VVQPGRSLRL SCAASGITFS SHGMHWVRQA PGKGLEWVTF ISYDGSIKSY  60
VDSVKGRFTI SRDNSKNTLY LQMNSLRAED TAVYYCATGL TGTGAFDIWG QGTMVTVSS   119

SEQ ID NO: 82          moltype = AA  length = 108
FEATURE                Location/Qualifiers
source                 1..108
                       mol_type = protein
                       organism = synthetic construct
SEQUENCE: 82
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYKRSPYTFG QGTKLEIK              108

SEQ ID NO: 83          moltype = AA  length = 119
FEATURE                Location/Qualifiers
source                 1..119
                       mol_type = protein
                       organism = synthetic construct
SEQUENCE: 83
QVQLVESGGG VVQPGRSLRL SCAASGITFS SHGMHWVRQA PGKGLEWVTF ASYDGSYKQY  60
VDSVKGRFTI SRDNSKNTLY LQMNSLRAED TAVYYCATGL TGTGAFDIWG QGTMVTVSS   119

SEQ ID NO: 84          moltype = AA  length = 108
FEATURE                Location/Qualifiers
source                 1..108
                       mol_type = protein
                       organism = synthetic construct
SEQUENCE: 84
EIVLTQSPGT LSLSPGERAT LSCRASQSVS SSYLAWYQQK PGQAPRLLIY GASSRNTGIP  60
DRFSGSGSGT DFTLTISRLE PEDFAVYYCQ QYKRSPYTFG QGTKLEIK              108

SEQ ID NO: 85          moltype = AA  length = 119
FEATURE                Location/Qualifiers
source                 1..119
                       mol_type = protein
                       organism = synthetic construct
SEQUENCE: 85
QVQLVESGGG VVQPGRSLRL SCAASGIYFS SHGMHWVRQA PGKGLEWVTF ISYDGSIKSY  60
VDSVKGRFTI SRDNSKNTLY LQMNSLRAED TAVYYCATGL TGTNAFDIWG QGTMVTVSS   119

SEQ ID NO: 86          moltype = AA  length = 108
FEATURE                Location/Qualifiers
source                 1..108
                       mol_type = protein
                       organism = synthetic construct
SEQUENCE: 86
EIVLTQSPGT LSLSPGERAT LSCRASQSVS SSYLAWYQQK PGQAPRLLIY YASSRNTGIP  60
DRFSGSGSGT DFTLTISRLE PEDFAVYYCQ QYGSSPYTFG QGTKLEIK              108

SEQ ID NO: 87          moltype = AA  length = 119
FEATURE                Location/Qualifiers
source                 1..119
                       mol_type = protein
                       organism = synthetic construct
SEQUENCE: 87
QVQLVESGGG VVQPGRSLRL SCAASGITFS SHGMHWVRQA PGKGLEWVTF ISYDSSYKLY  60
VDSVKGRFTI SRDNSKNTLY LQMNSLRAED TAVYYCATGL TGTGAFDIWG QGTMVTVSS   119

SEQ ID NO: 88          moltype = AA  length = 108
FEATURE                Location/Qualifiers
source                 1..108
                       mol_type = protein
                       organism = synthetic construct
SEQUENCE: 88
EIVLTQSPGT LSLSPGERAT LSCRASQSVS SSYLAWYQQK PGQAPRLLIY YASSRATGIP  60
DRFSGSGSGT DFTLTISRLE PEDFAVYYCH QYGSSPYTFG QGTKLEIK              108
```

```
SEQ ID NO: 89          moltype = AA  length = 119
FEATURE                Location/Qualifiers
source                 1..119
                       mol_type = protein
                       organism = synthetic construct
SEQUENCE: 89
QVQLVESGGG VVQPGRSLRL SCAASGIYFS SHGMHWVRQA PGKGLEWVTF ITYDGSYKSY  60
VDSVKGRFTI SRDNSKNTLY LQMNSLRAED TAVYYCATGL TGTGAFDIWG QGTMVTVSS   119

SEQ ID NO: 90          moltype = AA  length = 108
FEATURE                Location/Qualifiers
source                 1..108
                       mol_type = protein
                       organism = synthetic construct
SEQUENCE: 90
EIVLTQSPGT LSLSPGERAT LSCRASQSVS SSYLAWYQQK PGQAPRLLIY YASSRNTGIP  60
DRFSGSGSGT DFTLTISRLE PEDFAVYYCQ QYGSSPYTFG QGTKLEIK              108

SEQ ID NO: 91          moltype = AA  length = 119
FEATURE                Location/Qualifiers
source                 1..119
                       mol_type = protein
                       organism = synthetic construct
SEQUENCE: 91
QVQLVESGGG VVQPGRSLRL SCAASGITFS SHGMHWVRQA PGKGLEWVTF SSYDGSYKSY  60
VDSVKGRFTI SRDNSKNTLY LQMNSLRAED TAVYYCATGL TGTNAFDIWG QGTMVTVSS   119

SEQ ID NO: 92          moltype = AA  length = 108
FEATURE                Location/Qualifiers
source                 1..108
                       mol_type = protein
                       organism = synthetic construct
SEQUENCE: 92
EIVLTQSPGT LSLSPGERAT LSCRASQSVS SSYLAWYQQK PGQAPRLLIY GASSRNTGIP  60
DRFSGSGSGT DFTLTISRLE PEDFAVYYCQ QYKSSPYTFG QGTKLEIK              108

SEQ ID NO: 93          moltype = AA  length = 119
FEATURE                Location/Qualifiers
source                 1..119
                       mol_type = protein
                       organism = synthetic construct
SEQUENCE: 93
QVQLVESGGG VVQPGRSLRL SCAASGITFS SHGMHWVRQA PGKGLEWVTF ISYDGSYKSY  60
VDSVKGRFTI SRDNSKNTLY LQMNSLRAED TAVYYCATGL TGTGANDIWG QGTMVTVSS   119

SEQ ID NO: 94          moltype = AA  length = 108
FEATURE                Location/Qualifiers
source                 1..108
                       mol_type = protein
                       organism = synthetic construct
SEQUENCE: 94
EIVLTQSPGT LSLSPGERAT LSCRASQSVS SSYLAWYQQK PGQAPRLLIY YASSRATGIP  60
DRFSGSGSGT DFTLTISRLE PEDFAVYYCQ QYGSSPYTFG QGTKLEIK              108

SEQ ID NO: 95          moltype = AA  length = 6
FEATURE                Location/Qualifiers
source                 1..6
                       mol_type = protein
                       organism = synthetic construct
SEQUENCE: 95
HHHHHH                                                            6

SEQ ID NO: 96          moltype = AA  length = 198
FEATURE                Location/Qualifiers
source                 1..198
                       mol_type = protein
                       organism = synthetic construct
SEQUENCE: 96
HHHHHHETVR FQGPKPSISS NNSKPVEDKD AVAFTCEPEA QNTTYLWWVN GQSLPVSPRL  60
QLSNGNRTLT LFNVTRNDAR AYVCGIQNSV SANRSDPVTL DVLYGPDTPI ISPPDSSYLS  120
GANLNLSCHS ASNPSPQYSW RINGIPQQHT QVLFIAKITP NNNGTYACFV SNLATGRNNS  180
IVKSITVSAS GTSPGLSA                                               198

SEQ ID NO: 97          moltype = AA  length = 214
FEATURE                Location/Qualifiers
source                 1..214
                       mol_type = protein
                       organism = synthetic construct
```

-continued

```
SEQUENCE: 97
DIQLTQSPSF LSASVGDRVT ITCRASQGIS TYLAWYQQKP GKAPKFLIYA EKTLQSGVPS  60
RFSGSGSGTE FTLTISSLQP EDFATYYCQQ LASYPFTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 98          moltype = AA  length = 225
FEATURE                Location/Qualifiers
source                 1..225
                       mol_type = protein
                       organism = synthetic construct
SEQUENCE: 98
QVQLQESGPG LVKPSGTLSL TCAVSGGSIS SSDWWSWVRQ PPGKGLEWIG EIYHQGSTNY  60
NPSLKSRVTI SVDKSKNQFS LKLSSVTAAD TAVYYCARAS SSGYYGHDVW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCGG                225

SEQ ID NO: 99          moltype = AA  length = 5
FEATURE                Location/Qualifiers
source                 1..5
                       mol_type = protein
                       organism = synthetic construct
SEQUENCE: 99
PVGVV                                                            5

SEQ ID NO: 100         moltype = AA  length = 224
FEATURE                Location/Qualifiers
source                 1..224
                       mol_type = protein
                       organism = synthetic construct
SEQUENCE: 100
QVQLVESGGG VVQPGRSLRL SCAASGIYFS SHGMHWVRQA PGKGLEWVTF ISYDGSYKSY  60
VDSVKGRFTI SRDNSKNTLY LQMNSLRAED TAVYYCATGL TGTGAFDIWG QGTMVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCGG                 224

SEQ ID NO: 101         moltype = AA  length = 4
FEATURE                Location/Qualifiers
source                 1..4
                       mol_type = protein
                       organism = synthetic construct
SEQUENCE: 101
GFLG                                                             4

SEQ ID NO: 102         moltype = AA  length = 7
FEATURE                Location/Qualifiers
source                 1..7
                       mol_type = protein
                       organism = synthetic construct
SEQUENCE: 102
ETVRFQG                                                          7

SEQ ID NO: 103         moltype = AA  length = 19
FEATURE                Location/Qualifiers
source                 1..19
                       mol_type = protein
                       organism = synthetic construct
SEQUENCE: 103
DVLYGPDTPI ISPPDSSYL                                             19

SEQ ID NO: 104         moltype = AA  length = 18
FEATURE                Location/Qualifiers
source                 1..18
                       mol_type = protein
                       organism = synthetic construct
SEQUENCE: 104
IVKSITVSAS GTSPGLSA                                              18

SEQ ID NO: 105         moltype = AA  length = 668
FEATURE                Location/Qualifiers
source                 1..668
                       mol_type = protein
                       organism = synthetic construct
SEQUENCE: 105
KLTIESTPFN VAEGKEVLLL VHNLPQHLFG YSWYKGERVD GNRQIIGYVI GTQQATPGPA  60
YSGREIIYPN ASLLIQNIIQ NDTGFYTLHV IKSDLVNEEA TGQFRVYPEL PKPSISSNNS  120
KPVEDKDAVA FTCEPETQDA TYLWWVNNQS LPVSPRLQLS NGNRTLTLFN VTRNDTASYK  180
CETQNPVSAR RSDSVILNVL YGPDAPTISP LNTSYRSGEN LNLSCHAASN PPAQYSWFVN  240
GTFQQSTQEL FIPNITVNNS GSYTCQAHNS DTGLNRTTVT TITVYAEPPK PFITSNNSNP  300
```

-continued

```
VEDEDAVALT CEPEIQNTTY LWWVNNQSLP VSPRLQLSND NRTLTLLSVT RNDVGPYECG  360
IQNELSVDHS DPVILNVLYG PDDPTISPSY TYYRPGVNLS LSCHAASNPP AQYSWLIDGN  420
IQQHTQELFI SNITEKNSGL YTCQANNSAS GHSRTTVKTI TVSAELPKPS ISSNNSKPVE  480
DKDAVAFTCE PEAQNTTYLW WVNGQSLPVS PRLQLSNGNR TLTLFNVTRN DARAYVCGIQ  540
NSVSANRSDP VTLDVLYGPD TPIISPPDSS YLSGANLNLS CHSASNPSPQ YSWRINGIPQ  600
QHTQVLFIAK ITPNNNGTYA CFVSNLATGR NNSIVKSITV SASGTSPGLS AGATVGIMIG  660
VLVGVALI                                                           668

SEQ ID NO: 106          moltype = AA  length = 11
FEATURE                 Location/Qualifiers
source                  1..11
                        mol_type = protein
                        organism = synthetic construct
SEQUENCE: 106
XGLTGTGAFD I                                                       11

SEQ ID NO: 107          moltype = AA  length = 11
FEATURE                 Location/Qualifiers
source                  1..11
                        mol_type = protein
                        organism = synthetic construct
SEQUENCE: 107
TXLTGTGAFD I                                                       11

SEQ ID NO: 108          moltype = AA  length = 11
FEATURE                 Location/Qualifiers
source                  1..11
                        mol_type = protein
                        organism = synthetic construct
SEQUENCE: 108
TGXTGTGAFD I                                                       11

SEQ ID NO: 109          moltype = AA  length = 11
FEATURE                 Location/Qualifiers
source                  1..11
                        mol_type = protein
                        organism = synthetic construct
SEQUENCE: 109
TGLXGTGAFD I                                                       11

SEQ ID NO: 110          moltype = AA  length = 11
FEATURE                 Location/Qualifiers
source                  1..11
                        mol_type = protein
                        organism = synthetic construct
SEQUENCE: 110
TGLTXTGAFD I                                                       11

SEQ ID NO: 111          moltype = AA  length = 11
FEATURE                 Location/Qualifiers
source                  1..11
                        mol_type = protein
                        organism = synthetic construct
SEQUENCE: 111
TGLTGXGAFD I                                                       11

SEQ ID NO: 112          moltype = AA  length = 11
FEATURE                 Location/Qualifiers
source                  1..11
                        mol_type = protein
                        organism = synthetic construct
SEQUENCE: 112
TGLTGTXAFD I                                                       11

SEQ ID NO: 113          moltype = AA  length = 11
FEATURE                 Location/Qualifiers
source                  1..11
                        mol_type = protein
                        organism = synthetic construct
SEQUENCE: 113
TGLTGTGXFD I                                                       11

SEQ ID NO: 114          moltype = AA  length = 11
FEATURE                 Location/Qualifiers
source                  1..11
                        mol_type = protein
                        organism = synthetic construct
SEQUENCE: 114
TGLTGTGAXD I                                                       11
```

-continued

```
SEQ ID NO: 115          moltype = AA  length = 11
FEATURE                 Location/Qualifiers
source                  1..11
                        mol_type = protein
                        organism = synthetic construct
SEQUENCE: 115
TGLTGTGAFX I                                                       11

SEQ ID NO: 116          moltype = AA  length = 11
FEATURE                 Location/Qualifiers
source                  1..11
                        mol_type = protein
                        organism = synthetic construct
SEQUENCE: 116
TGLTGTGAFD X                                                       11

SEQ ID NO: 117          moltype = AA  length = 16
FEATURE                 Location/Qualifiers
source                  1..16
                        mol_type = protein
                        organism = synthetic construct
SEQUENCE: 117
KSITVSASGT SPGLSA                                                  16
```

ANTI-CEACAM5 ANTIBODY DRUG CONJUGATES

CROSS-REFERENCE TO RELATED APPLICATIONS

This application claims the benefit of U.S. provisional patent application Ser. No. 63/558,431, filed Feb. 27, 2024, and U.S. provisional patent application Ser. No. 63/678,883, filed Aug. 2, 2024, each of which is incorporated herein by reference in its entirety.

REFERENCE TO SEQUENCE LISTING SUBMITTED ELECTRONICALLY

The content of the electronically submitted sequence listing (Name: 3338_3370002_SequenceListing_ST26.xml; Size: 114,947 bytes; and Date of Creation: Feb. 25, 2025), filed with the application, is incorporated herein by reference in its entirety.

FIELD OF DISCLOSURE

The disclosure provides antibody drug conjugates (ADCs) comprising antibodies or antigen binding portions that specifically binds to carcinoembryonic antigen-related cell adhesion molecule-5 (CEACAM5) for use in a therapy.

BACKGROUND

CEACAM5 is a cell surface protein that is weakly expressed in normal epithelial tissues, including colon, esophagus, head and neck, stomach, and cervix tissue, but is highly expressed in several tumor types including colorectal, gastrointestinal, lung, and breast, with highest prevalence and expression occurring in greater than 80% of colorectal cancers. In normal tissue, CEACAM5 protects luminal organs from microbial invasion. In tumor cells, CEACAM5 is functionally associated with cell differentiation, cell adhesion, tumor invasion and metastasis.

CEACAM5 overexpression is often associated with poor prognosis. For example, in patients with stage I, II, and III colorectal cancer, 5-year survival was found to be inversely correlated with tissue expression of CEACAM5, and in patients with stage III disease, increased serum levels of CEACAM5 are associated with poor prognosis (Gazzah et al., Ann Oncol., 33(4):416-425). The consistent overexpression of CEACAM5 in many cancers has made it an accepted tumor biomarker and indicator of recurrence in patients with cancer, especially those with colorectal cancer.

Multiple therapeutic approaches targeting CEACAM5 in cancer are in development. However, to date, there are no FDA-approved CEACAM5-targeted therapies for cancer. Therefore, there remains an urgent need for effective treatments for CEACAM5-associated cancers, including antibodies specifically directed to CEACAM5 that do not cross-react with other molecules of the CEACAM family, as well as antibody drug conjugates (ADCs) which specifically kill CEACAM5-expressing cancer cells.

SUMMARY

The present disclosure provides an antibody drug conjugate (ADC) having the formula (I):

(I)

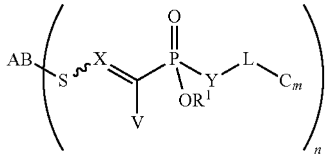

or a pharmaceutically acceptable salt, a stereoisomer, or a solvate thereof, wherein:

indicates that the configuration of the double bond is E or Z.

V is H or ($C_1$-$C_8$)alkyl;

X is $R^3$—C;

Y is $NR^5$, S, O, or $CR^6R^7$;

$R^1$ is a polyalkylene glycol unit comprising at least 3 alkylene glycol subunits;

$R^3$ and $R^5$-$R^7$ are each H, or an optionally substituted aliphatic or aromatic residue;

L is a linker;

C is a cytotoxic moiety;

m is an integer ranging from 1 to 10;

n ranges from 1 to 20; and

AB is an anti-CEACAM5 antibody or an antigen binding portion thereof comprising:

(a) a heavy chain variable region (VH) comprising complementarity determining region (CDR)1, CDR2, and CDR3 regions comprising the amino acid sequences set forth in SEQ ID Nos: 14, 15, and 16, respectively, and a light chain variable region (VL) comprising CDR1, CDR2, and CDR3 regions comprising the amino acid sequences set forth in SEQ ID Nos: 19, 20, and 21, or (b) a VH comprising CDR1, CDR2, and CDR3 regions which have at least 80%, 85%, 90%, 95%, 98%, or 99% sequence identity to the amino acid sequences set forth in SEQ ID Nos: 14, 15, and 16, respectively, and a VL comprising CDR1, CDR2, and CDR3 regions which have at least 85%, 90%, 95%, 98%, or 99% sequence identity to the amino acid sequences set forth in SEQ ID Nos: 19, 20, and 21, respectively.

The present disclosure provides an antibody drug conjugate having the formula (I), wherein the VH and the VL have at least 80%, 85%, 90%, 95%, 98%, or 99% sequence identity to:

(a) the amino acid sequence set forth in SEQ ID NOs: 38 and the amino acid sequence set forth in SEQ ID NO 43, respectively;

(b) the amino acid sequence set forth in SEQ ID NO: 49 and the amino acid sequence set forth in SEQ ID NO: 50; respectively;

(c) the amino acid sequence set forth in SEQ ID NO: 51 and the amino acid sequence set forth in SEQ ID NO: 52, respectively;

(d) the amino acid sequence set forth in SEQ ID NO: 67 and the amino acid sequence set forth in SEQ ID NO: 68, respectively;

(e) the amino acid sequence set forth in SEQ ID NO: 69 and the amino acid sequence set forth in SEQ ID NO: 70, respectively;

(f) the amino acid sequence set forth in SEQ ID NO: 71 and the amino acid sequence set forth in SEQ ID NO: 72, respectively;

(g) the amino acid sequence set forth in SEQ ID NO: 73 and the amino acid sequence set forth in SEQ ID NO: 74, respectively;

(h) the amino acid sequence set forth in SEQ ID NO: 75 and the amino acid sequence set forth in SEQ ID NO: 76, respectively;

(i) the amino acid sequence set forth in SEQ ID NO: 77 and the amino acid sequence set forth in SEQ ID NO: 78, respectively;

(j) the amino acid sequence set forth in SEQ ID NO: 79 and the amino acid sequence set forth in SEQ ID NO: 80, respectively;

(k) the amino acid sequence set forth in SEQ ID NO: 81 and the amino acid sequence set forth in SEQ ID NO: 82, respectively;

(l) the amino acid sequence set forth in SEQ ID NO: 83 and the amino acid sequence set forth in SEQ ID NO: 84, respectively;

(m) the amino acid sequence set forth in SEQ ID NO: 85 and the amino acid sequence set forth in SEQ ID NO: 86, respectively;

(n) the amino acid sequence set forth in SEQ ID NO: 87 and the amino acid sequence set forth in SEQ ID NO: 88, respectively;

(o) the amino acid sequence set forth in SEQ ID NO: 89 and the amino acid sequence set forth in SEQ ID NO: 90, respectively;

(p) the amino acid sequence set forth in SEQ ID NO: 91 and the amino acid sequence set forth in SEQ ID NO: 92, respectively; or (q) the amino acid sequence set forth in SEQ ID NO: 93 and the amino acid sequence set forth in SEQ ID NO: 94, respectively.

In certain embodiments, the anti-CEACAM5 antibody or antigen binding portion thereof is described in Table 10 and Table 11. In certain embodiments, the CDRs, VH, VL, heavy chain and/or light chain is described in Table 10. For example, the anti-CEACAM5 antibody comprises a heavy chain and the light chain comprise the amino acid sequence set forth in SEQ ID NO: 45 and the amino acid sequence set forth in SEQ ID NO: 46, respectively.

The present disclosure provides a method of preparing an ADC of the formula (I), comprising reacting a compound of the formula (III):

(III)

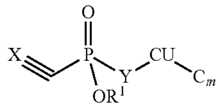

with a thiol containing compound, AB-(SH)$_n$, to obtain the ADC.

The present disclosure provides a method of treating cancer that expresses CEACAM5 in a subject in need thereof comprising administering to the subject a therapeutically effective amount of the ADC of the formula (I):

(I)

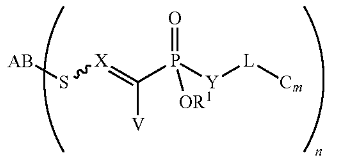

or a pharmaceutically acceptable salt, a stereoisomer, or a solvate thereof, wherein:

V is H or ($C_1$-$C_8$)alkyl;

X is $R^3$—C;

Y is $NR^5$, S, O, or $CR^6R^7$;

$R^1$ is a polyalkylene glycol unit comprising at least 3 alkylene glycol subunits;

$R^3$ and $R^5$-$R^7$ are each H, or an optionally substituted aliphatic or aromatic residue;

L is a linker;

C is a cytotoxic moiety;

m is an integer ranging from 1 to 10;

n ranges from 1 to 20; and

AB is an anti-CEACAM5 antibody or an antigen binding portion thereof comprising a VH and a VL wherein the VH and the VL have at least 80%, 85%, 90%, 95%, 98%, or 99% sequence identity to:

(a) the amino acid sequence set forth in SEQ ID NOs: 38 and the amino acid sequence set forth in SEQ ID NO 43, respectively;

(b) the amino acid sequence set forth in SEQ ID NO: 49 and the amino acid sequence set forth in SEQ ID NO: 50; respectively;

(c) the amino acid sequence set forth in SEQ ID NO: 51 and the amino acid sequence set forth in SEQ ID NO: 52, respectively;

(d) the amino acid sequence set forth in SEQ ID NO: 67 and the amino acid sequence set forth in SEQ ID NO: 68, respectively;

(e) the amino acid sequence set forth in SEQ ID NO: 69 and the amino acid sequence set forth in SEQ ID NO: 70, respectively;

(f) the amino acid sequence set forth in SEQ ID NO: 71 and the amino acid sequence set forth in SEQ ID NO: 72, respectively;

(g) the amino acid sequence set forth in SEQ ID NO: 73 and the amino acid sequence set forth in SEQ ID NO: 74, respectively;

(h) the amino acid sequence set forth in SEQ ID NO: 75 and the amino acid sequence set forth in SEQ ID NO: 76, respectively;

(i) the amino acid sequence set forth in SEQ ID NO: 77 and the amino acid sequence set forth in SEQ ID NO: 78, respectively;

(j) the amino acid sequence set forth in SEQ ID NO: 79 and the amino acid sequence set forth in SEQ ID NO: 80, respectively;

(k) the amino acid sequence set forth in SEQ ID NO: 81 and the amino acid sequence set forth in SEQ ID NO: 82, respectively;

(l) the amino acid sequence set forth in SEQ ID NO: 83 and the amino acid sequence set forth in SEQ ID NO: 84, respectively;

(m) the amino acid sequence set forth in SEQ ID NO: 85 and the amino acid sequence set forth in SEQ ID NO: 86, respectively;

(n) the amino acid sequence set forth in SEQ ID NO: 87 and the amino acid sequence set forth in SEQ ID NO: 88, respectively;

(o) the amino acid sequence set forth in SEQ ID NO: 89 and the amino acid sequence set forth in SEQ ID NO: 90, respectively;

(p) the amino acid sequence set forth in SEQ ID NO: 91 and the amino acid sequence set forth in SEQ ID NO: 92, respectively; or (q) the amino acid sequence set forth in SEQ ID NO: 93 and the amino acid sequence set forth in SEQ ID NO: 94, respectively.

In some aspects, the anti-CEACAM5 antibody or antigen binding portion thereof is described in Table 10 and Table 11. In some aspects, the CDRs, VH, VL, heavy chain and/or light chain is described in Table 10 and Table 11.

The present disclosure provides an antibody drug conjugate having the formula (II):

(h) the amino acid sequence set forth in SEQ ID NO: 75 and the amino acid sequence set forth in SEQ ID NO: 76, respectively;

(i) the amino acid sequence set forth in SEQ ID NO: 77 and the amino acid sequence set forth in SEQ ID NO: 78, respectively;

(j) the amino acid sequence set forth in SEQ ID NO: 79 and the amino acid sequence set forth in SEQ ID NO: 80, respectively;

(II)

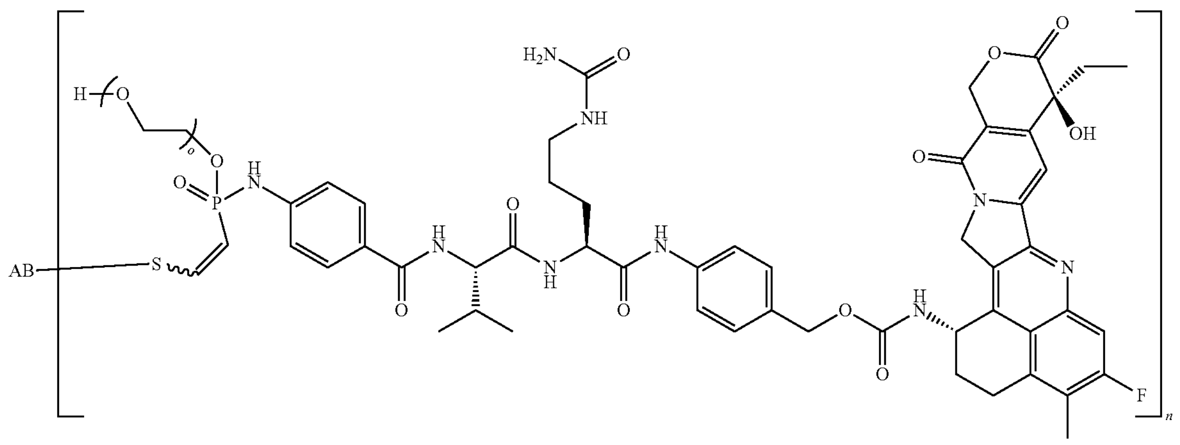

, (II), or a pharmaceutically acceptable salt, a stereoisomer, or a solvate thereof, wherein:

~~~ indicates that the configuration of the double bond is E or Z;

o is an integer from 8 to 30;

n ranges from 4 to 8; and

AB is an anti-CEACAM5 antibody or antigen binding portion thereof comprising a VH and a VL wherein the VH and the VL have at least 80%, 85%, 90%, 95%, 98%, or 99% sequence identity to:

(a) the amino acid sequence set forth in SEQ ID NOs: 38 and the amino acid sequence set forth in SEQ ID NO 43, respectively;

(b) the amino acid sequence set forth in SEQ ID NO: 49 and the amino acid sequence set forth in SEQ ID NO: 50; respectively;

(c) the amino acid sequence set forth in SEQ ID NO: 51 and the amino acid sequence set forth in SEQ ID NO: 52, respectively;

(d) the amino acid sequence set forth in SEQ ID NO: 67 and the amino acid sequence set forth in SEQ ID NO: 68, respectively;

(e) the amino acid sequence set forth in SEQ ID NO: 69 and the amino acid sequence set forth in SEQ ID NO: 70, respectively;

(f) the amino acid sequence set forth in SEQ ID NO: 71 and the amino acid sequence set forth in SEQ ID NO: 72, respectively;

(g) the amino acid sequence set forth in SEQ ID NO: 73 and the amino acid sequence set forth in SEQ ID NO: 74, respectively;

(k) the amino acid sequence set forth in SEQ ID NO: 81 and the amino acid sequence set forth in SEQ ID NO: 82, respectively;

(l) the amino acid sequence set forth in SEQ ID NO: 83 and the amino acid sequence set forth in SEQ ID NO: 84, respectively;

(m) the amino acid sequence set forth in SEQ ID NO: 85 and the amino acid sequence set forth in SEQ ID NO: 86, respectively;

(n) the amino acid sequence set forth in SEQ ID NO: 87 and the amino acid sequence set forth in SEQ ID NO: 88, respectively;

(o) the amino acid sequence set forth in SEQ ID NO: 89 and the amino acid sequence set forth in SEQ ID NO: 90, respectively;

(p) the amino acid sequence set forth in SEQ ID NO: 91 and the amino acid sequence set forth in SEQ ID NO: 92, respectively; or

(q) the amino acid sequence set forth in SEQ ID NO: 93 and the amino acid sequence set forth in SEQ ID NO: 94, respectively.

In some aspects, the anti-CEACAM5 antibody or antigen binding portion thereof is described in Table 10 and Table 11. In some aspects, the CDRs, VH, VL, heavy chain and/or light chain is described in Table 10 and Table 11.

The present disclosure provides an antibody drug conjugate having the structure:
~~~

[ADC 101]

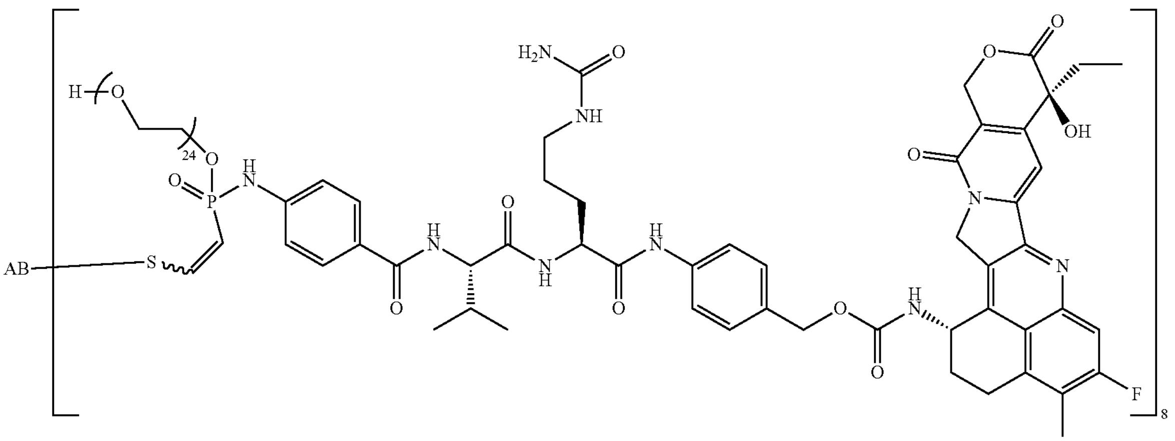

[ADC 101], or a pharmaceutically acceptable salt, a stereoisomer, or a solvate thereof, wherein

~~~ represents that the configuration of the double bond is E or Z; and

AB is an anti-CEACAM5 antibody or antigen binding portion thereof comprising a VH and a VL wherein the VH and the VL have at least 80%, 85%, 90%, 95%, 98%, or 99% sequence identity to:

(a) the amino acid sequence set forth in SEQ ID NOs: 38 and the amino acid sequence set forth in SEQ ID NO 43, respectively;

(b) the amino acid sequence set forth in SEQ ID NO: 49 and the amino acid sequence set forth in SEQ ID NO: 50; respectively;

(c) the amino acid sequence set forth in SEQ ID NO: 51 and the amino acid sequence set forth in SEQ ID NO: 52, respectively;

(d) the amino acid sequence set forth in SEQ ID NO: 67 and the amino acid sequence set forth in SEQ ID NO: 68, respectively;

(e) the amino acid sequence set forth in SEQ ID NO: 69 and the amino acid sequence set forth in SEQ ID NO: 70, respectively;

(f) the amino acid sequence set forth in SEQ ID NO: 71 and the amino acid sequence set forth in SEQ ID NO: 72, respectively;

(g) the amino acid sequence set forth in SEQ ID NO: 73 and the amino acid sequence set forth in SEQ ID NO: 74, respectively;

(h) the amino acid sequence set forth in SEQ ID NO: 75 and the amino acid sequence set forth in SEQ ID NO: 76, respectively;

(i) the amino acid sequence set forth in SEQ ID NO: 77 and the amino acid sequence set forth in SEQ ID NO: 78, respectively;

(j) the amino acid sequence set forth in SEQ ID NO: 79 and the amino acid sequence set forth in SEQ ID NO: 80, respectively;

(k) the amino acid sequence set forth in SEQ ID NO: 81 and the amino acid sequence set forth in SEQ ID NO: 82, respectively;

(l) the amino acid sequence set forth in SEQ ID NO: 83 and the amino acid sequence set forth in SEQ ID NO: 84, respectively;

(m) the amino acid sequence set forth in SEQ ID NO: 85 and the amino acid sequence set forth in SEQ ID NO: 86, respectively;

(n) the amino acid sequence set forth in SEQ ID NO: 87 and the amino acid sequence set forth in SEQ ID NO: 88, respectively;

(o) the amino acid sequence set forth in SEQ ID NO: 89 and the amino acid sequence set forth in SEQ ID NO: 90, respectively;

(p) the amino acid sequence set forth in SEQ ID NO: 91 and the amino acid sequence set forth in SEQ ID NO: 92, respectively; or

(q) the amino acid sequence set forth in SEQ ID NO: 93 and the amino acid sequence set forth in SEQ ID NO: 94, respectively.

In some aspects, the anti-CEACAM5 antibody or antigen binding portion thereof is described in Table 10 and Table 11. In some aspects, the CDRs, VH, VL, heavy chain and/or light chain is described in Table 10 and Table 11. For example, the anti-CEACAM5 antibody or antigen binding portion thereof comprises a heavy chain and the light chain comprise the amino acid sequence set forth in SEQ ID NO: 45 and the amino acid sequence set forth in SEQ ID NO: 46, respectively.

## BRIEF DESCRIPTION OF THE DRAWINGS

FIGS. **1**A-**1**B are tables that show competition and binning of selected anti-CEACAM5 binding antibodies.

FIGS. **2**A-**2**D are graphs that show cell-based binding of anti-CEACAM5 antibodies by flow cytometry (AF647). The anti-CEACAM5 antibodies were assayed to test their binding to the cell lines expressing different levels of human CEACAM5: BXPC-3 (FIG. **2**A), Ls174T (FIG. **2**B), MKN-45 (FIG. **2**C), and HCT-116 (FIG. **2**D), respectively.

FIGS. **3**A-**3**C are graphs depicting the percentage of cell death (% inhibition) induced by anti-CEACAM5 antibodies delivering the cytotoxic agent MMAE which has been conjugated to secondary VHH (FIG. **3**A), internalization (Red Area/Phase Area) rates (FIG. **3**B), and cytotoxicity levels of selected anti-CEACAM5 antibodies (Cytotoxicity AUC) as a function of internalization (Internalization AUC) (FIG. **3**C) in MKN45 cells.

FIGS. **4**A-**4**B are graphs that show percent growth inhibition of anti-CEACAM5 antibodies delivering cytotoxic
~~~

agent MMAE conjugated to a VHH secondary antibody (FIG. 4A) internalization (Red Area/Phase Area) rates (FIG. 4B) of selected anti-CEACAM5 antibodies in Ls174T cells.

FIG. 5A is a general description of the mutation analysis that was performed to generate single mutant libraries and for selection of progeny antibodies that bind human CEACAM5 and cynomolgus CEACAM5. FIG. 5B shows the mutational scan of MBN001. The CDR positions (by Kabat) are analyzed, and the mutations to germline VH include T7S, S40A, A68T, and P84A. FIGS. 5C-5N are the heat maps for human CEACAM5 and cynomolgus CEACAM5 that were generated using the mutational scan analysis of MBN001 antibody for LCDR1 substitutions (SEQ ID NO: 64, germline and parental) (FIG. 5I and FIG. 5J); LCDR2 substitutions (SEQ ID NO: 65, germline and parental) (FIG. 5K and FIG. 5L) LCDR3 substitutions (SEQ ID NO: 66, germline and parental) (FIG. 5M and FIG. 5N); HCDR1 substitutions (SEQ ID NO: 61, germline and parental) (FIG. 5C and FIG. 5D); HCDR2 substitutions (SEQ ID NO: 62, germline and parental) (FIG. 5E and FIG. 5F); and HCDR3 substitutions (SEQ ID NO: 63, germline and parental, (FIG. 5G and FIG. 511). Note that in the graphs described herein that ND indicates that enrichment ratios could not be determined because NGS counts in the starting library were too low.

Figure 8A:
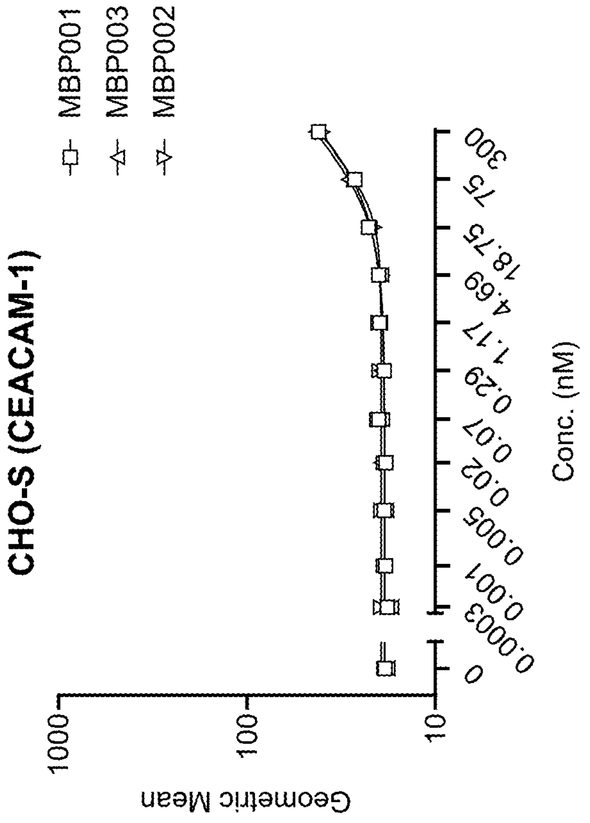
Figure 8B:
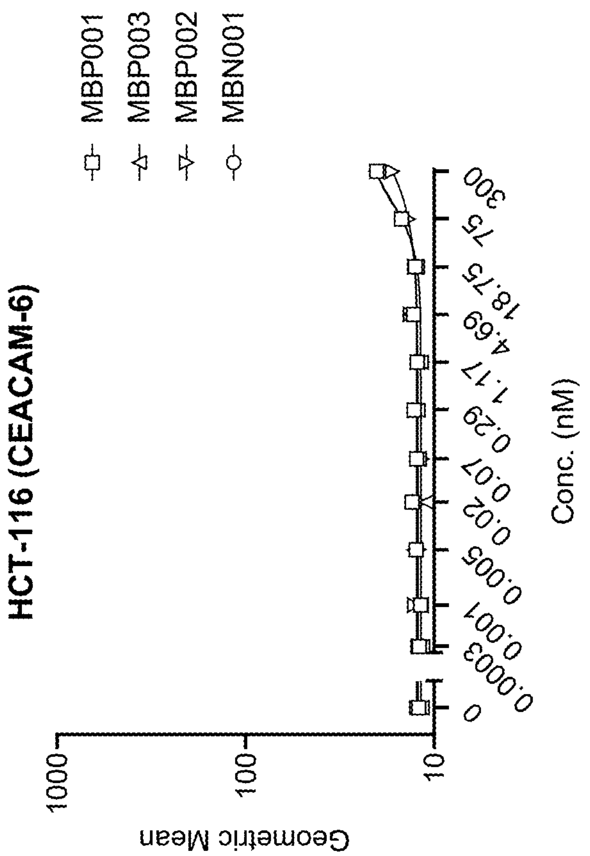

FIGS. 8A-8B are a set of graphs that show the absence of non-specific binding to cell lines engineered to express human CEACAM1 (CHO-S; FIG. 8A) and human CEACAM6 (HCT-116; FIG. 8B) by MBN001 and progeny mAbs MBP003, MBP001 and MBP002.

FIGS. 9A-9C are a set of graphs showing binding to CEACAM5-low expressing LS174T cells (FIG. 9A), CEACAM-medium expressing BxPC-3 cells (FIG. 9B), and CEACAM5-high expressing MKN45 cells (FIG. 9C) of anti-CEACAM5 mAbs MBN001, MBP001, MBP003, and MBP002 by FACS. EC50 values are shown in FIG. 9D (MBN001, MBP001, MBP002, and MBP003).

FIGS. 10A-10D are a set of graphs and tables showing the percent inhibition of anti-CEACAM5 antibodies conjugated to Compound A' across a panel of CEACAM5-expressing cell lines. The graphs show % growth inhibition for selected antibodies conjugated to Compound A' compared to isotype controls at the indicated antibody concentrations in: a low CEACAM5-expressing cell line Ls174T FIG. 10A), a medium CEACAM5-expressing cell line BxPC-3 (FIG. 10B), and high CEACAM5-expressing line MKN-45 (FIG. 10C). FIG. 10D is a table with IC50 values for the antibody-drug-conjugates.

Figure 11A:
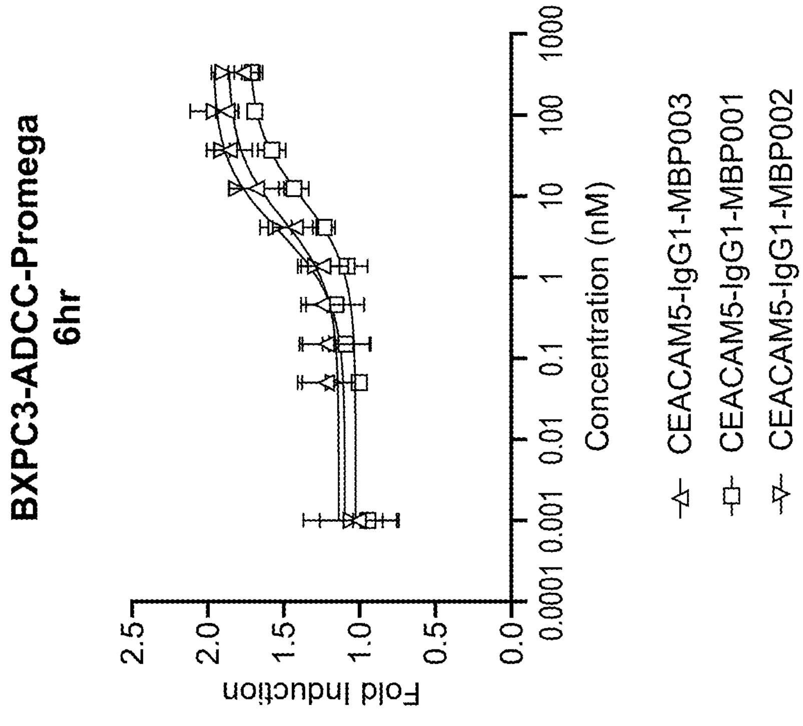
Figure 11B:
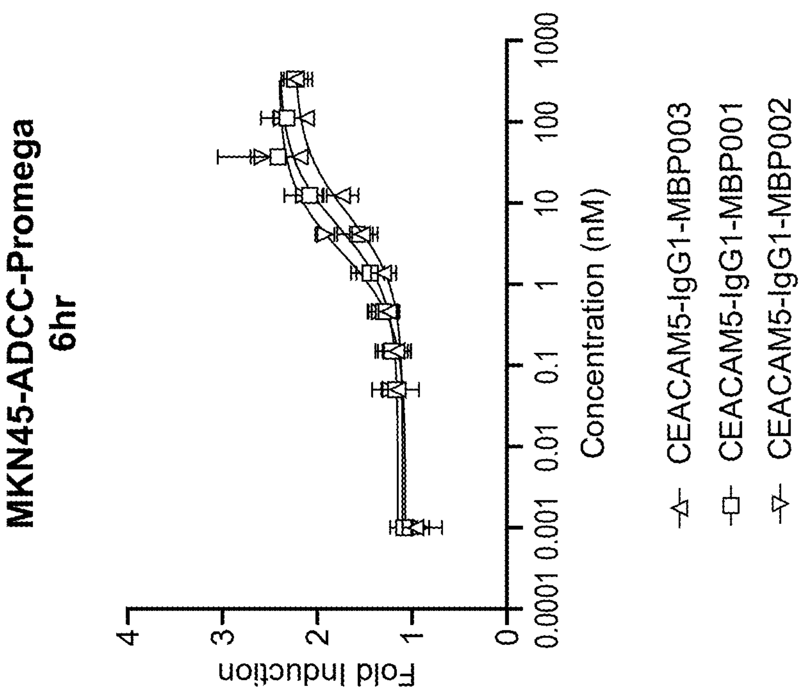

FIGS. 11A-11B are graphs showing the ADCC activity of anti-human CEACAM5 mAbs in Jurkat-NFAT-FcγRIIIa (Promega) cell assays across CEACAM5-medium expressing BxPC3 (FIG. 11A) and CEACAM5-high expressing MKN45 (FIG. 11B) cells.

Figure 12A:
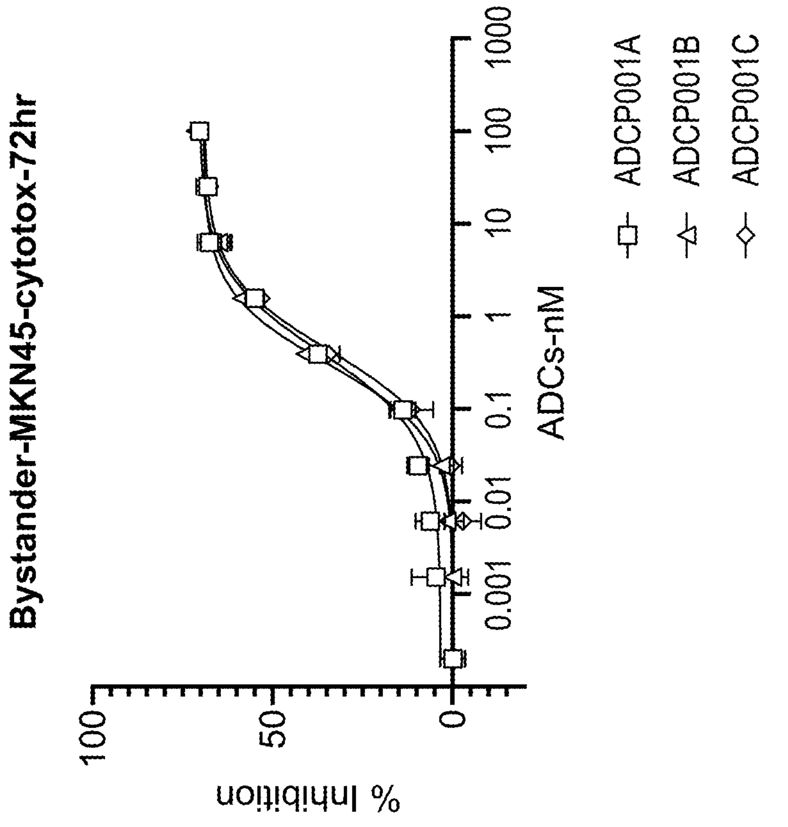
Figure 12B:
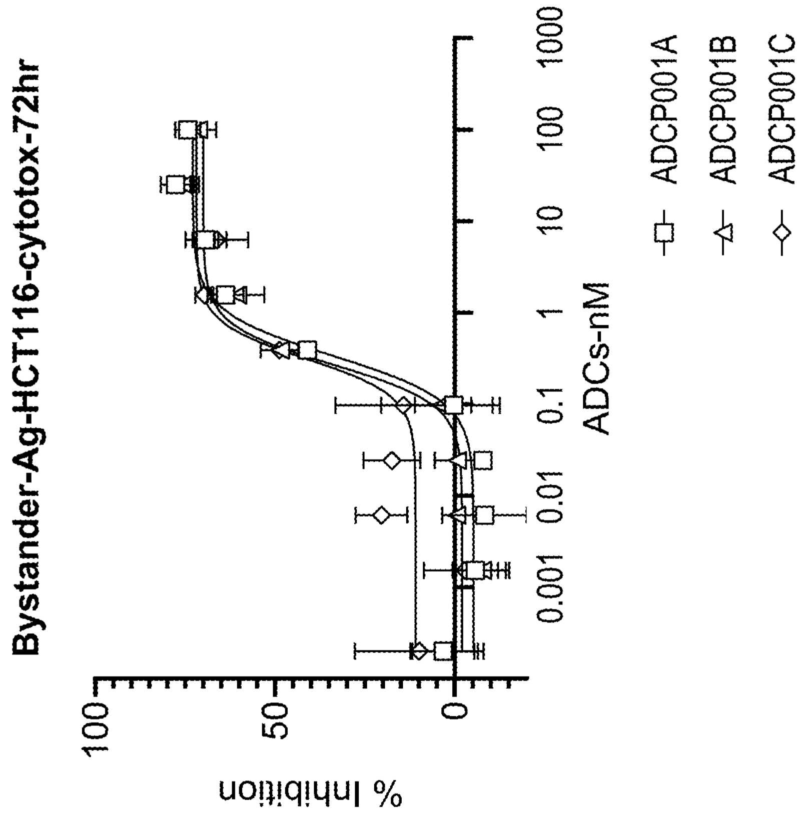
Figure 12C:
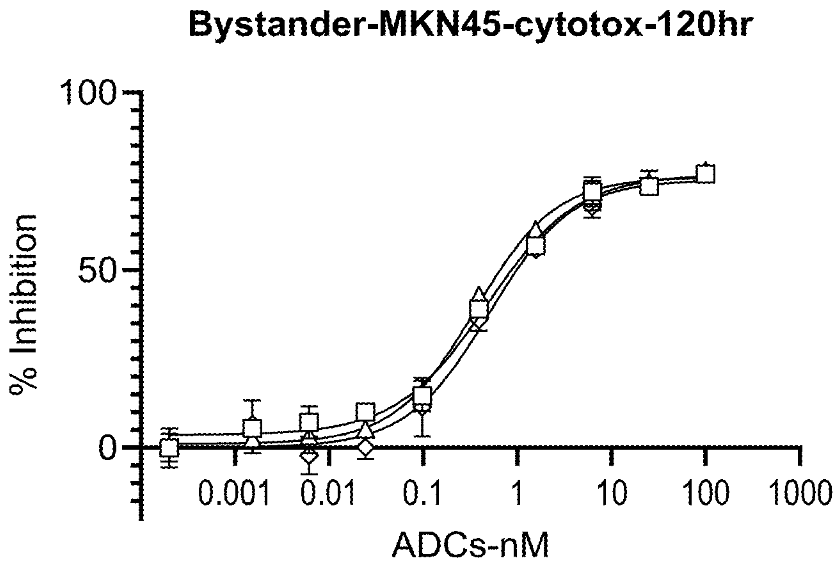
Figure 12D:
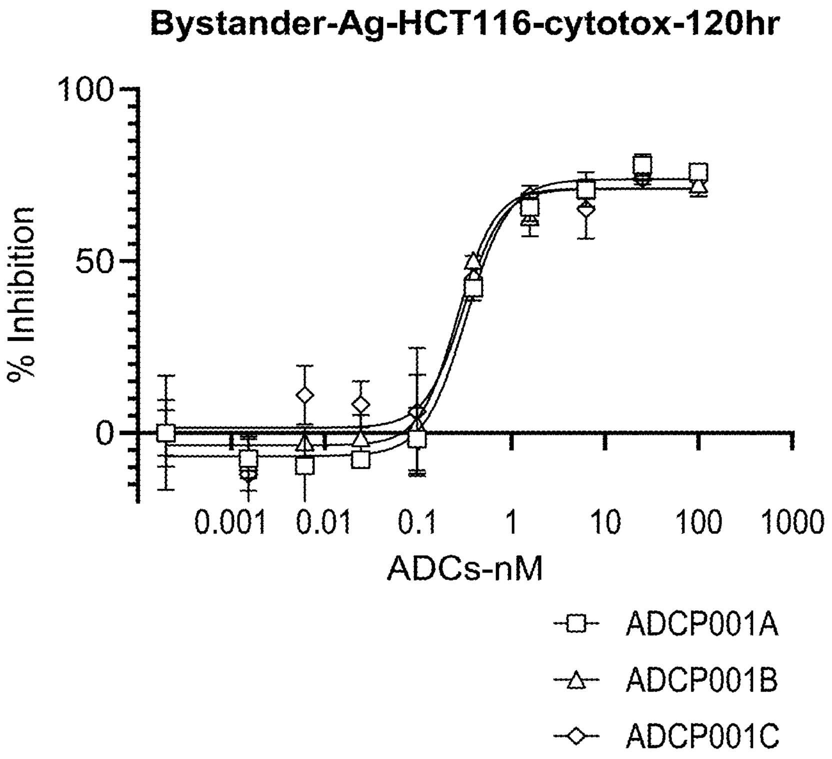

FIGS. 12A-12D are a set of graphs showing bystander kill effect at 72 and 120 hours by co-culturing of MKN45 cells (Ag+; FIG. 12A and FIG. 12C) and HCT-116 cells (Ag−; FIG. 12B and FIG. 12D) followed by treatment with ADP001A, ADCP001B, ADCP01C: ADCs having mAbs either MBP001, MBP002, or MBP003 conjugated to Compound A').

Figure 13C:
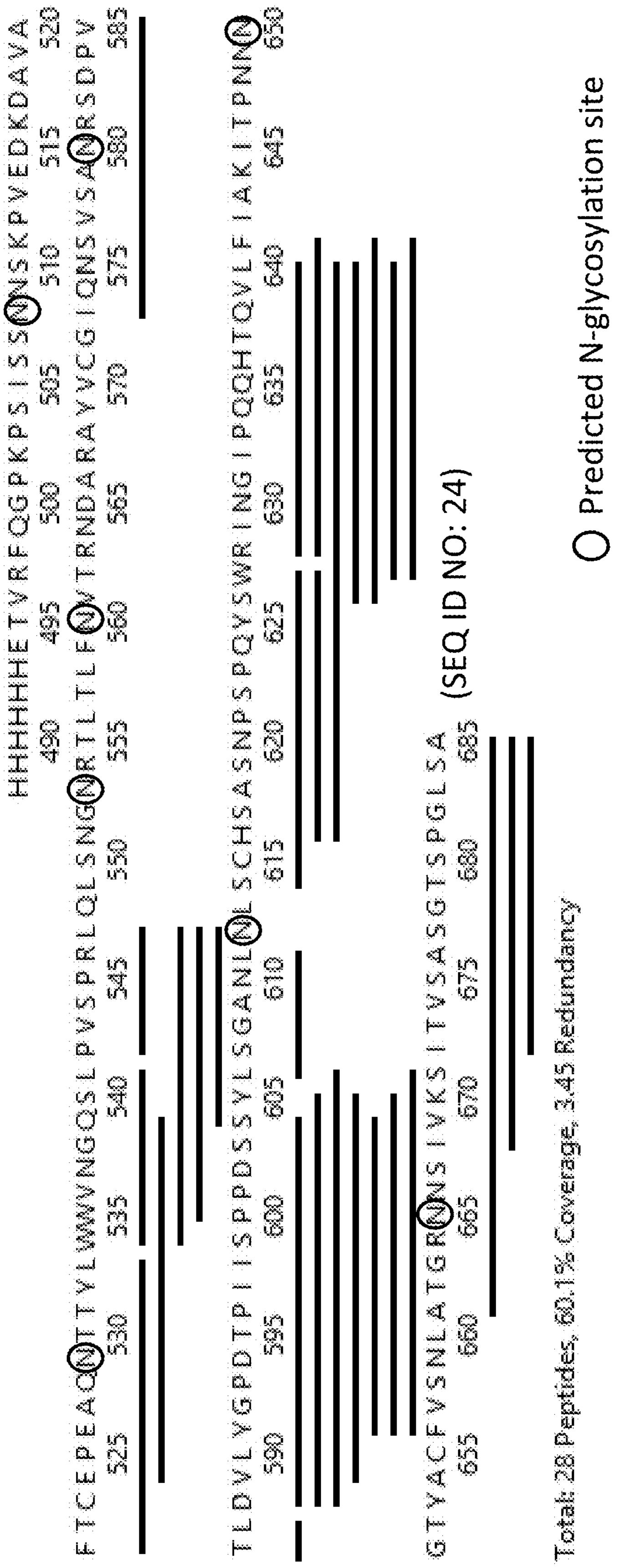
Figures 13D, 13E:
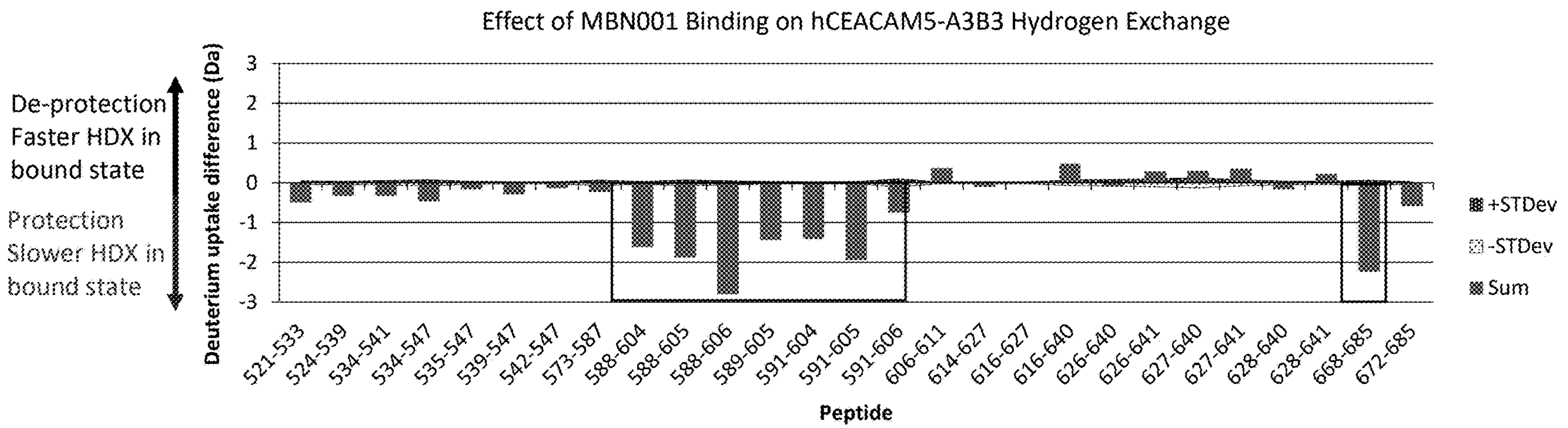

FIG. 13A is a ribbon representation of the 3D model of human CEACAM5 along with the separate structural domains. A box is added to this figure to highlight the A3 and B3 domains of human CEACAM5. FIG. 13B shows an amino acid sequence for hCEACAM5 (UniProt entry: P06731) with shading identifying the separate structural domains shown in FIG. 13A (SEQ ID NO: 25). FIG. 13C is a drawing showing peptic sequence coverage for hCEACAM5-A3-B3 construct (SEQ ID NO: 24). FIG. 13D is a graph showing differential deuterium uptake between hCEACAM5 bound to MBN001 vs. unbound hCEACAM5. Regions in hCEACAM5 with significant HDX reduction upon MBN001 binding are boxed. FIG. 13E is a drawing showing annotation on linear sequence of hCEACAM5, of HDX effects of MBN001 binding. Bold residues exhibit slower exchange, no information is available for residues in italics, no difference detected on straight type residues.

Figure 14A:
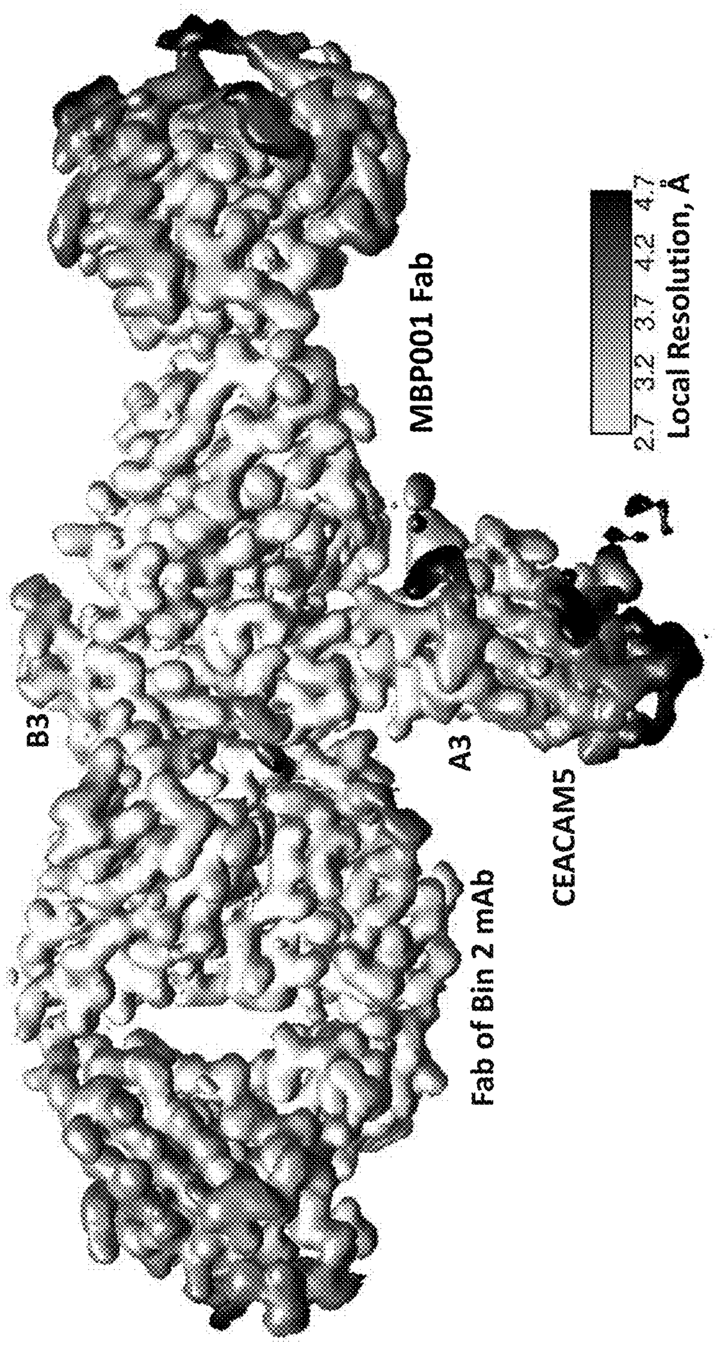
Figure 14B:
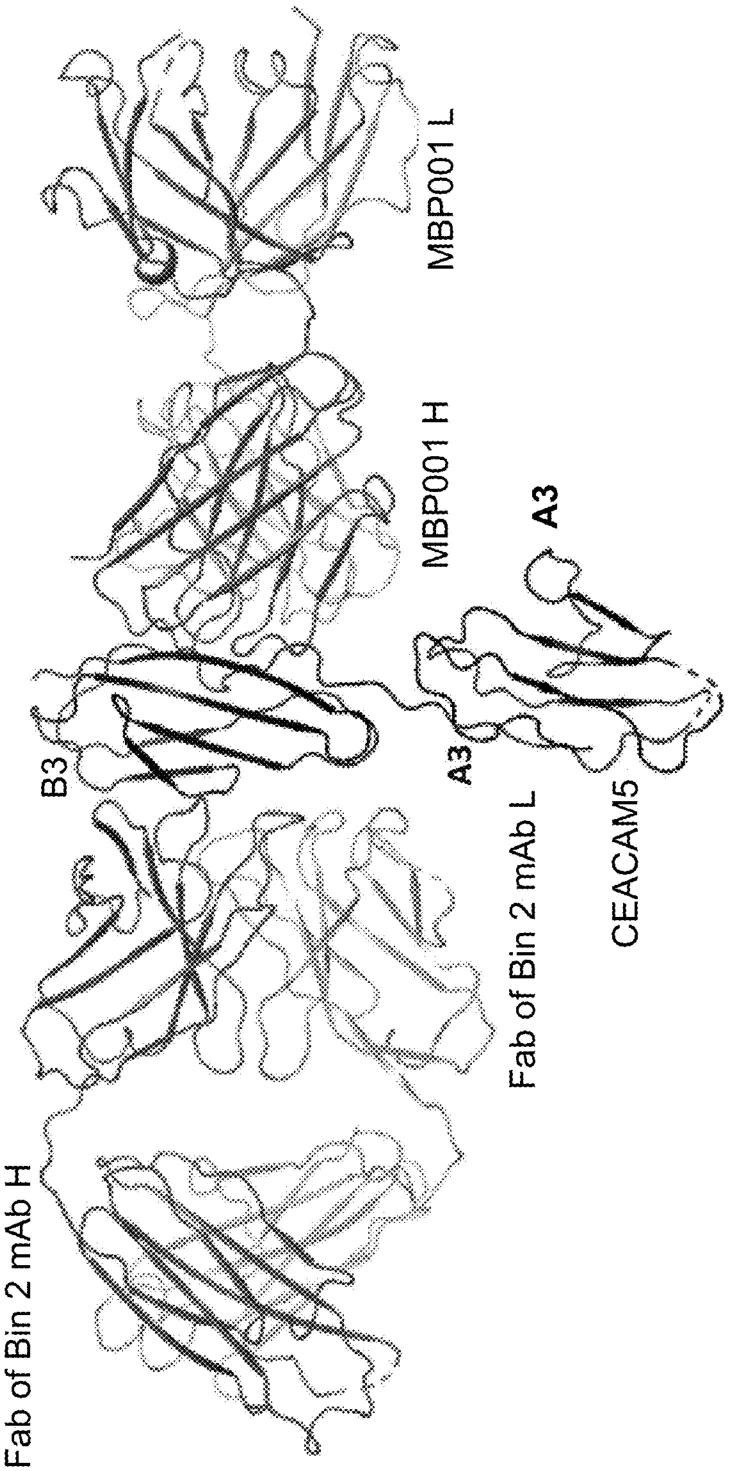
Figure 15B:
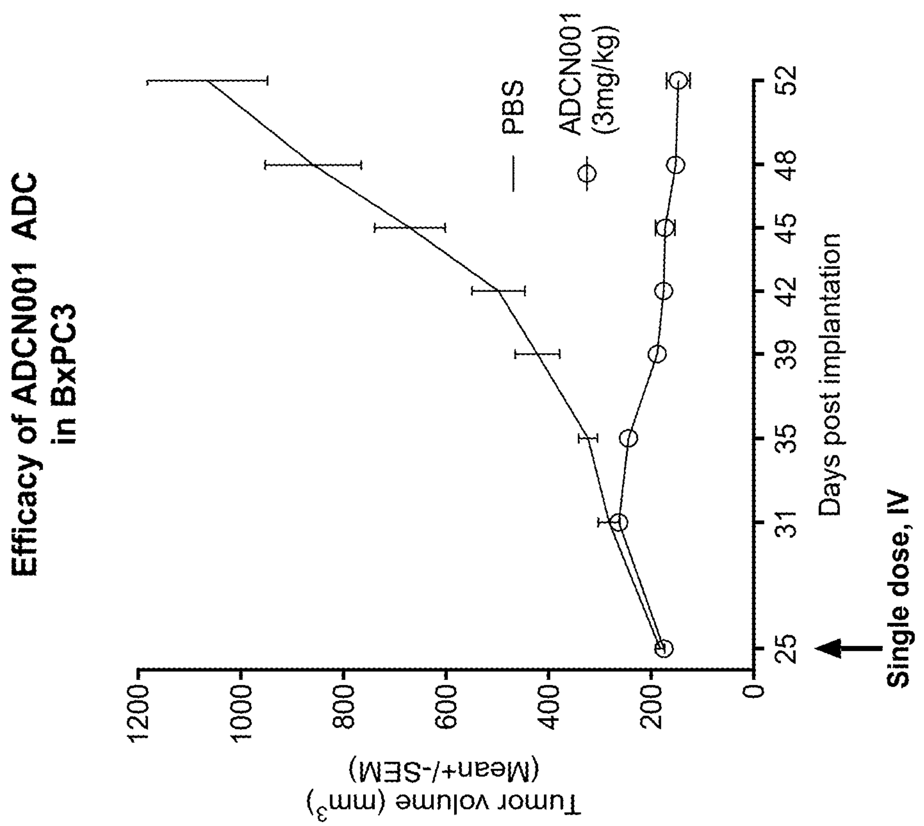
Figure 15A:
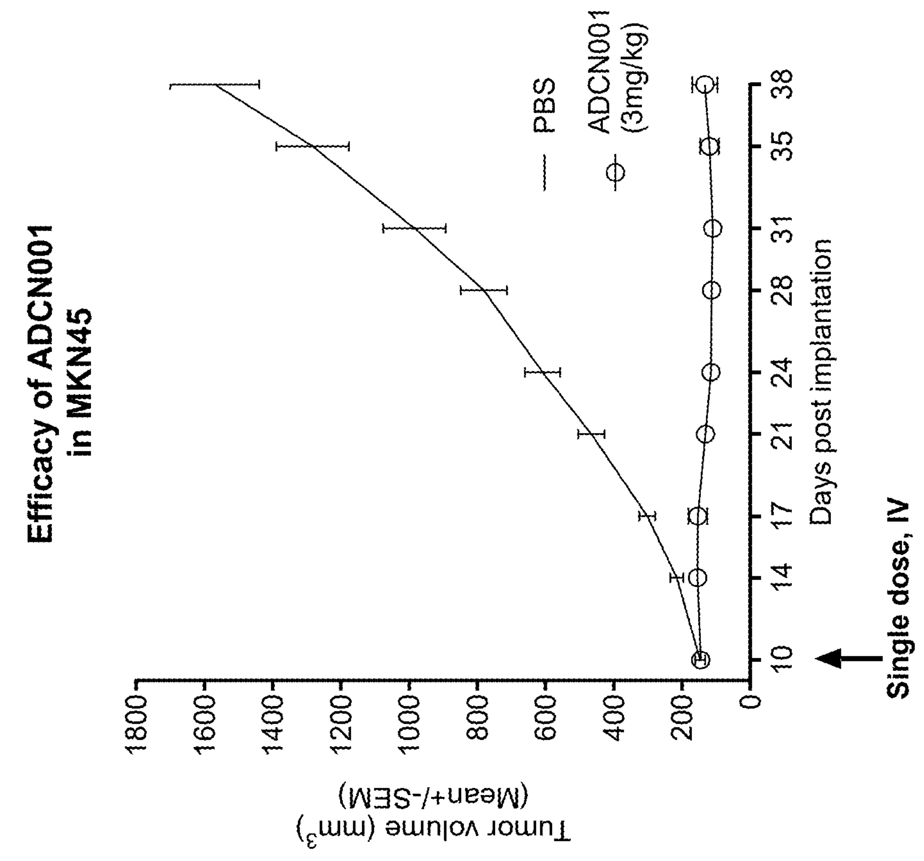
Figure 15C:
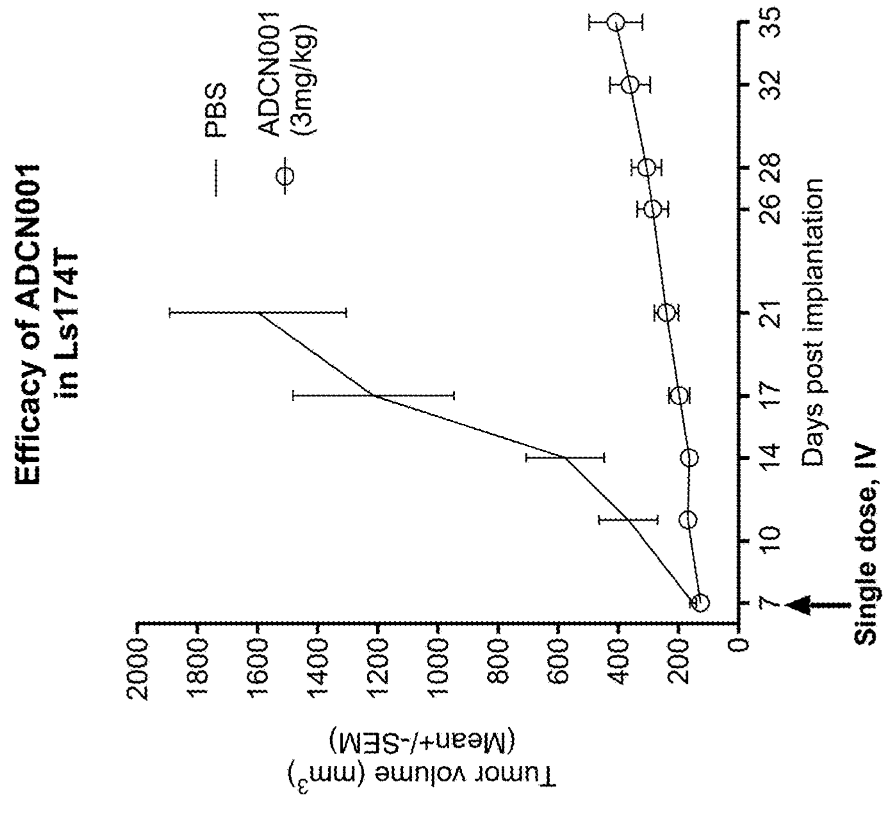
Figure 15D:
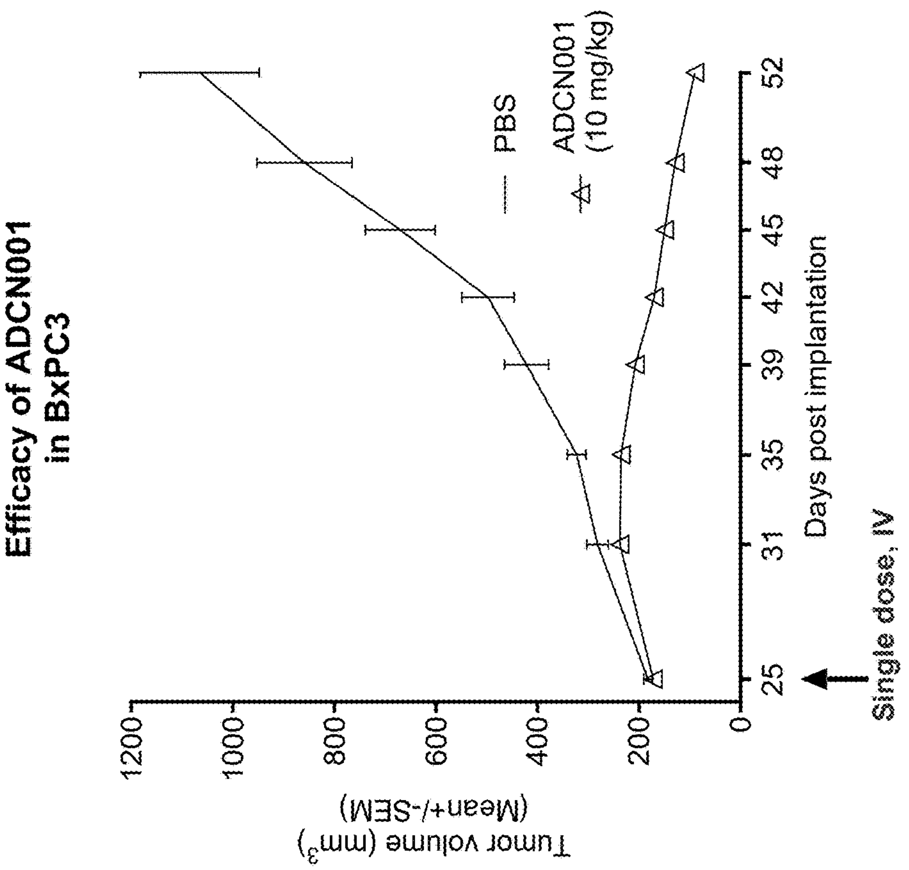
Figure 15E:
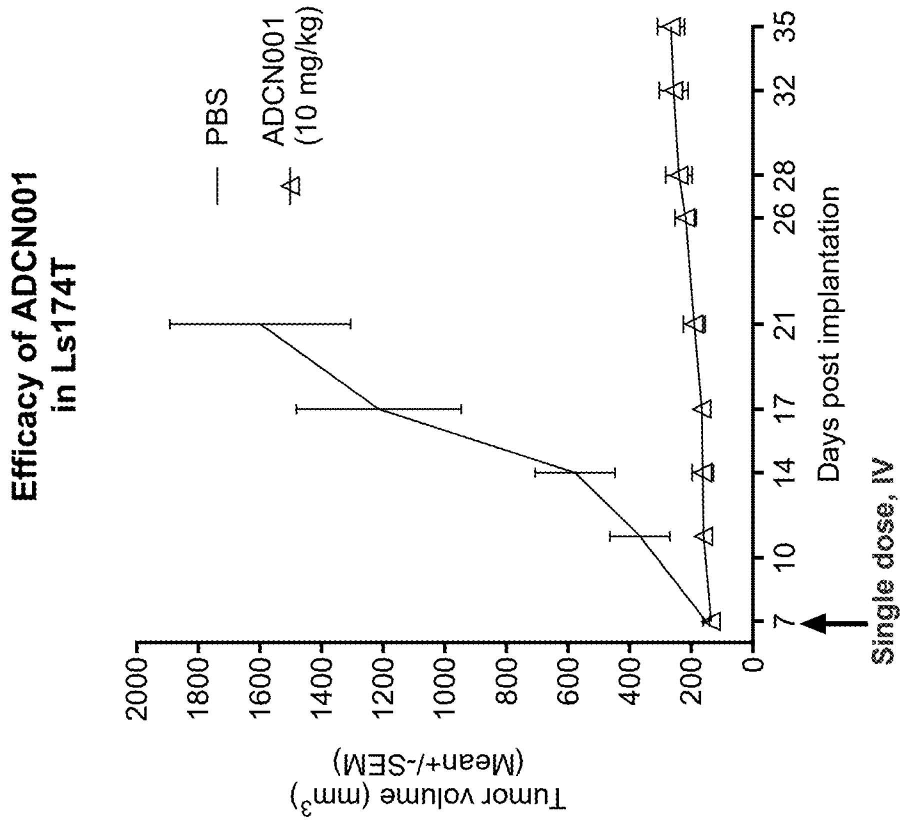

FIG. 14A is a map of the final cryoEM and FIG. 14B and FIG. 14C are ribbon diagrams of the final structure-based model derived from cryoEM showing the epitope and paratope interaction between human CEACAM5 and Fab construct of MBP001 and a Fab of a bin 2 mAb.

FIGS. 15A-15E are a set of graphs showing in vivo efficacy of ADCN001 (MBN001 (hIgG1.3) conjugated to Compound A' (DAR8)) in MKN45 CDX models (FIG. 15A), BxPC3 (FIG. 15B and FIG. 15D), and Ls174T (FIG. 15C and FIG. 15E) after a single intravenous injection with either 3 mg/kg (FIG. 15A, FIG. 15B and FIG. 15C) or 10 mg/kg (FIG. 15D and FIG. 15E) of the ADCs.

Figure 16A:
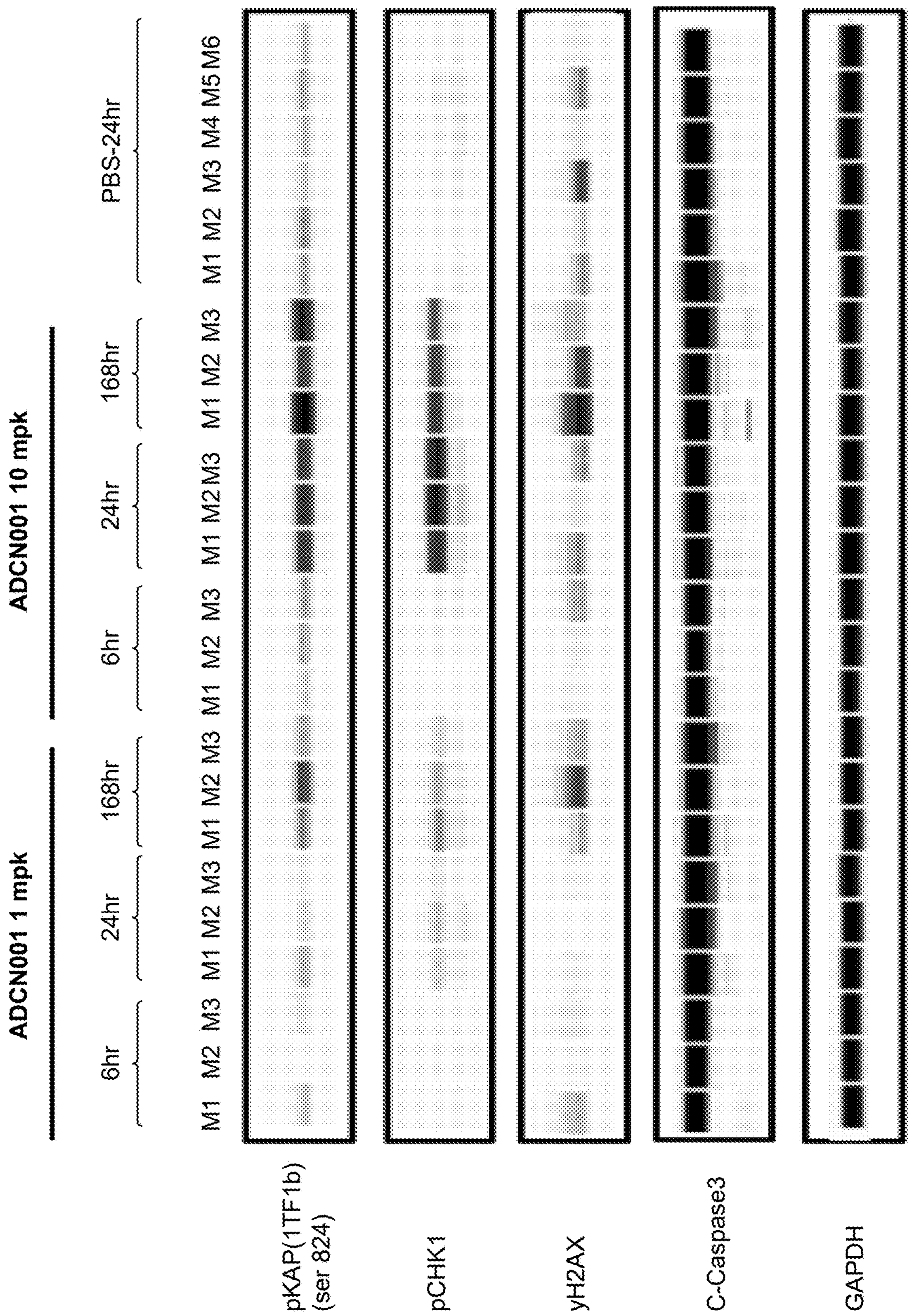
Figure 16B:
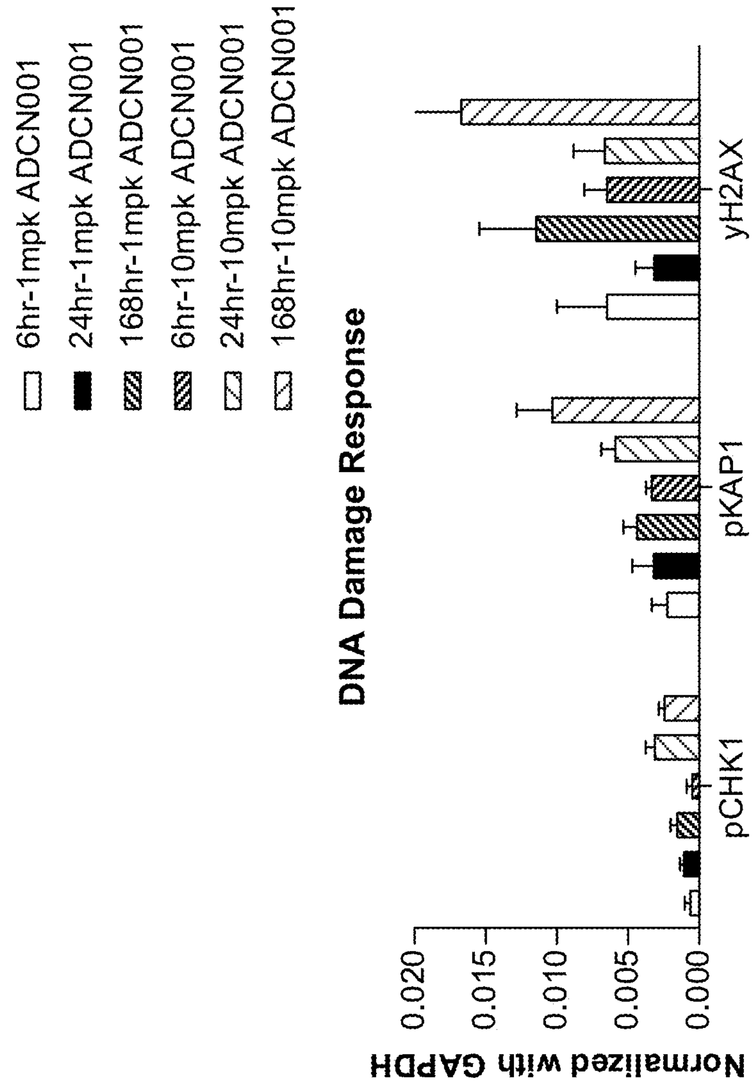
Figure 17B:
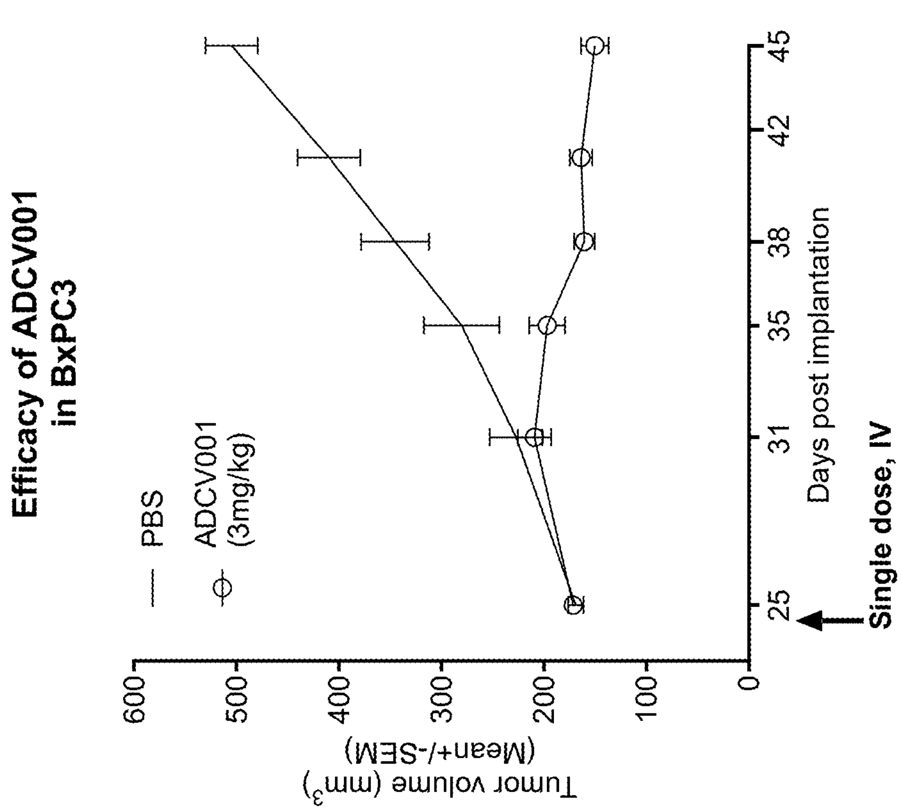
Figure 17A:
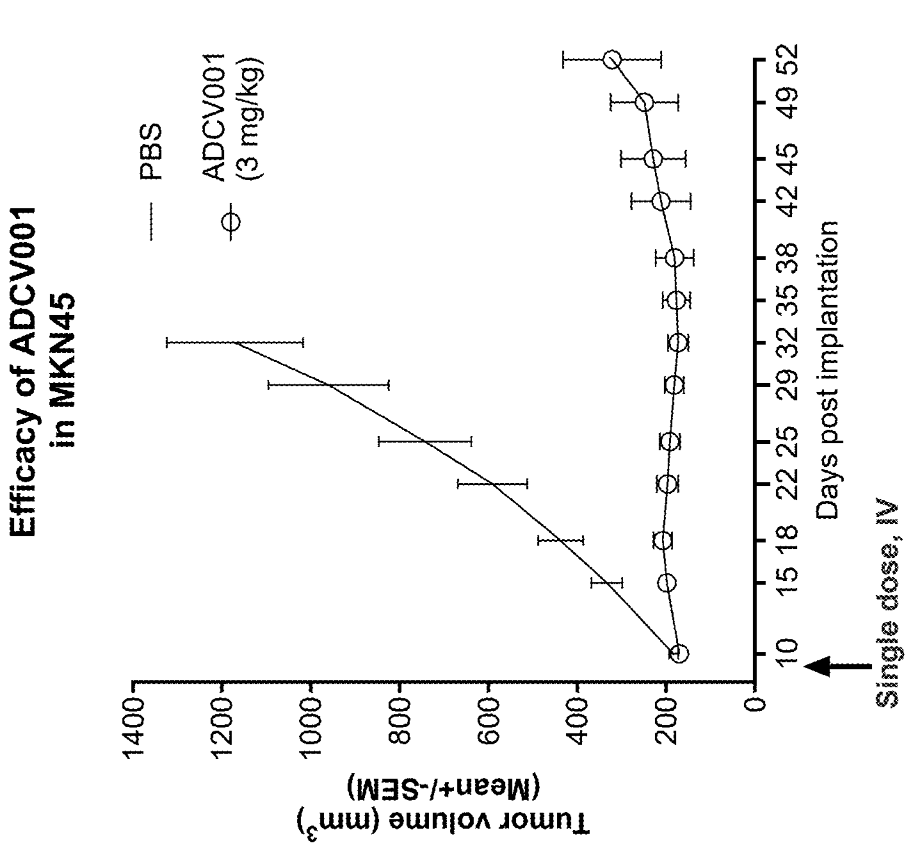
Figure 17C:
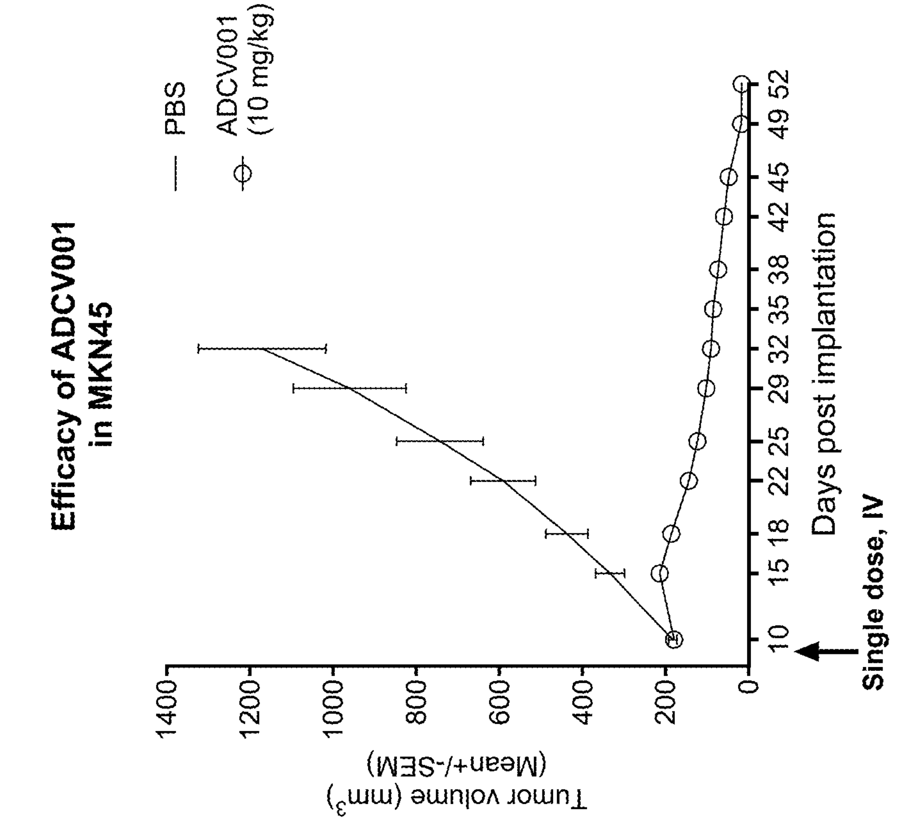
Figure 17D:
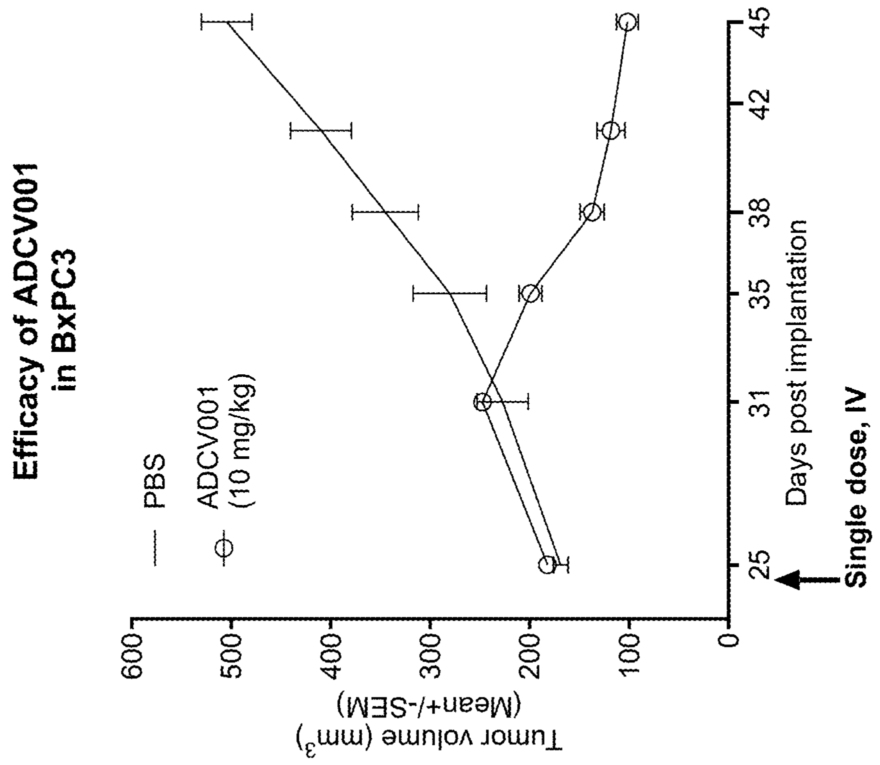
Figure 18A:
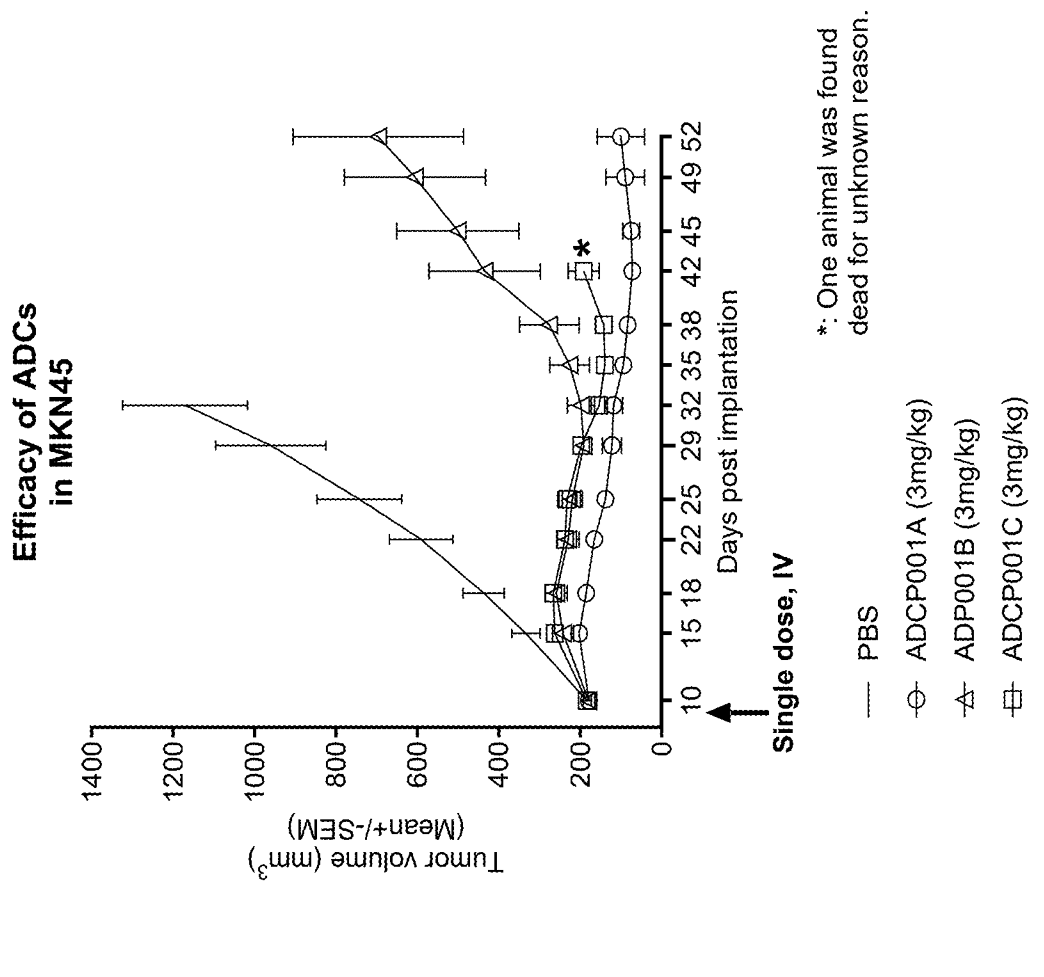
Figure 18B:
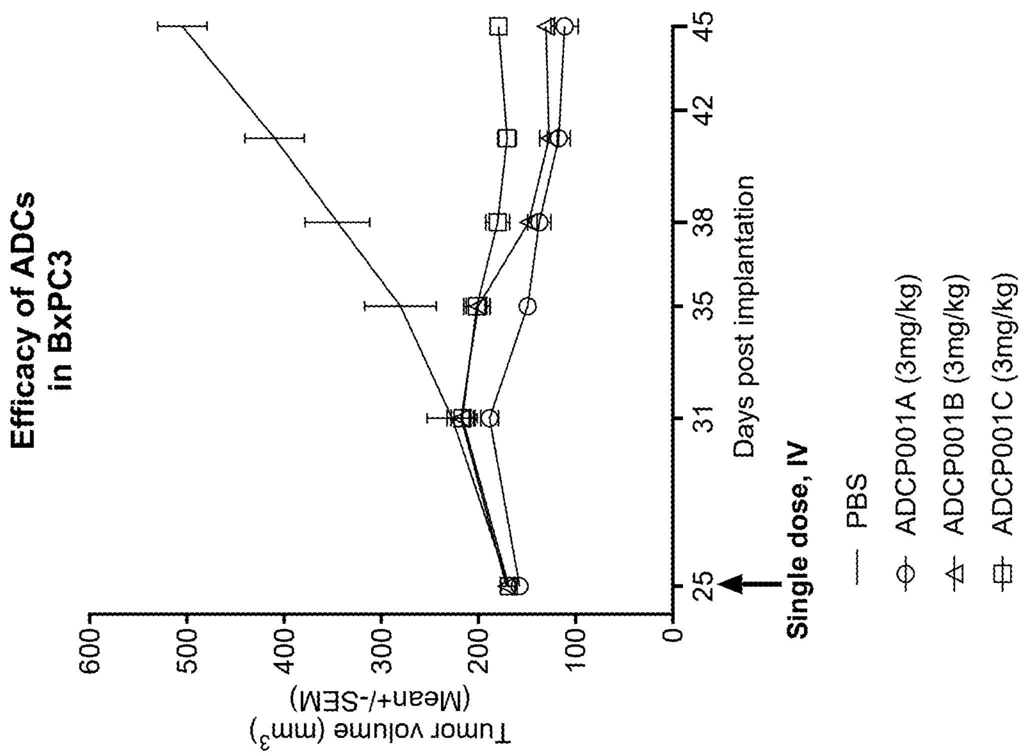
Figure 18C:
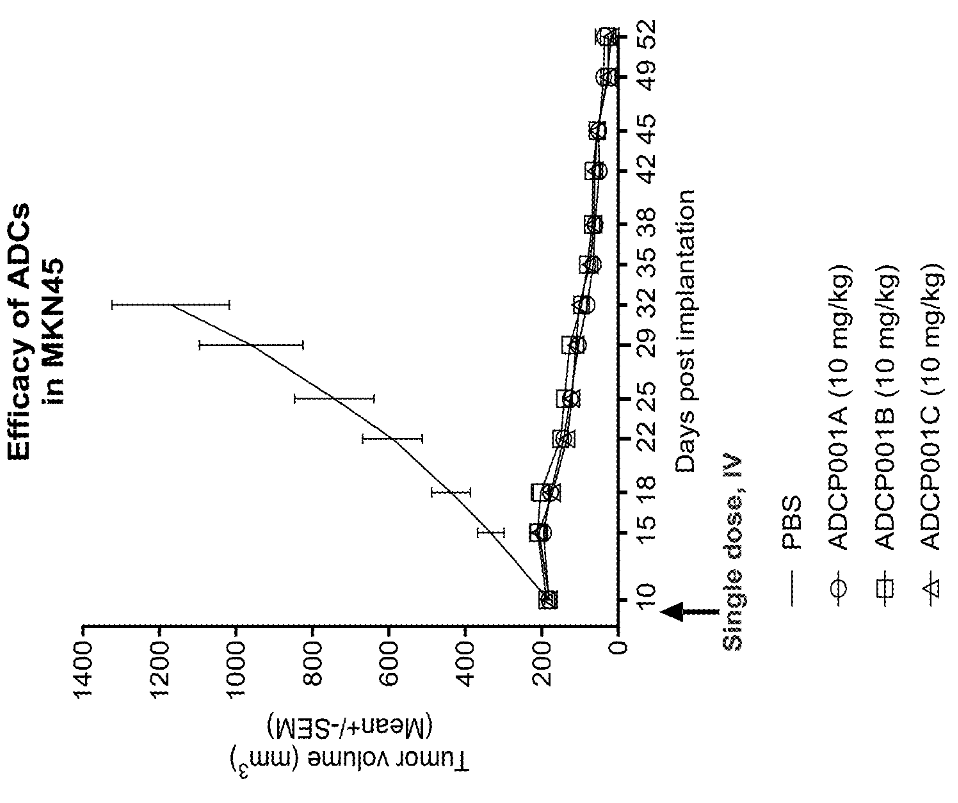
Figure 18D:
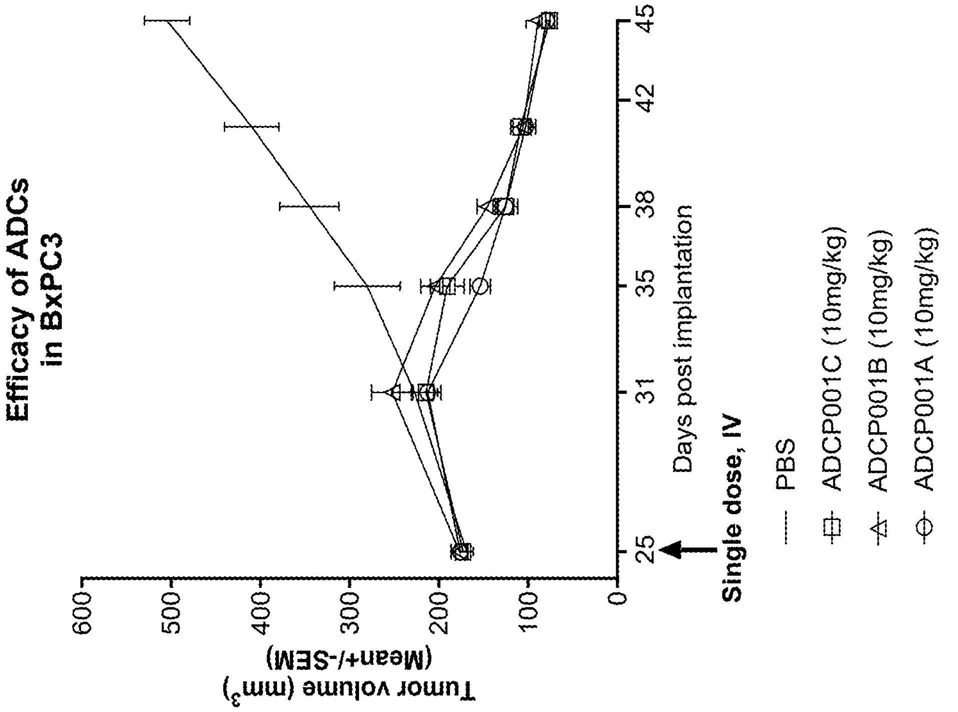

FIGS. 16A-16B are a Simple Western Blot image and a graph showing induction of the pharmacodynamic markers of DNA damage response, including pKAP, pCHK1 gH2AX, in addition to the apoptosis marker cleaved caspase-3 expression in tumors from MKN45 CDX model (n=3) at 6 hours, 24 hours, and 168 hours after a single intravenous injection with either 1 mg/kg or 10 mg/kg of ADCN001 (MBN001+ Compound A' ADC). Expression intensity of DNA damage response markers pKAP(1TF1b) (ser 824), pCHK1, yH2AX and apoptosis marker c-caspase 3 was normalized to that of the loading control GAPDH.

FIGS. 17A-17D are a set of graphs showing in vivo efficacy of ADCV001 (MBV001 (wild-type hIgG1 version of MBN001) conjugated to Compound A') in CDX models (MKN45 (FIG. 17A and FIG. 17C) and BxPC3 (FIG. 17B and FIG. 17D)) after a single intravenous injection with either 3 mg/kg (FIG. 17A and FIG. 17B) or 10 mg/kg (FIG. 17C and FIG. 17D) of ADCV001.

FIGS. 18A-18D are a set of graphs showing in vivo efficacy of ADCP001A (MBP001+ Compound A' ADC), ADCP001B (MBP002+ Compound A' ADC), and ADCP001C (MBP003+ Compound A' ADC) ADCs in CDX models (MKN45 (FIG. 18A and FIG. 18C) and BxPC3 (FIG. 18B and FIG. 18D)) after a single intravenous injection with either 3 mg/kg (FIG. 18A and FIG. 18B) or 10 mg/kg (FIG. 18C and FIG. 18D) of the ADCs.

Figure 19B:
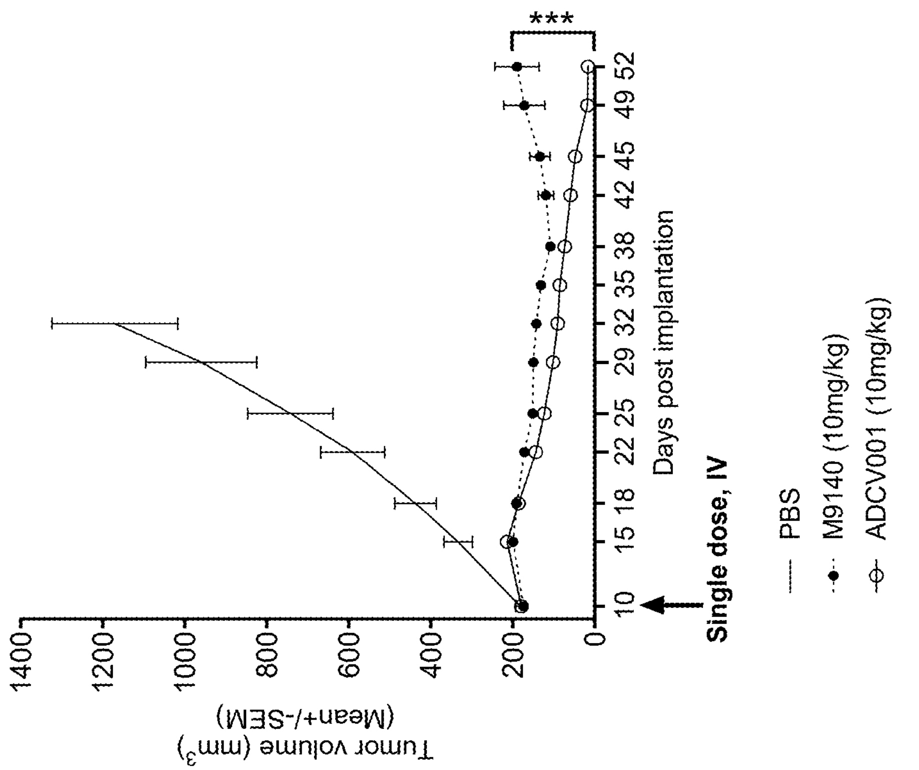
Figure 19A:
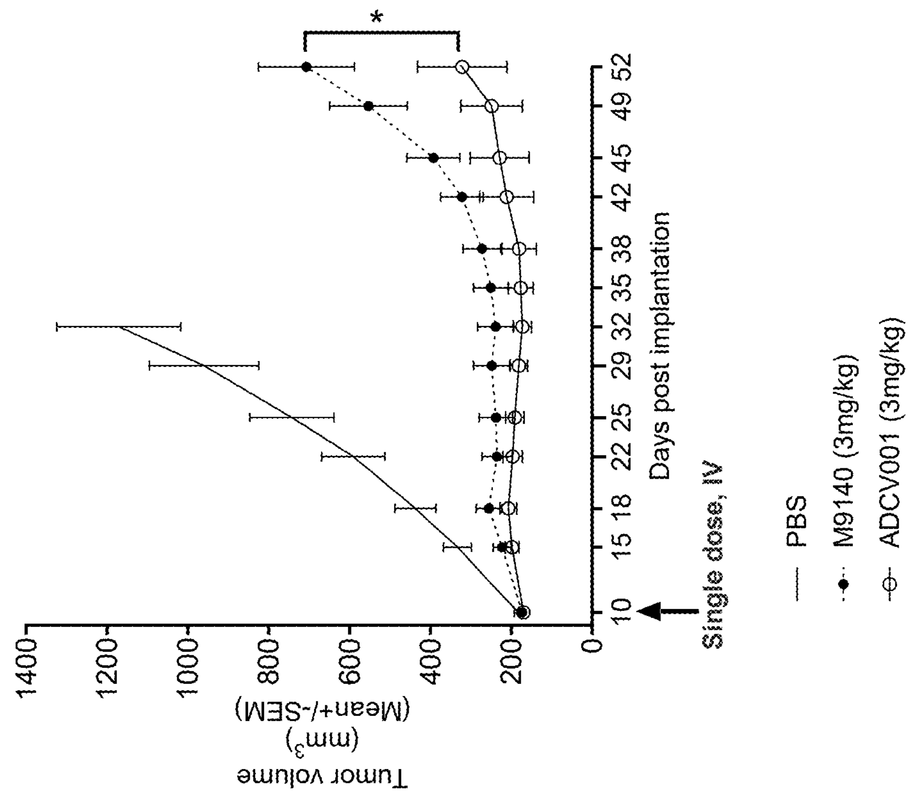
Figure 19C:
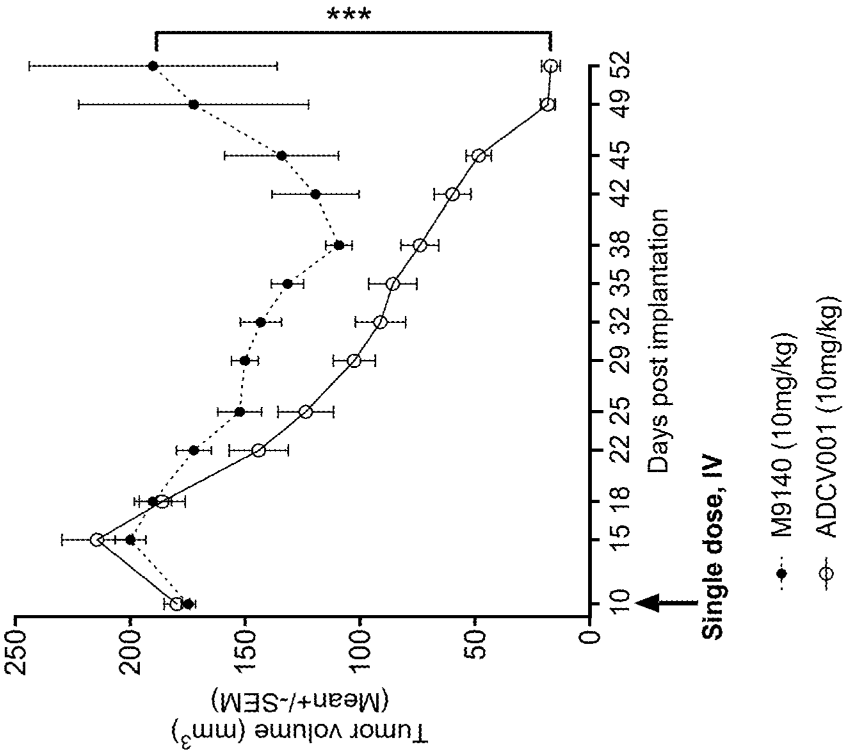

FIGS. 19A-19C are a set of graphs showing in vivo efficacy of ADCV001 and M9140 in CDX model MKN45 after a single intravenous injection with either 3 mg/kg (FIG. 19A) or 10 mg/kg (FIG. 19B and FIG. 19C) of the ADCV001 and Merck ADC1. FIG. 19C is an enlarged plot of FIG. 19B.

Figure 20:
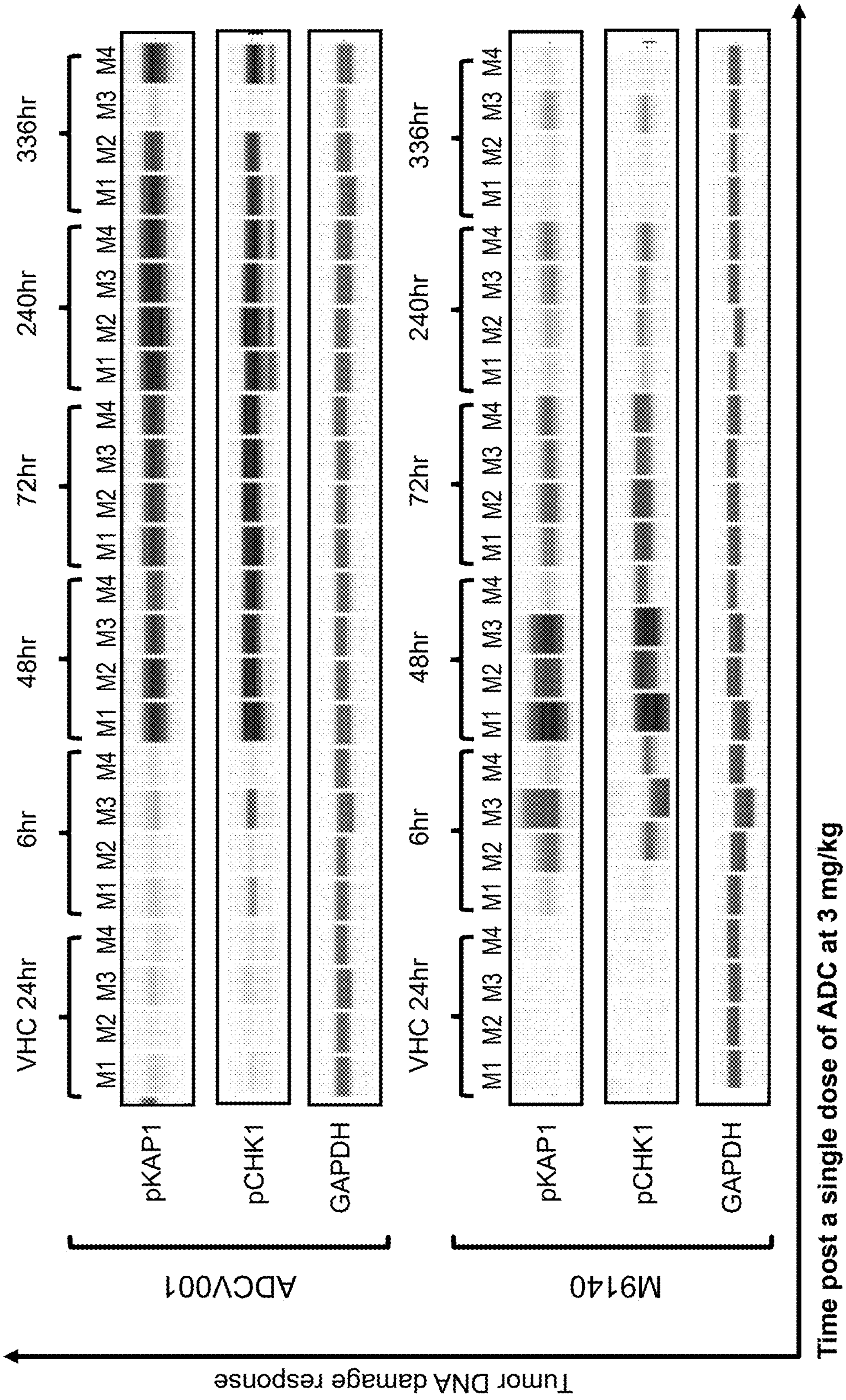

FIG. 20 is a Western Blot image showing sustained induction of the pharmacodynamic markers of DNA damage response, including pKAP1 and pCHK1 in tumors from MKN45 CDX model (n=4) at 6, 48, 72, 240, and 336 hours after a single intravenous injection with 3 mg/kg of ADCV001 and M9140.

DETAILED DESCRIPTION

The present disclosure provides an antibody drug conjugate (ADC) of the formula (I), (II) or ADC 101, a pharmaceutical composition comprising the ADC, the use of the ADC in a method of treating disease, such as cancer.

Definitions

In order for the following detailed description to be readily understood, certain terms are first defined. Additional definitions are provided throughout.

The term "alkyl" by itself or as part of another term in general refers to a substituted or unsubstituted straight chain or branched, saturated hydrocarbon having the indicated number of carbon atoms; e.g., "—$(C_1$-$C_8)$alkyl" or "—$(C_1$-$C_{10})$alkyl" refer to an alkyl group having from 1 to 8 or 1 to 10 carbon atoms, respectively). When the number of carbon atoms is not indicated, the alkyl group may have from 1 to 8 carbon atoms. Representative straight chain —$(C_1$-$C_8)$ alkyl groups include, but are not limited to, -methyl, -ethyl, -n-propyl, -n-butyl, -n-pentyl, -n-hexyl, -n-heptyl and -n-octyl; branched-$(C_1$-$C_5)$alkyl groups include, but are not limited to, -isopropyl, -sec-butyl, -isobutyl, -tert-butyl, -isopentyl, and -2-methylbutyl. In some aspects, an alkyl group may be unsubstituted. Optionally, an alkyl group may be substituted, e.g., with one or more groups.

The term "polyalkene glycol unit," refers to a repeating alkylene glycol subunit having the formula $—[(CH_2)_n—O]_y—$, where n is the number of methylene groups in the subunit and y is the number of subunits in the unit. The oxygen atom of the terminal subunit can be substituted with a hydrogen atom, a protecting group, or any other allowable functionality.

The term "substituted", "optionally substituted", "optionally may be substituted" or the like, unless otherwise indicated, in general means that one or more hydrogen atoms can be each independently replaced with a substituent. Typical substituents include, but are not limited to, —X, —R, —O—, —OR, —SR, $—S^-$, $—NR^2$, =NR, $—CX_3$, —CN, —OCN, —SCN, —N=C=O, —NCS, —NO, $—NO_2$, $=N_2$, $—N_3$, —NRC(=O)R, —C(=O)R, $—C(=O)NR^2$, $—SO_3—$, $—SO_3H$, $—S(=O)_2R$, $—OS(=O)_2OR$, $—S(=O)_2NR$, —S(=O)R, $—OP(=O)(OR)_2—P(=O)(OR)_2$, $—PO_4^{3-}$, $—PO_3H_2$, —C(=O)R, —C(=O)X, —C(=S)R, $—CO_2R$, $—CO_2H$, —C(=S)OR, —C(=O)SR, —C(=S)SR, $—C(=O)NR^2$, $—C(=S)NR^2$, or $—C(=NR)NR^2$, where each X is independently a halogen: —F, —Cl, —Br, or —I; and each R is independently —H, —$(C_1$-$C_{20})$alkyl (such as e.g. —$(C_1$-$C_{10})$alkyl or —$(C_1$-$C_8)$ alkyl), —$(C_6$-$C_{20})$aryl, (such as e.g. —$(C_6$-$C_{10})$aryl or, e.g., —$C_6$-aryl), —$(C_3$-$C_{14})$heterocycle (such as e.g. —$(C_3$-$C_{10})$ heterocycle or —$(C_3$-$C_8)$heterocycle), a protecting group, or a prodrug moiety. Typical substituents also include (=O).

The term "aliphatic or aromatic residue", as used herein, in general refers to an aliphatic substituent, such as e.g. but not limited to an alkyl residue, which, however, can be optionally substituted by further aliphatic and/or aromatic substituents. As non-limiting examples an aliphatic residue can be a nucleic acid, an enzyme, a co-enzyme, a nucleotide, an oligonucleotide, a monosaccharide, a polysaccharide, a polymer, a fluorophore, optionally substituted benzene, etc., as long as the direct link of such a molecule to the core structure (in case of R', e.g., the link to the nitrogen atom of the Y) is aliphatic. An aromatic residue is a substituent, wherein the direct link to the core structure is part of an aromatic system, e.g., an optionally substituted phenyl or triazolyl or pyridyl or nucleotide, as non-limiting example if the direct link of the nucleotide to the core structure is for example via a phenyl-residue. The term "aromatic residue", as used herein, also includes a heteroaromatic residue.

The term "antibody" as used to herein includes whole antibodies and any antigen binding portions (i.e., "antigen-binding portions") or single chains thereof. An "antibody" refers, in one aspect, to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. In certain naturally occurring antibodies, the heavy chain constant region is comprised of three domains, CH1, CH2, and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, $10^{-8}$ M or less, $1\times10^{-9}$ M or less, $1\times10^{-10}$ M or less, or $1\times10^{-11}$ M or less. In some aspects, the antibody specifically binds to an antigen with a $K_D$ between $10^{-8}$ M and $10^{-10}$ M or between $10^{-9}$ M and $10^{-11}$ M, but does not bind with high affinity to unrelated antigens.

An "antibody" according to the present disclosure includes, but is not limited to, naturally and non-naturally occurring antibodies, monoclonal antibodies, polyclonal antibodies, chimeric antibodies, humanized antibodies, human antibodies, nonhuman antibodies, bivalent antibodies, bispecific antibodies, multispecific antibodies, single chain antibodies, diabodies, and nanobodies.

An "isolated antibody," as used herein, refers to an antibody which is substantially free of other antibodies having different antigenic specificities.

The phrase "antigen binding portion" of an antibody, as used herein, refers to one or more fragments of an antibody that retain the ability to specifically bind to an antigen (e.g., human and/or cynomolgus CEACAM5). It has been shown that the antigen-binding function of an antibody can be performed by fragments of a full-length antibody. Examples of binding fragments of an antibody include (i) a Fab fragment, a monovalent fragment consisting of the $V_L$, $V_H$, CL and CH1 domains; (ii) a $F(ab')_2$ fragment, a bivalent fragment comprising two Fab fragments linked by a disulfide bridge at the hinge region; (iii) an Fd fragment consisting of the $V_H$ and CH1 domains; (iv) an Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Antigen-binding portions can be produced by recombinant DNA techniques, or by enzymatic or chemical cleavage of intact immunoglobulins.

Antibody fragments within the scope of the present invention also include F(ab')2 fragments which may be produced by enzymatic cleavage of an IgG by, for example, pepsin. Fab fragments may be produced by, for example, reduction of F(ab')2 with dithiothreitol or mercaptoethylamine. A Fab fragment is a VL-CL chain appended to a VH-CH1 chain by a disulfide bridge. A F(ab')2 fragment is two Fab fragments which, in turn, are appended by two disulfide bridges. The Fab portion of an F(ab')2 molecule includes a portion of the Fc region between which disulfide bridges are located.

As used herein, "isotype" refers to the antibody class (e.g., IgG (including IgG1, IgG2, IgG3, and IgG4), IgM, IgA (including IgA1 and IgA2), IgD, and IgE antibody) that is encoded by the heavy chain constant region genes of the antibody.

An antibody may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. Immunoglobulins, e.g., IgG1, exist in several allotypes, which differ from each other in at most a few amino acids.

As used herein, the term "allotype" refers to naturally occurring variants within a specific isotype group, where the variants differ in a few amino acids. Anti-CEACAM5 antibodies described herein can be of any allotype. Antibodies referred to herein as "IgG1.3f" are IgG1 antibodies of the allotype "f," i.e., having 214R, 356E and 358M according to the EU index. A triple mutant (L234A, L235E, G237A) IgG1.3f variant comprises an amino acid sequence set forth in SEQ ID NO: 30. The mutation of these residues would eliminate or decrease the binding of the antibodies to Fc7 receptors and/or C1q, and thus reduce activator efficacy of the Fc domain of the IgG1 component of an antibody.

As used herein, the term "hypervariable region" (sometimes referred to as the "variable region") refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al., (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, (1987) *J. Mol. Biol.* 196: 901-917).

As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing. Amino acid residues in antibodies can also be defined using other numbering systems, such as Chothia, enhanced Chothia, IMGT, Kabat/Chothia composite, Honegger (AHo), Contact, or any other conventional antibody numbering scheme.

The term "acceptor human framework" refers to a framework comprising the amino acid sequence of a $V_L$ framework, or a $V_H$ framework derived from a human immunoglobulin framework or a human consensus framework. An acceptor human framework "derived from" a human immunoglobulin framework or a human consensus framework may have the same amino acid sequence as the naturally occurring human immunoglobulin framework or human consensus framework, or it may have amino acid sequence changes compared to wild-type naturally occurring human immunoglobulin framework or human consensus framework. In some aspects, the number of amino acid changes are 10, 9, 8, 7, 6, 5, 4, 3, or 2, or 1. In some aspects, the $V_L$ acceptor human framework is identical in sequence to the $V_L$ human immunoglobulin framework sequence or human consensus framework sequence.

An "Fc region," "Fc domain," or "Fc" refers to the C-terminal region of the heavy chain of an antibody. Thus, an Fc region comprises the constant region of an antibody excluding the first constant region immunoglobulin domain (e.g., CH1 or CL).

An "effector function" refers to the interaction of an antibody Fc region with an Fc receptor or ligand, or a biochemical event that results therefrom. Exemplary "effector functions" include Clq binding, complement dependent cytotoxicity (CDC), Fc receptor binding, FcγR-mediated effector functions such as ADCC and antibody dependent cell-mediated phagocytosis (ADCP), and downregulation of a cell surface receptor (e.g., the B cell receptor; BCR). Such effector functions generally require the Fc region to be combined with a binding domain (e.g., an antibody variable domain).

The term "epitope" or "antigenic determinant" refers to a site on an antigen (e.g., human CEACAM5) to which an immunoglobulin or antibody specifically binds. Epitopes can be formed both from contiguous amino acids (usually a linear epitope) or noncontiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14, 15, 16, 17, 18, 19, 20, 21, or 22 amino acids in a unique spatial conformation.

The term "monoclonal antibody," as used herein, refers to an antibody that displays a single binding specificity and affinity for a particular epitope or a composition of antibodies in which all antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In one aspect, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell. Monoclonal antibodies include chimeric antibodies, human antibodies, and humanized antibodies and may occur naturally or be produced recombinantly.

The monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079, which are hereby incorporated by reference in their entireties). In one aspect, provided herein are single domain antibodies comprising two $V_H$ domains with modifications such that single domain antibodies are formed.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain aspects, however, such recombinant human antibodies can be subjected to in vitro mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

A "human" antibody refers to an antibody having variable regions in which both the framework and CDR regions are derived from human germline immunoglobulin sequences. Furthermore, if the antibody contains a constant region, the constant region also is derived from human germline immunoglobulin sequences. Also encompassed are antibodies derived from human germline immunoglobulin sequences that include normal somatic hypermutations which alter the germline immunoglobulin sequences relative to the wild-type germline immunoglobulin sequences.

A "humanized" antibody refers to an antibody in which some, most or all of the amino acids outside the CDR domains of a non-human antibody are replaced with corresponding amino acids derived from human immunoglobulins. In one aspect of a humanized form of an antibody, some, most or all of the amino acids outside the CDR domains have been replaced with amino acids from human immunoglobulins, whereas some, most or all amino acids within one or more CDR regions are unchanged. Any additions, deletions, insertions, substitutions or modifications of amino acids are permissible as long as they do not abrogate the ability of the antibody to bind to a particular antigen. A "humanized" antibody may retain an antigenic specificity similar to that of the original antibody.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody which comprises mouse immunoglobulin sequences only.

A "chimeric antibody" refers to an antibody in which the variable regions are derived from one or more species and the constant regions are derived from another species, such as an antibody in which the variable regions are derived from a mouse antibody and the constant regions are derived from a human antibody. See U.S. Pat. No. 4,816,567; and Morrison et al., (1984) *Proc. Natl. Acad. Sci. USA* 81: 6851-6855.

A "domain antibody" or "nanobody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992). Bifunctional antibodies include, for example, heterodimeric antibody conjugates (e.g., two antibodies or antibody fragments joined together with each having different specificities), antibody/cell surface-binding molecule conjugates (e.g., an antibody conjugated to a non-antibody molecule such as a receptor), and hybrid antibodies (e.g., an antibody having binding sites for two different antigens).

A "multispecific antibody" is an antibody (e.g., bispecific antibodies, tri-specific antibodies) that recognizes two or more different antigens or epitopes.

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker. For a review of scFvs, see Pluckthun (1994) The Pharmacology of Monoclonal Antibodies, vol. 113, Rosenburg and Moore eds. Springer-Verlag, New York, pp. 269-315.

As used herein, the term "diabodies" refer to small antibody fragments with two antigen-binding sites in which the fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

The term "immune cell engager" or "ICE" is used herein with reference to a multifunctional molecule comprising two or more binding specificities able to redirect immune effector cells against cancer cells. Exemplary immune cell engagers include T-cell engagers (e.g., bispecific T-cell engagers or BiTEs), NK-cell engagers (NKCEs), B-cell engagers, dendritic cell engagers, and macrophage cell engagers.

The terms "bispecific T cell engager" and "BiTE" are used herein interchangeably with reference to a bispecific molecule linking the targeting regions of two antibodies and/or protein binding domains, wherein one arm of the molecule is engineered to bind a protein (e.g., CD3) on the surface of a cytotoxic T cell (i.e., T cell engager), and the other arm is engineered to bind to a specific protein found primarily on tumor cells, such as CEACAM5. When both targets are engaged, the BiTE molecule forms a bridge between the cytotoxic T cell and the tumor cell, enabling the T cell to recognize and kill the tumor cell. The BiTE may or may not include immunoglobulin constant regions.

The terms "bispecific NK cell engager" and "NKCE" are used herein interchangeably with reference to a bispecific molecule comprising a CEACAM5 binding domain linked by a short flexible linker region to the binding domain of cell surface protein of an NK cell (i.e., NK cell engager).

The term "binds to the same epitope" is used with reference to two or more antibodies that bind to the same segment or same segments of amino acid residues. Techniques for determining whether antibodies bind to the same epitope may be determined by epitope mapping methods described herein. Other methods involve monitoring the binding of the antibody to antigen fragments (e.g., proteolytic fragments) or to mutated variations of the antigen where loss of binding due to a modification of an amino acid residue within the antigen sequence is often considered an indication of an epitope component, such as alanine scanning mutagenesis (Cunningham & Wells (1985) *Science* 244:1081), yeast display of mutant target sequence variants, or analysis of chimeras. In addition, computational combinatorial methods for epitope mapping can also be employed. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of another antibody to the target. Whether two antibodies compete with each other for binding to a target, i.e., whether and to what extent one antibody inhibits the binding of the other antibody to a target, may be determined using known binding competition experiments involving surface plasmon resonance (SPR) and bio-layer interferometry (BLI). In certain aspects, an antibody competes with, and inhibits binding of another antibody to a target by at least 50%, 60%, 70%, 80%, 90% or 100%. The level of inhibition or competition may be different depending on which antibody is the "blocking antibody" (i.e., the antibody that when combined with an antigen blocks another immunologic reaction with the antigen). Competition assays can be conducted as described, for example, in Ed Harlow and David Lane, Cold Spring Harb. Protoc. 2006; doi: 10.1101/pdb.prot4277 or in Chapter 11 of "Using Antibodies" by Ed Harlow and David Lane, Cold Spring Harbor Laboratory Press, Cold Spring Harbor, NY, USA 1999. Competing antibodies bind to the same epitope, an overlapping epitope, or to adjacent epitopes (e.g., as evidenced by steric hindrance). Two antibodies "cross-compete" if antibodies block each other both ways by at least 50%, i.e., regardless of whether one or the other antibody is contacted first with the antigen in the competition experiment.

Competitive binding assays for determining whether two antibodies compete or cross-compete for binding include competition for binding to cells expressing CEACAM5, e.g., by flow cytometry. Other methods include surface plasmon resonance (SPR) (e.g., BIACORE®), solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., Virology 176:546 (1990)); and direct labeled RIA. (Moldenhauer et al., *Scand. J. Immunol.* 32:77 (1990)).

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) using a predetermined antigen as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Any $K_D$ greater than about $10^{-4}$ M is generally considered to indicate nonspecific binding.

The term "$k_{assoc}$" or "$k_a$," as used herein, refers to the association rate of a particular antibody-antigen interaction, whereas the term "$k_{dis}$" or "$k_d$," as used herein, refers to the dissociation rate of a particular antibody-antigen interaction. The term "$K_D$," as used herein, is intended to refer to the dissociation constant, which is obtained from the ratio of $k_d$ to $k_a$ (i.e. $k_d/k_a$) and is expressed as a molar concentration (M). $K_D$ values for antibodies can be determined using methods well established in the art. A preferred method for determining the $K_D$ of an antibody is by using surface plasmon resonance, for example, using a biosensor system such as a BIACORE® system or flow cytometry and Scatchard analysis, or bio-layer interferometry.

The term "EC50" or "IC50" in the context of an in vitro or in vivo assay using an antibody or immunoconjugate refers to the concentration of an antibody that induces a response that is 50% of the maximal response, i.e., halfway between the maximal response and the baseline. In pharmacology, the potency of a compound is expressed as the half-maximal effective concentration (EC50), which refers to the concentration of a drug that induces a response halfway between the baseline and maximum. While expressing the potency of a compound by its EC50 value makes sense in a clinical context, it is counterintuitive in the context of bioactivity-guided purification, as the potency of a compound is inversely related to its EC50 value, and the most potent compound is the one with the lowest EC50. Half-maximal inhibitory concentration (IC50) is the most widely used and informative measure of a drug's efficacy. It indicates how much drug is needed to inhibit a biological process by half, thus providing a measure of potency of an antagonist drug in pharmacological research.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, the term "conjugate" is used with reference to an immunoconjugate or antibody drug conjugate comprising an anti-CEACAM5 antibody or antigen binding portion thereof described herein linked to a cytotoxic or therapeutic drug described herein.

The term "linker," as used herein, refers to a chemical moiety comprising a covalent bond and/or any chain of atoms that may be used to covalently attach e.g., a drug to the antibody. Linkers are known in the art and include e.g., disulfide groups, thioether groups, acid labile groups, photolabile groups, peptidase labile groups and esterase labile groups. Conjugation of an antibody of the present disclosure with cytotoxic drugs or other growth inhibitory agents may be performed e.g. using a variety of bifunctional protein coupling agents including but not limited to N-succinimidyl pyridyldithiobutyrate (SPDB), butanoic acid 4-[(5-nitro-2-pyridinyl)dithio]-2,5-dioxo-1-pyrrolidinyl ester (nitro-SPDB), 4-(Pyridin-2-yldisulfanyl)-2-sulfo-butyric acid (sulfo-SPDB), N-succinimidyl (2-pyridyldithio) propionate (SPDP), succinimidyl (N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl)-hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987). Carbon labeled 1-isothiocyanatobenzyl methyldiethylene triaminepentaacetic acid (MX-DTPA) is an exemplary chelating agent for conjugation of radionucleotide to an antibody (WO 94/11026).

In certain aspects, the linker is a "cleavable linker," which may facilitate release of the cytotoxic drug or other growth inhibitory agent inside of or in the vicinity of a cell, e.g., a tumor cell. In some aspects, the linker is a linker cleavable in an endosome of a mammalian cell. For example, an acid-labile linker, a peptidase-sensitive linker, an esterase labile linker, a photolabile linker or a disulfide-containing linker (see e.g., U.S. Pat. No. 5,208,020) may be used.

The term "nucleic acid molecule," as used herein, is used with reference to DNA molecules and RNA molecules. A nucleic acid molecule may be single-stranded or double-stranded, and may be a cDNA.

The term "isolated nucleic acid molecule," as used herein in reference to nucleic acids encoding antibodies or antibody fragments (e.g., $V_H$, $V_L$, CDR3), is intended to refer to a nucleic acid molecule in which the nucleotide sequences are essentially free of other genomic nucleotide sequences, e.g., those encoding antibodies that bind antigens other than CEACAM5, which other sequences may naturally flank the nucleic acid in human genomic DNA.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

Also provided are "conservative sequence modifications" of the sequences set forth herein, e.g., amino acid sequence modifications which do not abrogate the binding of the antibody encoded by the nucleotide sequence or containing the amino acid sequence, to the antigen. Such conservative sequence modifications include conservative nucleotide and amino acid substitutions, as well as nucleotide and amino acid additions and deletions. For example, modifications can be introduced into a sequence by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-CEACAM5 antibody can be replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10): 879-884 (1999); and Burks et al. *Proc. Natl. Acad. Sci. USA* 94:412-417 (1997)). Alternatively, in another aspect, mutations can be introduced randomly along all or part of an anti-CEACAM5 antibody coding sequence, such as by saturation mutagenesis, and the resulting modified anti-CEACAM5 antibodies can be screened for binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 80% to 85%, 85% to 90% or 90% to 95%, and at least about 98% to 99.5% of the nucleotides. Alternatively, substantial homology exists when the segments will hybridize under selective hybridization conditions, to the complement of the strand. For polypeptides, the term "substantial homology"

indicates that two polypeptides, or designated sequences thereof, when optimally aligned and compared, are identical, with appropriate amino acid insertions or deletions, in at least about 80% of the amino acids, usually at least about 80% to 85%, 85% to 90%, 90% to 95%, and at least about 98% to 99.5% of the amino acids.

The percent identity between two sequences is a function of the number of identical positions shared by the sequences (i.e., % homology=# of identical positions/total # of positions×100), considering the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or two amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

The term "recombinant host cell" (or simply "host cell"), as used herein, is intended to refer to a cell that comprises a nucleic acid that is not naturally present in the cell and may be a cell into which a recombinant expression vector has been introduced. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein.

The term "inhibition," as used herein, refers to any statistically significant decrease in biological activity, including partial and full blocking of the activity. For example, "inhibition" can refer to a statistically significant decrease of about 10%, 20%, 30%, 40%, 50%, 60%, 70%, 80%, 90%, 95%, 96%, 97%, 98%, 99%, or 100% in biological activity.

The term "immunotherapy" as used herein, refers to the treatment of a subject afflicted with, or at risk of contracting or suffering a recurrence of, a disease by a method comprising inducing, enhancing, suppressing or otherwise modifying an immune response.

The terms "immunostimulating therapy" and "immunostimulatory therapy," as used herein, refer to a therapy that results in an increase (e.g., inducing or enhancing) an immune response in a subject for, e.g., treating cancer.

As used herein, "immune cell" refers to the subset of blood cells known as white blood cells, which include mononuclear cells such as lymphocytes, monocytes, macrophages, and granulocytes.

As used herein, "abnormal" is used in the context of the activity or level or expression of a molecule which is outside of the normal activity or expression level (e.g., overexpressed) as compared to e.g., a control sample or reference sample exhibiting a normal activity/expression profile. The term "normal" is used herein in the context of the activity or level of expression of a protein found in a population of healthy, gender- and age-matched subjects. The minimal size of this healthy population may be determined using standard statistical measures, e.g., the practitioner could consider the incidence of the disease in the general population and the level of statistical certainty desired in the results. In some aspects, the normal range for activity, level or expression of a biomarker is determined from a population of subjects (e.g., at least five, ten or twenty subjects), for example from a population of at least forty or eighty subjects, and from more than 100 subjects.

"T effector" ("$T_{eff}$") cells refer to T cells (e.g., CD4+ and CD8+ T cells) with cytolytic activities as well as T helper (Th) cells, which secrete inflammatory cytokines and activate and direct other immune cells but does not include regulatory T cells (Treg cells).

As used herein, "administering" refers to the physical introduction of a CEACAM5 targeting agent, such as an ADC (comprising an anti-CEACAM5 antibody or antigen binding portion thereof described herein linked to a cytotoxic moiety described herein via a linker alone or in combination with another therapeutic agent) to a subject, using any of the various methods and delivery systems known to those skilled in the art. Preferred routes of administration for ADCs described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intra-lymphatic, intralesional, intracapsular, intra-orbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, "cancer" refers to a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream, and includes a variety of cancers, including but not limited to e.g., carcinomas, melanomas, sarcomas, leukemias, lymphomas, germ cell tumors, and blastomas. Exemplary cancers for treatment include cancers of the brain, bladder, breast, cervix, colon, head and neck, kidney, lung, non-small cell lung, mesothelioma, ovary, prostate, stomach and uterus, leukemia, and medulloblastoma.

As used herein, the term "small molecule drug" refers to a molecular entity, often organic or organometallic, that is not a polymer, that has medicinal activity, and that has a molecular weight less than about 2 kilodaltons (kDa), less than about 1 kDa, less than about 900 daltons (Da), less than about 800 Da or less than about 700 Da. The term encompasses most medicinal compounds termed "drugs" other than protein or nucleic acids, although a small peptide or nucleic acid analog can be considered a small molecule drug. Examples include chemotherapeutic anticancer drugs and enzymatic inhibitors. Small molecule drugs can be derived synthetically, semi-synthetically (i.e., from naturally occurring precursors), or biologically.

The terms "treat," "treating," and "treatment," as used herein, refer to any type of intervention or process performed on, or administering an active agent (e.g., ADC comprising an anti-CEACAM5 antibody or antigen binding portion thereof described herein linked to a cytotoxic moiety via a linker as described herein) to, the subject with the objective of preventing, reversing, alleviating, ameliorating, inhibiting, or slowing down or preventing the progression, development, severity or recurrence of a symptom, complication, condition or biochemical indicia associated with a disease. Treatment can be of a subject having a disease or a subject who does not have a disease (e.g., for prophylaxis).

As used herein, "adjunctive" or "combined" administration (co-administration) includes simultaneous administration of an ADC (comprising an anti-CEACAM5 antibody or antigen binding portion thereof described herein linked to a cytotoxic moiety described herein via a linker) and one or more additional agents and/or compounds in the same or different dosage form, or combined administration in separate dosages concurrently or sequentially. Thus, an ADC (comprising an anti-CEACAM5 antibody or antigen binding portion thereof described herein linked to a cytotoxic moiety described herein via a linker), and second, third, or more agents and/or compounds (e.g., small molecules) can be simultaneously administered in a single formulation or formulated for separate administration and are administered concurrently or sequentially.

"Combination" therapy, as used herein, means administration of two or more therapeutic agents in a coordinated fashion, and includes, but is not limited to, concurrent and sequential dosing. Specifically, combination therapy encompasses both co-administration (e.g., administration of a co-formulation or simultaneous administration of separate therapeutic compositions) and serial or sequential administration, provided that administration of one therapeutic agent is conditioned in some way on administration of another therapeutic agent. For example, one therapeutic agent may be administered only after a different therapeutic agent has been administered and allowed to act for a prescribed period of time. (See, e.g., Kohrt et al. (2011) *Blood* 117:2423). For example, the ADC (comprising an anti-CEACAM5 antibody linked to a cytotoxic moiety described herein via a linker) can be administered first followed by (e.g., immediately followed by) the administration of a second agent (e.g., an antibody or antigen binding portion thereof, and anti-cancer agent), or vice versa. In one aspect, the ADC is administered prior to administration of the second agent. In another aspect, the ADC is administered, for example, a few minutes (e.g., within about 30 minutes) or at least one hour of the second agent. Such concurrent or sequential administration can result in both the ADC and the second agent being simultaneously present in treated patients.

The administration of effective amounts of the ADC (comprising an anti-CEACAM5 antibody or antigen binding portion thereof described herein linked to a cytotoxic moiety described herein via a linker) alone, or the ADC combined with another compound or agent (e.g., an immune checkpoint inhibitor such as an anti-PD-1 antibody), according to any of the methods provided herein, can result in at least one therapeutic effect, including, for example, reduced tumor growth or size, reduced number of indicia of cancer (e.g., metastatic lesions) appearing over time, complete remission, partial remission, or stable disease. For example, the methods of treatment may produce a comparable clinical benefit rate (CBR=complete remission (CR)+ partial remission (PR)+stable disease (SD) lasting ≥6 months) better than that achieved without administration of the ADC, or than that achieved with administration of any one of the ADC and the second agent, e.g., the improvement of clinical benefit rate is about 20% 20%, 30%, 40%, 50%, 60%, 70%, 80% or more.

As used herein, the terms "inhibit" and "block" (e.g., with regard to inhibition/blocking of CEACAM5 binding or functional activity) are used interchangeably and encompass both partial and complete inhibition/blocking by the anti-CEACAM5 antibody or fragment thereof in the ADC, or other inhibition/blocking of a functional activity by a therapeutic agent. The degree of inhibition may be at least 20%, 30%, 40%, 50%, 60%, 70%, 80%, 90%, 95%, or 100% (i.e., 2-fold or 2×), 3-fold, 5-fold or 10-fold relative to a control antibody or reference antibody. Additionally, the degree of inhibition may be between 20%-95%, 20%-80%, 20%-50%, 40%-95%, 40%-80%, 40%-60%, 50%-90%, 50%-70%, 75%-95%, 75%-85%, 2-fold to 20-fold, 2-fold to 10-fold, 2-fold to 5-fold, 4-fold to 12-fold, or 4-fold to 8-fold.

The term "effective dose" or "effective dosage" is defined as an amount sufficient to achieve or at least partially achieve a desired effect. A "therapeutically effective amount" or "therapeutically effective dosage" of a drug (e.g., ADC (comprising anti-CEACAM5 antibody or antigen binding portion thereof described herein linked to a cytotoxic moiety described herein via a linker)) is any amount of the drug or therapeutic agent that, when used alone or in combination with another therapeutic agent, promotes disease regression evidenced by a decrease in severity of disease symptoms, an increase or therapeutic agent in frequency and duration of disease symptom-free periods, or a prevention of impairment or disability due to the disease affliction. A therapeutically effective amount or dosage of a drug or therapeutic agent includes a "prophylactically effective amount" or a "prophylactically effective dosage," which is any amount of the drug or therapeutic agent that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example, for the treatment of tumors, a therapeutically effective amount or dosage of the drug or therapeutic agent (e.g., ADC (comprising anti-CEACAM5 antibody or antigen binding portion thereof described herein linked to a cytotoxic moiety described herein via a linker) inhibits tumor cell growth by at least about 20%, by at least about 30% by at least about 40%, by at least about 50%, by at least about 60%, by at least above 70%, by at least about 80%, or by at least about 90% relative to untreated subjects. In some aspects, a therapeutically effective amount or dosage of the drug or therapeutic agent completely inhibits cell growth or tumor growth, i.e., inhibits cell growth or tumor growth by 100%. The ability of a compound or therapeutic agent, including an antibody, to inhibit tumor growth can be evaluated using the assays described herein. Alternatively, this property of a composition comprising the compound or therapeutic agent can be evaluated by examining the ability of the composition to inhibit cell growth; such inhibition can be measured in vitro by assays known to the skilled practitioner.

The term "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, cats, dogs, cows, chickens, amphibians, and reptiles.

The term "sample" refers to tissue, bodily fluid, or a cell (or a fraction of any of the foregoing) taken from a patient or a subject. Normally, the tissue or cell will be removed from the patient, but in vivo diagnosis is also contemplated. In the case of a solid tumor, a tissue sample can be taken from a surgically removed tumor and prepared for testing. In the case of lymphomas and leukemias, lymphocytes, leukemic cells, or lymph tissues can be obtained (e.g., leukemic cells from blood) and appropriately prepared. Other samples, including e.g., urine, tears, serum, plasma, cerebrospinal fluid, feces, sputum, and cell extracts can also be useful for particular cancers.

The terms "detection" or "detected", as used herein refer to qualitative and/or quantitative detection (measuring levels) with or without reference to a control.

The term "diagnosing", as used herein, means the determination of the nature of a medical condition intended to identify a pathology which affects the subject from a number of collected data.

As used herein, "comprising" is synonymous with "including," "containing," "having" or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising," "consisting essentially of," and "consisting of" may be optionally replaced with either of the other two terms, thus describing alternative aspects of the scope of the subject matter. The invention illustratively described herein suitably may be practiced in the absence of any element or elements, limitation or limitations which is not specifically disclosed herein.

As used herein, the singular forms "a," "an," and "the" include plural referents unless the context clearly dictates otherwise. The use of "or" or "and" means "and/or" unless stated otherwise. Furthermore, use of the term "including" as well as other forms, such as "include," "includes," and "included," is not limiting.

The term "about" as used herein when referring to a measurable value such as an amount, a temporal duration and the like, encompasses variations of up to ±10% from the specified value. Unless otherwise indicated, all numbers expressing e.g., quantities of ingredients or properties (e.g., molecular weight, reaction conditions) described herein are to be understood as being modified by the term "about."

As used herein, "and/or" is to be taken as specific disclosure of each of the two specified features or components with or without the other. Thus, the term "and/or" as used in a phrase such as "A and/or B" includes "A and B," "A or B," "A" alone, and "B" alone. Likewise, the term "and/or" as used in a phrase such as "A, B, and/or C" encompasses each of the following: A, B, and C; A, B, or C; A or C; A or B; B or C; A and C; A and B; B and C; A alone; B alone; and C alone.

As used herein, recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3% are expressly enumerated in this specification. These are only examples of what is specifically intended, and all possible combinations of numerical values between and including the lowest value and the highest value enumerated are to be considered to be expressly stated in this disclosure.

As used herein, the term "stereoisomer" refers to isomers of identical constitution that differ in the arrangement of their atoms in space. Enantiomers and diastereomers are examples of stereoisomers. Geometric isomers are also examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity. Geometric isomers of C=C double bonds can also be present in the ADCs, and all such stable isomers are contemplated in the present invention. Cis- and trans-(or E- and Z-) geometric isomers of the ADCs of the present invention are described and may be isolated as a mixture of isomers or as separated isomeric forms.

The term "ADC 101" refers to a compound having the formula:

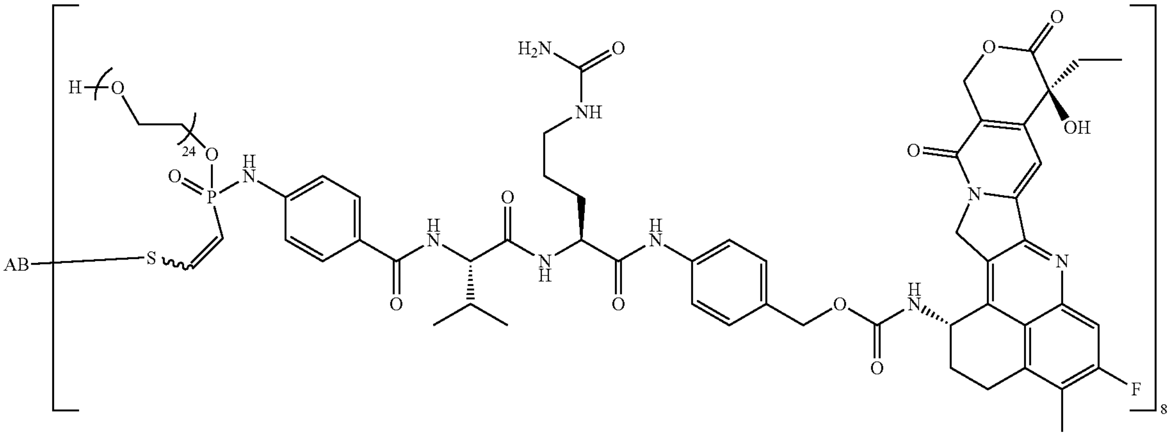

AB is an anti-CEACAM5 antibody or an antigen binding portion thereof described herein; wherein o is an integer of 24, which is also understood to be identical to the compound having the formula:

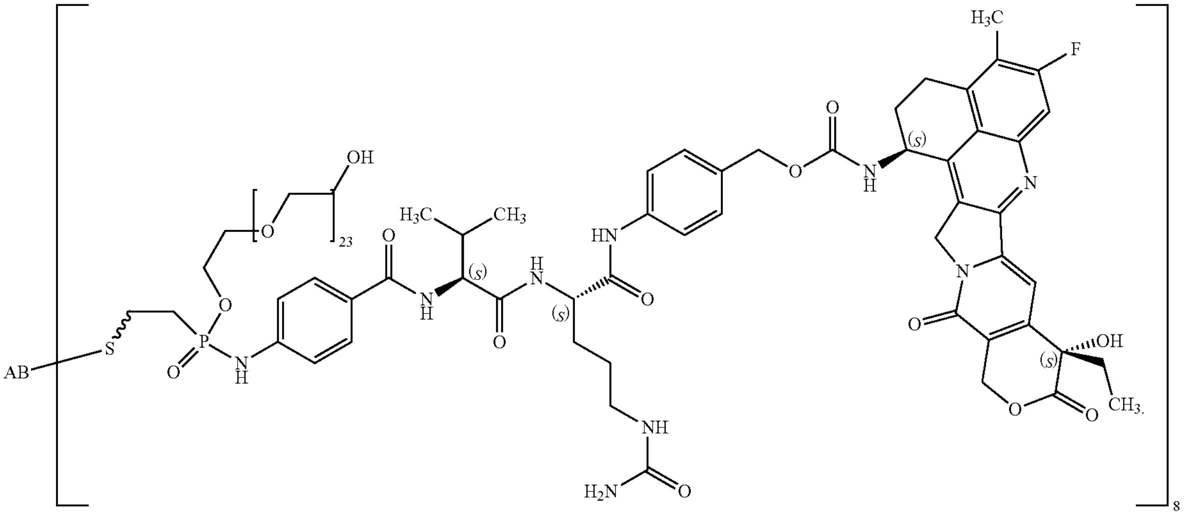

As the two structures are presumed to be identical, the two representations are interchangeable. Either structure can be used to represent the same structure.

In some aspects, the anti-CEACAM5 antibody or antigen binding portion thereof is described in Table 10 and Table 11. In some aspects, the CDRs, VH, VL, heavy chain and/or light chain is described in Table 10 and Table 11.

Various aspects described herein are described in further detail in the following subsections.

I. Antibody Drug Conjugates

The present disclosure provides an antibody drug conjugate comprising an anti-CEACAM5 antibody or antigen binding portion thereof described herein which is linked or conjugated via a phosphorus (V) moiety (also denoted as "P5") and a linker to a cytotoxic moiety, i.e., camptothecin or derivatives and analogs thereof.

In some aspects, the ADC of the present disclosure has the formula (I):

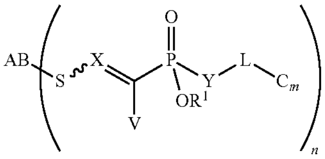

(I)

or a pharmaceutically acceptable salt, a stereoisomer, or a solvate thereof, wherein:

∿∿ indicates that the configuration of the double bond is E or Z;

V is H or $(C_1-C_8)$alkyl;

X is $R^3$—C;

Y is $NR^5$, S, O, or $CR^6R^7$;

$R^1$ is a polyalkylene glycol unit comprising at least 3 alkylene glycol subunits;

$R^3$ and $R^5$-$R^7$ are each H, or an optionally substituted aliphatic or aromatic residue;

L is a linker;

C is a cytotoxic moiety;

m is an integer ranging from 1 to 10;

n ranges from 1 to 20; and

AB is an anti-CEACAM5 antibody or an antigen-binding portion thereof comprising (a) a heavy chain variable region (VH) comprising complementarity determining region (CDR)1, CDR2, and CDR3 regions comprising the amino acid sequences set forth in SEQ ID NOs: 14, 15, and 16, respectively, and a light chain variable region (VL) comprising CDR1, CDR2, and CDR3 regions comprising the amino acid sequences set forth in SEQ ID NOs: 19, 20, and 21, or;

(b) a VH comprising CDR1, CDR2, and CDR3 regions which have at least 80%, 85%, 90%, 95%, 98%, or 99% sequence identity to the amino acid sequences set forth in SEQ ID NOs: 14, 15, and 16, respectively, and a VL comprising CDR1, CDR2, and CDR3 regions which have at least 85%, 90%, 95%, 98%, or 99% sequence identity to the amino acid sequences set forth in SEQ ID NOs: 19, 20, and 21, respectively.

In some aspects, $R^3$ is H or an optionally substituted aliphatic or aromatic residue. In some aspects, $R^3$ is H or $(C_1$-$C_8)$alkyl. In some aspects, $R^3$ is H.

In some aspects, $R^1$ comprises 3 to 100 subunits having the structure:

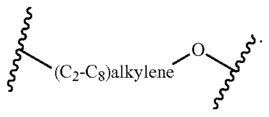

In some aspects, $R^1$ is

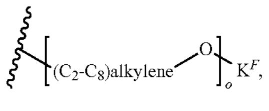

wherein:  indicates the position of the O; $K^F$ is selected from the group consisting of —H, —$PO_3H$, —$(C_1$-$C_{10})$alkyl, —$(C_1$-$C_{10})$alkyl-$SO_3H$, —$(C_2$-$C_{10})$alkyl-$CO_2H$, —$(C_2$-$C_{10})$alkyl-OH, —$(C_2$-$C_{10})$alkyl-$NH_2$, —$(C_2$-$C_{10})$alkyl-NH$(C_1$-$C_3)$alkyl and —$(C_2$-$C_{10})$alkyl-N($(C_1$-$C_3)$ alkyl$)_2$; and o is an integer ranging from 3 to 100.

In some aspects, $R^1$ comprises 3 to 50 subunits having the structure:

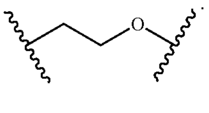 [SMILES: "." ; *CCO*]

In some aspects, $R^1$ is:

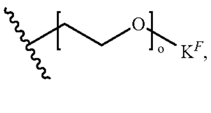

wherein  indicates the position of the O; $K^F$ is selected from the group consisting of —H, —$(C_1$-$C_{10})$alkyl, and —$(C_2$-$C_{10})$alkyl-OH; and o is an integer ranging from 3 to 50.

In some aspects, $K^F$ is H.

In some aspects, o is an integer ranging from 8 to 30, e.g., from 8 to 16, from 10 to 30, or from 20 to 28, e.g., 10, 11, 12, 13 14, 22, 23, 24, 25 or 26.

In some aspects, the linker L is cleavable.

In some aspects, the linker L is cleavable by a protease, a glucuronidase, a sulfatase, a phosphatase, an esterase, or by disulfide reduction.

In some aspects, the linker is cleaved under physiological conditions, in particular inside a cell by e.g., a lysosomal or endosomal protease to release the attached cytotoxic moiety. In some aspects, the cleavable linkers are designed to release the free cytotoxic moiety in an unmodified form. Cleavable linkers include, e.g., disulfide linkers, acid labile linkers, photolabile linkers, peptidase labile linkers, and esterase labile linkers. Typically, a peptidyl linker is at least two amino acids long or at least three amino acids long.

Peptidase labile linkers can be used to cleave certain peptides inside or outside cells. In one aspect, the cleavable linker is cleaved under mild conditions, i.e., conditions within a cell under which the activity of the cytotoxic moiety is not affected.

Depending on the linker design, membrane permeable (lipophilic) toxins that are released inside target positive cells can pass the cell membrane and kill other cells that are in close proximity, including neighboring cancer cells that lack antigen expression (bystander effect) (Kovtun, Y. V. et al. (2006) Cancer Res. 66 (6), 3214-3221). The ability of such cytotoxic drugs to mediate local bystander killing is one selection criterium for the ADCs according to the present disclosure.

Cleaving agents can include e.g., cathepsins B and D and plasmin, all of which are known to hydrolyze dipeptide drug derivatives resulting in the release of active drug inside target cells. For example, a peptidyl linker that is cleavable by the thiol-dependent protease cathepsin-B, which is highly expressed in cancerous tissue, can be used (e.g., a Phe-Leu or a Gly-Phe-Leu-Gly (SEQ ID NO: 101) linker). In specific aspects, the peptidyl linker cleavable by an intracellular protease is a valine-citrulline (Val-Cit) linker or a phenylalanine-lysine (Phe-Lys) linker. One advantage of using intracellular proteolytic release of the therapeutic agent is that the agent is typically attenuated when conjugated and the serum stabilities of the conjugates are typically high.

A variety of linkers may be used in the conjugates described herein. In some aspects, the linker comprises a peptidyl linker, such as dipeptide valine (Val)-citrulline (Cit) (vc), which can be cleaved by cathepsin inside tumor cells. Additional peptidyl linkers include, but are not limited to Val-Cit, Ala-Val, Val-Ala-Val, Lys-Lys, Pro-Val-Gly-Val-Val (SEQ ID NO: 99), Ala-Asn-Val, Val-Leu-Lys, Ala-Ala-Asn, Cit-Cit, Val-Lys, Lys, Cit, Ser, or Glu. In some aspects, the linker L is cleavable by a protease, for example cathepsins B and D.

In some aspects, the linker L has the formula:

$$*\text{-A-W}_{1\text{-}8}\text{-B}_{0\text{-}1}\text{-}\#,$$

wherein unit A is a first spacer unit; W is an amino acid; B is a second spacer unit, * denotes the attachment point to the —Y— and # denotes the attachment point to the cytotoxic moiety.

In some aspects, the first spacer unit A has the structure:

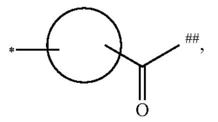

wherein

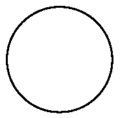

is a 5- or 6-membered carbocycle; * denotes the attachment point to the —Y— and ## denotes the attachment point to W. A preferred unit A is

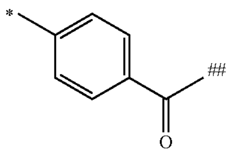

In some aspects, W is a dipeptide ($W_2$).

In some aspects, the dipeptide is selected from the group consisting of valine-citrulline (Val-Cit) and valine-alanine (Val-Ala).

In some aspects, the second spacer unit B is a PAB group having the following structure:

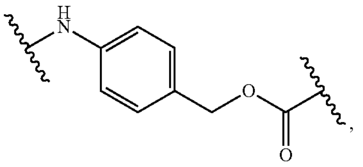 [SMILES: *Nc1ccc(COC(*)=O)cc1 ; ","]

wherein the NH group is bonded to —W— and the C(O) group is bonded to the cytotoxic moiety.

In some aspects, the linker has the following structure:

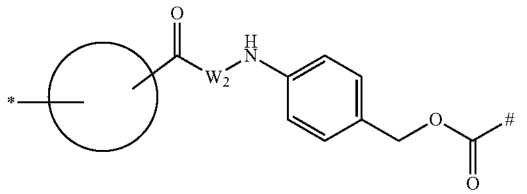

wherein $W_2$ is a dipeptide,

* indicates the attachment point to the Y, and # indicates the attachment point to the cyctotoxic moiety.

In some aspects, the linker L is *-A-$W_2$—$B_1$-#, having the structure:

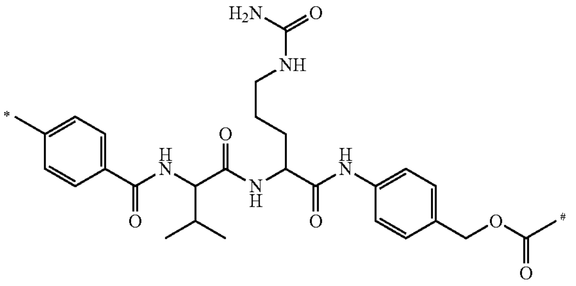

wherein * indicates the attachment point to the Y and # indicates the attachment point to the cytotoxic moiety.

In some aspects, C is a cytotoxic moiety. The term "cytotoxic moiety" or sometimes "payload," refer to a chemical or biochemical moiety that is conjugated to the anti-CEACAM5 antibody described herein via a linker.

In some aspects, the cytotoxic moiety is an anti-cancer agent. Accordingly, the drug may be selected from the group consisting of maytansinoids, calicheamycins, tubulysins, amatoxins, dolastatins and auristatins such as monomethyl auristatin E (MMAE) or monomethyl auristatin F (MMAF), pyrrolobenzodiazepine dimers, indolino-benzodiazepine dimers, emetine, radioisotopes, therapeutic proteins and peptides, (or fragments thereof), kinase inhibitors, CDK inhibitors, histone deacetylase (HDAC) inhibitors, MEK inhibitors, KSP inhibitors, topoisomerase inhibitors, and analogues or prodrugs thereof. In preferred embodiments, the cytotoxic moiety is topoisomerase I inhibitor. In some aspects, the cytotoxic moiety is topoisomerase I inhibitor produced by nature, camptothecin or a derivative or analog thereof. In some aspects, the cytotoxic moiety is a camptothecin derivative, e.g., exatecan. The structure of exatecan is shown below.

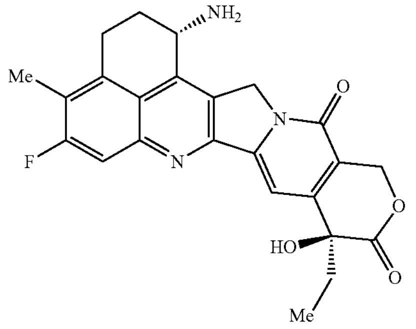 [SMILES: CC[C@@]1(O)C(=O)OCc2c1cc1n(c2=O)Cc2c-1nc1cc(F)c(C)c3c1c2[C@@H](N)CC3]

All stereoisomers of the exatecan are contemplated for the ADCs disclosed herein.

In some aspects, the n in the ADC of the formula (I) is 7 or 8. In some aspects, the n in the ADC is 5 or 6. In some aspects, the n in the ADC is 9 or 10. In some aspects, the n in the ADC is 7. In some aspects, the n in the ADC is 8.

In some aspects, in formula (I), AB is an anti-CEACAM5 antibody or an antigen-binding portion thereof discloses herein; V is H; Y is NH; $R^3$ is H; n ranges from 4-8; $R^1$ is a polyalkylene glycol unit having the structure:

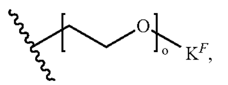

wherein: indicates the position of the O;

$K^F$ is H; and o is an integer ranging from 8 to 30;

L is a linker having the following structure:

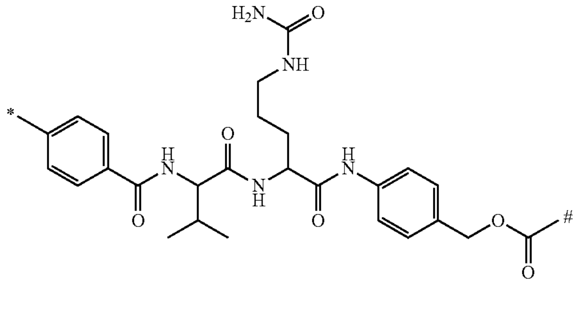

wherein * indicates the attachment point to the Y and # indicates the attachment point to the cytotoxic moiety; C is exatecan; and m is 1.

In some aspects, o is an integer ranging from 8 to 30, from 10 to 30, from 15 to 30, from 20 to 30, or from 20 to 25. In some aspects, o is 20, 21, 22, 23, 24, or 25.

In some aspects, n is an integer ranging from 2 to 10. In some aspects, o is an integer ranging from 20 to 28. In some aspects, o is 22, 23, 24, 25, or 26.

In some aspects, n is an integer ranging from 2 to 10.

In some aspects, the anti-CEACAM5 antibody or antigen binding portion thereof is described in Table 10 and Table 11. In some aspects, the CDRs, VH, VL, heavy chain and/or light chain is described in Table 10 and Table 11.

In some aspects, the ADC of the present disclosure has the formula (II):

(II)

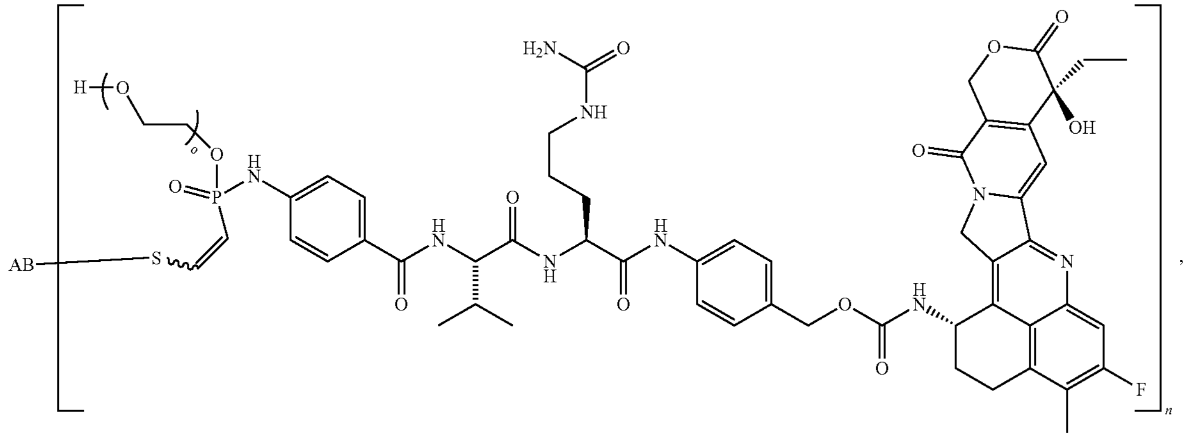

(II), or a pharmaceutically acceptable salt, a stereoisomer, or a solvate thereof, wherein o is an integer from 8 to 30;

n ranges from 4 to 8; and

AB is an anti-CEACAM5 antibody or antigen binding portion thereof disclosed herein (e.g., Table 10 and Table 11); and indicates that the configuration of the double bond is E or Z. It is also possible that the linker is present as a mixture of the E and Z isomers.

In some aspects, the ADC of the present disclosure has the formula (II):

(II)

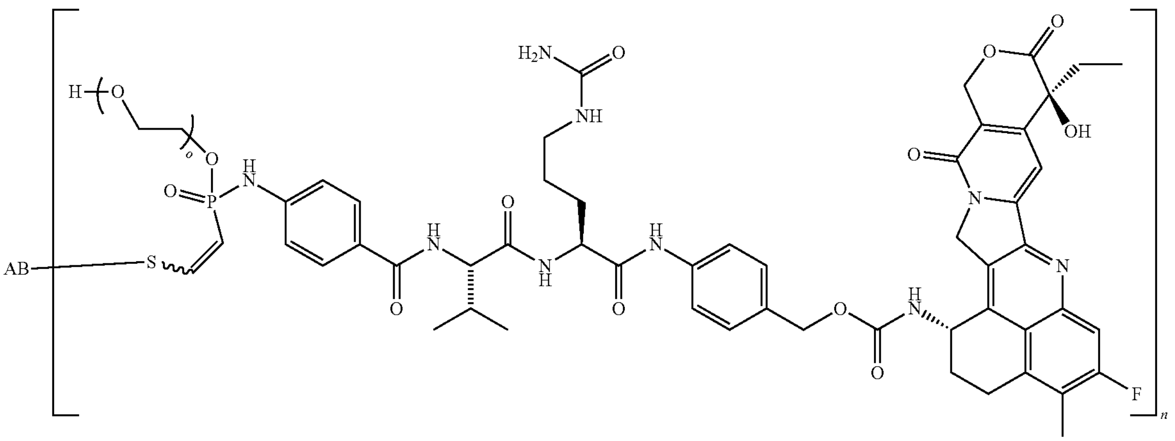

or a pharmaceutically acceptable salt, a stereoisomer or a solvate thereof, wherein:

∿∿ indicates that the configuration of the double bond is E or Z;

n ranges from 4 to 8; and have at least 85%, 90%, 95%, 98%, or 99% sequence identity to the amino acid sequences set forth in SEQ ID NOs: 19, 20, and 21, respectively.

In some aspects, the ADC of the present disclosure has the formula (ADC 101):

(ADC 101)

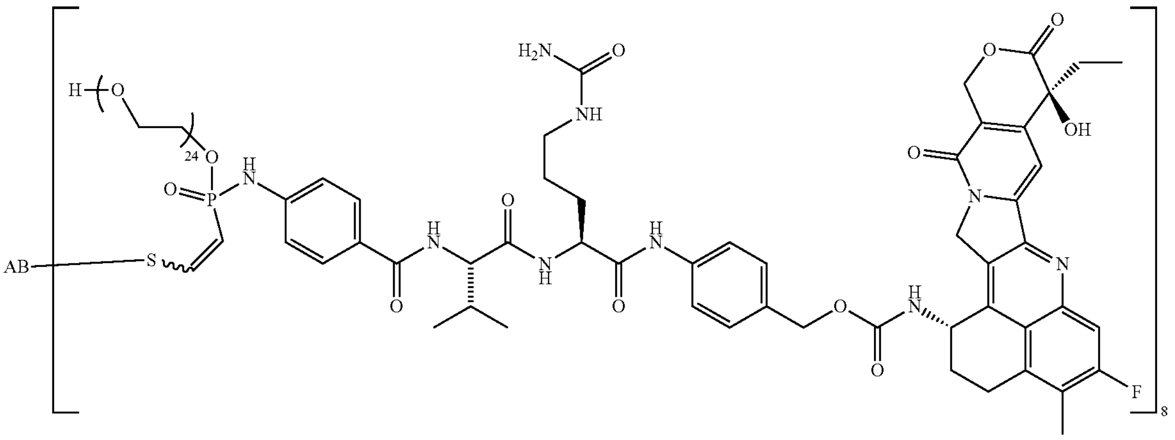

o is an integer from 8 to 30;

AB is an anti-CEACAM5 antibody or an antigen binding portion of an anti-CEACAM5 antibody, which specifically binds to a carcinoembryonic antigen-related cell adhesion molecule-5 (CEACAM5), comprising:

(a) a heavy chain variable region (VH) comprising complementarity determining region (CDR)1, CDR2, and CDR3 regions comprising the amino acid sequences set forth in SEQ ID NOs: 14, 15, and 16, respectively, and a light chain variable region (VL) comprising CDR1, CDR2, and CDR3 regions comprising the amino acid sequences set forth in SEQ ID NOs: 19, 20, and 21, or;

(b) a VH comprising CDR1, CDR2, and CDR3 regions which have at least 80%, 85%, 90%, 95%, 98%, or 99% sequence identity to the amino acid sequences set forth in SEQ ID NOs: 14, 15, and 16, respectively, and a VL comprising CDR1, CDR2, and CDR3 regions which or a pharmaceutically acceptable salt, a stereoisomer or a solvate thereof, wherein:

∿∿ indicates that the configuration of the double bond is E or Z;

AB is an anti-CEACAM5 antibody or an antigen binding portion of an anti-CEACAM5 antibody, which specifically binds to a carcinoembryonic antigen-related cell adhesion molecule-5 (CEACAM5), comprising:

(a) a heavy chain variable region (VH) comprising complementarity determining region (CDR)1, CDR2, and CDR3 regions comprising the amino acid sequences set forth in SEQ ID NOs: 14, 15, and 16, respectively, and a light chain variable region (VL) comprising CDR1, CDR2, and CDR3 regions comprising the amino acid sequences set forth in SEQ ID NOs: 19, 20, and 21, or;

(b) a VH comprising CDR1, CDR2, and CDR3 regions which have at least 80%, 85%, 90%, 95%, 98%, or 99% sequence identity to the amino acid sequences set forth in SEQ ID NOs: 14, 15, and 16, respectively, and a VL comprising CDR1, CDR2, and CDR3 regions which have at least 85%, 90%, 95%, 98%, or 99% sequence identity to the amino acid sequences set forth in SEQ ID NOs: 19, 20, and 21, respectively.

In certain embodiments, AB is an anti-CEACAM5 antibody or antigen binding portion thereof described in Table 10 and Table 11. In certain embodiments, AB is an anti-CEACAM5 antibody or antigen binding portion thereof that comprises:

(a) a heavy chain variable region (VH) comprising complementarity determining region (CDR)1, CDR2, and CDR3 regions comprising the amino acid sequences set forth in SEQ ID Nos: 14, 15, and 16, respectively, and a light chain variable region (VL) comprising CDR1, CDR2, and CDR3 regions comprising the amino acid sequences set forth in SEQ ID Nos: 19, 20, and 21, or (b) a VH comprising CDR1, CDR2, and CDR3 regions which have at least 80%, 85%, 90%, 95%, 98%, or 99% sequence identity to the amino acid sequences set forth in SEQ ID Nos: 14, 15, and 16, respectively, and a VL comprising CDR1, CDR2, and CDR3 regions which have at least 85%, 90%, 95%, 98%, or 99% sequence identity to the amino acid sequences set forth in SEQ ID Nos: 19, 20, and 21, respectively.

is 14. In some aspects, o is 15. In some aspects o is 16. In some aspects o is 17. In some aspects, o is 18. In some aspects, o is 19.

In some aspects, n is 1, 2, 3, 4, 5, 6, 7, 8, 9, or 10. In some aspects, n is 4. In some aspects, n is 5. In some aspects, n is 6. In some aspects, n is 7. In some aspects, n is 8. Preferably, o is 24 and n is 8.

The present disclosure also provides a compound of the formula (III):

(III)

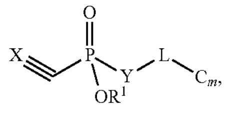

or a pharmaceutically acceptable salt, a stereoisomer, or a solvate thereof, wherein X, $R^1$, Y, L, C, and m are as defined in the formula (I).

In some aspects, the present disclosure provides a method of preparing an ADC of the formula (I), comprising reacting a compound of the formula (III) with a thiol containing compound, AB-$(SH)_n$, wherein AB is the anti-CEACAM5 antibody or antigen binding portion thereof disclosed herein, n ranges from 1 and 10, to yield the ADC of the formula (I):

In some aspects, the compounds of the formula (III) have the structure:

(Compound A)

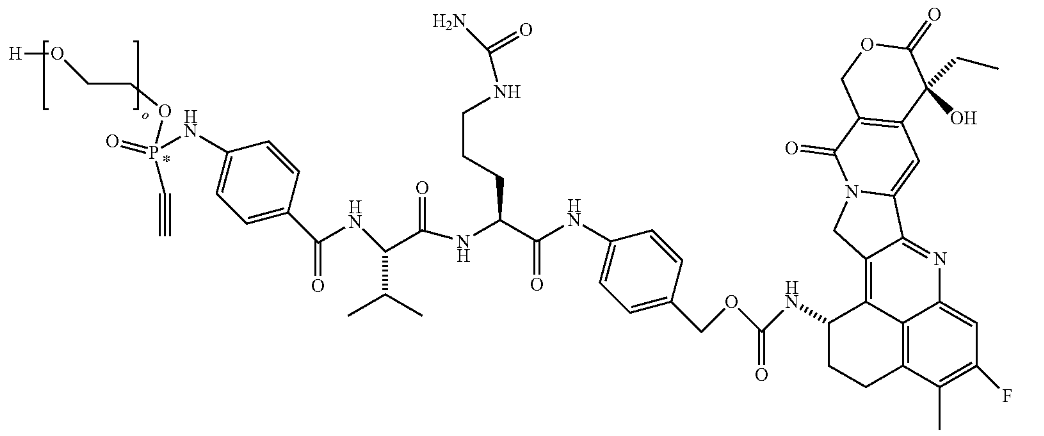

,

In some aspects, o is an integer of 8, 9, 10, 11, 12, 13, 14, 15, 16, 17, 18, 19, 20, 21, 22, 23, 24, 25, 26, 27, 28, 29, or 30. In some aspects, o is an integer between 20 to 30, e.g., 23. In some aspects, o is an integer between 20 and 25, e.g., 24. In some aspects, o is an integer of 24. In some aspects, o is 24. In some aspects, o is 25. In some aspects, o is 23. In some aspects, o is 22. In some aspects, o is 21. In some aspects, o is 20. In some aspects, o is an integer between 26 and 30. In some aspects, o is 26. In some aspects o is 27. In some aspects, o is 28. In some aspects o is 29. In some aspects, o is 30. In some aspects o is an integer between 8 and 19. In some aspects, o is 8. In some aspects, o is 9. In some aspects, o is 10. In some aspects o is 11. In some aspects o is 12. In some aspects o is 13. In some aspects, o (Compound A), or a pharmaceutically acceptable salt a stereoisomer, or a solvate thereof, wherein o is an integer ranging from 8-25, e.g., 24, * represents a chiral center. All stereoisomers of Compound A are contemplated for the synthesizing the ADCs disclosed herein.

In some aspects, the present disclosure provides a method of preparing an ADC of the formula (II), comprising reacting Compound A with a thiol containing compound, AB-$(SH)_n$, wherein AB is the anti-CEACAM5 antibody or antigen binding portion thereof disclosed herein (e.g., disclosed in Table 10 and Table 11), to obtain the ADC of the formula (II):

(II)

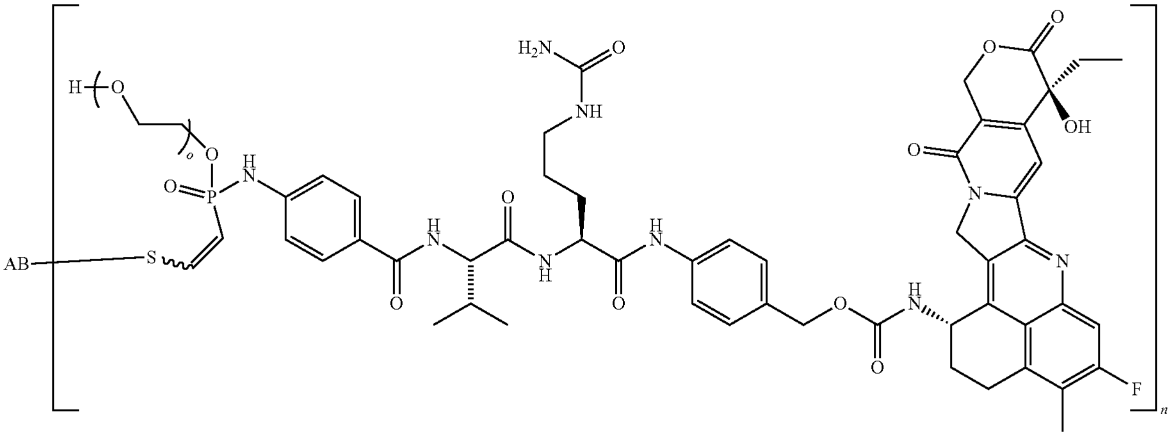

(II), or a pharmaceutically acceptable salt, a stereoisomer, or a solvate thereof, wherein o and n are as defined above. Methods of selective bioconjugation reaction of ethynylphosphonamideates with cysteine containing compounds have been described in WO2018041985A1 (published Mar. 8, 2018), WO2019170710A2 (published Sep. 12, 2019), WO2022223783A1 (published Oct. 27, 2022), WO2023083900A1 (published May 19, 2023), WO2023083919A1 (published May 19, 2023), each of which is incorporated herein by reference.

The number of cytotoxic moieties linked to the antigen binding moiety of a CEACAM5-ADC (drug-to-antibody ratio: DAR) can vary and will be limited only by the number of available attachments sites on the antigen binding moiety and the number of agents linked to a single linker.

The DAR value can vary with the nature of the antigen binding moiety (e.g. any antibody or the antigen-binding portion thereof described herein) and the drug used along with the experimental conditions used for the conjugation (DAR, reaction time, nature of the solvents and/or cosolvents). Thus, the contact between the antibody and the drug may in an ADC lead to a mixture comprising several conjugates differing from one another by different drug-to-antibody ratios and may further include free antibodies and/or aggregates. The DAR that is determined is thus a mean value. DARs may be analyzed by UV spectrometry, monomer content may be analyzed by SEC-HPLC, and free drug content may be analyzed by RP-HPLC.

In some aspects, a linker will link a single cytotoxic moiety to the antigen binding moiety (e.g., any antibody or the antigen-binding portion thereof described herein) of a conjugate. In some aspects where the conjugate include more than one cytotoxic moiety, each moiety may be the same or different. As long as the conjugate does not exhibit unacceptable levels of aggregation under the conditions of use and/or storage, conjugates with DARs of twenty, or even higher, are contemplated. In some aspects, the conjugates described herein may have a DAR in the range of about 1-10, 2-10, 1-8, 2-8, 1-6, 2-6, 1-4, or 2-4. In some specific aspects, the conjugate may have a DAR of 2, 3, 4 or 5. In some aspects, the DAR is 6. In some aspects, the DAR is 7. In some aspects, the DAR is 8. In some aspects, the DAR is 9. In some aspects, the DAR is 6 or 7. In some aspects, the DAR is 7, 7.5 or 8. In some aspects, the DAR is 7-8.

In some aspects, an ADC of the present disclosure has the following structure:

(ADC 101)

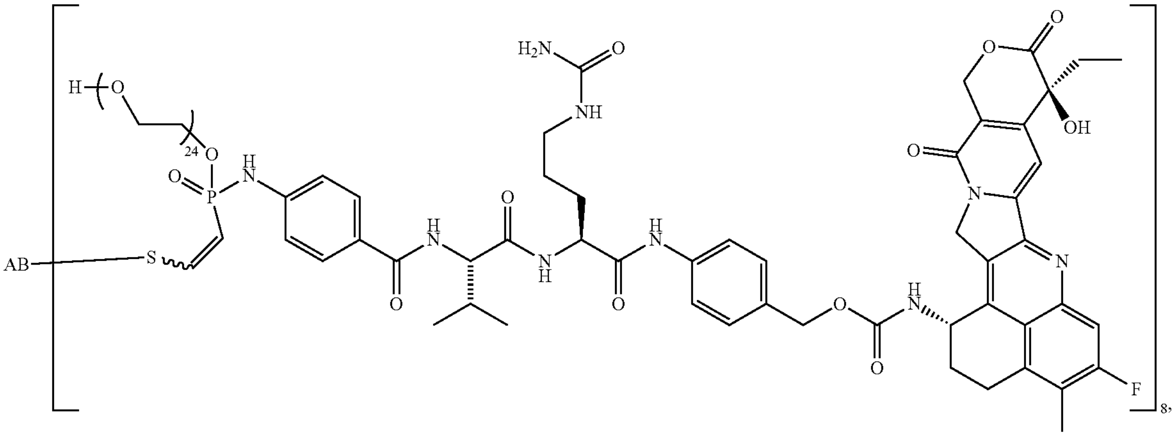

or a pharmaceutically acceptable salt, a stereoisomer, or a solvate thereof, wherein represents that the configuration of the double bond is E or Z; AB is the antibody, or antigen binding portion thereof that binds CEACAM5, comprising a VH and a VL, which comprise the amino acid sequences set forth in SEQ ID NOs: 38 and 43, respectively.

In some aspects, the disclosure provides ADC 101:

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 69 and the amino acid sequence set forth in SEQ ID NO: 70, respectively.

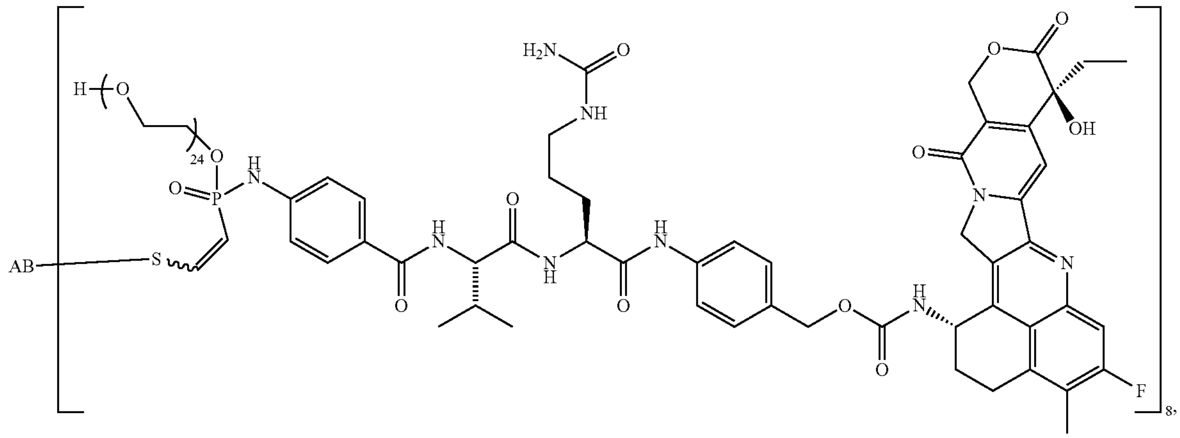

or a pharmaceutically acceptable salt thereof, wherein AB is the anti-CEACAM5 antibody, or antigen binding portion thereof, comprising (a) a heavy chain variable region (VH) comprising complementarity determining region (CDR)1, CDR2, and CDR3 regions comprising the amino acid sequences set forth in SEQ ID NOs: 14, 15, and 16, respectively, and a light chain variable region (VL) comprising CDR1, CDR2, and CDR3 regions comprising the amino acid sequences set forth in SEQ ID NOs: 19, 20, and 21, or;

(b) a VH comprising CDR1, CDR2, and CDR3 regions which have at least 80%, 85%, 90%, 95%, 98%, or 99% sequence identity to the amino acid sequences set forth in SEQ ID NOs: 14, 15, and 16, respectively, and a VL comprising CDR1, CDR2, and CDR3 regions which have at least 85%, 90%, 95%, 98%, or 99% sequence identity to the amino acid sequences set forth in SEQ ID NOs: 19, 20, and 21, respectively.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 49 and the amino acid sequence set forth in SEQ ID NO: 50, respectively.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 49 and the amino acid sequence set forth in SEQ ID NO: 50, respectively.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 67 and the amino acid sequence set forth in SEQ ID NO: 68, respectively.

In some aspects, the disclosure provides ADC 101, or a pharmaceutically acceptable salt thereof, wherein AB is the anti-CEACAM5 the antibody, or antigen binding portion thereof, comprising a VH and a VL which comprise the amino acid sequence set forth in SEQ ID NO: 71 and the amino acid sequence set forth in SEQ ID NO: 72; respectively.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 73 and the amino acid sequence set forth in SEQ ID NO: 74; respectively.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 75 and the amino acid sequence set forth in SEQ ID NO: 76; respectively.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 77 and the amino acid sequence set forth in SEQ ID NO: 78; respectively.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 79 and the amino acid sequence set forth in SEQ ID NO: 80; respectively.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 81 and the amino acid sequence set forth in SEQ ID NO: 82; respectively.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 83 and the amino acid sequence set forth in SEQ ID NO: 84; respectively.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 85 and the amino acid sequence set forth in SEQ ID NO: 86; respectively.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 87 and the amino acid sequence set forth in SEQ ID NO: 88; respectively.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 89 and the amino acid sequence set forth in SEQ ID NO: 90; respectively and wherein the cytotoxic moiety comprises Compound 101.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 91 and the amino acid sequence set forth in SEQ ID NO: 92; respectively.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 93 and the amino acid sequence set forth in SEQ ID NO: 94; respectively.

In some aspects, the disclosure provides ADC 101, or a pharmaceutically acceptable salt thereof, wherein AB is the anti-CEACAM5 antibody, or antigen binding portion thereof, comprising a VH and a VL which comprise the amino acid sequence set forth in SEQ ID NO: 17 and the amino acid sequence set forth in SEQ ID NO: 22; respectively.

In some aspects, the VH and the VL comprise the amino acid sequence set forth in SEQ ID NO: 49 and the amino acid sequence set forth in SEQ ID NO: 50, respectively. In some aspects, the VH and the VL comprise the amino acid sequence set forth in SEQ ID NO: 51 and the amino acid sequence set forth in SEQ ID NO: 52, respectively. In some aspects, the VH and the VL comprise the amino acid sequence set forth in SEQ ID NO: 67 and the amino acid sequence set forth in SEQ ID NO: 68, respectively. In some aspects, the VH and the VL comprise the amino acid sequence set forth in SEQ ID NO: 69 and the amino acid sequence set forth in SEQ ID NO: 70, respectively. In some aspects, the VH and the VL comprise the amino acid sequence set forth in SEQ ID NO: 71 and the amino acid sequence set forth in SEQ ID NO: 72, respectively. In some aspects, the VH and the VL comprise the amino acid sequence set forth in SEQ ID NO: 73 and the amino acid sequence set forth in SEQ ID NO: 74, respectively. In some aspects, the VH and the VL comprise the amino acid sequence set forth in SEQ ID NO: 75 and the amino acid sequence set forth in SEQ ID NO: 76, respectively. In some aspects, the VH and the VL comprise the amino acid sequence set forth in SEQ ID NO: 69 and the amino acid sequence set forth in SEQ ID NO: 70, respectively. In some aspects, the VH and the VL comprise the amino acid sequence set forth in SEQ ID NO: 73 and the amino acid sequence set forth in SEQ ID NO: 74, respectively. In some aspects, the VH and the VL comprise the amino acid sequence set forth in SEQ ID NO: 75 and the amino acid sequence set forth in SEQ ID NO: 76, respectively. In some aspects, the VH and the VL comprise the amino acid sequence set forth in SEQ ID NO: 77 and the amino acid sequence set forth in SEQ ID NO: 78, respectively. In some aspects, the VH and the VL comprise the amino acid sequence set forth in SEQ ID NO: 79 and the amino acid sequence set forth in SEQ ID NO: 80, respectively. In some aspects, the VH and the VL comprise the amino acid sequence set forth in SEQ ID NO: 81 and the amino acid sequence set forth in SEQ ID NO: 82, respectively. In some aspects, the VH and the VL comprise the amino acid sequence set forth in SEQ ID NO: 83 and the amino acid sequence set forth in SEQ ID NO: 84, respectively. In some aspects, the VH and the VL comprise the amino acid sequence set forth in SEQ ID NO: 85 and the amino acid sequence set forth in SEQ ID NO: 86, respectively. In some aspects, the VH and the VL comprise the amino acid sequence set forth in SEQ ID NO: 87 and the amino acid sequence set forth in SEQ ID NO: 88, respectively. In some aspects, the VH and the VL comprise the amino acid sequence set forth in SEQ ID NO: 89 and the amino acid sequence set forth in SEQ ID NO: 90, respectively. In some aspects, the VH and the VL comprise the amino acid sequence set forth in SEQ ID NO: 91 and the amino acid sequence set forth in SEQ ID NO: 92, respectively. In some aspects, the VH and the VL comprise the amino acid sequence set forth in SEQ ID NO: 93 and the amino acid sequence set forth in SEQ ID NO: 94, respectively. In some aspects, the VH and the VL comprise the amino acid sequence set forth in SEQ ID NO: 17 and the amino acid sequence set forth in SEQ ID NO: 22, respectively. In some aspects, the heavy chain and the light chain comprise the amino acid sequence set forth in SEQ ID NO: 45 and the amino acid sequence set forth in SEQ ID NO: 46, respectively.

In some aspects, the disclosure provides an antibody drug conjugate (ADC) having the formula (II):

(II)

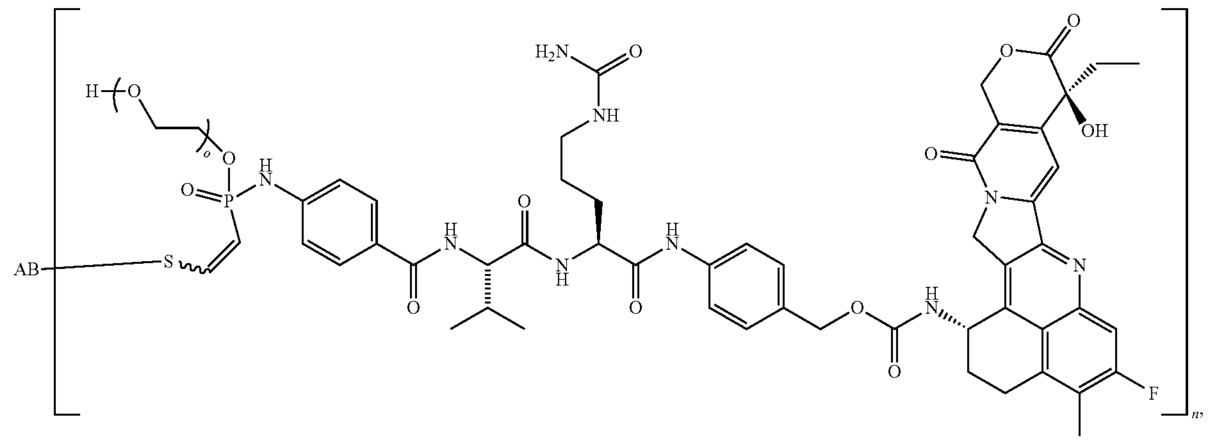

or a pharmaceutically acceptable salt, a stereoisomer or a solvate thereof, wherein n ranges from 4 to 8; o is an integer ranging from 10 to 30; AB is an anti-CEACAM5 antibody or antigen binding portion thereof comprising a VH and a VL, which comprise the amino acid sequence set forth in SEQ ID NO: 67 and the amino acid sequence set forth in SEQ ID NO: 68, respectively.

In some aspects, the disclosure provides an antibody drug conjugate (ADC) having the formula (II):

(II)

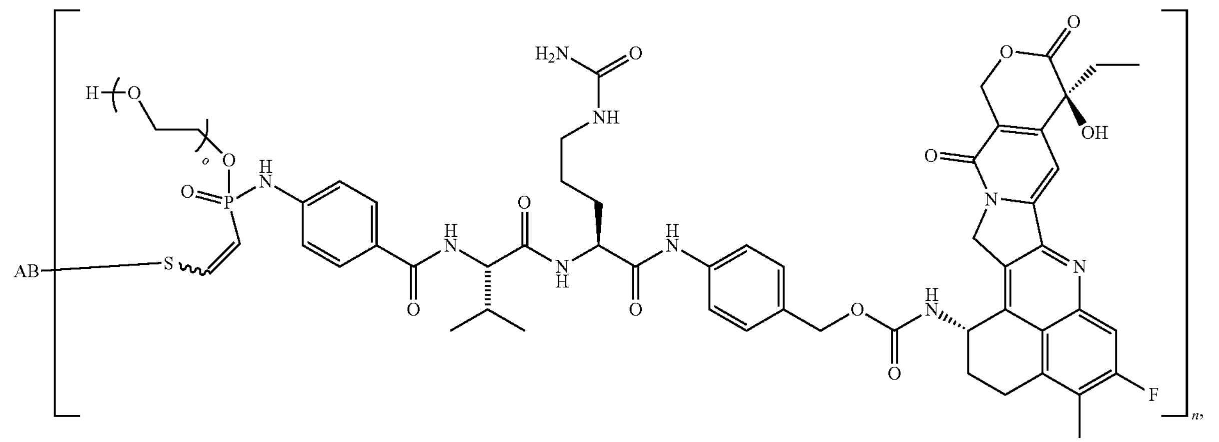

or a pharmaceutically acceptable salt, a stereoisomer, or solvate thereof, wherein n ranges from 4 to 8; o is an integer ranging from 10 to 30; AB is an anti-CEACAM5 antibody or antigen binding portion thereof comprising a VH and a VL, which comprise the amino acid sequence set forth in SEQ ID NO: 69 and the amino acid sequence set forth in SEQ ID NO: 70, respectively.

In some aspects, the disclosure provides an antibody drug conjugate (ADC) having the formula (II):

(II)

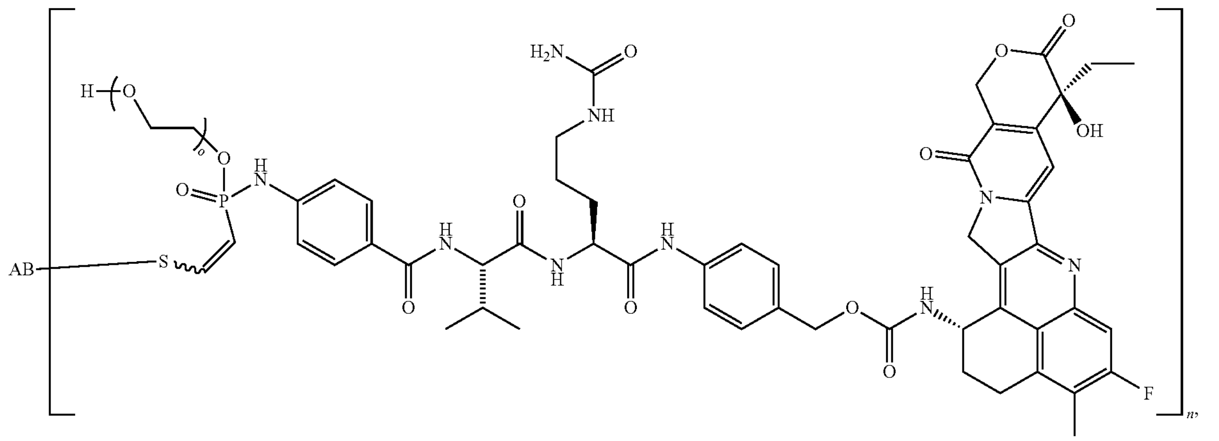

or a pharmaceutically acceptable salt, a stereoisomer, or a solvate thereof; wherein n ranges from 4 to 8; o is an integer ranging from 10 to 30; AB is an anti-CEACAM5 antibody or antigen binding portion thereof comprising a VH and a VL, which comprise the amino acid sequence set forth in SEQ ID NO: 71 and the amino acid sequence set forth in SEQ ID NO: 72, respectively.

In some aspects, the disclosure provides an antibody drug conjugate (ADC) having the formula (II):

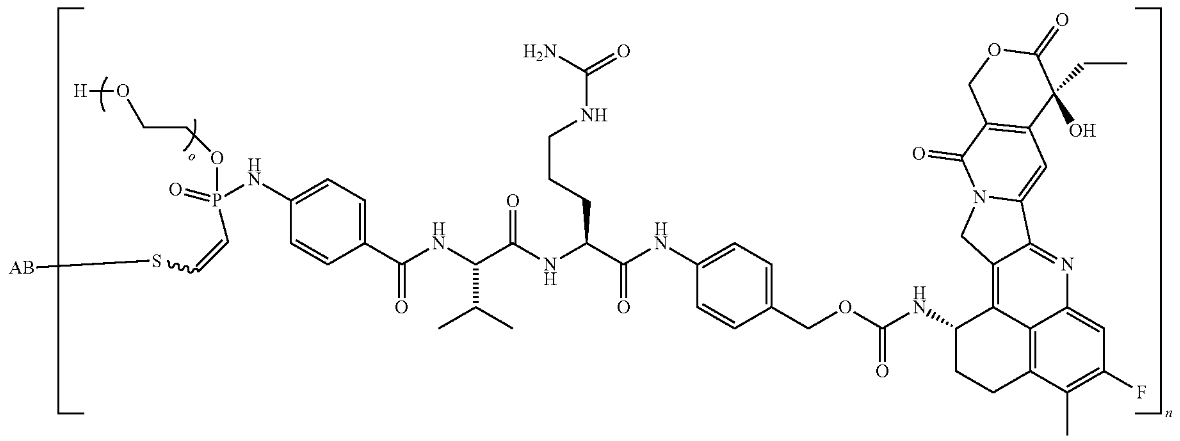

or a pharmaceutically acceptable salt, a stereoisomer, or a solvate thereof; wherein n ranges from 4 to 8; o is an integer ranging from 10 to 30; AB is an anti-CEACAM5 antibody or antigen binding portion thereof comprising a VH and a VL, which comprise the amino acid sequence set forth in SEQ ID NO: 73 and the amino acid sequence set forth in SEQ ID NO: 74, respectively.

In some aspects, the disclosure provides an antibody drug conjugate (ADC) having the formula (II):

(II)

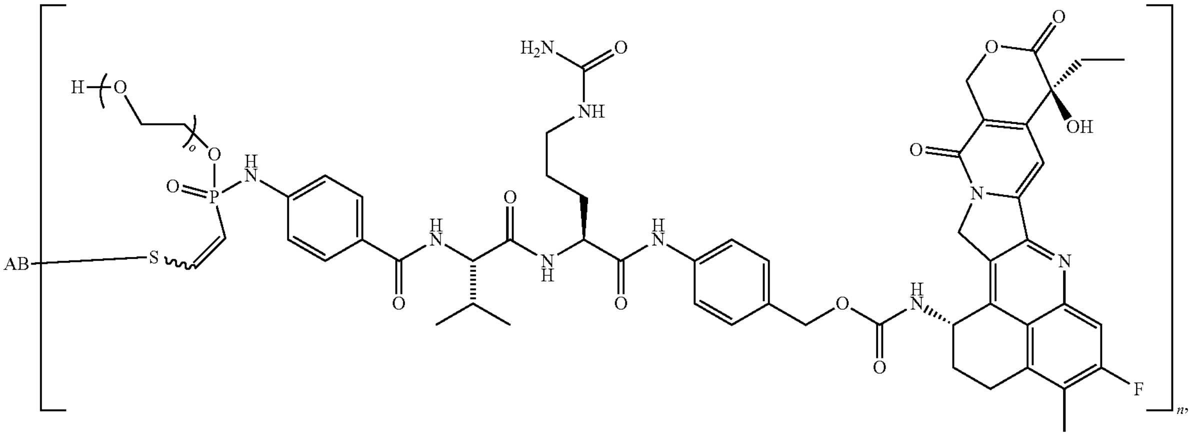

or a pharmaceutically acceptable salt, a stereoisomer, or a solvate thereof; wherein n is an integer ranging from 4 to 8; o is an integer ranging from 10-30; AB is an anti-CEACAM5 antibody or antigen binding portion thereof comprising a VH and a VL, which comprise the amino acid sequence set forth in SEQ ID NO: 75 and the amino acid sequence set forth in SEQ ID NO: 76, respectively.

In some aspects, the disclosure provides an antibody drug conjugate (ADC) having the formula (II):

(II)

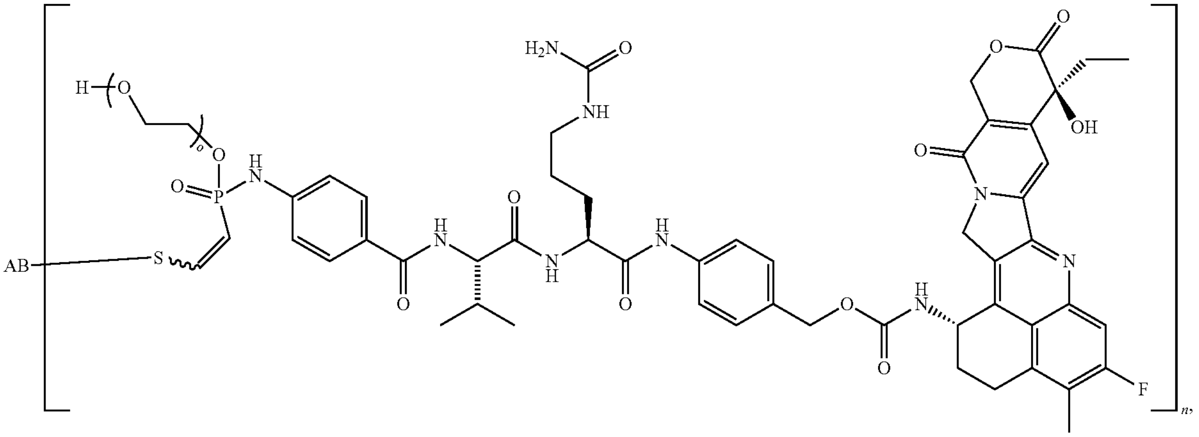

or a pharmaceutically acceptable salt, a stereoisomer, or a solvate thereof; wherein n is an integer ranging from 4 to 8; o is an integer ranging from 10 to 30; AB is an anti-CEACAM5 antibody or antigen binding portion thereof comprising a VH and a VL, which comprise the amino acid sequence set forth in SEQ ID NO: 77 and the amino acid sequence set forth in SEQ ID NO: 78, respectively.

In some aspects, the disclosure provides an antibody drug conjugate (ADC) having the formula (II):

(II)

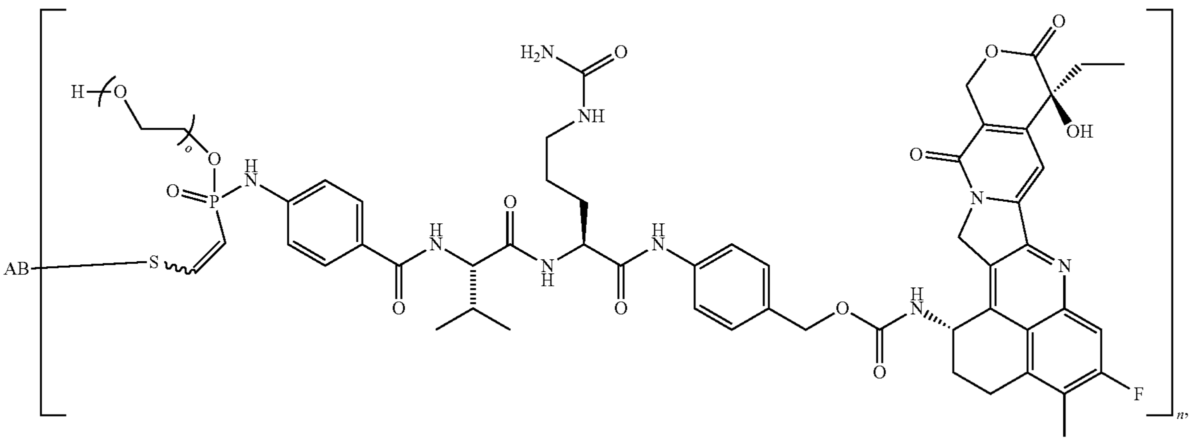

or a pharmaceutically acceptable salt, a stereoisomer, or a solvate thereof; wherein n ranges from 4 to 8; o Is an integer ranging from 10 to 30; AB is an anti-CEACAM5 antibody or antigen binding portion thereof comprising a VH and a VL, which comprise the amino acid sequence set forth in SEQ ID NO: 79 and the amino acid sequence set forth in SEQ ID NO: 80, respectively.

In some aspects, the disclosure provides an antibody drug conjugate (ADC) having the formula (II):

(II)

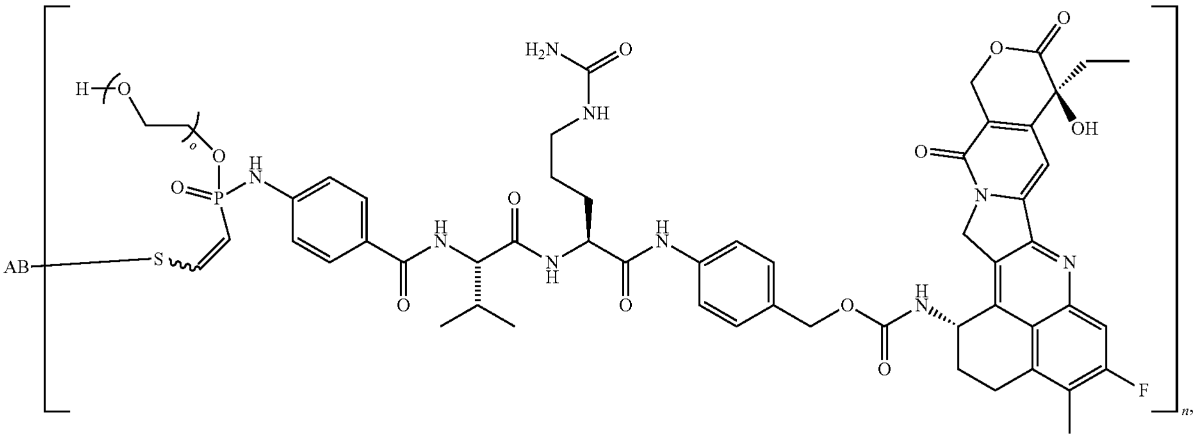

or a pharmaceutically acceptable salt, a stereoisomer, or a solvate thereof, wherein n ranges from 4 to 8; o is an integer ranging from 10 to 30; AB is an anti-CEACAM5 antibody or antigen binding portion thereof comprising a VH and a VL, which comprise the amino acid sequence set forth in SEQ ID NO: 81 and the amino acid sequence set forth in SEQ ID NO: 82, respectively.

In some aspects, the disclosure provides an antibody drug conjugate (ADC) having the formula (II):

(II)

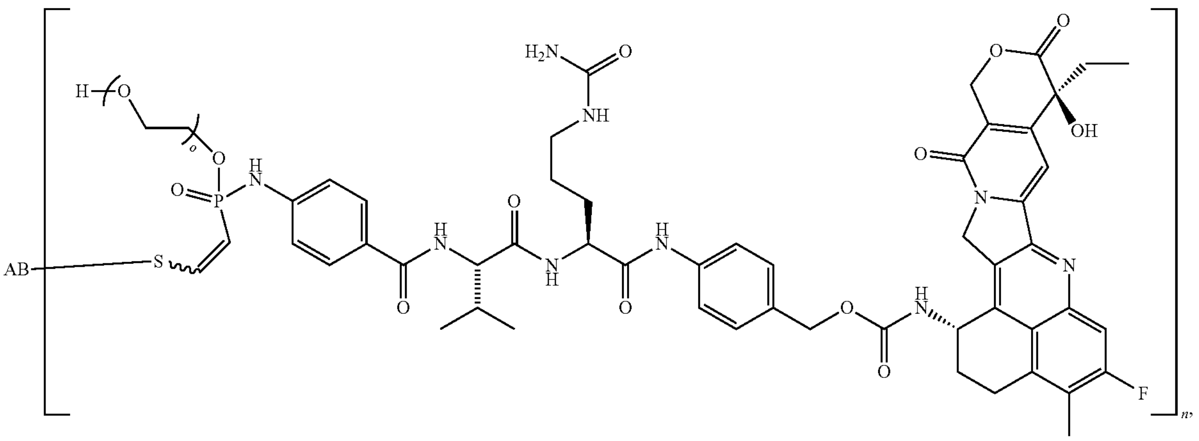

or a pharmaceutically acceptable salt, a stereoisomer, or a solvate thereof; wherein n ranges from 4 to 8; o is an integer ranging from 10 to 30; AB is an anti-CEACAM5 antibody or antigen binding portion thereof comprising a VH and a VL, which comprise the amino acid sequence set forth in SEQ ID NO: 83 and the amino acid sequence set forth in SEQ ID NO: 84, respectively.

In some aspects, the disclosure provides an antibody drug conjugate (ADC) having the formula (II):

(II)

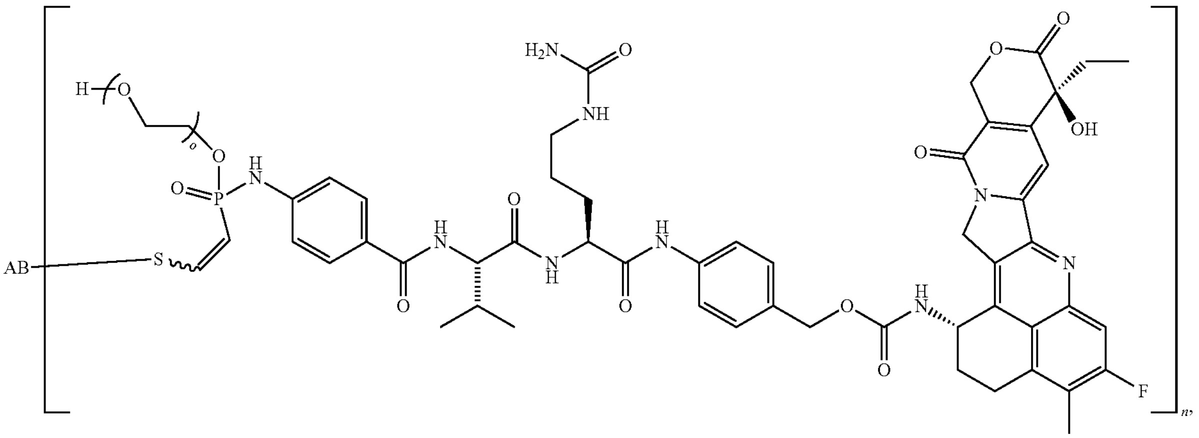

or a pharmaceutically acceptable salt, a stereoisomer, or a solvate thereof; wherein n ranges from 4 to 8; o is an integer ranging from 10 to 30; AB is an anti-CEACAM5 antibody or antigen binding portion thereof comprising a VH and a VL, which comprise the amino acid sequence set forth in SEQ ID NO: 85 and the amino acid sequence set forth in SEQ ID NO: 86, respectively.

In some aspects, the disclosure provides an antibody drug conjugate (ADC) having the formula (II):

(II)

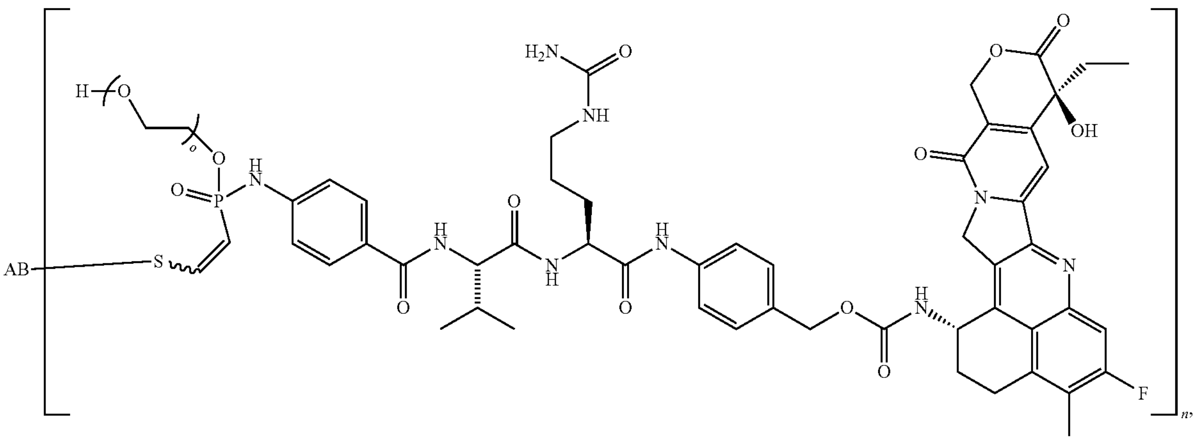

or a pharmaceutically acceptable salt, a stereoisomer, or a solvate thereof; wherein n ranges from 4 to 8; o Is an integer ranging from 10 to 30; AB is an anti-CEACAM5 antibody or antigen binding portion thereof comprising a VH and a VL, which comprise the amino acid sequence set forth in SEQ ID NO: 87 and the amino acid sequence set forth in SEQ ID NO: 88, respectively.

In some aspects, the disclosure provides an antibody drug conjugate (ADC) having the formula (II):

(II)

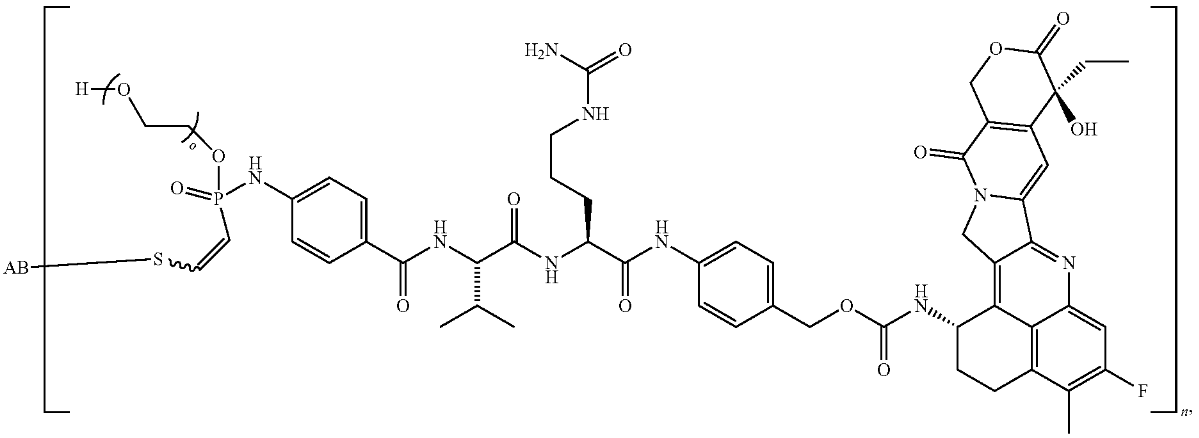

or a pharmaceutically acceptable salt, a stereoisomer, or a solvate thereof; wherein n ranges from 4 to 8; o is an integer ranging from 10 to 30; AB is an anti-CEACAM5 antibody or antigen binding portion thereof comprising a VH and a VL, which comprise the amino acid sequence set forth in SEQ ID NO: 89 and the amino acid sequence set forth in SEQ ID NO: 90, respectively.

In some aspects, the disclosure provides an antibody drug conjugate (ADC) having the formula (II):

(II)

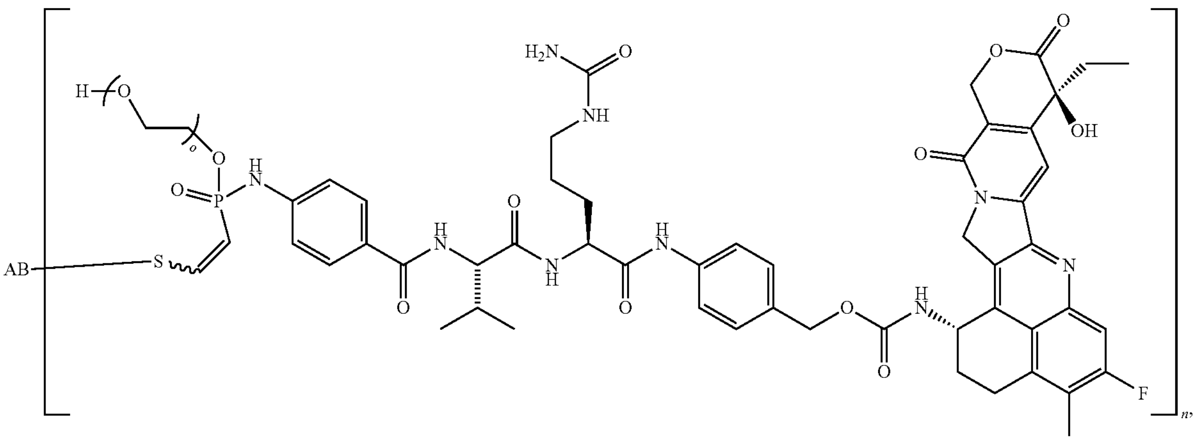

or a pharmaceutically acceptable salt, a stereoisomer, or a solvate thereof; wherein n ranges from 4 to 8; o Is an integer ranging from 10 to 30; AB is an anti-CEACAM5 antibody or antigen binding portion thereof comprising a VH and a VL, which comprise the amino acid sequence set forth in SEQ ID NO: 91 and the amino acid sequence set forth in SEQ ID NO: 92, respectively.

In some aspects, the disclosure provides an antibody drug conjugate (ADC) having the formula (II):

(II)

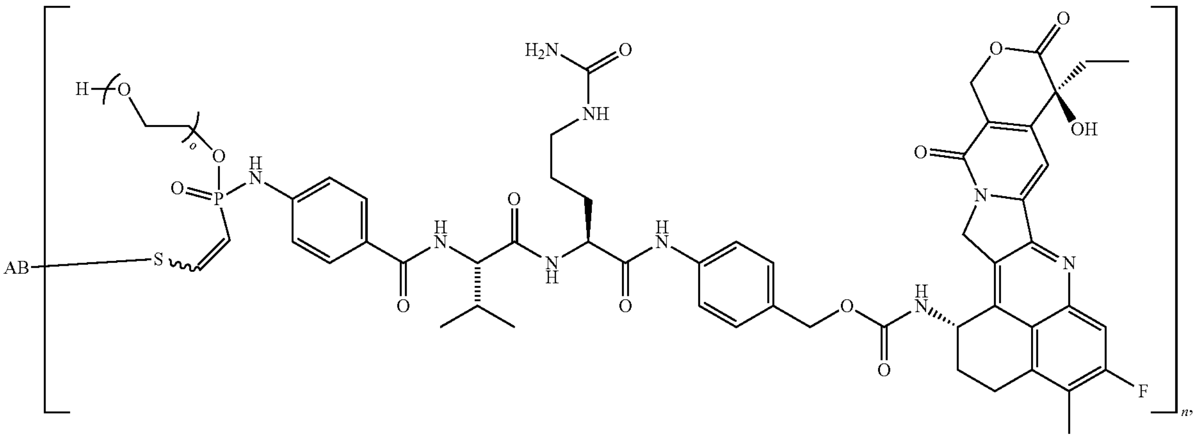

or a pharmaceutically acceptable salt, a stereoisomer, or a solvate thereof; wherein n ranges from 4 to 8; o is an integer ranging from 10 to 30; AB is an anti-CEACAM5 antibody or antigen binding portion thereof comprising a VH and a VL, which comprise the amino acid sequence set forth in SEQ ID NO: 93 and the amino acid sequence set forth in SEQ ID NO: 94, respectively.

In some aspects, the disclosure provides an antibody drug conjugate (ADC) having the formula (II):

(II)

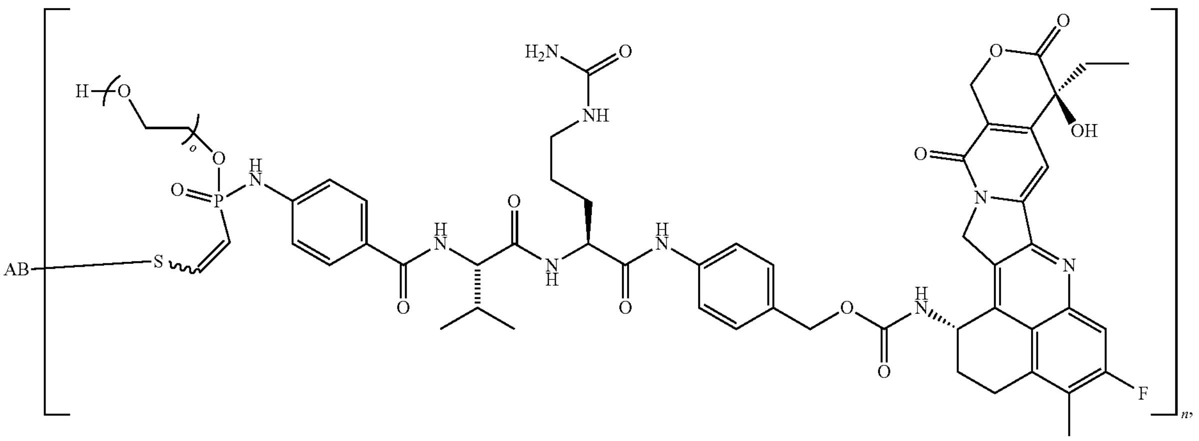

or a pharmaceutically acceptable salt, a stereoisomer, or solvate thereof; wherein n ranges from 4 to 8; o is an integer ranging from 10 to 30; AB is an anti-CEACAM5 antibody or antigen binding portion thereof comprising a VH and a VL which comprise the amino acid sequence set forth in SEQ ID NO: 17 and the amino acid sequence set forth in SEQ ID NO: 22, respectively.

In some aspects, n is 4, 5, 6, 7, 8, or 9. In some aspects, n is 6. In some aspects, n is 7. In some aspects, n is 8. In some aspects, n is 9.

In some aspects, the disclosure provides an antibody drug conjugate (ADC) comprising the formula (II):

polypeptide possessing a desired biological activity (e.g., lymphokines, tumor necrosis factor, IFNγ, growth factors).

Techniques for conjugating toxins or therapeutic moieties to antibodies are known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And (II)

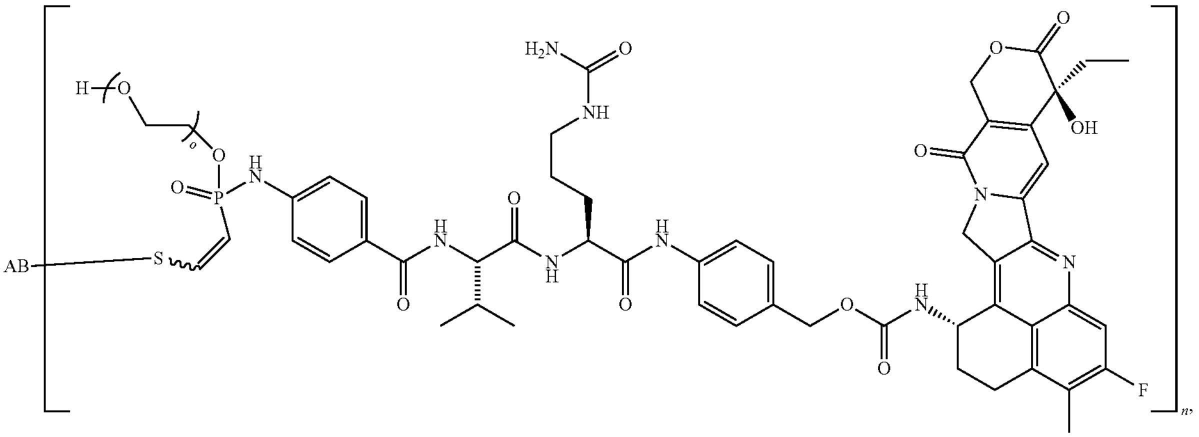

or a pharmaceutically acceptable salt, a stereoisomer, or a solvate thereof; wherein n ranges from 4 to 8; o is an integer ranging from 10 to 30; AB is an anti-CEACAM5 antibody or antigen binding portion thereof comprising a heavy chain and a light chain comprising the amino acid sequence as set forth in SEQ ID NO: 45 and the amino acid sequence as set forth in SEQ ID NO: 46, respectively.

ADCs can also be used to modify a given biological response, where the cytotoxic moiety should not be construed as limited to classical chemical therapeutic agents. For example, the cytotoxic moiety may be a protein or Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

IA. Anti-CEACAM5 Antibodies and Antigen Binding Portions

The anti-CEACAM5 antibodies useful for the ADC of the disclosure can be defined by particular structural features.

As used herein, the terms "Carcinoembryonic antigen-related cell adhesion molecule-5" and "CEACAM5" are used interchangeably with reference to human CEACAM5 or cynomolgus (*Macaca fascicularis*) CEACAM5, unless the context clearly dictates otherwise. The human CEACAM5 precursor polypeptide (with signal peptide) contains the amino acid sequence set forth in the SEQ ID NO: 1 (GenBank: AAH34671.1). The cynomolgus CEACAM5 precursor polypeptide (with signal peptide) contains the amino acid sequence set forth in SEQ ID NO: 3 (NCBI: XP_005589491.2). The amino acid sequence and nucleic acid sequences of human a cynomolgus CEACAM5 are disclosed in Table 10.

The term "CEACAM5" further includes counterparts from other species and other naturally occurring allelic, splice variants, and processed forms thereof, unless the context clearly dictates otherwise.

Antibody Sequences

In some aspects, the isolated anti-CEACAM5 antibody (e.g., recombinant humanized, chimeric, or human antibody) or antigen binding portion thereof (e.g., useful for conjugation to a cytotoxic moiety described herein to produce an ADC and useful for being the antibody in the ADC) is found in Table 10. The anti-CEACAM5 antibody or antigen binding portion thereof binds to and internalizes into CEACAM5-expressing cells. Thus, the anti-CEACAM5 antibody or antigen binding portion is useful for the ADC (comprising the antibody or antigen binding portion thereof linked to a cytotoxic moiety) by effectively delivering the cytotoxic moiety to kill cells, for example cancer cells.

Anti-CEACAM5 antibodies useful for the ADC include all known forms of antibodies and other protein scaffolds with antibody-like properties. For example, the antibody can be a monoclonal antibody, a humanized antibody, a human antibody, a bispecific antibody, an immunoconjugate, a chimeric antibody, or a protein scaffold with antibody-like properties, such as fibronectin or ankyrin repeats. The antibody also can be a Fab, $F(ab')_2$, scFv, AFFIBODY, avimer, nanobody, single chain antibody, or a domain antibody. The antibody also can have any isotype or allotype, including any of the following isotypes: IgG1, IgG2, IgG3, IgG4, IgM, IgA1, IgA2, secretory IgA (SIgA), IgD, IgE, and allotypes thereof. Full-length antibodies can be prepared from VH and VL sequences using standard recombinant DNA techniques and nucleic acid encoding the desired constant region sequences to be operatively linked to the variable region sequences.

In some aspects, the anti-CEACAM5 antibody, or antigen binding portion thereof, useful for the ADC comprises a VH comprising CDR1, CDR2, and CDR3 regions which have at least 60%, at least 70%, at least 80%, at least 85%, at least 90%, at least 95%, at least 98%, or at least 99% sequence identity to the amino acid sequences set forth in SEQ ID NOs: 14, 15, and 16, respectively, and a VL comprising CDR1, CDR2, and CDR3 regions which have at least 60%, at least 70%, at least 80%, at least 85%, at least 90%, at least 95%, at least 98%, or at least 99% sequence identity to the amino acid sequences set forth in SEQ ID NOs: 19, 20, and 21, respectively. In some aspects, the anti-CEACAM5 antibody, or antigen binding portion thereof, which specifically binds to CEACAM5 comprises: a VH comprising CDR1, CDR2, and CDR3 regions which comprises the amino acid sequences set forth in SEQ ID NOs: 14, 15, and 16, respectively, and a VL comprising CDR1, CDR2, and CDR3 regions which comprise the amino acid sequences set forth in SEQ ID NOs: 19, 20, and 21, respectively.

In some aspects, the anti-CEACAM5 antibody, or antigen binding portion thereof, useful for the ADC comprises a VH comprising CDR1, CDR2, and CDR3 regions which have at least 60%, at least 70%, at least 80%, at least 85%, at least 90%, at least 95%, at least 98%, at least 99%, or 100% sequence identity to the amino acid sequences set forth in SEQ ID NOs: 14, 15, and 16, respectively, and a VL comprising CDR1, CDR2, and CDR3 regions which have at least 60%, at least 70%, at least 80%, at least 85%, at least 90%, at least 95%, at least 98%, at least 99%, or 100% sequence identity to, and wherein the VH comprises an amino acid sequence having at least 80%, at least 85%, at least 90%, at least 95%, at least 98%, at least 99%, or 100% sequence identity to the amino acid sequence as set forth in SEQ ID NO: 38. In some aspects, the anti-CEACAM5 antibody, or antigen binding portion thereof, useful for the ADC comprises a VH comprising CDR1, CDR2, and CDR3 regions which have at least 60%, at least 70%, at least 80%, at least 85%, at least 90%, at least 95%, at least 98%, at least 99%, or 100% sequence identity to the amino acid sequences set forth in SEQ ID NOs: 14, 15, and 16, respectively, and a VL comprising CDR1, CDR2, and CDR3 regions which have at least 60%, at least 70%, at least 80%, at least 85%, at least 90%, at least 95%, at least 98%, at least 99%, or 100% sequence identity to, and wherein the VH comprises an amino acid sequence having at least 80%, at least 85%, at least 90%, at least 95%, at least 98%, at least 99%, or 100% sequence identity to the amino acid sequence as set forth in SEQ ID NO: 17. In some aspects, the anti-CEACAM5 antibody, or antigen binding portion thereof, useful for the ADC comprises a VH comprising CDR1, CDR2, and CDR3 regions which have at least 60%, at least 70%, at least 80%, at least 85%, at least 90%, at least 95%, at least 98%, at least 99%, or 100% sequence identity to the amino acid sequences set forth in SEQ ID NOs: 14, 15, and 16, respectively, and a VL comprising CDR1, CDR2, and CDR3 regions which have at least 60%, at least 70%, at least 80%, at least 85%, at least 90%, at least 95%, at least 98%, at least 99%, or 100% sequence identity to, and wherein the VH comprises an amino acid sequence having at least 80%, at least 85%, at least 90%, at least 95%, at least 98%, at least 99%, or 100% sequence identity to the amino acid sequence as set forth in SEQ ID NO: 49, SEQ ID NO: 51, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, or SEQ ID NO: 93.

In some aspects, the anti-CEACAM5 antibody, or antigen binding portion thereof, useful for the ADC comprises a VH comprising CDR1, CDR2, and CDR3 regions which have at least 60%, at least 70%, at least 80%, at least 85%, at least 90%, at least 95%, at least 98%, at least 99%, or 100% sequence identity to the amino acid sequences set forth in SEQ ID NOs: 14, 15, and 16, respectively, and a VL comprising CDR1, CDR2, and CDR3 regions which have at least 60%, at least 70%, at least 80%, at least 85%, at least 90%, at least 95%, at least 98%, at least 99%, or 100% sequence identity to, and wherein the VL comprises an amino acid sequence having at least 80%, at least 85%, at least 90%, at least 95%, at least 98%, at least 99%, or 100% sequence identity to the amino acid sequence as set forth in SEQ ID NO: 43. In some aspects, the anti-CEACAM5 antibody, or antigen binding portion thereof, useful for the ADC comprises a VH comprising CDR1, CDR2, and CDR3 regions which have at least 60%, at least 70%, at least 80%, at least 85%, at least 90%, at least 95%, at least 98%, at least 99%, or 100% sequence identity to the amino acid sequences set forth in SEQ ID NOs: 14, 15, and 16, respectively, and a VL comprising CDR1, CDR2, and CDR3 regions which have at least 60%, at least 70%, at least 80%, at least 85%, at least 90%, at least 95%, at least 98%, at least 99%, or 100% sequence identity to, and wherein the VH comprises an amino acid sequence having at least 80%, at least 85%, at least 90%, at least 95%, at least 98%, at least 99%, or 100% sequence identity to the amino acid sequence as set forth in SEQ ID NO: 22. In some aspects, the anti-CEACAM5 antibody, or antigen binding portion thereof, useful for the ADC comprises a VH comprising CDR1, CDR2, and CDR3 regions which have at least 60%, at least 70%, at least 80%, at least 85%, at least 90%, at least 95%, at least 98%, at least 99%, or 100% sequence identity to the amino acid sequences set forth in SEQ ID NOs: 14, 15, and 16, respectively, and a VL comprising CDR1, CDR2, and CDR3 regions which have at least 60%, at least 70%, at least 80%, at least 85%, at least 90%, at least 95%, at least 98%, at least 99%, or 100% sequence identity to, and wherein the VH comprises an amino acid sequence having at least 80%, at least 85%, at least 90%, at least 95%, at least 98%, at least 99%, or 100% sequence identity to the amino acid sequence as set forth in SEQ ID NO: 50, SEQ ID NO: 52, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, or SEQ ID NO: 94.

In some aspects, the anti-CEACAM5 antibody, or antigen binding portion thereof, useful for the ADC comprises a VH and a VL comprising the amino acid sequence set forth in SEQ ID NO: 38 and the amino acid sequence set forth in SEQ ID NO: 43, respectively. In some aspects, the anti-CEACAM5 antibody, or antigen binding portion thereof, useful for the ADC comprises a VH and a VL comprising the amino acid sequence set forth in SEQ ID NO: 49 and the amino acid sequence set forth in SEQ ID NO: 50; respectively. In some aspects, the anti-CEACAM5 antibody, or antigen binding portion thereof, useful for the ADC comprises a VH and a VL comprising the amino acid sequence set forth in SEQ ID NO: 51 and the amino acid sequence set forth in SEQ ID NO: 52, respectively. In some aspects, the anti-CEACAM5 antibody, or antigen binding portion thereof, useful for the ADC comprises a VH and a VL comprising the amino acid sequence set forth in SEQ ID NO: 67 and the amino acid sequence set forth in SEQ ID NO: 68, respectively. In some aspects, the anti-CEACAM5 antibody, or antigen binding portion thereof, useful for the ADC comprises a VH and a VL comprising the amino acid sequence set forth in SEQ ID NO: 69 and the amino acid sequence set forth in SEQ ID NO: 70, respectively. In some aspects, the anti-CEACAM5 antibody, or antigen binding portion thereof, useful for the ADC comprises a VH and a VL comprising the amino acid sequence set forth in SEQ ID NO: 71 and the amino acid sequence set forth in SEQ ID NO: 72, respectively. In some aspects, the anti-CEACAM5 antibody, or antigen binding portion thereof, useful for the ADC comprises a VH and a VL comprising the amino acid sequence set forth in SEQ ID NO: 73 and the amino acid sequence set forth in SEQ ID NO: 74, respectively. In some aspects, the anti-CEACAM5 antibody, or antigen binding portion thereof, useful for the ADC comprises a VH and a VL comprising the amino acid sequence set forth in SEQ ID NO: 75 and the amino acid sequence set forth in SEQ ID NO: 76, respectively. In some aspects, the anti-CEACAM5 antibody, or antigen binding portion thereof, useful for the ADC comprises a VH and a VL comprising the amino acid sequence set forth in SEQ ID NO: 77 and the amino acid sequence set forth in SEQ ID NO: 78, respectively. In some aspects, the anti-CEACAM5 antibody, or antigen binding portion thereof, useful for the ADC comprises a VH and a VL comprising the amino acid sequence set forth in SEQ ID NO: 79 and the amino acid sequence set forth in SEQ ID NO: 80, respectively. In some aspects, the anti-CEACAM5 antibody, or antigen binding portion thereof, useful for the ADC comprises a VH and a VL comprising the amino acid sequence set forth in SEQ ID NO: 81 and the amino acid sequence set forth in SEQ ID NO: 82, respectively. In some aspects, the anti-CEACAM5 antibody, or antigen binding portion thereof, useful for the ADC comprises a VH and a VL comprising the amino acid sequence set forth in SEQ ID NO: 83 and the amino acid sequence set forth in SEQ ID NO: 84, respectively. In some aspects, the anti-CEACAM5 antibody, or antigen binding portion thereof, useful for the ADC comprises a VH and a VL comprising the amino acid sequence set forth in SEQ ID NO: 85 and the amino acid sequence set forth in SEQ ID NO: 86, respectively. In some aspects, the anti-CEACAM5 antibody, or antigen binding portion thereof, useful for the ADC comprises a VH and a VL comprising the amino acid sequence set forth in SEQ ID NO: 87 and the amino acid sequence set forth in SEQ ID NO: 88, respectively. In some aspects, the anti-CEACAM5 antibody, or antigen binding portion thereof, useful for the ADC comprises a VH and a VL comprising the amino acid sequence set forth in SEQ ID NO: 89 and the amino acid sequence set forth in SEQ ID NO: 90, respectively. In some aspects, the anti-CEACAM5 antibody, or antigen binding portion thereof, useful for the ADC comprises a VH and a VL comprising the amino acid sequence set forth in SEQ ID NO: 91 and the amino acid sequence set forth in SEQ ID NO: 92, respectively. In some aspects, the anti-CEACAM5 antibody, or antigen binding portion thereof, useful for the ADC comprises a VH and a VL comprising the amino acid sequence set forth in SEQ ID NO: 93 and the amino acid sequence set forth in SEQ ID NO: 94, respectively. In some aspects, the anti-CEACAM5 antibody, or antigen binding portion thereof, useful for the ADC comprises a VH and a VL comprising the amino acid sequence set forth in 17 and the amino acid sequence set forth in SEQ ID NO: 22, respectively. In some aspects, the anti-CEACAM5 antibody comprises a heavy chain and the light chain comprise the amino acid sequence set forth in SEQ ID NO: 45 and the amino acid sequence set forth in SEQ ID NO: 46, respectively.

In some aspects, the anti-CEACAM5 antibody, or antigen binding portion thereof, which binds human CEACAM5 and is useful for conjugation to the cytotoxic moiety for producing the ADC has at least one amino acid mutation described in Table 11.

In some aspects, the anti-CEACAM5 antibody, or antigen binding portion thereof, useful for the ADC specifically binds to CEACAM5 with a $K_D$ less than $1\times10^{-6}$M. In some aspects, the anti-CEACAM5 antibody, or antigen binding portion thereof, useful for the ADC specifically binds to CEACAM5 with a $K_D$ less than $1\times10^{-7}$M. In some aspects, the anti-CEACAM5 antibody, or antigen binding portion thereof, useful for the ADC specifically binds to CEACAM5 with a $K_D$ less than $1\times10^{-8}$M. In some aspects, the anti-CEACAM5 antibody, or antigen binding portion thereof, useful for the ADC specifically binds to CEACAM5 with a $K_D$ less than $5\times10^{-9}$M. In some aspects, the anti-CEACAM5 antibody, or antigen binding portion thereof, useful for the ADC specifically binds to CEACAM5 with a $K_D$ less than $1\times10^{-9}$M. In some aspects, the anti-CEACAM5 antibody, or antigen binding portion thereof, useful for the ADC specifically binds to CEACAM5 with a $K_D$ less than $5\times10^{-10}$M.

Antibody Binding

The anti-CEACAM5 antibodies or antigen binding portions thereof (e.g., useful for being the antigen binding moiety in an ADC) bind to CEACAM5 (e.g., human CEACAM5) in solution, to CEACAM5 attached to a solid surface, such as a microtiter plate, and/or to CEACAM5 (e.g., human CEACAM5) anchored to the membrane of a cell. In some aspects, the anti-CEACAM5 antibody or antigen binding portion thereof (e.g., useful for conjugation to a cytotoxic moiety described herein for producing an ADC) binds to human CEACAM5, cyno CEACAM5, or both.

In some aspects, the anti-CEACAM5 antibody or antigen binding portion thereof (e.g., useful for being the antigen binding moiety in an ADC) binds to human and/or cynomolgus CEACAM5 with a $K_D$ of 100 nM or less, such as 90 nM or less, 80 nM or less, 70 nM or less, 60 nM or less, 50 nM or less, such as 40 nM or less, 30 nM or less, 20 nM or less, 10 nM or less, 5 nM or less, 3 nM or less, 1 nM or less, 0.9 nM or less, 0.8 nM or less, 0.7 nM or less, 0.6 nM or less, 0.5 nM or less, 0.4 nM or less, 0.3 nM or less, 0.2 nM or less, 0.1 nM or less, as measured by any detection method known in the art or described herein, for example, in Examples 3 and 4.

In some aspects, the anti-CEACAM5 antibody or antigen binding portion thereof (e.g., useful for being the antigen binding moiety in an ADC) binds to human and/or cynomolgus CEACAM5 with a $K_D$ between 0.1 nM and 100 nM, between 0.1 nM and 50 nM, between 0.1 nM and 25 nM, between 0.1 nM and 10 nM, between 0.1 nM and 5 nM, between 0.1 nM and 2 nM, between 0.1 nM and 1 nM, between 0.1 nM and 0.5 nM, between 1 nM and 100 nM, between 1 nM and 50 nM, between 1 nM and 25 nM, between 1 nM and 10 nM, between 1 nM and 5 nM, between 1 nM and 2 nM, between 5 nM and 100 nM, between 5 nM and 50 nM, between 5 nM and 25 nM, between 5 nM and 10 nM, between 10 nM and 100 nM, between 10 nM and 50 nM, between 10 nM and 25 nM, between 25 nM and 100 nM, between 25 nM and 50 nM, or between 50 nM and 100 nM, as measured by any detection method known in the art or described herein.

Binding of an anti-CEACAM5 antibody or antigen binding portion thereof (and absence of binding) useful for being the antigen binding moiety in the ADC may be assessed qualitatively or quantitatively by any method known in the art. Exemplary binding methodologies include immunohistochemistry, flow cytometry using, e.g., CEACAM5-overexpressing cells (e.g., MKN-45 or HCT116-CEACAM5), surface plasmon resonance (SPR) using, e.g., BIACORE® system (Cytiva), or bio-layer interferometry (BLI) using, e.g., the Octet platform (ForteBio).

In some aspects, the CEACAM5 antibody or antigen binding portion thereof (useful for being the antigen binding moiety in the ADC) does not bind to or does not cross-react with other carcinoembryonic antigens (CEAs), such as CEACAM1, CEACAM3, CEACAM4, CEACAM5, CEACAM6, CEACAM7, CEACAM8, CEACAM16, CEACAM18, CEACAM19, CEACAM20, and/or CEACAM21, e.g., as assessed by, e.g., flow cytometry using cells that overexpress one of the foregoing CEAs, or by SPR or BLL. For example, in some aspects, the anti-CEACAM5 antibody or antigen binding portion thereof useful for the ADC binds to one of the foregoing CEAs with a signal or affinity that is not significantly above the signal seen with a control antibody (e.g., isotype control) or the signal seen in the absence of the anti-CEACAM5 antibody.

In some aspects, the anti-CEACAM5 antibody or antigen binding portion thereof useful for being the antigen binding moiety in the ADC (comprising the CEACAM5 antibody or antigen binding portion and a cytotoxic moiety) binds to all or a portion of amino acids of human CEACAM5 (SEQ ID NO: 1) as described in Example 16. In some aspects, the anti-CEACAM5 antibody or antigen binding portion thereof useful for the ADC binds to all or a portion of amino acids of human CEACAM5 (SEQ ID NO: 1) as described in Example 17.

In some aspects, the anti-CEACAM5 antibody or antigen binding portion thereof useful for the ADC binds to (or is determined to bind to) CEACAM5-overexpressing cancer cell lines or tumor cells. In some aspects, the anti-CEACAM5 antibody or antigen binding portion thereof useful for the ADC binds to CEACAM5 on these cells as assessed e.g., by flow cytometry. For example, in some aspects, at least 5%, at least 10%, at least 20% at least 50%, at least 75%, or at least 90% of CEACAM5-expressing cells can be detected by binding of the anti-CEACAM5 antibody (e.g., display a signal above that seen with an isotype control antibody) by any detection method known in the art or described herein.

In some aspects, the anti-CEACAM5 antibody or antigen binding portion thereof useful for the ADC (comprising the CEACAM5 antibody or antigen binding portion and a cytotoxic moiety) binds to CEACAM5 expressed on cells (e.g., human and/or cynomolgus CEACAM5 expressed on, e.g., MKN-45 cells) with an $EC_{50}$ of 1000 ng/ml or less, 500 ng/ml or less, 200 ng/ml or less, 150 ng/ml or less, 100 ng/ml or less, 50 ng/ml or less, 25 ng/ml or less, 10 ng/ml or less, 5 ng/ml or less, 2 ng/ml or less, or 1 ng/ml or less, as measured by any detection method known in the art or described herein.

In some aspects, the anti-CEACAM5 antibody or antigen binding portion thereof useful for the ADC (comprising the CEACAM5 antibody or antigen binding portion and a cytotoxic moiety) binds to CEACAM5 expressed on cells with an $EC_{50}$ between about 1 ng/ml and about 1000 ng/ml, between about 1 ng/ml and about 500 ng/ml, between about 1 ng/ml and about 200 ng/ml, between about 1 ng/ml and about 100 ng/ml, between about 1 ng/ml and about 50 ng/ml, between about 1 ng/ml and about 25 ng/ml, between about 1 ng/ml and about 10 ng/ml, between about 1 ng/ml and about 5 ng/ml, between about 5 ng/ml and about 500 ng/ml, between about 5 ng/ml and about 200 ng/ml, between about 5 ng/ml and about 100 ng/ml, between about 5 ng/ml and about 50 ng/ml, between about 5 ng/ml and about 25 ng/ml, between about 5 ng/ml and about 10 ng/ml, between about 10 ng/ml and about 500 ng/ml, between about 10 ng/ml and about 200 ng/ml, between about 10 ng/ml and about 100 ng/ml, between about 10 ng/ml and about 50 ng/ml, between about 10 ng/ml and about 25 ng/ml, between about 25 ng/ml and about 500 ng/ml, between about 25 ng/ml and about 200 ng/ml, between about 25 ng/ml and about 100 ng/ml, between about 25 ng/ml and about 50 ng/ml, between about 50 ng/ml and about 500 ng/ml, between about 50 ng/ml and about 200 ng/ml, between about 50 ng/ml and about 100 ng/ml, between about 100 ng/ml and about 500 ng/ml, or between about 100 ng/ml and about 200 ng/ml, as measured by any detection method known in the art or described herein.

The binding of the anti-CEACAM5 antibody or antigen binding portion thereof to CEACAM5 described herein and useful for the ADC (comprising the CEACAM5 antibody or antigen binding portion and a cytotoxic moiety) may also be defined using quantitative immunofluorescence by flow cytometry, which allows the number of antibody molecules bound per cell or the number of CEACAM5-expressing cells to be quantified. In some aspects, the number of CEACAM5 molecules expressed per cell or number of CEACAM5-expressing cells in a cell line or tumor sample may be quantified by quantitative immunofluorescence using an anti-CEACAM5 antibody or fragment thereof described herein.

An anti-CEACAM5 antibody or antigen binding portion thereof described herein and useful for the ADC (comprising the CEACAM5 antibody or antigen binding portion and a cytotoxic moiety) binds to soluble or membrane-bound human and/or cynomolgus CEACAM5 with high affinity, for example, with a $K_D$ of $10^{-7}$ M or less, $10^{-8}$ M or less, $10^{-9}$ M or less, $10^{-10}$ M or less, $10^{-11}$ M or less, $10^{-12}$ M or less, $10^{-12}$ M to $10^{-7}$ M, $10^{-11}$ M to $10^{-7}$ M, $10^{-10}$ M to $10^{-7}$ M, or $10^{-9}$ M to $10^{-7}$ M, as measured by, e.g., surface plasmon resonance or other art-recognized methods.

In some aspects, the anti-CEACAM5 antibody or antigen binding portion thereof described herein and useful for the ADC (comprising the CEACAM5 antibody or antigen binding portion and a cytotoxic moiety) binds to soluble or membrane-bound human and/or cynomolgus CEACAM5 with a $K_D$ of between $10^{-7}$ M and $10^{-12}$ M, between $10^{-7}$ M and $10^{-11}$ M, between $10^{-7}$ M and $10^{-10}$ M, between $10^{-7}$ M and $10^{-9}$ M, between $10^{-7}$ M and $10^{-8}$ M, between $10^{-8}$ M and $10^{-12}$ M, between $10^{-8}$ M and $10^{-11}$ M, between $10^{-8}$ M and $10^{-11}$ M, between $10^{-8}$ M and $10^{-9}$ M, between $10^{-9}$ M and $10^{-12}$ M, between $10^{-9}$ M and $10^{-11}$ M, between $10^{-9}$ M and $10^{-10}$ M, between $10^{-10}$ M and $10^{-12}$ M, between $10^{-10}$ M and $10^{-11}$ M, or between $10^{-11}$ M and $10^{-12}$ M, as measured by, e.g., surface plasmon resonance or other art-recognized methods.

Competing Antibodies and Antibodies that Bind to the Same Epitope

The anti-CEACAM5 antibodies and antigen binding portions described herein (e.g., useful for being the antigen binding moiety in an ADC) are distinguished by the characteristic epitope(s) (i.e., site(s) on CEACAM5) to which they bind, e.g., Example 16 and Example 17. The epitope(s) to which the antibody or fragment binds can be determined using art-recognized methods. An anti-CEACAM5 antibody or antigen binding portion thereof useful for the ADC is considered to bind to the same epitope as a reference anti-CEACAM5 antibody (for example, MBN001) if it, e.g., contacts one or more of the same residues on human CEACAM5 as the reference antibody or contacts all of the same residues at all of the same regions of human CEACAM5 as the reference antibody.

Antibodies sharing common epitope binding characteristics may considered to fall within a common "epitope bin." In some cases, a CEACAM5-binding "test antibody" may be determined to fall within a common "epitope bin" by comparison to the sequence of a given "reference" antibody (e.g., MBN001) known to fall within a particular epitope bin. In other cases, epitope binning experiments may be performed to determine whether a test antibody falls into the same "bin" as an antibody based on common binding characteristics with a reference antibody. Antibodies that reduce binding of the antibodies disclosed herein by sequence to, e.g., an immobilized CEACAM5 protein or protein fragment, particularly at roughly stoichiometric concentrations, are likely to bind at the same, overlapping, or adjacent epitopes, and thus may share the desirable functional properties as one or more of the antibodies disclosed herein.

In some aspects, antibodies falling into the same epitope bin are determined by assaying for antibodies that compete for binding to CEACAM5 with particular anti-CEACAM5 antibodies described herein. Methods of determining antibody competition are known in the art.

In some aspects, BIACORE analysis can be used to assess the ability of the antibodies to compete. The ability of a test antibody to inhibit the binding of an anti-CEACAM5 antibody useful for the ADC to CEACAM5 demonstrates that the test antibody can compete with the antibody for binding to CEACAM5.

Inhibition or blocking by one antibody relative to another may be carried out by performing any suitable competitive inhibition experiment using art-recognized methods or those described herein, including but not limited to surface plasmon resonance (SPR) using e.g., the BIACORE® system (Cytiva), bio-layer interferometry (BLI) using e.g., the Octet platform (ForteBio), enzyme-linked immunoassay (ELISA), and flow cytometry. In some aspects, epitope binning of the anti-CEACAM5 antibodies useful for the ADC may be performed using a recombinant CEACAM5 protein or fragment, which is biotinylated and captured onto, e.g., Streptavidin biosensors which are bound by the first antibody until saturation is achieved. In some aspects, epitope binning may be carried out using a cell-based competition binding FACS assay.

Unless otherwise indicated, an antibody will be considered to compete with an anti-CEACAM5 antibody if it reduces binding of the selected antibody to human CEACAM5 (SEQ ID NO: 1), cynomolgus CEACAM5 (SEQ ID NO: 3), or fragment thereof by at least 20% when used at a roughly equal molar concentration with the selected antibody, as measured in competition ELISA experiments as outlined in the preceding two paragraphs.

In some aspects, the anti-CEACAM5 antibodies or antigen binding portions thereof useful for the ADC binds to a linear epitope. In some aspects, the anti-CEACAM5 antibodies or antigen binding portions thereof useful for the ADC binds to a conformational epitope.

In some aspects, the anti-CEACAM5 antibodies useful for the ADC are screened for high affinity binding to human CEACAM5, and selected antibodies therefrom are studied, e.g., using yeast display assays in which sequence variants of CEACAM5 are presented on the surface of yeast cells, MS-based protein footprinting, such as HDX-MS and Fast Photochemical Oxidation of Proteins (FPOP), and structural methods, such as X-ray crystal structure determination, molecular modeling, and nuclear magnetic resonance (NMR) spectroscopy, including NMR determination of the H-D exchange rates of labile amide hydrogens in CEACAM5 when free and when bound in a complex with an antibody of interest. Such methods can provide atomic resolution of the precise epitope bound by the antibody. In recent years, SP-cryo-EM has emerged as a complementary technique to crystallography and NMR for determining near-atomic level structures suitable for application in drug discovery (Renaud et al. *Nat Rev Drug Discov* 2018; 17:471-92; Scapin et al. *Cell Chem Biol* 2018; 25:1318-25; Ceska et al. *Biochemical Society Transactions* 2019: p. BST20180267).

Anti-CEACAM5 antibodies which bind to and compete for the same or similar epitopes to the antibodies disclosed herein may be raised using immunization protocols similar to those described herein, for example, in Example 1. In some aspects the immunization may be carried out with a construct containing the epitope bound by the anti-CEACAM5 antibodies disclosed herein. The resulting antibodies can be screened for high affinity binding to human CEACAM5 by FACS, ELISA, or SPR and/or screened for the ability to block binding of a reference antibody disclosed herein as determined by ELISA or by blocking their ability to bind to cells expressing CEACAM5 on their surface, e.g., by FACS or SPR. A test antibody can be contacted with a CEACAM5 protein, protein fragment, or CEACAM5-expressing cell prior to, at the same time as, or after the addition of the reference antibody.

Alternatively, variants of anti-CEACAM5 antibodies or antigen-binding portions thereof useful for the ADC can be obtained by mutagenesis of cDNA sequences encoding the heavy and light chains of the antibody.

Antibody Internalization

In another aspect, an anti-CEACAM5 antibody, or antigen binding portion thereof, useful for the ADC binds to human and/or cynomolgus CEACAM5 and induces internalization of the anti-CEACAM5 antibody or antigen binding portion thereof in accordance with, e.g., the conditions and results described in the examples. In some aspects, an ADC (comprising the anti-CEACAM5 antibody, or antigen binding portion thereof linked to a cytotoxic moiety described herein) binds to and is internalized by CEACAM5-expressing cells.

The identification of internalizing anti-CEACAM5 antibodies, or antigen binding portions thereof, useful for the ADC is important for development of effective ADCs. An anti-CEACAM5 antibody, or antigen binding portion thereof, useful for the ADC can be evaluated for its ability to internalize into cells as determined by any well-known method in the art, including but not limited to use of the IncuCyte live-cell analysis system, Amnis IMAGESTREAM® Imaging Flow Cytometry Analysis, or laser scanning confocal microscopy.

The internalizing anti-CEACAM5 antibody, or antigen binding portion thereof, useful for the ADC can be characterized or ranked in terms of their "degree of internalization" or "level of internalization," which can relate to the degree (e.g., cell percentage) or level of internalization (total amount of internalized antibodies) at a given antibody concentration (e.g., 100 nM) or following a given period of time (e.g., 2 minutes, 5 minutes, 10 minutes or 30 minutes) relative to a control antibody (e.g., MBN001), such as a non-internalizing antibody, control IgG, or other control antibody (e.g., benchmark antibody).

In some aspects, the anti-CEACAM5 antibody, or antigen binding portion thereof, useful for the ADC internalizes into at least about 20%, 30%, 40%, 50%, 60%, 70%, 80%, 90% or 100% of CEACAM5-expressing cells in a cell population. In some aspects, the anti-CEACAM5 antibody, or antigen binding portion thereof, useful for the ADC internalizes into a CEACAM5-expressing cell or population of CEACAM5-expressing cells at a level at least 2-fold, at least 5-fold, at least 20-fold, at least 100-fold, at least 500-fold, or at least 2,000-fold greater level than a control antibody (e.g., non-internalizing antibody, control IgG, other antibody, benchmark antibody).

In some aspects, the level of internalization of an anti-CEACAM5 antibody, or antigen binding portion thereof, into CEACAM5-expressing cells (e.g., MKN45 or HCT-116-hu/cyno CEACAM5) is determined by comparing area under time-course (AUC) immunofluorescence levels relative to a reference antibody, e.g., as described in Example 6. In some aspects, the anti-CEACAM5 antibody, or antigen binding portion thereof, useful for the ADC internalizes into a CEACAM5-expressing cell or population of CEACAM5-expressing cells at antibody/cell concentrations resulting in an AUC immunofluorescence level that is at least 50%, at least 75%, at least 2-fold, at least 3-fold, at least 5-fold, at least 10-fold, at least 25-fold, at least 50-fold, or at least 100-fold greater compared to a control antibody, as described herein. In some aspects, the anti-CEACAM5 antibody, or antigen binding portion thereof, useful for the ADC internalizes into a CEACAM5-expressing cell e.g., in accordance with the conditions and results set forth in Example 6 and Table 9.

In some aspects, the anti-CEACAM5 antibody, or antigen binding portion thereof, useful for the ADC may be characterized by its "rate of internalization" represented, e.g., by its $T_{1/2}$ of internalization, which is defined as the time at which half of the maximal internalization is achieved, as measured from the time the antibody is added to the cells. In some aspects, the $T_{1/2}$ of internalization for the anti-CEACAM5 antibody, or antigen binding portion thereof, useful for the ADC may be enhanced or increased by at least 10%, 30%, 50%, 75%, 2-fold, 3-fold, 5-fold or more, resulting in a reduction of the $T_{1/2}$ by at least 10%, 30%, 50%, 75%, 2-fold, 3-fold, 5-fold or more compared to a control antibody, as described herein. For example, instead of having a $T_{1/2}$ of 10 minutes, the anti-CEACAM5 antibody, or antigen binding portion thereof, useful for the ADC may exhibit an increased rate of internalization and thereby reduce the $T_{1/2}$ to 5 minutes (i.e., a two-fold increase in rate of internalization or a two-fold decrease in $T_{1/2}$). In some aspects, the $T_{1/2}$ is reduced by at least 10 minutes, 30 minutes, or 1 hour.

In some aspects, the anti-CEACAM5 antibody, or antigen binding portion thereof, useful for the ADC may be characterized by its maximal level of internalization into a CEACAM5-expressing cell or population of CEACAM5-expressing cells, where the maximal level of internalization is represented by the level of internalization at the plateau of a graph representing the internalization plotted against antibody concentrations or times. In some aspects, the anti-CEACAM5 antibody, or antigen binding portion thereof, useful for the ADC exhibits a maximal level of internalization, which is at least 10%, 30%, 50%, 75%, 2-fold, 3-fold, 5-fold or more relative to a control antibody, as described herein.

Another way to compare internalization efficacies of the anti-CEACAM5 antibody, or antigen binding portion thereof, useful for the ADC is to compare their level of internalization at a given antibody concentration (e.g., 100 nM) and/or at a given time (e.g., 2 minutes, 5 minutes, 10 minutes or 30 minutes).

In some aspects, the anti-CEACAM5 antibody, or antigen binding portion thereof, useful for the ADC may be characterized by level of internalization, which ability to internalize may be determined using area under time-course (AUC) immunofluorescence analysis representing the antibody concentration at which 50% of the maximum level of internalization is obtained, as measured from the time the antibody is added to the cells, for example, as described in Example 6.

In some aspects, the anti-CEACAM5 antibody, or antigen binding portion thereof, useful for the ADC exhibits an EC50 binding value less than 50 nM, less than 40 nM, less than 30 nM, less than 25 nM, less than 20 nM, less than 15 nM, less than 10 nM, less than 8 nM, less than 6 nM, less than 4 nM or less than 3 nM. In some aspects, the anti-CEACAM5 antibody, or antigen binding portion thereof, useful for the ADC exhibits an EC50 internalization value between 1 nM and 50 nM, between 4 nM and 50 nM, between 10 nM and 50 nM, between 20 nM and 50 nM, between 30 nM and 50 nM, between 4 nM and 40 nM, between 4 nM and 30 nM, between 4 nM and 20 nM, between 8 nM and 40 nM, between 8 nM and 30 nM, between 8 nM and 20 nM, between 12 nM and 40 nM, between 12 nm and 30 nM, or between 12 nM and 25 nM.

In some aspects, the level of binding of the anti-CEACAM5 antibody, or antigen binding portion thereof, useful for the ADC can be defined relative to that of a given control antibody, as described herein, and expressed as a percentage of the EC50 value obtained compared to the control antibody. In some aspects, the extent of binding reflected in the EC50 value can be enhanced by at least 10%, 30%, 50%, 75%, 2-fold, 3-fold, 5-fold or more, as compared to a control antibody.

In some aspects, the anti-CEACAM5 antibody, or antigen binding portion thereof, useful for the ADC comprises a modified constant region conferring increased internalization relative to the same anti-CEACAM5 antibody, or antigen binding portion thereof, without the modified constant region, or relative to a control antibody, as described herein. Modified constant regions for use in these aspects are described in U.S. Pat. No. 10,653,791, the contents of which are herein incorporated by reference in their entirety. For example, in some aspects, the anti-CEACAM5 antibody, or antigen binding portion thereof, useful for the ADC comprises an IgG2 hinge or a substitution of a non-IgG2 hinge with an IgG2 hinge. In some aspects, the anti-CEACAM5 antibody, or antigen binding portion thereof, useful for the ADC comprises a hinge and/or a CH1 domain that is not an IgG2 hinge and/or IgG2 CH1 domain is replaced with an IgG2 hinge and/or IgG2 CH1 domain.

In some aspects, the anti-CEACAM5 antibody useful for the present ADC comprises a lysine at the C-terminus of the heavy chain. In some aspects, the anti-CEACAM5 antibody useful for the present ADC does not comprise a lysine at the C-terminus of the heavy chain. In some aspects, the anti-CEACAM5 antibody useful for the present disclosure is a compostions comprising a mixture of at least two antibodies, one without C terminus lysine, and another with C terminus lysine.

In some aspects, the anti-CEACAM5 antibody, or antigen binding portion thereof, useful for the ADC comprising the modified constant region has a rate of internalization (as measured by $T_{1/2}$) that is increased by at least 10%, 30%, 50%, 75%, 2 fold, 3 fold, 5 fold or more, resulting in a reduction of the $T_{1/2}$ by at least 10%, 30%, 50%, 75%, 2 fold, 3 fold, 5 fold or more relative to the same anti-CEACAM5 antibody, or antigen binding portion thereof, without the modified constant region, or relative to a control antibody, as described herein.

Antibody Physical Properties

Each antibody or antigen binding portion thereof will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. In addition, each antibody or antigen binding portion thereof will have a characteristic melting temperature, with a higher melting temperature indicating greater overall stability in vivo (Krishnamurthy R and Manning MC (2002) *Curr Pharm Biotechnol* 3:361-71). In general, the $T_{M1}$ (the temperature of initial unfolding) may be greater than 60° C., greater than 65° C., or greater than 70° C. The melting point of an antibody or fragment can be measured using differential scanning calorimetry (Chen et al (2003) *Pharm Res* 20:1952-60; Ghirlando et al (1999) *Immunol Lett* 68:47-52) or circular dichroism (Murray et al. (2002) *J. Chromatogr Sci* 40:343-9). In a further aspect, the antibodies and antigen binding portions thereof are selected that do not degrade rapidly. Degradation of an antibody or antigen binding portion thereof can be measured using capillary electrophoresis (CE) and MALDI-MS (Alexander A J and Hughes D E (1995) Anal Chem 67:3626-32).

In some aspects, the anti-CEACAM5 antibody or antigen binding portion thereof useful for the ADC has minimal aggregation effects, which can otherwise lead to the triggering of an unwanted immune response and/or altered or unfavorable pharmacokinetic properties. Generally, antibodies and antigen binding portions thereof are acceptable with aggregation of 25% or less, 20% or less, 15% or less, 10% or less, or 5% or less. Aggregation can be measured by several techniques, including size-exclusion column (SEC), high performance liquid chromatography (HPLC), and light scattering.

IB. Bispecific or Multispecific Molecules

In some aspects, provided herein are ADCs conjugated by the formula (I) wherein the ADC comprises a bispecific molecule or multispecific molecule (e.g., bispecific antibodies or multispecific antibodies). In some aspects, the bispecific molecule useful for the ADC comprises at least one binding region (e.g., antibody or antigen binding portion thereof) for a particular epitope on CEACAM5 (e.g., human CEACAM5), as described herein, and at least one other binding region that binds another antigen. In some aspects, the multispecific molecule useful for the ADC comprises the antibody, or antigen binding portion thereof, disclosed herein and at least two binding regions, each of which binds other antigens. Bispecific and/or multispecific molecules can be prepared as full-length antibodies or antibody binding portions (e.g., $F(ab')_2$ antibodies).

Methods for making bispecific or multispecific molecules are known in the art (see, e.g., PCT Publication numbers WO 05117973 and WO 06091209). For example, production of full length bispecific or multispecific molecules, e.g., antibodies, can be based on the co-expression of two paired immunoglobulin heavy chain-light chains, where the two or more chains have different specificities. Various techniques for making and isolating bispecific or multispecific molecules directly from recombinant cell culture are also known. For example, bispecific or multispecific molecules can be produced using leucine zippers. Another strategy for making bispecific or multispecific molecules by the use of single-chain Fv (sFv) dimers has also been reported.

Examples of suitable bispecific or multispecific molecule platforms include, but are not limited to, Dual Targeting (DT)-Ig (GSK/Domantis), Two-in-one Antibody (Genentech), Cross-linked Mabs (Karmanos Cancer Center), Fcab and $mAb^2$ (F-Star), CovX-body (CovX/Pfizer), Dual Variable Domain (DVD)-Ig (Abbott), IgG-like Bispecific (ImClone/Eli Lilly), Ts2Ab (MedImmune/AZ) and BsAb (Zymogenetics), HERCULES (Biogen Idee), TvAb (Roche), ScFv/Fc Fusions, SCORPION (Emergent BioSolutions/Trubion, Zymogenetics/BMS), Dual Affinity Retargeting Technology (Fc-DART) (MacroGenics), Dual(ScFv)2-Fab (National Research Center for Antibody Medicine—China), F(ab)2 (Medarex/AMGEN), Dual-Action or Bis-Fab (Genentech), Dock-and-Lock (DNL) (ImmunoMedics), Bivalent Bispecific (Biotecnol), SEED (EMD Serono), $mAb^2$ (F-star), Fab-Fv (UCB-Celltech), Bispecific T Cell Engager (BiTE) (Micromet, Tandem Diabody (Tandab) (Affimed), Dual Affinity Retargeting Technology (DART) (MacroGenics), Single-chain Diabody (Academic), TCR-like Antibodies (AIT, ReceptorLogics), COMBODY (Epigen Biotech), dual targeting nanobodies (Ablynx), and Fc-engineered IgGl (Xencor).

In some aspects, the bispecific molecule useful for the ADC comprises a first binding region (e.g., antibody or antigen binding portion thereof) which binds to CEACAM5 derivatized or linked to another functional molecule, e.g., another peptide or protein (e.g., another antibody or ligand for a receptor) to generate a bispecific molecule that binds to CEACAM5 and a non-CEACAM5 target molecule. In some aspects, the multispecific molecule comprises a first binding region (e.g., antibody or antigen binding portion thereof) which binds to CEACAM5 derivatized or linked to two or more functional molecules, e.g., different peptides or proteins (e.g., other antibodies or ligands for a receptor) to generate a multispecific molecule that binds to CEACAM5 and two or more non-CEACAM5 target molecules. An antibody or antigen binding portion thereof may be derivatized or linked to more than one other functional molecule to generate bispecific or multispecific molecules that bind to more than two or more different binding sites and/or target molecules. To create a bispecific or multispecific molecule, an antibody or antigen binding portion thereof disclosed herein can be functionally linked (e.g., by chemical coupling, genetic fusion, noncovalent association or otherwise) to one or more other binding molecules, such as another antibody, antibody fragment, peptide, receptor, or binding mimetic, such that a multispecific molecule results.

Accordingly, bispecific molecules, for example, bispecific antibodies and bifunctional antibodies, comprising at least a first binding specificity for a particular epitope on CEACAM5 (e.g., human CEACAM5) and a second binding specificity for a second target are contemplated. In some aspects, multispecific molecules, for example, multispecific antibodies and multifunctional antibodies, comprising at least a first binding specificity for a particular epitope on CEACAM5 (e.g., human CEACAM5), a second binding specificity for a second target, and a third binding specificity for a third target, wherein the second target and the third target are not the same, are contemplated. In some aspects, the second binding region and/or the third binding region specifically binds to a tumor-associated antigen.

In some aspects, the second and/or third binding region has agonistic properties when binding to a target.

In some aspects, the antibody is a trispecific antibody comprising first, second, and third binding regions, wherein the first binding region comprises the binding specificity (e.g., antigen-binding region) of an anti-CEACAM5 antibody described herein, and the second and third binding regions bind to two different targets (or different epitopes on the same target), for example, the targets described herein.

In some aspects, the antibody is a bifunctional antibody comprising an anti-CEACAM5 antibody described herein and a receptor molecule.

In one aspect, the multispecific molecules comprise as a binding specificity at least one antibody, or an antigen binding portion thereof, including, e.g., a Fab, Fab', F(ab')2, Fv, or a single chain Fv. The antibody may also be a light chain or heavy chain dimer, or any minimal fragment thereof such as a Fv or a single chain construct, as described in Ladner et al. U.S. Pat. No. 4,946,778.

In some aspects, provided herein is a bispecific or multispecific immune cell engager (ICE) comprising a CEACAM5 binding domain linked by a short flexible linker region to at least one binding domain of a cell surface protein in an immune effector cell. Exemplary immune effector cells include T cells, NK cells, B cells, dendritic cells, and macrophage cells. Compositions and methods for preparing and using immune cell engagers are disclosed in U.S. Patent Publication No. 2017/368169, the disclosures of which are incorporated by reference herein.

In some aspects, the immune cell engager is a bispecific (BiTE) or trispecific (TriKE) T cell engager molecule comprising a CEACAM5 binding domain linked by a short flexible linker region to at least one binding domain of a T cell surface protein (i.e., T cell engager domain) in a T cell effector, such as a cytotoxic T cell. A CEACAM5-targeted BiTE or TriKE can bring $CD8^+$ CTLs into close proximity to a CEACAM5-expressing tumor cell, resulting in a high binding affinity. $CD8^+$ CTLs, like all T cells, express variable T-cell receptors (TCRs) associated with invariable CD3 subunits. In some aspects, a CEACAM5-targeted BiTE comprises a CEACAM5 binding fragment linked to a CD3$\epsilon$ binding domain engages the CD3$\delta$ unit of the TCR complex to form a synapse on the surface of the tumor cell, activating T cells directly and triggering cell death signaling pathways with the subsequent release of granzymes and perforins. By engaging the CD3$\epsilon$ unit, the CEACAM-based BiTE is not limited by TCR specificity and can potentially redirect the entire repertoire of T cells in a TCR-peptide-major histocompatibility complex (MHC) independent manner, which avoids the potential for immunotherapy driven downregulation of MHC-I and immune escape. Advantageously, CEACAM5-targeted BiTEs provide a means for activating exhausted T cells induced by long term exposure to CEACAM5. Exemplary T cell engager binding domains for inclusion in the BiTE or TriKE include CD3, TCRa, TCRp, TCRy, TCRC, ICOS, CD28, CD27, HVEM, LIGHT, CD40, 4-1BB, OX40, DR3, GITR, CD30, TIMI, SLAM, CD2, CD226, or a combination thereof.

In some aspects, a bispecific T cell engager molecule comprises a CEACAM5 binding domain linked by short flexible linker regions to a checkpoint inhibitor binding domain (a bispecific checkpoint inhibitory engager), e.g., CTLA-4, PD-1, PD-L1, PD-L2, LAG-3, TIM-3, Galectin 9, CEACAM-1, BTLA, CD69, Galectin-1, TIGIT, CD113, CD155, GPR56, VISTA, B7-H3, B7-H4, 2B4, CD48, GARP, PD1H, LAIR1, TIM-1, or TIM-4.

In some aspects, the immune cell engager is a bispecific or trispecific natural killer (NK) cell engager (NKCE) molecule comprising a CEACAM5 binding domain linked by a short flexible linker region to at least one binding domain of an NK cell surface protein (i.e., an NK cell engager binding domain). In some aspects, the NKCE comprises an antigen binding domain, or ligand that binds to (e.g., activates) CD16 (e.g., CD16a, CD16b, or both), NKp46, NKp30, NKp40, NKp44, NKp46, NKG2D, DNAM1, DAP10, CD16 (e.g., CD16a, CD16b, or both), CRTAM, CD27, PSGL1, CD96, CD 100 (SEMA4D), NKp80, CD244 (also known as SLAMF4 or 2B4), SLAMF6, SLAMF7, KIR2DS2, KIR2DS4, KIR3DS 1, KIR2DS3, KIR2DS5, KIR2DS 1, CD94, NKG2C, NKG2E, CD160, or a combination thereof.

The bispecific or multispecific molecules can be prepared by conjugating the constituent binding specificities, e.g., the anti-FcR and anti-CEACAM5 binding specificities, using methods known in the art. For example, each binding specificity of the multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC). In some aspects, conjugating agents are SATA and sulfo-SMCC, both available from Pierce Chemical Co. (Rockford, IL).

When the binding specificities are antibodies, they can be conjugated via sulfhydryl bonding of the C-terminus hinge regions of the two heavy chains. In some aspects, the hinge region is modified to contain an odd number of sulfhydryl residues, for example, one, prior to conjugation.

Alternatively, both binding specificities can be encoded in the same vector and expressed and assembled in the same host cell. This method is particularly useful where the multispecific molecule is a mAb×mAb, mAb×Fab, Fab×F (ab')2 or ligand×Fab fusion protein. A bispecific or multispecific molecule can be a single chain molecule comprising one single chain antibody and a binding determinant, or a single chain bispecific or multispecific molecule comprising two binding determinants. Bispecific or multispecific molecules may comprise at least two single chain molecules. Methods for preparing bispecific or multispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific or multispecific molecules to their specific targets can be confirmed by, for example, enzyme-linked immunosorbent assay (ELISA), radioimmunoassay (RIA), FACS analysis, bioassay (e.g., growth inhibition), or simple western blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antigen binding portion which recognizes and specifically binds to the antibody-FcR complexes. Alternatively, the complexes can be detected using any of a variety of other immunoassays. For example, the antibody can be radioactively labeled and used in a radioimmunoassay (RIA). The radioactive isotope can be detected by such means as the use of a α γ-β counter or a scintillation counter or by autoradiography.

IIC. Antibody Engineering

The ADC or its components (e.g., anti-CEACAM5 antibody or antigen binding portion thereof) as disclosed herein can be modified or engineered to improve their physical and functional properties.

Antibody Engineering of the Fc Region

The ADC or its components (e.g., anti-CEACAM5 antibody or antigen binding portion thereof) described herein may include modifications to their respective Fc regions, typically to alter one or more of their physical or functional properties, such as effector function (e.g., antigen-dependent cellular cytotoxicity), Fc receptor binding, serum half-life, and complement fixation). Furthermore, the ADC or its components (e.g., anti-CEACAM5 antibody or antigen binding portion thereof) can be chemically modified (e.g., one or more chemical moieties can be attached to the antibody) or be modified to alter its glycosylation, again to alter one or more properties of the antibody or fragment. In the context of Fc region modifications, the numbering of residues in the Fc region is that of the EU index of Kabat.

The ADC or its components (e.g., anti-CEACAM5 antibody or antigen binding portion thereof) disclosed herein also include antibodies and fragments with modified (or blocked) Fc regions to provide altered effector functions as described in e.g., U.S. Pat. No. 5,624,821; U.S. Patent Publication numbers US2009/280114 and US2011/142858; and PCT Publication Number WO2006/0057702. Such modifications can further include alterations to enhance or suppress various reactions of the immune system, with possible beneficial effects in diagnosis and therapy.

Altered Effector Functions

In some aspects, the ADC or its components (e.g., anti-CEACAM5 antibody or antigen binding portion thereof) comprises a variant Fc region that is modified (e.g., by amino acid substitution, deletion and/or insertion) relative to a parent Fc sequence (e.g., an unmodified Fc polypeptide that is subsequently modified to generate a variant) to increase or reduce the ability of the antibody or antigen-binding portions thereof to mediate one or more effector function(s) and/or to increase or decrease its binding to the Fc-gamma receptors (FcγRs), while retaining its antigen binding ability. Thus, in exemplary aspects, the ADC or its components (e.g., anti-CEACAM5 antibody or antigen binding portion thereof) may include one or more amino acid changes altering affinity for an effector ligand, such as an Fc receptor or the C1 component of complement. This approach is described in further detail in U.S. Pat. Nos. 5,624,821 and 5,648,260.

The interaction between the constant region of an antigen binding protein (such as an anti-CEACAM5 antibody, or antigen binding portion thereof,) and various Fc receptors (FcR), including FcγRI (CD64), FcγRII (CD32) and FcγRIII (CD16), is believed to mediate the effector functions, such as ADCC and CDC, of the antigen binding protein. The Fc receptor is also important for antibody cross-linking, which can be important for anti-tumor immunity. In exemplary aspects, modifications can be made in the Fc region in order to generate an Fc variant promoting (a) increased or decreased antibody-dependent cell-mediated cytotoxicity (ADCC), (b) increased or decreased complement mediated cytotoxicity (CDC), (c) increased or decreased affinity for C1q, (d) increased or decreased affinity for a Fc receptor relative to the parent Fc, and/or (e) increased or decreased pharmacokinetic stability.

Alterations of the Fc region may include amino acid changes, such as substitutions, deletions, insertions, glycosylation, deglycosylation, and/or addition of multiple Fc regions. Combining amino acid modifications may be particularly desirable. For example, the variant Fc region may include two, three, four, five, or more substitutions therein, e.g., of the specific Fc region positions identified herein. In some aspects, the Fc region is altered by replacing at least one amino acid residue with a different amino acid residue such that the antibody has an altered affinity for an effector ligand but retains the antigen-binding ability of the parent antibody. For example, one or more amino acids selected from amino acid residues 234, 235, 236, 237, 297, 318, 320 and 322 can be replaced with a different amino acid residue. The effector ligand to which affinity is altered can be, for example, an Fc receptor or the C1 component of complement. This approach is described in further detail in U.S. Pat. Nos. 5,624,821 and 5,648,260, both by Winter et al. In some aspects, the C1q binding site may be removed from the Fc region by deleting or substituting, for example, the EKK sequence of human IgG1. In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In another example, one or more amino acid residues within amino acid positions 231 and 239 are altered to change the ability of the antibody to fix complement. This approach is described further in U.S. Pat. No. 6,180,377.

In some aspects, provided herein are effector function-less versions of the anti-CEACAM5 antibodies or antigen binding portions thereof having e.g., a mutant hIgG1f allotype (hIgG1.3f) described herein, for example comprising the amino acid sequence set forth in SEQ ID NO: 30. The hIgG1.3f variant is a triple mutant version of hIgG1f (L234A, L235E, G237A) which lacks FcγR binding and effector function.

In some aspects, the ADC or its components (e.g., anti-CEACAM5 antibody or antigen binding portion thereof) may be engineered to have different affinities and selectivities for Fc gamma receptors (FcγRs) by mutating the heavy chain constant region, including the hinge and Fc domains. Mutations can be introduced to either enhance or reduce FcγR binding. These mutations can increase or decrease FcγR-mediated cross-linking and/or signaling. For therapeutic targets, such as CEACAM5, FcγR-mediated cross-linking of anti-CEACAM5 antibodies have the potential to provide undesirable agonist signaling and potential for toxicity absent the introduction of certain modification to obviate this problem.

Binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A, which has been shown to exhibit enhanced FcγRIIIa binding and ADCC activity (Shields et al., 2001). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys (Lazar et al., 2006). Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys (Lazar et al., 2006).

In some aspects, the ADC or its components (e.g., anti-CEACAM5 antibody or antigen binding portion thereof) may be engineered for reduced FcγR binding and potential for cross-linking and/or signaling, specifically, reduced engagement of the "low affinity" FcγRs hCD32a/FcγRIIa, hCD32b/FcγRIIb, hCD16a/FcγRIIIa, and hCD16b/FcγRIIIb. Engagement of the "high affinity" receptor CD64/FcγRI is generally believed to be of lower concern due to saturation of this receptor with serum IgG. Therefore, in some aspects, the ADC or its components (e.g., anti-CEACAM5 antibody or antigen binding portion thereof) may comprise an IgG1.3 Fc region, which is essentially devoid of binding to CD16, CD32a, CD32b and CD64 and lacks ADCC, ADCP and CDC functions (see U.S. Pat. No. 10,077,306 and U.S. Patent Publication No. US2022/0106400).

In some aspects, the Fc region may be engineered for increased ADCC and/or increased FcγR binding by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439 (as described e.g., in U.S. Pat. No. 6,737,056) wherein the numbering of the residues in the Fc region is that of the EU index as in Kabat. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F/324T. Other modifications for enhancing FcγR and complement interactions include but are not limited to substitutions 298A, 333A, 334A, 326A, 2471, 339D, 339Q, 280H, 290S, 298D, 298V, 243L, 292P, 300L, 396L, 3051, and 396L. These and other modifications are reviewed in Strohl, 2009, Current Opinion in Biotechnology 20:685-691.

In some aspects, the Fc region is modified to decrease the ability of the anti-CEACAM5 antibody or antigen binding portion thereof described herein to mediate effector function and/or to increase anti-inflammatory properties by modifying residues 243 and 264. In one aspect, the Fc region of the ADC or its components (e.g., anti-CEACAM5 antibody or antigen binding portion thereof) is modified by changing the residues at positions 243 and 264 to alanine. In another aspect, the Fc region is modified to decrease the ability of the ADC or its components (e.g., anti-CEACAM5 antibody or antigen binding portion thereof) to mediate effector function and/or to increase anti-inflammatory properties by modifying residues 243, 264, 267 and 328.

Other Fc modifications to the Fc region include those for reducing or ablating binding to FcγRs and/or complement proteins, thereby reducing or ablating Fc-mediated effector functions, such as ADCC, ADCP, and CDC. Modifications for altering binding to FcγRIIb include one or more substitutions, insertions, and deletions at positions 234, 235, 236, 237, 239, 266, 267, 268, 269, 325, 326, 327, 328, and 332, wherein numbering is according to the EU index. In one aspect, the Fc variants provide selectively enhanced affinity to FcγRIIb relative to one or more activating receptors. Exemplary substitutions include but are not limited to 234G, 235G, 236R, 237K, 267R, 269R, 325L, and 328R. Other Fc variants for enhancing binding to FcγRIIb include 235Y/267E, 236D/267E, 236R/328R, 239D/268D, 239D/267E, 267E/268D, 267E/268E, and 267E/328F. Other modifications for reducing FcγR and complement interactions include substitutions 297A, 234A, 235A, 237A, 318A, 228P, 236E, 268Q, 309L, 3305, 331 S, 2205, 226S, 2295, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691.

In certain aspects, the Fc region may be modified to remove an ADCC site. ADCC sites can be found, for example, in Molec. Immunol. 29 (5): 633-9 (1992) with regard to ADCC sites in IgG1. In addition, IgG1 mutants containing L235V, F243L, R292P, Y300L and P396L mutations were found to exhibit enhanced binding to FcγRIIIa and concomitantly enhanced ADCC activity in transgenic mice expressing human FcγRIIIa in models of B cell malignancies and breast cancer (Stavenhagen et al., 2007; Nordstrom et al., 2011). Other Fc mutants that may be used include: S298A/E333A/L334A, S239D/I332E, S239D/I332E/A330L, L235V/F243L/R292P/Y300L/P396L, and M428L/N434S. Specific examples of variant Fc domains are disclosed for example, in U.S. Pat. No. 6,096,871 and PCT Publication number WO 97/34631.

Optionally, the Fc region may comprise a non-naturally occurring amino acid residue at additional and/or alternative positions (see, e.g., U.S. Pat. Nos. 5,624,821; 6,277,375; 6,737,056; 6,194,551; 7,317,091; 8,101,720; PCT Patent Publication numbers WO 00/42072; WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114).

In one aspect, the hinge region of Fc is modified such that the number of cysteine residues in the hinge region is altered, e.g., increased or decreased. For example, in one aspect, the number of cysteine residues in the hinge region of CH1 is increased to provide increased the stability of the antibody or decreased to provide enhanced assembly of the light and heavy chains or as described in U.S. Pat. No. 5,677,425.

In some aspects, the changes to the Fc region may be made to increase the biological half-life of the ADC so as to facilitate less frequent dosing, with the concomitant increase convenience and decreases use of material (Presta (2005) J. Allergy Clin. Immunol. 116:731 at 734-35). Various approaches may be employed. For example, in certain aspects, this may be achieved by increasing the binding affinity of the Fc region for the neonatal Fc receptor (FcRn). For example, one or more of more of following residues can be mutated: 252, 254, 256, 433, 435, 436, as described in U.S. Pat. No. 6,277,375. Specific exemplary substitutions include one or more of the following: T252L, T254S, and/or T256F. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

Other Fc variants for increased binding to FcRn and/or improved pharmacokinetic properties include substitutions at positions 259, 308, 428, and 434, including for example 2591, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 307Q, 311A, 312A, 376A, 378Q, 380A, 382A, 434A (Shields et al, Journal of Biological Chemistry, 2001, 276(9):6591-6604), 252F, 252T, 252Y, 252W, 254T, 256S, 256R, 256Q, 256E, 256D, 256T, 309P, 311 S, 433R, 433S, 4331, 433P, 433Q, 434H, 434F, 434Y, 252Y/254T/256E, 433K/434F/436H, 308T/309P/311S (Dall'Acqua et al. Journal of Immunology, 2002, 169:5171-5180, Dall'Acqua et al., 2006, Journal of Biological Chemistry 281:23514-23524). Other modifications for modulating FcRn binding are described in Yeung et al., 2010, J Immunol, 182:7663-7671.

In another aspect, the Fc hinge region may be mutated to decrease the biological half-life of the antibody or fragment. For example, one or more amino acid mutations may be introduced into the CH2-CH3 domain interface region of the Fe hinge fragment such that the antibody or fragment has impaired Staphylococcal protein A (SpA) binding relative to native Fc-hinge domain SpA binding as described in U.S. Pat. No. 6,165,745.

In certain aspects, hybrid IgG isotypes with particular biological characteristics may be used. For example, in certain aspects, one or more regions and/or mutations from an IgG2 or IgG4. In one aspect, the ADC described herein comprises an IgG4 isotype antibody or fragment comprising a serine to proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system). When using an IgG4 constant domain, it is usually to include the substitution S228P, which mimics the hinge sequence in IgG1 and thereby stabilizes IgG4 molecules.

In another aspect, an IgG1/IgG3 hybrid variant may be constructed by substituting IgG1 positions in the CH2 and/or CH3 region with the amino acids from IgG3 at positions where the two isotypes differ. Thus, a hybrid variant IgG antibody may be constructed that comprises one or more substitutions, e.g., 274Q, 276K, 300F, 339T, 356E, 358M, 384S, 392N, 397M, 4221, 435R, and 436F. In other aspects described herein, an IgG1/IgG2 hybrid variant may be constructed by substituting IgG2 positions in the CH2 and/or CH3 region with amino acids from IgG1 at positions where the two isotypes differ. Thus, a hybrid variant IgG antibody may be constructed that comprises one or more substitutions, e.g., one or more of the following amino acid substitutions: 233E, 234L, 235L, 236G (referring to an insertion of a glycine at position 236), and 327A.

In some aspects, the variant Fc region may also comprise a sequence alteration wherein amino acids involved in disulfide bond formation are removed or replaced with other amino acids. Such removal may avoid reaction with other cysteine-containing proteins present in the host cell used to produce the antibodies described herein. Even when cysteine residues are removed, single chain Fc domains can still form a dimeric Fc domain that is held together non-covalently. In other aspects, the Fc region may be modified to make it more compatible with a selected host cell. For example, one may remove the PA sequence near the N-terminus of a typical native Fc region, which may be recognized by a digestive enzyme in *E. coli* such as proline iminopeptidase.

The ADC or its components (e.g., anti-CEACAM5 antibody or antigen binding portion thereof) disclosed herein may contain one or more glycosylation sites. Such glycosylation sites may result in increased immunogenicity of the antibody or fragment or an alteration of the pK of the antibody due to altered antigen-binding (Marshall et al. (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N-X-S/T sequence.

Therefore, in some aspects, the glycosylation properties of the ADC or its components (e.g., anti-CEACAM5 antibody or antigen binding portion thereof) described herein may be modified. For example, one or more glycosylation sites within the Fc domain may be modified or removed. Residues that are typically glycosylated (e.g., asparagine) may confer a cytolytic response. Such residues may be deleted or substituted with unglycosylated residues (e.g., alanine) to produce an aglycosylated antibody. In certain aspects, glycosylation can be altered to, for example, increase the affinity of the antibody for antigen. For example, one or more amino acid substitutions can be made that result in elimination of one or more variable region framework glycosylation sites to thereby eliminate glycosylation at that site. The resulting aglycosylation may increase the affinity of the antibody for antigen. Such an approach is described in further detail in U.S. Pat. Nos. 5,714,350 and 6,350,861 by Co et al. Glycosylation of the constant region on N297 may be prevented by mutating the N297 residue to another residue, e.g., N297A, and/or by mutating an adjacent amino acid, e.g., 298 to thereby reduce glycosylation on N297.

Additionally, or alternatively, an ADC or its components (e.g., anti-CEACAM5 antibody or antigen binding portion thereof) described herein can be engineered with an altered type of glycosylation, such as a hypofucosylated antibody having reduced amounts of fucosyl residues or an antibody having increased bisecting GlcNac structures. Non-fucosylated antibodies harbor a tri-mannosyl core structure of complex-type N-glycans of Fc without fucose residue. These glycoengineered antibodies that lack core fucose residue from the Fc N-glycans may exhibit stronger ADCC than fucosylated equivalents due to enhancement of FcγRIIIa binding capacity. Such carbohydrate modifications can be accomplished by, for example, expressing the antibody in a host cell with altered glycosylation machinery.

Cells with altered glycosylation machinery can be used as host cells in which to express recombinant antibodies described herein to thereby produce an antibody with altered glycosylation. For example, EP 1,176,195 by Hanai et al. describes a cell line with a functionally disrupted FUT8 gene, which encodes a fucosyl transferase (i.e., alpha-1,6-fucosyltransferase), such that antibodies expressed in such a cell line exhibit hypofucosylation. Recombinant host cells which have been genetically modified to inactivate the FUT8 gene encoding an alpha-1,6-fucosyltransferase are available. See, e.g., the POTELLIGENT™ technology system available from BioWa, Inc. (Princeton, N.J.) in which CHOK1SV cells lacking a functional copy of the FUT8 gene produce monoclonal antibodies having enhanced ADCC activity that is increased relative to an identical monoclonal antibody produced in a cell with a functional FUT8 gene. Aspects of the POTELLIGENT™ technology system are described in U.S. Pat. Nos. 7,214,775 and 6,946,292, and PCT Publication numbers WO00/61739 and WO02/31240.

PCT Publication number WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication number WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180).

Another modification of the antibodies described herein is pegylation. In some aspects, the ADC or its components (e.g., anti-CEACAM5 antibody or antigen binding portion thereof) described herein is pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. In some aspects, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain aspects, the antibody to be pegylated is an aglycosylated antibody. Methods for pegylating proteins can be applied to the antibodies or antigen binding portions thereofs described herein. See for example, European patent number EP 0 154 316 by Nishimura et al. and European patent number EP 0 401 384 by Ishikawa et al.

Effector functions can be measured in a number of ways including for example via binding of the FcγRIII to Natural Killer cells or via FcγRI to monocytes/macrophages to measure for ADCC effector function. For example, an antigen binding protein of the present invention can be assessed for ADCC effector function in a Natural Killer cell assay. Examples of such assays can be found in Shields et al., 2001 *J. Biol. Chem., Vol.* 276, p 6591-6604; Chappel et al., 1993 J. Biol. Chem., Vol 268, p 25124-25131; Lazar et al., 2006 PNAS, 103; 4005-4010.

The affinities and binding properties of an Fc region for its ligand may be determined by a variety of in vitro assay methods (biochemical or immunological based assays) including, but not limited to, equilibrium methods (e.g., enzyme-linked immunosorbent assay (ELISA), or radioimmunoassay (RIA)), or kinetics (e.g., BIACORE analysis), and other methods such as indirect binding assays, competitive inhibition assays, fluorescence resonance energy transfer (FRET), gel electrophoresis, and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

With regard to the above-described modifications for increasing or decreasing one or more of the functional properties described herein (e.g., biochemical, immunochemical, cellular, physiological or other biological activities, as determined using methods known to the art and described herein), the resulting increase in a given parameter may represent a statistically significant increase of at least 10% of the measured parameter, for example at least 20%, 30%, 40%, 50%, 60%, 70%, 80%, 90%, 95%, or 100% (i.e., 2-fold), 3-fold, 5-fold or 10-fold. Conversely, the resulting decrease in a measured parameter may represent a statistically significant decrease of at least 10% of the measured parameter, e.g., at least 20%, 30%, 40%, 50%, 60%, 70%, 80%, 90%, 95%, or 100%, 3-fold, 5-fold or 10-fold.

Any of the above-described modifications may be employed alone or in combination with any of the above-described modifications or those described in the next section in order to further enhance or decrease effector functions or other desirable properties (e.g., stability, expression).

Antibody Engineering of Variable Regions

In some aspects, the ADC or its components (e.g., anti-CEACAM5 antibody or antigen binding portion thereof) are engineered with modifications to framework residues within the variable domains of the parental antibody, e.g., to improve the properties of the antibody or antigen binding portion thereof. Typically, such framework modifications are made to decrease the immunogenicity of the anti-CEACAM5 antibodies or antigen binding portions thereof. This is usually accomplished by replacing non-CDR residues in the variable domains (i.e., framework residues) in a parental (e.g., rodent) antibody with analogous residues from the immune repertoire of the species in which the antibody is to be used, e.g., human residues in the case of human therapeutics. Such an antibody is referred to as a "humanized" antibody. In some cases, it is desirable to increase the affinity, or alter the specificity of an engineered (e.g., humanized) antibody. One approach is to "back-mutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived. Another approach is to revert to the original parental (e.g., rodent) residue at one or more positions of the engineered (e.g., humanized) antibody, e.g., to restore binding affinity that may have been lost in the process of replacing the framework residues. (See, e.g., U.S. Pat. Nos. 5,693,762, 5,585,089 and 5,530,101).

In certain aspects, the anti-CEACAM5 antibodies and antigen binding portions thereof in an ADC are engineered (e.g., humanized) to include modifications in the framework and/or CDRs to improve their properties. Such engineered changes can be based on molecular modeling. A molecular model for the variable region for the parental (non-human) antibody sequence can be constructed to understand the structural features of the antibody and used to identify potential regions on the antibody that can interact with the antigen. Conventional CDRs are based on alignment of immunoglobulin sequences and identifying variable regions. Kabat et al., (1991) Sequences of Proteins of Immunological Interest, Kabat, et al.; National Institutes of Health, Bethesda, Md.; 5th ed.; NIH Publ. No. 91-3242; Kabat (1978) *Adv. Prot. Chem.* 32:1-75; Kabat, et al., (1977) *J. Biol. Chem.* 252:6609-6616. Chothia and coworkers carefully examined conformations of the loops in crystal structures of antibodies and proposed hypervariable loops. Chothia, et al., (1987) *J Mol. Biol.* 196:901-917 or Chothia, et al., (1989) *Nature* 342:878-883. There are variations between regions classified as "CDRs" and "hypervariable loops". Later studies (Raghunathan et al., (2012) *J. Mol Recog.* 25, 3, 103-113) analyzed several antibody-antigen crystal complexes and observed that the antigen binding regions in antibodies do not necessarily conform strictly to the "CDR" residues or "hypervariable" loops. The molecular model for the variable region of the non-human antibody can be used to guide the selection of regions that can potentially bind to the antigen. In practice, the potential antigen binding regions based on model differ from the conventional "CDR"s or "hyper variable" loops. Commercial scientific software such as MOE (Chemical Computing Group) can be used for molecular modeling. Human frameworks can be selected based on best matches with the non-human sequence both in the frameworks and in the CDRs. For FR4 (framework 4) in VH, VJ regions for the human germlines are compared with the corresponding non-human region. In the case of FR4 (framework 4) in VL, J-kappa and J-Lambda regions of human germline sequences are compared with the corresponding non-human region. Once suitable human frameworks are identified, the CDRs are grafted into the selected human frameworks. In some cases, certain residues in the VL-VH interface can be retained as in the non-human (parental) sequence. Molecular models can also be used for identifying residues that can potentially alter the CDR conformations and hence binding to antigen. In some cases, these residues are retained as in the non-human (parental) sequence. Molecular models can also be used to identify solvent exposed amino acids that can result in unwanted effects such as glycosylation, deamidation and oxidation. Developability filters can be introduced early on in the design stage to eliminate/minimize these potential problems.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Pat. No. 7,125,689. In certain aspects, one or more glycosylation sites in either the light or heavy chain immunoglobulin variable regions, such as the framework regions, may be modified or removed to reduce immunogenicity. In particular aspects, it will be desirable to change certain amino acids containing exposed side-chains to another amino acid residue in order to provide for greater chemical stability of the final antibody, so as to avoid deamidation or isomerization. The deamidation of asparagine may occur on NG, DG, NG, NS, NA, NT, QG or QS sequences and result in the creation of an isoaspartic acid residue that introduces a kink into the polypeptide chain and decreases its stability (isoaspartic acid effect). Isomerization can occur at DG, DS, DA or DT sequences. In certain aspects, the antibodies provided herein do not contain deamidation or asparagine isomerism sites. For example, an asparagine (Asn) residue may be changed to Gln or Ala to reduce the potential for formation of isoaspartate at any Asn-Gly sequences, particularly within a CDR.

A similar problem may occur at an Asp-Gly sequence. Reissner and Aswad (2003) *Cell. Mol. Life Sci.* 60:1281. Isoaspartate formation may debilitate or completely abrogate binding of an antibody to its target antigen. See, Presta (2005) *J. Allergy Clin. Immunol.* 116:731 at 734.

In various aspect, the asparagine is changed to glutamine (Gln). It may also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) *J. Chromatog.* 662:261. In addition, any methionine residues (typically solvent exposed Met) in CDRs may be changed to Lys, Leu, Ala, or Phe or other amino acids in order to reduce the possibility that the methionine sulfur would oxidize, which could reduce antigen-binding affinity and also contribute to molecular heterogeneity in the final antibody preparation. Id. Additionally, in order to prevent or minimize potential scissile Asn-Pro peptide bonds, it may be desirable to alter any Asn-Pro combinations found in a CDR to Gln-Pro, Ala-Pro, or Asn-Ala. Antibodies with such substitutions are subsequently screened to ensure that the substitutions do not decrease the affinity or specificity of the antibody for CEACAM5, or other desired biological activity to unacceptable levels. See Table 1 for exemplary stabilizing CDR variants.

TABLE 1

Exemplary stabilizing CDR variants

| CDR Residue | Stabilizing Variant Sequence |
|---|---|
| Asn-Gly (N-G) | Gln-Gly, Ala-Gly, or Asn-Ala (Q-G), (A-G), or (N-A) |

TABLE 1-continued

Exemplary stabilizing CDR variants

| CDR Residue | Stabilizing Variant Sequence |
|---|---|
| Asp-Gly (D-G) | Glu-Gly, Ala-Gly or Asp-Ala (E-G), (A-G), or (D-A) |
| Met (M) | Lys, Leu, Ala, or Phe (K), (L), (A), or (F) |
| Asn (N) | Gln or Ala (Q) or (A) |
| Asn-Pro (N-P) | Gln-Pro, Ala-Pro, or Asn-Ala (Q-P), (A-P), or (N-A) |

III. Pharmaceutical Compositions

Also provided herein are pharmaceutical compositions comprising an ADC as disclosed herein and a carrier (e.g., pharmaceutically acceptable carrier). Such compositions are useful for various therapeutic applications, such as cancer treatment.

In some aspects, the pharmaceutical compositions may further include other compounds, drugs, and/or agents for various therapeutic applications. Such compounds, drugs, and/or agents can include, for example, an anti-cancer agent, a chemotherapeutic agent, an immunosuppressive agent, an immunostimulatory agent, an immune checkpoint inhibitor, and/or an anti-inflammatory agent. Exemplary compounds, drugs, and agents that can be formulated together or separately with the ADC described in the next section.

As used herein, "pharmaceutically acceptable carrier" includes any and all solvents, dispersion media, coatings, antibacterial and antifungal agents, isotonic and absorption delaying agents, and the like that are physiologically compatible. In some aspects, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein may also include a pharmaceutically acceptable antioxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. Except insofar as any media or agent is incompatible with the active compound, use thereof in the pharmaceutical compositions described herein is contemplated. A pharmaceutical composition may comprise a preservative or may be devoid of a preservative. Supplementary active compounds can be incorporated into the compositions.

A composition described herein can be administered via one or more routes of administration using one or more of a variety of methods. The route and/or mode of administration can vary depending upon the desired results. Routes of administration for the ADC described herein include e.g., intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an ADC described herein can be administered via a non-parenteral route, such as a topical, epidermal or mucosal route of administration, for example, intranasally, orally, vaginally, rectally, sublingually or topically.

IV. Uses and Methods

The ADC described herein have numerous in vitro and in vivo utilities as described herein.

Cancer Treatment

In one aspect, provided herein is a method of treating cancer comprising administering to a subject in need thereof an ADC in an effective amount so that the growth of a cancerous tumor is inhibited or reduced and/or that regression and/or that prolonged survival is achieved.

In some aspects, the ADC described herein may be administered in combination with additional cytotoxic or therapeutic agent(s), for example as described herein.

Cancers that express CEACAM5 whose growth may be inhibited using the ADC described herein include, but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer (e.g. estrogen-receptor positive breast cancer HER2-positive breast cancer; triple negative breast cancer); cancer of the peritoneum; cervical cancer; cholangiocarcinoma; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; liver cancer (e.g., hepatocellular carcinoma; hepatoma); intra-epithelial neoplasm; kidney or renal cancer; larynx cancer; leukemia; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; teratocarcinoma; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblasts leukemia; and post-transplant lymphoproliferative disorder (PTLD), as well as abnormal vascular proliferation associated with phakomatoses, edema (such as that associated with brain tumors), tumors of primitive origins and Meigs' syndrome.

Additional cancers which express CEACAM5 and can be treated using the ADC described herein include metastatic pancreatic cancer, metastatic adenocarcinoma of the pancreas, stomach cancer, fibrotic cancer, glioma, malignant glioma, diffuse intrinsic pontine glioma, recurrent childhood brain neoplasm renal cell carcinoma, clear-cell metastatic renal cell carcinoma, metastatic castration resistant prostate cancer, stage IV prostate cancer, metastatic melanoma, malignant melanoma, recurrent melanoma of the skin, melanoma brain metastases, malignant melanoma of head and neck, squamous cell non-small cell lung cancer, metastatic breast cancer, follicular lymphoma, advanced B-cell NHL, HL including diffuse large B-cell lymphoma (DLBCL), multiple myeloma, chronic myeloid leukemia, adult acute myeloid leukemia in remission, adult acute myeloid leukemia with Inv(16)(p13.1q22), CBFB-MYH11, adult acute myeloid leukemia with t(16:16) (p13.1:q22), CBFB-MYH11, adult acute myeloid leukemia with t(8:21)(d22:q22), RUNX1-RUNX1T1, adult acute myeloid leukemia with t(9:11)(p22:q23), MLLT3-MLL, adult acute promyelocytic leukemia with tO15:17)(q22:ql2), PML-RARA, alkylating agent-related acute myeloid leukemia, Richter's syndrome, adult glioblastoma, adult gliosarcoma, recurrent glioblastoma, recurrent childhood rhabdomyosarcoma, recurrent Ewing sarcoma/peripheral primitive neuroectodermal tumor, recurrent neuroblastoma, recurrent osteosarcoma, colorectal cancer, MSI positive colorectal cancer, MSI negative colorectal cancer, nasopharyngeal nonkeratinizing carcinoma, recurrent nasopharyngeal undifferentiated carcinoma, cervical adenocarcinoma, cervical adenosquamous carcinoma; cervical squamous cell carcinoma, recurrent cervical carcinoma, anal canal squamous cell carcinoma, metastatic anal canal carcinoma, recurrent anal canal carcinoma, recurrent head and neck cancer, squamous cell of head and neck, head and neck squamous cell carcinoma (HNSCC), ovarian carcinoma, colon cancer, advanced GI cancer, gastric adenocarcinoma, gastroesophageal junction adenocarcinoma, bone neoplasms, soft tissue sarcoma, bone sarcoma, thymic carcinoma, urothelial carcinoma, Merkel cell carcinoma, recurrent Merkel cell carcinoma, mycosis fungoides, Sezary syndrome, neuroendocrine cancer, nasopharyngeal cancer, basal cell skin cancer, squamous cell skin cancer, dermatofibrosarcoma trotuberans, glioma, mesothelioma, myelodysplastic syndromes (MDS), myelofibrosis (MF), myeloproliferative neoplasms, and acute myeloid leukemia (AML).

In some aspects, the cancer comprises: colorectal cancer, breast cancer, lung cancer including non-small cell lung carcer (NSCLC), ovarian cancer, pancreatic cancer, bladder cancer, uterine/cervical cancer, prostate cancer, testicular cancer, esophageal cancer, gastric cancer, gastrointestinal cancer, colon cancer, kidney cancer, head and neck cancer, stomach cancer, germ cell cancer, bone cancer, liver cancer, thyroid cancer, skin cancer, neoplasm of the central nervous system, lymphoma, leukemia, myeloma, sarcoma, or myelodysplastic syndromes. In some aspects, the cancer treatable with the present ADC comprises colorectal cancer (CRC), non-small cell lung cancer (NSCLC), or gastric cancer (GC).

Cancers may be, e.g., metastatic or primary cancers; desmoplastic or non-desmoplastic cancers; or recurrent cancers.

In some aspects, the cancer is associated with fibrosis. In some aspects, the cancer is associated with infiltration of CD4+ regulatory T cells. In some aspects, the cancer is associated with infiltration of CD8+ regulatory T cells. In some aspects, the cancer is associate with infiltration of regulatory B cells. In some aspects, the cancer is associated with infiltration of myeloid-derived suppressor cells. In some aspects, the cancer is associated with infiltration of tumor-associated macrophages. In some aspects, the cancer is associated with infiltration of innate lymphoid cells. In some aspects, the cancer is associated with infiltration of cancer-associated fibroblasts. In some aspects, the cancer is associated with a radiation-related increase in the above cell types.

In some aspects, the ADCs described herein are used to treat myelodysplastic syndromes (MDSs). MDSs are a diverse group of malignant disorders marked by bone marrow failure due to defective hematopoiesis and production of dysplastic cells. TGF-β is a primary driver in MDS (Geyh et al., Haematologica 2018; 103:1462-71) and agents that inhibit the function of TGF-β have been proposed as therapeutics (Mies et al., Curr Hematol Malig Rep 2016; 11:416-24). Furthermore, MDSCs are known to be dysregulated in MDS (Chen et al., JCI 2013; 123:4595-611) and agents that reduce MDSC levels in the bone marrow are potential therapeutics.

In some aspects, the cancer is resistant to checkpoint inhibitor(s). In some aspects, the cancer is intrinsically refractory or resistant (e.g., resistant to a PD-1 pathway inhibitor, PD-1 pathway inhibitor, or CTLA-4 pathway inhibitor). In some aspects, the resistance or refractory state of the cancer is acquired. In some aspects, the ADC described herein can be used in combination with checkpoint inhibitors to overcome resistance of the cancer to the checkpoint inhibitors. In some aspects, the ADC described herein can be used to treat tumors with a mesenchymal and/or EMT signature together with checkpoint inhibitors in combination or sequentially with agents that induce a mesenchymal phenotype, such as MAPK pathway inhibitors.

In some aspects, the ADCs described herein are used to enhance the viability of immune cells ex vivo, e.g., in adoptive NK cell transfer. Accordingly, in some aspects, ADCs are used in combination with adoptively transferred NK cells to treat cancer. In some aspects, the ADC described herein are used to treat tumors with MHC loss or MHC down-regulation, as monotherapy or in combination with NK activating or enhancing treatment.

Combination Therapy

The ADCs described herein can be used in combination with various treatments or agents (or in the context of a multispecific antibody or bifunctional partner) known in the art for the treatment of disease or condition, as described herein.

In some aspects, a method of treating cancer comprises administering to a subject in need thereof an effective amount of an ADC described herein in combination with another therapeutic agent, such as a second antibody, a therapeutic protein or a small molecule drug. In some aspects, the therapeutic protein is a checkpoint inhibitor. In some aspects, the small molecule drug is a chemotherapeutic agent as described herein. In some aspects, the another therapeutic agent comprises an anti-cancer agent.

Suitable anti-cancer agents for use in combination therapy with the ADC described herein include, but are not limited to, surgery, chemotherapeutic agents, growth inhibitory agents, cytotoxic agents, radiotherapy and agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC (Imatinib Mesylate)), COX-2 inhibitors (e.g., celecoxib), interferons, and cytokines; antagonists (e.g., neutralizing antibodies) that bind to and/or neutralize the activity of one or more of the following targets: PD-1, PD-L1, PD-L2 (e.g., pembrolizumab; nivolumab; MK-3475; AMP-224; MPDL3280A; MEDI0680; MSB0010718C; and/or MEDI4736); CTLA4 (e.g., tremelimumab (PFIZER) and ipilimumab); LAG3 (e.g., BMS-986016); CD 103; TIM-3 and/or other TIM family members; anti-VEGF antibodies (e.g., Bevacizumab); CEACAM1, CEACAM6, and/or other CEACAM family members; ErbB2, ErbB3, ErbB4, PDGFR-beta, BlyS, APRIL, BCMA or VEGF receptor(s), TRAIL/Apo2, PARP inhibitors (e.g., AZD-2281, Lynparza OCEACAM5arib, Rubraca Rucaparib; (Zejula) niraparib), DNA damage repair inhibitors (e.g., ATMi, ATRi, DNAPKi), and other bioactive and organic chemical agents, including those described in section VII. Combinations thereof are also specifically contemplated for the methods described herein.

In some aspects, the ADC is administered with an anti-cancer agent, such as an EGFR inhibitor; a HER2 inhibitor; a histone deacetylase inhibitor; a hormone; a mitotic inhibitor; a phosphatidylinositol-3-kinase (PI3K) inhibitor; an Akt inhibitor; a mammalian target of rapamycin (mTOR) inhibitor; a proteasomal inhibitor; a poly(ADP-ribose) polymerase (PARP) inhibitor; a Ras/MAPK pathway inhibitor; a centrosome declustering agent; a multi-kinase inhibitor; a serine/threonine kinase inhibitor; a tyrosine kinase inhibitor; a VEGF/VEGFR inhibitor; a microtubule targeting drug; a topoisomerase poison drug; or a combination thereof.

In some aspects, the ADC is administered along with an immune checkpoint inhibitor. Exemplary immune checkpoint inhibitors include, but are not limited to, agents (e.g., antibodies) that bind to PD-1, PD-L1, PD-L2, LAG-3, CTLA4, TIGIT, ICOS, OX40, PVR, PVRIG, VISTA, TIM3, SIRPa, ILT2, ILT3, ILT4, or ILT5.

Any anti-PD-1 antibody can be used in combination with the ADC in the presently described methods. Various human monoclonal antibodies that bind specifically to PD-1 with high affinity have been disclosed in U.S. Pat. No. 8,008,449.

In some aspects, the anti-PD-1 antibody is pembrolizumab, nivolumab, cemiplimab, spartalizumab, camrelizumab, sintilimab, tislelizumab, toripalimab, dostarlimab, retifanlimab, pimivalimab, dostarlimab, serplulimab, zimberelimab, acrixolimab, MEDI-0680, AM-0001, STI-1110, AGEN2034, BCD-100, sasanlimab, BI 754091, or SSI-361.

In some aspects, the anti-PD-1 antibody used in combination with the ADC comprises the CDRH1, CDRH2, CDRH3, CDRL1, CDRL2, CDRL3, the VH and the VL, and/or the heavy and light chains of any of pembrolizumab, nivolumab, cemiplimab, spartalizumab, camrelizumab, sintilimab, tislelizumab, toripalimab, dostarlimab, retifanlimab, pimivalimab, MEDI-0680, GLS-010, AM-0001, STI-1110, AGEN2034, BCD-100, sasanlimab, BI 754091, or SSI-361.

In some aspects, the anti-PD-1 antibody used in combination with the ADC is selected from the group consisting of nivolumab (OPDIVO®; formerly designated $5C_4$, BMS-936558, MDX-1106, or ONO-4538), pembrolizumab (KEYTRUDA®; formerly designated lambrolizumab and MK-3475; see WO 2008/156712A1), PDR001 (see WO 2015/112900), MEDI-0680 (formerly designated AMP-514; see WO 2012/145493), REGN-2810 see WO 2015/112800), JS001 (see Liu and Wu, 2017), BGB-A317 (see WO 2015/035606 and US 2015/0079109), INCSHR1210 (SHR-1210; see WO 2015/085847; Liu and Wu, 2017), TSR-042 (ANBO11; see WO 2014/179664), GLS-010 (WBP3055; see Liu and Wu, 2017), AM-0001 (see WO 2017/123557), STI-1110 (see WO 2014/194302), AGEN2034 (see WO 2017/040790), and MGD013 (see WO 2017/106061).

In some aspects, the anti-PD-1 antibody used in combination with the ADC is pembrolizumab (Merck; also known as KEYTRUDA®, lambrolizumab, and MK-3475; see, for example, WO 2008/156712). Pembrolizumab is a humanized monoclonal IgG4 (S228P) antibody directed against human cell surface receptor PD-1 (programmed death-1 or programmed cell death-1). Pembrolizumab is described, for example, in U.S. Pat. Nos. 8,354,509 and 8,900,587.

In some aspects, the anti-PD-1 antibody used in combination with the ADC comprises nivolumab (also known as OPDIVO®, 5C4, BMS-936558, MDX-1106, and ONO-4538). Nivolumab is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (see, for example, U.S. Pat. No. 8,008,449; Wang et al., 2014 Cancer Immunol Res. 2(9):846-56).

In some aspects, the anti-PD-1 antibody used in combination with the ADC is cemiplimab (Regeneron; also known as LIBTAYO or REGN-2810; see, for example, WO 2015/112800 and U.S. Pat. No. 9,987,500).

In some aspects, the anti-PD-1 antibody used in combination with the ADC is spartalizumab (Novartis; also known as PDR001; see, for example, WO 2015/112900 and U.S. Pat. No. 9,683,048).

In some aspects, the anti-PD-1 antibody used in combination with the ADC is camrelizumab (Jiangsu Hengrui Medicine; also known as SHR-1210 or INCSHR1210; see, for example, WO 2015/085847; Si-Yang Liu et al., J. Hematol. Oncol. 10:136 (2017)).

In some aspects, the anti-PD-1 antibody used in combination with the ADC is MEDI-0680 (AstraZeneca; also known as AMP-514; see, for example, WO 2012/145493). In some aspects, the anti-PD-1 antibody is pimivalimab (also known as JTX-4014; see, for example, Papadopoulos, et al., 2022, IOTECH, Vol. 16, Supplement 1, 100284). In some aspects, the anti-PD-1 antibody is toripalimab (TAIZHOU JUNSHI PHARMA; also known as JS001; see, for example, Si-Yang Liu et al., J. Hematol. Oncol. 10:136 (2017)). In some aspects, the anti-PD-1 antibody is tislelizumab (Beigene; also known as BGB-A317; see, for example, WO 2015/35606 and US 2015/0079109). In some aspects, the anti-PD-1 antibody is dostarlimab (Tesaro Biopharmaceutical; also known as ANBO11 or TSR-042; see, for example, WO2014/179664). In some aspects, the anti-PD-1 antibody is GLS-010 (Wuxi/Harbin Gloria Pharmaceuticals; also known as WBP3055; see, for example, Si-Yang Liu et al., J. Hematol. Oncol. 10:136 (2017)). In some aspects, the anti-PD-1 antibody is AM-0001 (Armo BioSciences).

In some aspects, the anti-PD-1 antibody is STI-1110 (Sorrento Therapeutics; see, for example, WO 2014/194302). In some aspects, the anti-PD-1 antibody is AGEN2034 (Agenus; see, for example, WO 2017/040790). In some aspects, the anti-PD-1 antibody is retifanlimab (Macrogenics, also known as MGA012, AEX-1188, and INCMGA-00012; see, for example, WO 2017/19846). In some aspects, the anti-PD-1 antibody is BCD-100 (Biocad; see, for example, Kaplon et al., mAbs 10(2):183-203 (2018). In some aspects, the anti-PD-1 antibody is sintilimab (Innovent; also known as IBI308; see, for example, WO 2017/024465, WO 2017/025016, WO 2017/132825, and WO 2017/133540). In some aspects, the anti-PD-1 antibody is sasanlimab (Pfizer; also known as PF-06801591; see, for example, US 2016/0159905). In some aspects, the anti-PD-1 antibody is BI 754091 (Boehringer Ingelheim; see, for example, Zettl M et al., Cancer. Res. (2018); 78(13 Suppl): Abstract 4558). In some aspects, the anti-PD-1 antibody is SSI-361 (Lyvgen Biopharma Holdings Limited, see, for example, US 2018/0346569).

Other anti-PD-1 monoclonal antibodies suitable for the methods of the present disclosure have been described in, for example, U.S. Pat. Nos. 6,808,710, 7,488,802, 8,168,757, 8,354,509, and 9,205,148, US Publication No. 2016/0272708, and PCT Publication Nos. WO 2012/145493, WO 2008/156712, WO 2015/112900, WO 2012/145493, WO 2015/112800, WO 2014/206107, WO 2015/35606, WO 2015/085847, WO 2014/179664, WO 2017/020291, WO 2017/020858, WO 2016/197367, WO 2017/024515, WO 2017/025051, WO 2017/123557, WO 2016/106159, WO 2014/194302, WO 2017/040790, WO 2017/133540, WO 2017/132827, WO 2017/024465, WO 2017/025016, WO 2017/106061, WO 2017/19846, WO 2017/024465, WO 2017/025016, WO 2017/132825, and WO 2017/133540 each of which is incorporated by reference in its entirety.

Examples of anti-PD-L1 antibodies useful in combination with the ADC according to the methods of the present disclosure include the antibodies disclosed in U.S. Pat. No. 9,580,507. In some aspects, the anti-PD-L1 antibody is atezolizumab, durvalumab, avelumab, envafolimab, cosibelimab, BMS-936559, STI-1014, CX-072, LY3300054, FAZ053, CS-1001, SHR-1316, CBT-502, KNO35, or BGB-A333.

In some aspects, the anti-PD-L1 antibody is BMS-936559 (also known as 12A4, MDX-1105; see, e.g., U.S. Pat. No. 7,943,743 and WO 2013/173223).

In some aspects, the anti-PD-L1 antibody is STI-1014 (Sorrento; see, for example, WO 2013/181634). STI-104 is designated H6 in U.S. Pat. No. 9,175,082. In some aspects, the anti-PD-L1 antibody is CX-072 (Cytomx; see, for example, WO 2016/149201). In some aspects, the anti-PD-L1 antibody is LY3300054 (Eli Lilly Co.; see, e.g., WO 2017/034916). In some aspects, the anti-PD-L1 antibody is FAZ053 (Novartis). In some aspects, the anti-PD-L1 antibody is CK-301 (Checkpoint Therapeutics; see, for example, Gorelik et al., AACR:Abstract 4606 (April 2016)). CK-301 is also referred to as cosibelimab. In some aspects, the anti-PD-L1 antibody is CS-1001. See, for example, Zhou et al., Journal of Clinical Oncology, Meeting Abstract, 2020 ASCO Annual Meeting I, Lung Cancer—Non-Small Cell Metastatic, e21687, and Zhang et al., Cancer Research, 2020, 80 (16_Supplement): 3260. In some aspects, the anti-PD-L1 antibody is SHR-1316. See, for example, Mu et al., Thorac Cancer, 2021 May; 12(9):1373-1381, and Wu et al., Anals of Oncology, Abstract, Vol. 33, Supplement 2, S72, April 2022. In some aspects, the anti-PD-L1 antibody is CBT-502 (also known as TQB2450; see, for example, Wei et al., Mol Cancer Ther (2018) 17 (1_Supplement): A200). In some aspects, the anti-PD-L1 antibody is KN035 (3D Med/Alphamab; also referred to as envafolimab; see, for example, Zhang et al., Cell Discov. 7:3 (March 2017) and Shimizu et al., Invest New Drugs, 2022 October; 40(5): 1021-1031).

In some aspects, the anti-PD-L1 antibody is BGB-A333 (BeiGene; see, for example, Desai et al., JCO 36 (15suppl): TPS3113 (2018) and Desai et al., 2023, British Journal of Cancer 128, 1418-1428). In certain aspects, the PD-L1 antibody is atezolizumab. Atezolizumab is a fully humanized IgG1 monoclonal anti-PD-L1 antibody. Atezolizumab (Roche) is also known as TECENTRIQ®; MPDL3280A, RG7446. See, for example, U.S. Pat. No. 8,217,149 and Herbst et al. (2013) J. Clin. Oncol. 31 (suppl):3000). Atezolizumab is designated YW243.55570 in U.S. Pat. No. 8,217,149. In certain aspects, the PD-L1 antibody is durvalumab. Durvalumab is a human IgG1 kappa monoclonal anti-PD-L1 antibody. Durvalumab (AstraZeneca) is also known as IMIFINZI® or MEDI-4736. Durvalumab is designated 2.14H90PT in U.S. Pat. No. 8,779,108. See, for example, WO 2011/066389. In certain aspects, the PD-L1 antibody is avelumab. Avelumab is a human IgG1 lambda monoclonal anti-PD-L1 antibody. Avelumab (Pfizer) is also known as BAVENCIO® or MSB0010718C. Avelumab is designated A09-246-2 in U.S. Pat. No. 9,624,298. See, for example, WO 2013/079174.

In some aspects, the anti-CTLA-4 antibody useful in combination with the ADC is tremelimumab, ipilimumab, botensilimab, BMS-986218, BMS-986288, BMS-986249, IBI310, MK-1308 (quavonlimab), AGEN-1884 (zalifrelimab), ONC-392, ADG116, or CS1002.

In some aspects, the anti-CTLA-4 antibody useful in combination with the ADC is MK-1308. MK-1308 is also known as quavonlimab. See, for example, Perets et al. 2021, Ann Oncol 32(3):395-403.

In some aspects, the anti-CTLA-4 antibody useful in combination with the ADC is AGEN-1884. AGEN-1884 is also known as zalifrelimab. See, for example, WO 2016/196237.

In some aspects, the anti-CTLA-4 antibody useful in combination with the ADC is tremelimumab. Tremelimumab, sold under the brand name IMJUDO®, is a fully human monoclonal antibody used for the treatment of hepatocellular carcinoma and non-small cell lung cancer. Tremelimumab (AstraZeneca) is also known as ticilimumab, CP-675,206; see WO 2000/037504 and Ribas, Update Cancer Ther. 2(3): 133-39 (2007)).

In some aspects, the anti-CTLA-4 antibody useful in combination with the ADC is ipilimumab. Ipilimumab (sold under the brand name YERVOY®, which was first approved for the treatment of metastatic melanoma, has since been approved for use in other cancers. Hoos et al. (2010) Semin. Oncol. 37:533; Hodi et al. (2010) N. Engl. J. Med. 363:711; Pardoll (2012) Nat. Immunol. 13(12):1129. In 2011, ipilimumab is a human antibody, which has an IgG1 constant region, was approved in the US and EU for the treatment of unresectable or metastatic melanoma based on an improvement in overall survival in a phase III trial of previously treated patients with advanced melanoma. Hodi et al. (2010) N. Engl. J. Med. 363:711. Tumor regressions and disease stabilization were frequently observed. Ipilimumab is also known as MDX-010 and 10D1. See U.S. Pat. No. 6,984,720.

In some aspects, the anti-CTLA-4 antibody is an activatable anti-CTLA-4 antibody, such as an activatable anti-CTLA-4 antibody wherein the light chains of the antibody comprise a cleavable moiety and a masking moiety at the amino termini. The masking moiety interferes with binding to CTLA-4, but is preferentially released in the tumor microenvironment after cleavage of the cleavable moiety by proteases that are more prevalent and/or active in tumors than in peripheral tissues (see, in particular, WO 2018/085555). Such preferential cleavage in the tumor microenvironment enables full CTLA-4 blocking, promoting anti-tumor immune response, while minimizing CTLA-4 blockade in normal tissue, thereby reducing the risk of potential systemic toxicity of an anti-CTLA-4 antibody. In some aspects, the activatable anti-CTLA-4 antibody is an activatable form of ipilimumab, such as an antibody comprising light chains modified to comprise a masking moiety and a cleavable moiety, as disclosed, for example, in WO 2018/085555. An example of an activatable anti-CTLA-4 antibody that has entered human clinical trials is BMS-986249 (NCT03369223: "A Study of BMS-986249 Alone and in Combination with Nivolumab in Advanced Solid Tumors"). In some aspects, the anti-CTLA-4 antibody is BMS-986249.

In some aspects, the anti-CTLA-4 antibody shows an enhanced Fcγ receptor (CD16) binding. Whether an anti-CTLA-4 antibody shows an enhanced Fcγ receptor binding is assessed by comparison with the Fcγ receptor binding of ipilimumab. Anti-CTLA-4 antibodies with enhanced Fcγ receptor (CD16) binding have been proposed as therapeutic agents for treatment of cancer through depletion of Treg cells. See, in particular, WO 2014/089113. In some aspects, the anti-CTLA-4 antibody shows an Fcγ receptor (CD16) binding that is at least two-fold enhanced when compared to the Fcγ receptor binding of ipilimumab.

Examples of anti-CTLA-4 antibodies that show enhanced Fc receptor (i.e., FcγRIIIA or CD16) binding are nonfucosylated anti-CTLA-4 antibodies. In some aspects, the anti-CTLA-4 antibody is a nonfucosylated anti-CTLA-4 antibody. Non-fucosylated anti-CTLA-4 antibodies lack fucose residues in its N-linked glycans. In some aspects, the nonfucosylated anti-CTLA-4 antibody is produced by expressing the chains of the antibody in a mammalian cell under conditions that prevent fucosylation, including but not limited to use of mammalian cells with genetic modifications preventing fucosylation, or growth of the cells expressing the antibody in medium containing one or more chemical compounds that inhibit fucosylation. In some aspects, the genetic modification that prevents fucosylation is inactivation, e.g. knock-out, of the FUT8 gene. In some aspects, the anti-CTLA-4 antibody is a hypofucosylated anti-CTLA-4 antibody.

An exemplary nonfucosylated anti-CTLA-4 antibody that has entered human clinical trials is BMS-986218 (e.g., NCT03110107: "First-In-Human Study of Monoclonal Antibody BMS-986218 by Itself and in Combination with Nivolumab in Participants with Advanced Solid Tumors"). BMS-986218 is a nonfucosylated antibody developed to increase the effects of CTLA-4 blockade by enhancing binding to Fcγ receptor, thus promoting APC-mediated T cell priming. In some aspects, the anti-CTLA-4 antibody is BMS-986218. See, for example, PCT/US18/19868.

In some aspects, the Fc region of the anti-CTLA-4 antibody contains amino acid substitutions in the antibody constant region to enhance binding to activating Fcγ receptors. Exemplary substitutions are G236A, S239D, A330L and 1332E (all residue numbering per the EU numbering system). In some aspects, the anti-CTLA-4 antibody comprises a human IgG1 constant domain with S239D, A330L and 1332E mutations.

In some aspects, the anti-CTLA-4 antibody is an activatable and nonfucosylated anti-CTLA-4 antibody.

Human monoclonal antibodies that bind specifically to CTLA-4 with high affinity that are suitable for the methods of the present disclosure have been disclosed in U.S. Pat. No. 6,984,720. Other anti-CTLA-4 monoclonal antibodies have been described in, for example, U.S. Pat. Nos. 5,977,318, 6,051,227, 6,682,736, and 7,034,121 and International Publication Nos. WO 2012/122444, WO 2007/113648, WO 2016/196237, and WO 2000/037504, each of which is incorporated by reference herein in its entirety.

In some aspects, the anti-LAG-3 antibody useful in combination with the CEACAM5 targeting agent according to the methods of the present disclosure is relatlimab (BMS-986016), IMP731 (H5L7BW), MK4280 (28G-10, favezelimab), REGN3767 (fianlimab), GSK2831781, humanized BAP050, IMIP-701 (LAG525, ieramilimab), aLAG-3 (0414), aLAG-3(0416), Sym022, TSR-033, TSR-075, XmAb841 (XmAb22841), MGD013 (tebotelimab), B1754111, FS118, P 13B02-30, AVA-017, 25F7, AGEN1746, R07247669, INCAGN02385, 1131-110, EMB-02, IBI-323, LBL-007, or ABL501.

In some aspects, the anti-LAG-3 antibody useful in combination with the CEACAM5 targeting agent comprises the CDRH1, CDRH2, CDRH3, CDRL1, CDRL2, CDRL3, the VH and the VL, and/or the heavy and light chains of any of relatlimab (BMS-986016), IMIP731 (H5L7BW), MK4280 (28G-10, favezelimab), REGN3767 (fianlimab), GSK2831781, humanized BAP050, IMIP-701 (LAG525, ieramilimab), aLAG-3(0414), aLAG-3(0416), Sym022, TSR-033, TSR-075, XmAb841 (XmAb22841), MGD013 (tebotelimab), BI754111, FS118, P 13B02-30, AVA-017, 25F7, AGEN1746, R07247669, INCAGNO2385, IBI-110, EMB-02, IBI-323, LBL-007, or ABL501.

In some aspects, the anti-LAG-3 antibody useful in combination with the ADC comprises relatlimab (BMS-986016). In some aspects, the anti-LAG-3 antibody comprises IMP731 (H5L7BW). In some aspects, the anti-LAG-3 antibody comprises MK4280 (28G-10, favezelimab). MK-4280 (28G-10, favezelimab) described in WO2016028672 and U.S. Publication No. 2020/0055938. In some aspects, the anti-LAG-3 antibody comprises REGN3767 (fianlimab). REGN3767 (fianlimab) is described, for example, in Burova E, et al., J. Immunother. Cancer (2016); 4(Supp. 1):P195 and U.S. Pat. No. 10,358,495. In some aspects, the anti-LAG-3 antibody comprises GSK2831781. In some aspects, the anti-LAG-3 antibody comprises humanized BAP050. Humanized BAP050 is described, for example, in WO2017/019894. In some aspects, the anti-LAG-3 antibody comprises IMP-701 (LAG525, ieramilimab) IMP-701 (LAG525; ieramilimab) is described, for example, in U.S. Pat. No. 10,711,060 and U.S. Publ. No. 2020/0172617. In some aspects, the anti-LAG-3 antibody comprises aLAG-3 (0414). In some aspects, the anti-LAG-3 antibody comprises aLAG-3(0416). In some aspects, the anti-LAG-3 antibody comprises Sym022. In some aspects, the anti-LAG-3 antibody comprises TSR-033. In some aspects, the anti-LAG-3 antibody comprises TSR-075. In some aspects, the anti-LAG-3 antibody comprises XmAb841 (XmAb22841). In some aspects, the anti-LAG-3 antibody comprises MGD013 (tebotelimab). In some aspects, the anti-LAG-3 antibody comprises B1754111. In some aspects, the anti-LAG-3 antibody comprises FS118. In some aspects, the anti-LAG-3 antibody comprises P 13B02-30. In some aspects, the anti-LAG-3 antibody comprises AVA-017. In some aspects, the anti-LAG-3 antibody comprises 25F7. 25F7 is described, for example, in U.S. Publ. No. 2011/0150892. In some aspects, the anti-LAG-3 antibody comprises AGEN1746. In some aspects, the anti-LAG-3 antibody comprises R07247669. In some aspects, the anti-LAG-3 antibody comprises INCAGNO2385. In some aspects, the anti-LAG-3 antibody comprises IBI-110. In some aspects, the anti-LAG-3 antibody comprises EMB-02. In some aspects, the anti-LAG-3 comprises IBI-323. In some aspects, the anti-LAG-3 antibody comprises LBL-007. In some aspects, the anti-LAG-3 antibody comprises ABL501.

In general, any anti-LAG-3 antibody useful in combination with the ADC can be used. Antibodies that bind to LAG-3 have been disclosed in Int'l Publ. No. WO/2015/042246 and U.S. Publ. Nos. 2014/0093511 and 2011/0150892, each of which is incorporated by reference herein in its entirety. Disclosure relating to the anti-LAG-3 antibodies described herein and other anti-LAG-3 antibodies useful in the methods of the present disclosure can be found in, for example: U.S. Pat. No. 10,188,730, WO 2016/028672, WO 2017/106129, WO2017/062888, WO2009/044273, WO2018/069500, WO2016/126858, WO2014/179664, WO2016/200782, WO2015/200119, WO2017/019846, WO2017/198741, WO2017/220555, WO2017/220569, WO2018/071500, WO2017/015560, WO2017/025498, WO2017/087589, WO2017/087901, WO2018/083087, WO2017/149143, WO2017/219995, US2017/0260271, WO2017/086367, WO2017/086419, WO2018/034227, WO2018/185046, WO2018/185043, WO2018/217940, WO19/011306, WO2018/208868, WO2014/140180, WO2018/201096, WO2018/204374, and WO2019/018730. The contents of each of these references are incorporated by reference in their entirety.

Several experimental treatment protocols involve ex vivo activation and expansion of antigen specific T cells and adoptive transfer of these cells into recipients in order to generate antigen-specific T cells against tumors. Ex vivo activation in the presence of the anti-CEACAM5 antibodies described herein with or without an additional immunostimulating therapy (e.g., an immune checkpoint inhibitor) can be expected to increase the frequency and activity of the adoptively transferred T cells.

In some aspects, the ADC described herein may also be administered with a standard of care treatment, or another treatment, such as radiation, surgery, or chemotherapy. The ADC may be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

V. Kits

Also provided are kits comprising an ADC described herein and instructions for use.

In some aspects, the kits comprise the ADC in unit dosage form, such as in a single dose vial or a single dose pre-loaded syringe, optionally contained in a single vial or container, along with e.g., instructions for use in treating a cancer using the ADC as described herein.

The present disclosure is further illustrated by the following examples, which should not be construed as further limiting. The contents of all figures and all references, Genbank sequences, issued patents, and published patent applications cited throughout this disclosure are expressly incorporated herein by reference.

EXAMPLES

Commercially available reagents referred to in the Examples below were used according to manufacturer's instructions unless otherwise indicated. Unless otherwise noted, the present disclosure uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture,* 1987; Coligan et al., *Current Protocols in Immunology,* 1991.

The following Examples describe the isolation and characterization of anti-CEACAM5 monoclonal antibodies. The CDR sequences, variable region sequences, and full-length heavy and light chain sequences of anti-CEACAM5 antibodies are provided below, for example, in Table 10.

Example 1: Generation of Anti-CEACAM5 Antibodies

Human anti-CEACAM5 monoclonal antibodies (mAbs) were generated by immunizing BMS proprietary chimeric mouse strains. Hybridomas were generated. Positive human and cynomolgus CEACAM5 cross-reactive binders (not recognizing either human CEACAM1 protein or human CEACAM6 protein) were selected. A single B cell cloning (SBC) approach was additionally utilized to isolate CEACAM5 mAbs from the mice immunized as described above. Immune libraries were also generated from the mouse B cells. The libraries were expressed by yeast display and selected against CEACAM5 to identify additional human/cynomolgus cross reactive antibodies that demonstrated specificity over CEACAM1 and CEACAM6.

The VH and VL regions from the positive human CEACAM5 mAbs identified above were sequenced by NGS using a MiSeq sequencing system (Illumina). Approximately 380 sequence-unique clones binding either human or cynomolgus CEACAM5 were identified, comprising 173 sequence families (as defined by 80% sequence homology in HCDR3). Of these CEACAM5 positive sequences, 188 antibodies (57 sequence families) were shown to bind both human and cynomolgus CEACAM5 expressed on HCT116 cells (as described below), and 75 clones (31 sequences families) demonstrated specificity over CEACAM1 and CEACAM6. Further characterization (as described herein) led to the isolation of multiple antibodies including MBN001. The amino acid sequences of the VH and VL CDRs are provided in Table 10.

Example 2: Epitope Binning

High throughput SPR-based epitope binning sandwich assays were performed using the Carterra LSA Platform to group the anti-CEACAM5 mAbs into bins sharing common binding epitopes. Pairwise competition experiments were performed by high-throughput Carterra SPR microfluidics under a classic sandwich format using a microarray-based 96×96 microfluidic system array. Binning results were analyzed using Carterra microfluidics' binning software for heat map generation and network plotting. The competing antibody relationships allow for the anti-CEACAM5 antibodies to be clustered into bins, where a bin represents a family of anti-CEACAM5 antibodies sharing an identical blocking profile when tested against the other anti-CEACAM5 antibodies. See FIG. 1A. Based on the assay results, the newly generated antibodies binned to 7 distinct epitope groups. MBN001 mAb was identified as being a Bin 1 binder of CEACAM5. Cross-reactivity to other CEACAM5 family members, including CEACAM1 and CEACAM6 were determined by SPR as described above, and epitope bins 4, 6, 7 and 8 were determined to cross-react with CEACAM1 and CEACAM6. See FIG. 1B.

Example 3: Binding Specificity of Anti-CEACAM5 Antibodies in Cell Lines Expressing CEACAM5

Figure 2A:
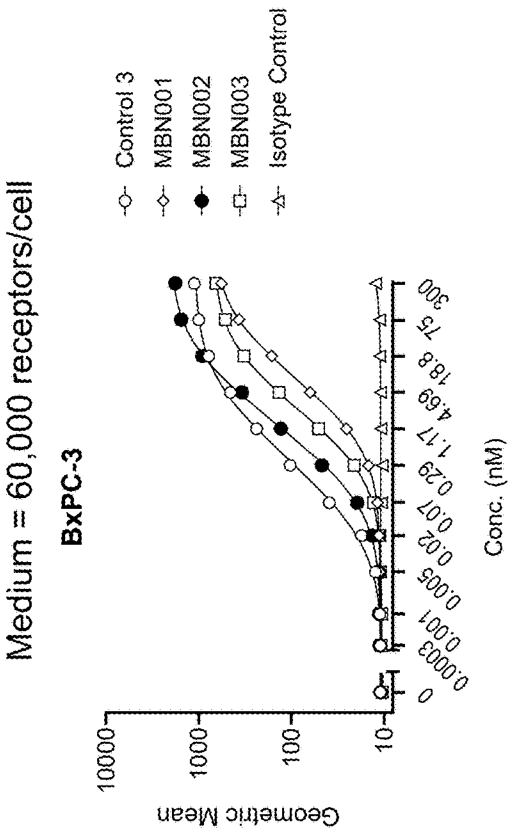
Figure 2B:
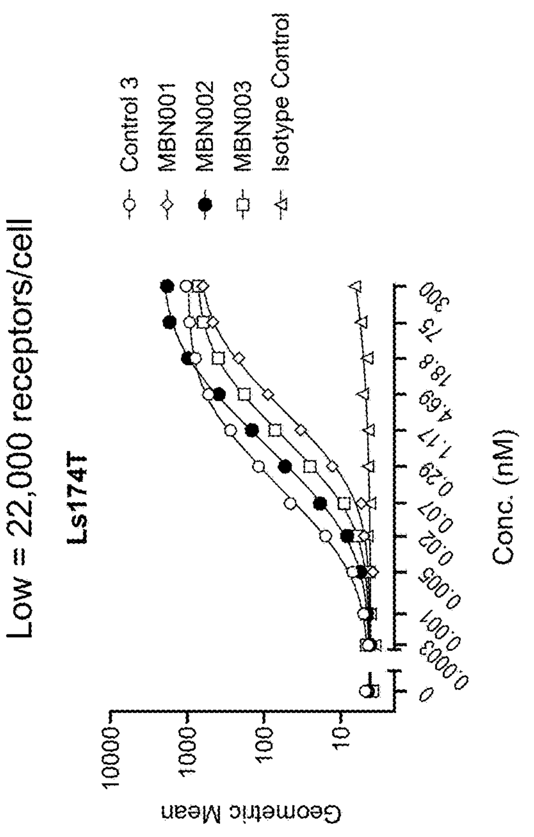
Figure 2C:
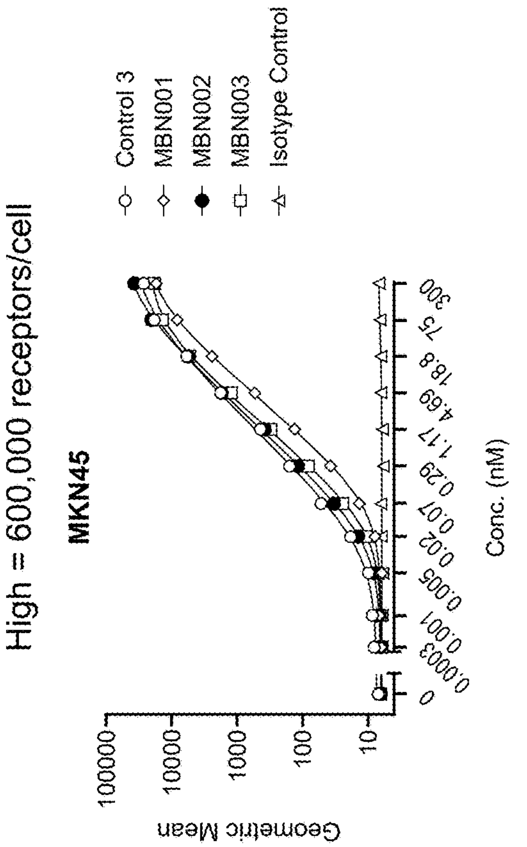
Figure 2D:
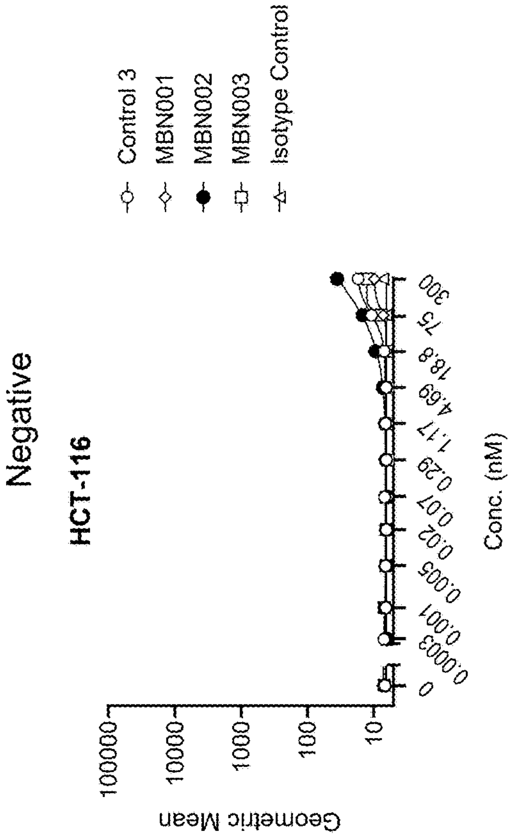

This Example analyzed the cell binding specificity of the anti-human CEACAM5 mAbs (e.g., MBN001, MBN002, and MBN003) described in Example 6. FIG. 2A, FIG. 2B, FIG. 2C and FIG. 2D are a set of graphs showing cell-based binding of antibodies against cell lines expressing different levels of human CEACAM5: medium BXPC-3 (FIG. 2A), low Ls174T cells (FIG. 2B), high MKN45 (FIG. 2C), and negative HCT-116 (FIG. 2D). Each of the tested antibodies (mAb MBN001, mAb MBN002, and mAb MBN003) bound the cells expressing human CEACAM5 comparable to mAb Control 3. Each of the mAbs was further evaluated for binding specificity using human colorectal carcinoma cell lines (HCT-116) or CHOS cell lines overexpressing human CEACAM5, cynomolgus CEACAM5, human CEACAM1 and human CEACAM6. As shown in Table 2, the antibody MBN001 exhibited specific binding to human CEACAM5 and cynomolgus CEACAM5, but not to human CEACAM1 or CEACAM6.

TABLE 2

Specificity of binding of anti-CEACAM5 mAbs to human and cynomolgus CEACM5- and/or CEACAM6-expressing cell lines.

| mAb | HCT116-parental single-point MFI (Mean) | HCT116-huCEACAM5 single-point MFI (Mean) | HCT116-cyCEACAM5 single-point MFI (Mean) | HCT116-huCEACAM6 single-point MFI (Mean) | CHO-S-huCEACAM1 single-point MFI (Mean) |
|---|---|---|---|---|---|
| MBN001 | 32.8 | 12758 | 8348 | 29.5 | 41.9 |

CEACAM5 mAbs such as MBN002, MBP018, MBP003, MBP001 and MBP002 were examined for binding to human CEACAM7 (R&D Systems catalog #9010-CM-050) by SPR using CEACAM7 mAb (R&D Systems catalog #MAB44782) as a positive control. No binding was observed for the CEACAM5 mAbs (data not shown). The CEACAM5 mAbs were similarly examined for binding to human CEACAM8 (R&D Systems catalog #9639-CM-050). Commercial CEACAM8 mAb (R&D Systems catalog #MAB4246) showed binding to CEACAM8 but no binding was observed for the CEACAM5 mAbs (data not shown).

Example 4: Binding Kinetics of Anti-CEACAM5 Antibodies

Analytical binding studies were carried out by surface plasmon resonance (SPR) to characterize the binding kinetics of selected anti-CEACAM5 antibody MBN001 to full-length human CEACAM5 and cynomolgus CEACAM5 and to the A3-B3 regions of human CEACAM5 and cynomolgus CEACAM5 (all internally generated proteins).

SPR analyses were conducted at 37° C. using a Biacore 8K instrument primed with 1×HBSP+ running water and docked with a CM5 sensor chip equilibrated to room temperature, followed by re-priming of the instrument. The chip surface was activated by injecting an ethyl(dimethylaminopropyl) carbodiimide (EDC)/N-hydroxysuccinimide (NHS) mixture for 7 minutes at 10 μL/min. The activated chip surface was then immobilized with an anti-human Fc capture reagent (at 25 μg/mL in acetate pH 5 buffer) injected on the chip surface for 7 minutes at 10 μL/min to yield an immobilization level of about 9000 RU. The remaining chip surface was blocked by injecting ethanolamine for 7 minutes at 10 μL/min.2

To analyze the kinetics of antibody binding, anti-CEACAM5 antibody (10 nm in HBSP+ buffer) was first captured onto the chip for 20 seconds at 10 μL/min for binding to the Fc capture reagent, followed by CEACAM5 analyte binding in which each of a series of recombinant full-length CEACAM5 or A3-B3 CEACAM5 proteins diluted 3× from 500 nM to 0.23 nM in HBSP+ buffer was flowed across the chip The analyte association time was 3 minutes at 30 μL/min; the antigen dissociation time was 10 minutes at 30 μl/min; and regeneration involved two injections of 3M magnesium chloride ($MgCl_2$) for 30 seconds at 30 μL/min.

The kinetic data for anti-CEACAM5 mAb:CEACAM5 binding were fit to a 1:1 Langmuir binding with Rmax to provide estimates of the kinetic and affinity values for the corresponding interactions. Estimates of the binding kinetics and affinities for the selected antibody to full length CEACAM5 (hu/cy) and A3-B3 regions of CEACAM5 (hu/cy) are shown in Tables 3-6.

TABLE 3

Kinetics of anti-CEACAM5 mAb binding to full-length huCEACAM5.

| mAb | Full-length huCEACAM5 ka (1/Ms) | Full-length huCEACAM5 kd (1/s) | Full-length huCEACAM5 $K_D$ (M) | Full-length huCEACAM5 % Rmax |
|---|---|---|---|---|
| MBN001 | 6.86E+04 | 6.15E−03 | 8.96E−08 | 98 |

TABLE 4

Kinetics of anti-CEACAM5 mAb binding to full-length cyCEACAM5.

| mAb | Full-length cyCEACAM5 ka (1/Ms) | Full-length cyCEACAM5 kd (1/s) | Full-length cyCEACAM5 KD (M) | Full-length cyCEACAM5 % Rmax |
|---|---|---|---|---|
| MBN001 | 1.91E+04 | 1.19E−02 | 6.21E−07 | 23 |

TABLE 5

Kinetics of anti-CEACAM5 mAb binding to A3-B3 huCEACAM5.

| mAb | A3-B3 huCEACAM5 ka (1/Ms) | A3B3 huCEACAM5 kd (1/s) | A3-B3 huCEACAM5 KD (M) | A3-B3 huCEACAM 5% Rmax |
|---|---|---|---|---|
| MBN001 | 6.31E+04 | 8.12E−03 | 1.29E−07 | 84 |

TABLE 6

Kinetics of anti-CEACAM5 mAb antibody binding to A3-B3 cyCEACAM5.

| mAb | A3-B3 cyCEACAM5 ka (1/Ms) | A3-B3 cyCEACAM5 kd (1/s) | A3-B3 cyCEACAM5 KD (M) | A3-B3 cyCEACAM5 % Rmax |
|---|---|---|---|---|
| MBN001 | 3.43E+04 | 2.49E−02 | 7.26E−07 | 24 |

Example 5: In Vitro Binding of Anti-CEACAM5 Antibodies in CEACAM5-Expressing Cell Lines Selected anti-CEACAM5 antibody MBN001 was evaluated for binding to the CEACAM5-expressing cell lines MKN45, HCT116-huCEACAM5, and HCT116-cyCEACAM5, along with the HCT-116 parent control. The results of these experiments are shown in Table 7 (EC50 values) and Table 8 (Amax values).

TABLE 7

| EC50 values for selected anti-CEACAM5 mAb | | | | |
|---|---|---|---|---|
| mAb | EC50 MKN45 (nM) | EC50 HCT-116 huCEACAM5 (nM) | EC50 HCT-116 cyCECAM5 (nM) | EC50 HCT-116 (nM) |
| MBN001 | 33.8 | 3.33 | 82.2 | Weak |
| Control #1 | 63.73 | ND | 82.02 | Weak |
| Control #2 | 5.74 | 5.47 | 14.51 | Weak |

TABLE 8

| Amax values for selected anti-CEACAM5 mAb | | | | |
|---|---|---|---|---|
| mAb | Amax MKN45 (MFI) | Amax HCT-116 huCEACAM5 (MFI) | Amax HCT-116 cyCECAM5 (MFI) | Amax HCT-116 (MFI) |
| MBN001 | 4159 | 6793 | 25518 | 43.9 |

Data show that the MBN001 bound both huCEACAM5 expressing lines and cynoCEACAM-5 expressing lines. Furthermore, MBN001 had improved cellular binding compared to control antibodies.

Example 6: Screening of Anti-CEACAM5 mAbs Capable of Internalizing into Cells Anti-CEACAM5 mAbs were screened for their ability to internalize into huCEACAM5-expressing cells. The internalization assay utilized the MKN-45 cell line, the HCT116-huCEACAM5 cell line, the parental HCT-116 control cell line and the LS174T cell line. The internalization assay was performed in 96-well plates using the IncuCyte S3 Live-Cell Analysis System. Plates were scanned for phase contrast and red fluorescence and images were automatically analyzed using the integrated INCUCYTE® software for phase confluence (measure of cell area) and red fluorescence object area. As the labeled antibodies internalize into the acidic environment of endosomes and lysosomes, the intensity of red fluorescence inside the cells increases. The internalization signals are represented as red fluorescence object areas normalized to the total cell areas (phase confluence).

Briefly, a number ($1\times10^4$) of viable cells from the MKN-45, HCT116-huCEACAM5, LS174T and HCT-116 parental cell lines were added to 96-well plates and incubated at 37° C./5% $CO_2$ for about four hours prior to adding the antibody treatments. Antibody treatments were prepared by combining test antibodies or isotype control antibodies with PHRODO™ red secondary Fab reagent (ThermoFisher Scientific) to provide final concentrations of test antibodies (25 nM) to pHrodo reagent (75 nM) following addition to the cells. Following an incubation at 37° C. for 30 minutes, 50 µl of each antibody treatment was added to 50 µl of cells in 96-well plates. The plates were then inserted in the INCUCYTE® system and further incubated at 37° C. for 30 minutes prior to the reading by the IncuCyte detection machine. The IncuCyte settings were set to a 24-hour duration with reads every 30 minutes, a 10× objective with 3 images/well, and with both phase and red fluorescent channels.

Table 9 shows a quantitative assessment of the internalization of the antibodies MBN001, MBN002 and MBN003 as described herein and as measured by an area under time-course (AUC) analysis. Internalization data were collected for selected antibodies in the MKN45, LS 174T and HCT 116-CEACAM5 cell lines. The data show the tested antibodies were internalized into the test cell lines and that in many cases the antibodies had improved, or comparable internalization compared to the control antibodies.

Figure 3A:
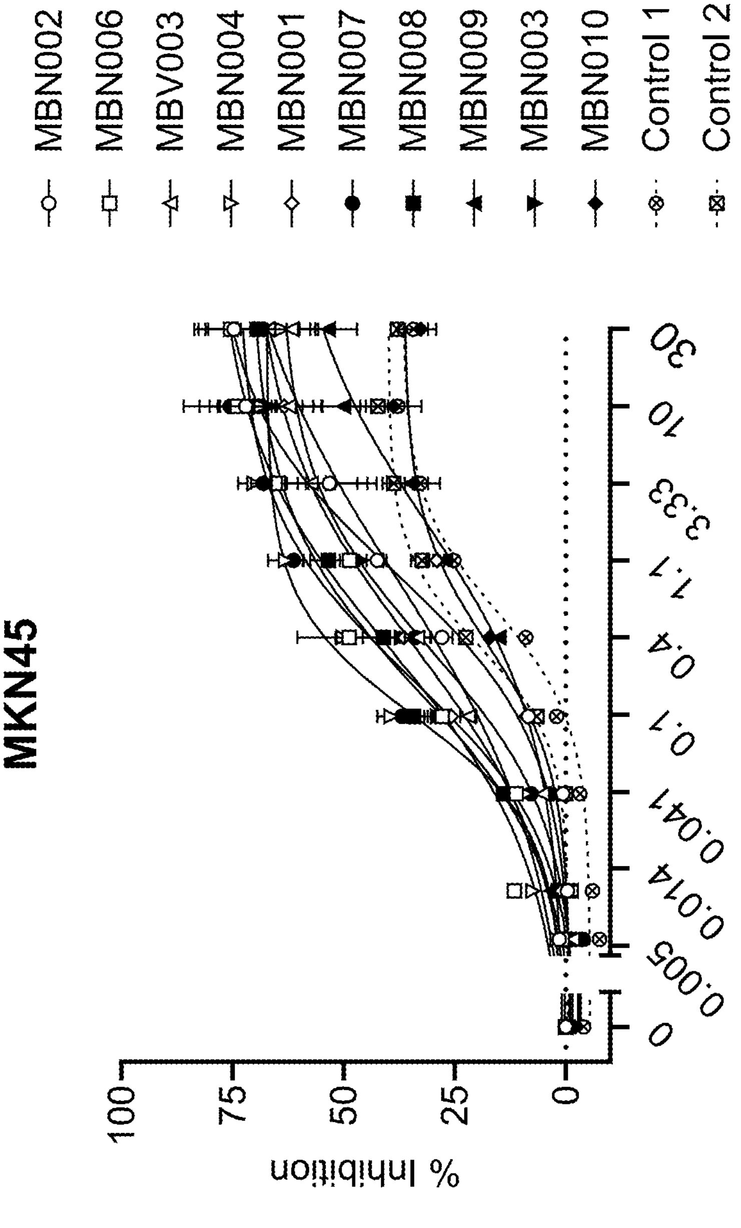
Figure 3B:
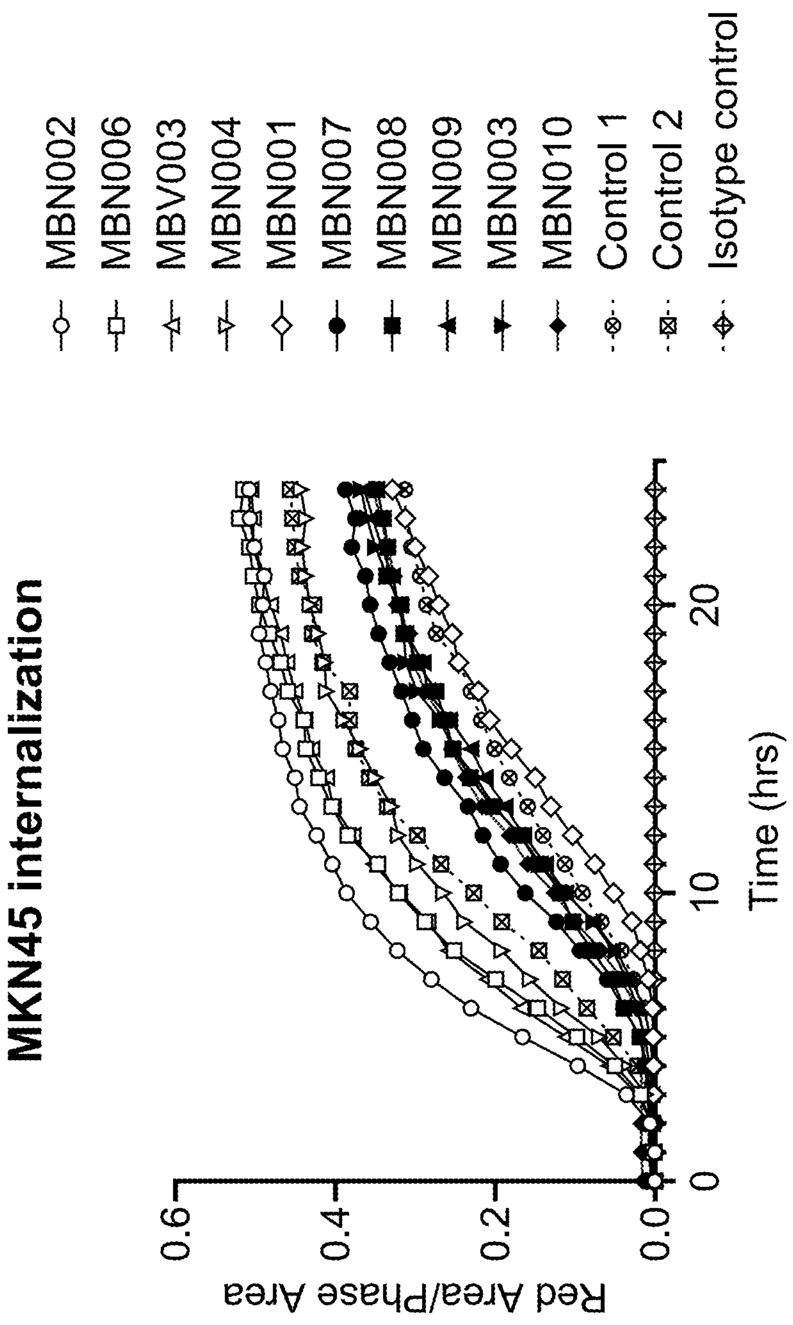
Figure 3C:
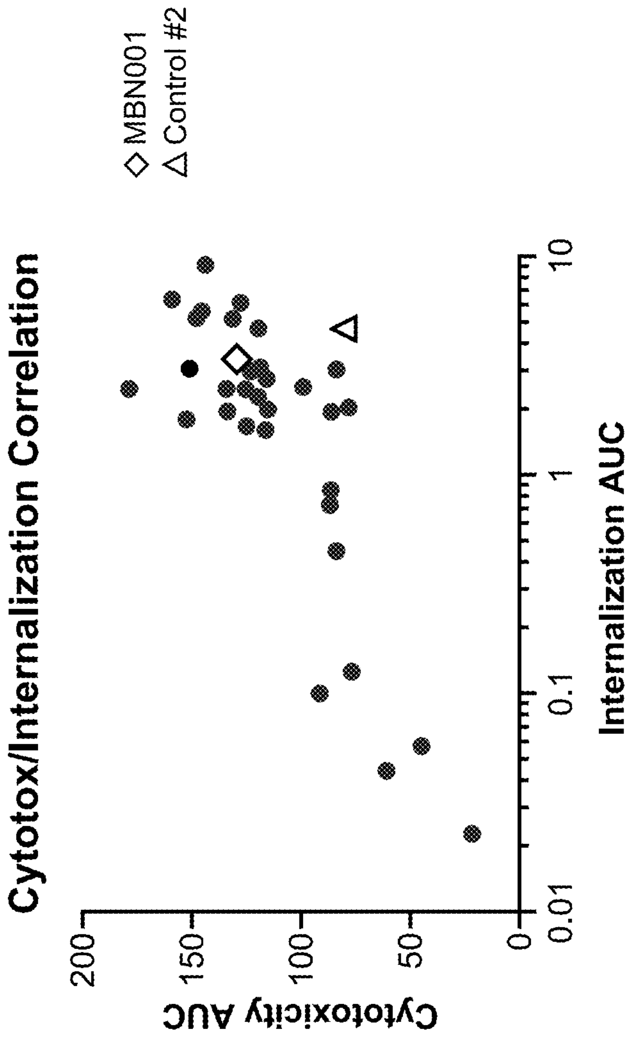
Figure 4A:
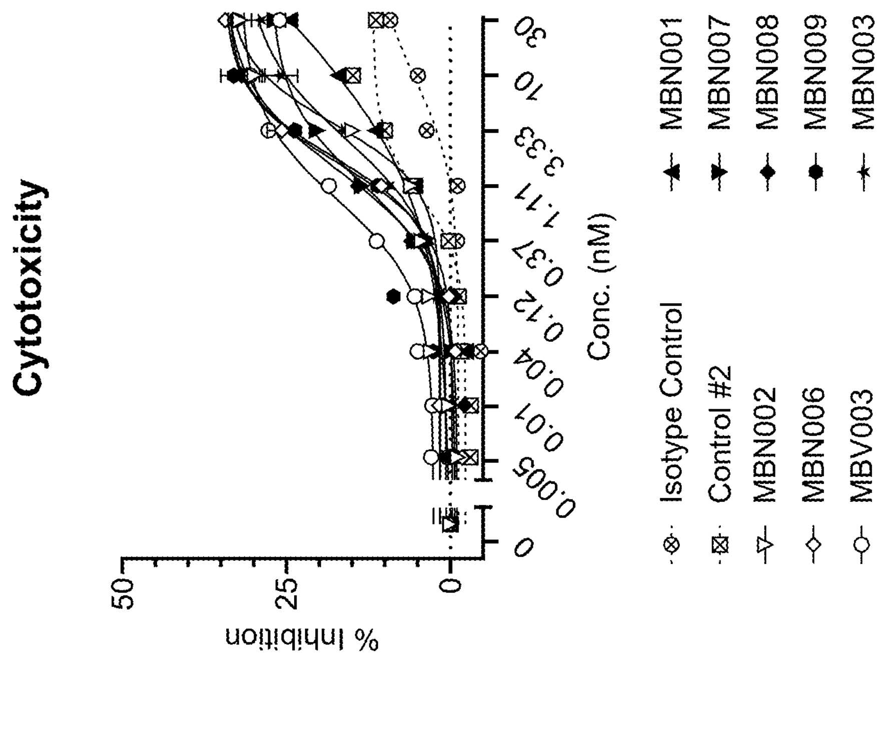
Figure 4B:
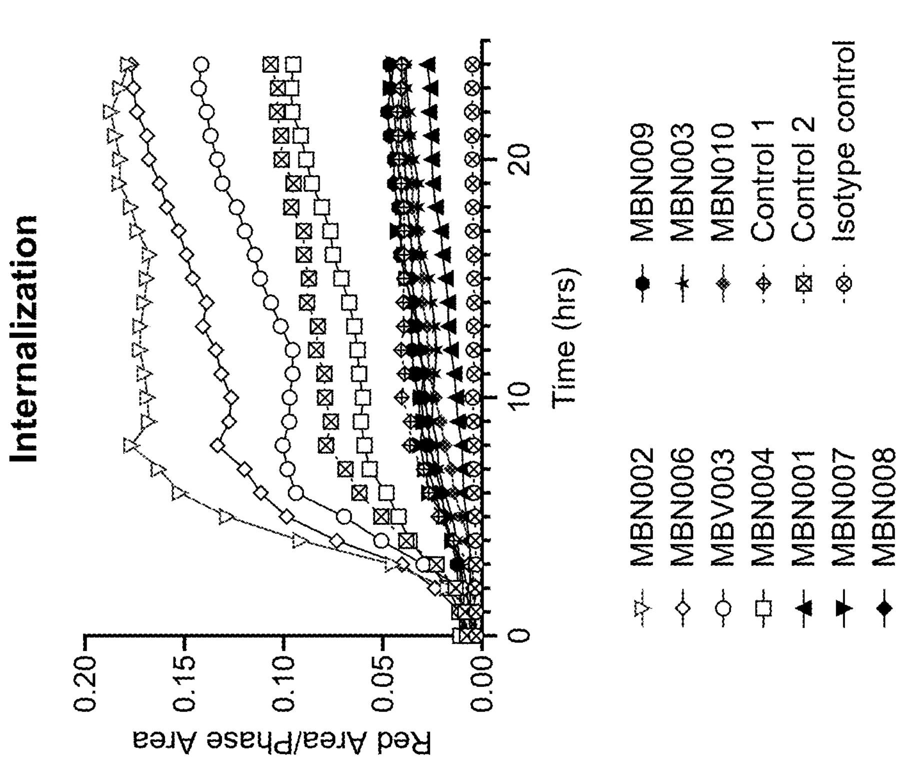

Additional assays were run and data show that MBN001 was effectively internalized by different CEACAM5-expressing cells (FIG. 3B and FIG. 4B). To facilitate high throughput cytotoxicity screening, MMAE, a microtubule inhibitor, was conjugated to a VHH, a targeting agent for human kappa light chain. Data show that the MBN001-VHH complex had the ability to be internalized by the CEACAM5-expressing cells and effectively delivered the cytotoxic agent to kill the CEACAM5-expressing cells. See FIG. 3A, FIG. 3C, and FIG. 4A.

TABLE 9

| Internalization of antibodies into HCT-116-huCEACAM5 and MKN-45 cell lines. | | |
|---|---|---|
| Antibody | HCT 116 CEACAM5 (AUC) | MKN-45 (AUC) |
| Control-1 | 2.232 | 4.668 |
| Control-2 | 0.8051 | 1.952 |
| Unstained | 0.00174 | 0.04971 |
| hIgG1.3f isotype | 0.004163 | 0.01135 |
| Secondary-only | 0.005398 | 0.01089 |

TABLE 10

| Summary table of amino acid sequences and nucleic acid sequences | | |
|---|---|---|
| Description | Amino acid Sequence or nucleic acid sequence | SEQ ID NO. |
| *H. sapiens* CEACAM5 amino acid sequence GenBank: AAH34671.1 | MESPSAPPHRWCIPWORLLLTASLLTFWNPPTTAKLTIESTPFNVAEGKEVLL<br>LVHNLPQHLFGYSWYKGERVDGNRQIIGYVIGTQQATPGPAYSGREIIYPNAS<br>LLIQNIIQNDTGFYTLHVIKSDLVNEEATGQFRVYPELPKPSISSNNSKPVED<br>KDAVAFTCEPETQDATYLWWVNNQSLPVSPRLQLSNGNRTLTLFNVTRNDSAS<br>YKCETQNPVSARRSDSVILNVLYGPDAPTISPLNTSYRSGENLNLSCHAASNP<br>PAQYSWFVNGTFQQSTQELFIPNITVNNSGSYTCQAHNSDTGLNRTTVTTITV<br>YAEPPKPFITSNNSNPVEDEDAVALTCEPEIQNTTYLWWVNNQSLPVSPRLQL<br>SNDNRTLTLLSVTRNDVGPYECGIQNELSVDHSDPVILNVLYGPDDPTISPSY<br>TYYRPGVNLSLSCHAASNPPAQYSWLIDGNIQQHTQELFISNITEKNSGLYTC<br>QANNSASGHSRTTVKTITVSAELPKPSISSNNSKPVEDKDAVAFTCEPEAQNT<br>TYLWWVNGQSLPVSPRLQLSNGNRTLTLFNVTRNDARAYVCGIQNSVSANRSD<br>PVTLDVLYGPDTPIISPPDSSYLSGANLNLSCHSASNPSPQYSWRINGIPQQH<br>TQVLFIAKITPNNNGTYACFVSNLATGRNNSIVKSITVSASGTSPGLSAGATV<br>GIMIGVLVGVALI | 1 |

TABLE 10-continued

Summary table of amino acid sequences and nucleic acid sequences

| Description | Amino acid Sequence or nucleic acid sequence | SEQ ID NO. |
|---|---|---|
| *H. sapiens*<br>CEACAM5<br>nucleotide<br>sequence<br>GenBank:<br>BC034671.1 | GGACAGCAGACCAGACAGTCACAGCAGCCTTGACAAAACGTTCCTGGAACTCA<br>AGCTCTTCTCCACAGAGGAGGACAGAGCAGACAGCAGAGACCATGGAGTCTCC<br>CTCGGCCCCTCCCCACAGATGGTGCATCCCCTGGCAGAGGCTCCTGCTCACAG<br>CCTCACTTCTAACCTTCTGGAACCCGCCCACCACTGCCAAGCTCACTATTGAA<br>TCCACGCCGTTCAATGTCGCAGAGGGGAAGGAGGTGCTTCTACTTGTCCACAA<br>TCTGCCCCAGCATCTTTTTGGCTACAGCTGGTACAAAGGTGAAAGAGTGGATG<br>GCAACCGTCAAATTATAGGATATGTAATAGGAACTCAACAAGCTACCCCAGGG<br>CCCGCATACAGTGGTCGAGAGATAATATACCCCAATGCATCCCTGCTGATCCA<br>GAACATCATCCAGAATGACACAGGATTCTACACCCTACACGTCATAAAGTCAG<br>ATCTTGTGAATGAAGAAGCAACTGGCCAGTTCCGGGTATACCCGGAGCTGCCC<br>AAGCCCTCCATCTCCAGCAACAACTCCAAACCCGTGGAGGACAAGGATGCTGT<br>GGCCTTCACCTGTGAACCTGAGACTCAGGACGCAACCTACCTGTGGTGGGTAA<br>ACAATCAGAGCCTCCCGGTCAGTCCCAGGCTGCAGCTGTCCAATGGCAACAGG<br>ACCCTCACTCTATTCAATGTCACAAGAAATGACTCAGCAAGCTACAAATGTGA<br>AACCCAGAACCCAGTGAGTGCCAGGCGCAGTGATTCAGTCATCCTGAATGTCC<br>TCTATGGCCCGGATGCCCCCACCATTTCCCCTCTAAACACATCTTACAGATCA<br>GGGGAAAATCTGAACCTCTCCTGCCACGCAGCCTCTAACCCACCTGCACAGTA<br>CTCTTGGTTTGTCAATGGGACTTTCCAGCAATCCACCCAAGAGCTCTTTATCC<br>CCAACATCACTGTGAATAATAGTGGATCCTATACGTGCCAAGCCCATAACTCA<br>GACACTGGCCTCAATAGGACCACAGTCACGACGATCACAGTCTATGCAGAGCC<br>ACCCAAACCCTTCATCACCAGCAACAACTCCAACCCCGTGGAGGATGAGGATG<br>CTGTAGCCTTAACCTGTGAACCTGAGATTCAGAACACAACCTACCTGTGGTGG<br>GTAAATAATCAGAGCCTCCCGGTCAGTCCCAGGCTGCAGCTGTCCAATGACAA<br>CAGGACCCTCACTCTACTCAGTGTCACAAGGAATGATGTAGGACCCTATGAGT<br>GTGGAATCCAGAACGAATTAAGTGTTGACCACAGCGACCCAGTCATCCTGAAT<br>GTCCTCTATGGCCCAGACGACCCCACCATTTCCCCCTCATACACCTATTACCG<br>TCCAGGGGTGAACCTCAGCCTCTCCTGCCATGCAGCCTCTAACCCACCTGCAC<br>AGTATTCTTGGCTGATTGATGGGAACATCCAGCAACACACACAAGAGCTCTTT<br>ATCTCCAACATCACTGAGAAGAACAGCGGACTCTATACCTGCCAGGCCAATAA<br>CTCAGCCAGTGGCCACAGCAGGACTACAGTCAAGACAATCACAGTCTCTGCGG<br>AGCTGCCCAAGCCCTCCATCTCCAGCAACAACTCCAAACCCGTGGAGGACAAG<br>GATGCTGTGGCCTTCACCTGTGAACCTGAGGCTCAGAACACAACCTACCTGTG<br>GTGGGTAAATGGTCAGAGCCTCCCAGTCAGTCCCAGGCTGCAGCTGTCCAATG<br>GCAACAGGACCCTCACTCTATTCAATGTCACAAGAAATGACGCAAGAGCCTAT<br>GTATGTGGAATCCAGAACTCAGTGAGTGCAAACCGCAGTGACCCAGTCACCCT<br>GGATGTCCTCTATGGGCCGGACACCCCCATCATTTCCCCCCCAGACTCGTCTT<br>ACCTTTCGGGAGCGAACCTCAACCTCTCCTGCCACTCGGCCTCTAACCCATCC<br>CCGCAGTATTCTTGGCGTATCAATGGGATACCGCAGCAACACACACAAGTTCT<br>CTTTATCGCCAAAATCACGCCAAATAATAACGGGACCTATGCCTGTTTTGTCT<br>CTAACTTGGCTACTGGCCGCAATAATTCCATAGTCAAGAGCATCACAGTCTCT<br>GCATCTGGAACTTCTCCTGGTCTCTCAGCTGGGGCCACTGTCGGCATCATGAT<br>TGGAGTGCTGGTTGGGGTTGCTCTGATATAGCAGCCCTGGTGTAGTTTCTTCA<br>TTTCAGGAAGACTGACAGTTGTTTTGCTTCTTCCTTAAAGCATTTGCAACAGC<br>TACAGTCTAAAATTGCTTCTTTACCAAGGATATTTACAGAAAAGACTCTGACC<br>AGAGATCGAGACCATCCTAGCCAACATCGTGAAACCCCATCTCTACTAAAAAT<br>ACAAAAATGAGCTGGGCTTGGTGGCGCGCACCTGTAGTCCCAGTTACTCGGGA<br>GGCTGAGGCAGGAGAATCGCTTGAACCCGGGAGGTGGAGATTGCAGTGAGCCC<br>AGATCGCACCACTGCACTCCAGTCTGGCAACAGAGCAAGACTCCATCTCAAAA<br>AGAAAAGAAAAGAAGACTCTGACCTGTACTCTTGAATACAAGTTTCTGATACC<br>ACTGCACTGTCTGAGAATTTCCAAAACTTTAATGAACTAACTGACAGCTTCAT<br>GAAACTGTCCCCCAAGATCAAGCAGAGAAAATAATTAATTTCATGGGACTAAA<br>TGAACTAATGAGGATAATATTTTCATAATTTTTTATTTGAAATTTTGCTGATT<br>CTTTAAATGTCTTGTTTCCCAGATTTCAGGAAACTTTTTTTCTTTTAAGCTAT<br>CCACAGCTTACAGCAATTTGATAAAATATACTTTTGTGAACAAAAAAAAAAAA<br>AAAAAAAAAAAAAAAAAAAAAAAAA | 2 |
| *Macaca*<br>*fascicularis*<br>CEACAM5<br>amino acid<br>sequence<br>NCBI<br>XP_005589491.2 | MGSPSAPLHRWCIPWQTLLLTASLLTFWNPPTTAQLTIESRPFNVAEGKEVLL<br>LAHNVSQNLFGYIWYKGERVDASRRIGSCVIRTQQITPGPAHSGRETIDFNAS<br>LLIHNVTQSDTGSYTIQVIKEDLVNEEATGQFRVYPELPKPYISSNNSNPVED<br>KDAVALTCEPETQDTTYLWWVNNQSLPVSPRLELSSDNRTLTVFNIPRNDTTS<br>YKCETQNPVSVRRSDPVTLNVLYGPDAPTISPLNTPYRAGENLNLSCHAASNP<br>AAQYSWFVNGTFQQSTQELFIPNITVNNSGSYMCQAHNSATGLNRTTVTAITV<br>YAELPKPYITSNNSNPIEDKDAVTLTCEPETQDTTYLWWVNNQSLSVSSRLEL<br>SNDNRTLTVFNIPRNDTTFYECETQNPVSVRRSDPVTLNVLYGPDAPTISPLN<br>TPYRAGENLNLSCHAASNPAAQYSWFVNGTFQQSTQELFIPNITVNNSGSYMC<br>QAHNSATGLNRTTVTAITVYVELPKPYISSNNSNPIEDKDAVTLTCEPVAENT<br>TYLWWVNNQSLSVSPRLQLSNGNRILTLLSVTRNDTGPYECGIONSESAKRSD<br>PVTLNVTYGPDTPIISPPDLSYRSGANLNLSCHSDSNPSPQYSWLINGTLRQH<br>TQVLFISKITSNNNGAYACFVSNLATGRNNSIVKNISVSSGDSAPGSSGLSAR<br>ATVGIIIGMLVGVALM | 3 |
| *Macaca*<br>*fascicularis*<br>CEACAM5<br>nucleotide | GATGCCGAGAAGTACTCCTGCTGTAGGAGGAGACTCAGGACAGAGGGAGGAAG<br>GACAGCAGACCAGGCAGTCACAGCTGCCCTGACAAGAGCGTTCCTAGAGCTCA<br>GGATCTTCTCCACAGAAGAGGACAGAGCAGACAGCAGAGACCATGGGGTCTCC<br>CTCGGCCCCTCTTCACAGATGGTGCATCCCCTGGCAGACGCTCCTGCTCACAG | 4 |

TABLE 10-continued

| Summary table of amino acid sequences and nucleic acid sequences | | |
|---|---|---|
| Description | Amino acid Sequence or nucleic acid sequence | SEQ ID NO. |
| sequence NCBI: XM_005589434.3 | CCTCACTTCTAACCTTCTGGAACCCGCCCACCACTGCCCAGCTCACTATTGAA<br>TCCAGGCCGTTCAATGTTGCAGAGGGGAAGGAGGTTCTTCTACTTGCCCACAA<br>TGTGTCCCAGAATCTTTTTGGCTACATCTGGTACAAGGGAGAAAGAGTGGATG<br>CCAGCCGTCGAATTGGATCATGTGTAATAAGAACTCAACAAATTACCCCAGGG<br>CCCGCACACAGCGGTCGAGAGACAATAGACTTCAATGCATCCCTGCTGATCCA<br>CAATGTCACCCAGAGTGACACAGGATCCTACACCATACAAGTCATAAAGGAAG<br>ATCTTGTGAATGAAGAAGCAACTGGCCAGTTCCGGGTATACCCGGAGCTGCCC<br>AAGCCCTACATCTCCAGCAACAACTCCAACCCTGTGGAGGACAAGGATGCTGT<br>GGCCTTAACCTGTGAACCTGAGACTCAGGACACAACCTACCTGTGGTGGGTAA<br>ACAATCAGAGCCTCCCGGTCAGTCCCAGGCTGGAGCTGTCCAGTGACAACAGG<br>ACCCTCACTGTATTCAATATTCCAAGAAATGACACAACATCCTACAAATGTGA<br>AACCCAGAACCCAGTGAGTGTCAGACGCAGCGACCCAGTCACCCTGAATGTCC<br>TCTATGGCCCGGATGCGCCCACCATTTCCCCTCTAAACACACCTTACAGAGCA<br>GGGGAAAATCTGAACCTCTCCTGCCACGCAGCCTCTAACCCAGCTGCACAGTA<br>CTCTTGGTTTGTCAATGGGACGTTCCAGCAATCCACACAAGAGCTCTTTATAC<br>CCAACATCACCGTGAATAATAGCGGATCCTATATGTGCCAAGCCCATAACTCA<br>GCCACTGGCCTCAATAGGACCACAGTCACGGCGATCACAGTCTACGCGGAGCT<br>GCCCAAGCCCTACATCACCAGCAACAACTCCAACCCCATAGAGGACAAGGATG<br>CTGTGACCTTAACCTGTGAACCTGAGACTCAGGACACAACCTACCTGTGGTGG<br>GTAAACAATCAGAGCCTCTCGGTCAGTTCCAGGCTGGAGCTGTCCAATGACAA<br>CAGGACCCTCACTGTATTCAATATTCCAAGAAACGACACAACGTTCTACGAAT<br>GTGAAACCCAGAACCCAGTGAGTGTCAGACGCAGCGACCCAGTCACCCTGAAT<br>GTCCTCTATGGCCCGGATGCGCCCACCATTTCCCCTCTAAACACACCTTACAG<br>AGCAGGGGAAAATCTGAACCTCTCCTGCCACGCAGCCTCTAACCCAGCTGCAC<br>AGTACTCTTGGTTTGTCAATGGGACGTTCCAGCAATCCACACAAGAGCTCTTT<br>ATACCCAACATCACCGTGAATAATAGCGGATCCTATATGTGCCAAGCCCATAA<br>CTCAGCCACTGGCCTCAATAGGACCACAGTCACGGCGATCACAGTCTATGTGG<br>AGCTGCCCAAGCCCTACATCTCCAGCAACAACTCCAACCCCATAGAGGACAAG<br>GATGCTGTGACCTTAACCTGTGAACCTGTGGCTGAGAACACAACCTACCTGTG<br>GTGGGTAAACAATCAGAGCCTCTCGGTCAGTCCCAGGCTGCAGCTCTCCAATG<br>GCAACAGGATCCTCACTCTACTCAGTGTCACACGGAATGACACAGGACCCTAT<br>GAATGTGGAATCCAGAACTCAGAGAGTGCAAAACGCAGTGACCCAGTCACCCT<br>GAATGTCACCTATGGCCCAGACACCCCCATCATATCCCCCCCAGACTTGTCTT<br>ACCGTTCGGGAGCAAACCTCAACCTCTCCTGCCACTCGGACTCTAACCCATCC<br>CCGCAGTATTCTTGGCTTATCAATGGGACACTGCGGCAACACACACAAGTTCT<br>CTTTATCTCCAAAATCACATCAAACAATAACGGGGCCTATGCCTGTTTTGTCT<br>CTAACTTGGCTACTGGTCGCAATAACTCCATAGTCAAGAACATCTCAGTCTCC<br>TCTGGCGATTCAGCACCTGGAAGTTCTGGTCTCTCAGCTAGGGCTACTGTCGG<br>CATCATAATTGGAATGCTGGTTGGGGTTGCTCTGATGTAGCAGCCGTGGTGTA<br>GTTTCTGCAATTAAGAAAGACTGACAGTTGTTTTGATTCTTCCTTAAAGCATT<br>TGCAACAGCTACAGTCTAAAATTGCCTCTTTACCAAGGATATTTATAGAAAAG<br>ACTCTGACCAGAGATCGAGACCATCCTAGCCAATATGGTGAAACCCCATCTCT<br>ACGGAATTAGCTGGGCGTGGTGGTGTGCTCCTGTAGTCCCAGCTACTCGGGAG<br>GCTGAGGCAGGAGAATCGCTTGAACCTGGGAAGCAGAGATTGCAGTGAGCCAA<br>GATCGCGCCACTGCACTCCAGCCTGGCGACAGAGCAAGACTCCATATCAAAAA<br>AAAAAAAAAAAGTATATATATATATGAAAGAAAAGACTCTGACCTGTACTCT<br>TGAATGAAAGTTTCTGATACCACTGGACTGTCTGAGAATTTCCAAAACGTAAT<br>GAACAAACTGACAGCTTCATGAAACTGCCGACCAAGATCAAGCAAAGAAAATA<br>ATTAATTTCATGGGACCAAATGAACTAATGAGGATAATATTTTCATAAATTTT<br>TTTTGAAATTTTGCTGATTCTTTAAATGTCTTGTTTCCCAGATTTCAGGAAAC<br>TTTTTTTCCTTTGCGCTATCTACAGCTTACAACAATTTGATAAAATATACTTT<br>TGTGAATAAACATTGAGACATTTACATTTTCTCCCTATGTGGTCGCTCCAGAC<br>TTGGGAAACTATTCATGAATATTTATATTGTATGGTAATATGTTTATTGTATA<br>AGTTCAATAACTCTGCTCTTTGTATAACAGAA | |
| MBN001 HCDR1 amino acid sequence | SHGMH | 14 |
| MBN001 HCDR2 amino acid sequence | FISYDGSYKSYVDSVKG | 15 |
| MBN001 HCDR3 amino acid sequence | GLTGTGAFDI | 16 |
| MBN001 VH amino acid sequence | QVQLVETGGGVVQPGRSLRLSCAASGITFSSHGMHWVRQSPGKGLEWVTFISY<br>DGSYKSYVDSVKGRFAISRDNSKNTLYLQMNSLRPEDTAVYYCATGLTGTGAF<br>DIWGQGTMVTVSS | 17 |
| MBN001 VH nucleotide sequence | CAGGTGCAGCTGGTGGAGACTGGGGGAGGCGTGGTCCAGCCTGGGAGGTCCCT<br>GAGACTCTCCTGTGCAGCCTCTGGAATCACCTTCAGTAGCCATGGCATGCACT<br>GGGTCCGCCAGTCTCCAGGCAAGGGGCTGGAGTGGGTGACATTTATATCATAT<br>GATGGAAGTTATAAATCCTATGTCGACTCCGTGAAGGGCCGATTCGCCATCTC<br>CAGAGACAATTCCAAGAACACGCTGTATCTGCAAATGAACAGCCTGAGACCTG | 18 |

TABLE 10-continued

Summary table of amino acid sequences and nucleic acid sequences

| Description | Amino acid Sequence or nucleic acid sequence | SEQ ID NO. |
|---|---|---|
| | AGGACACGGCTGTGTATTACTGTGCGACCGGATTAACTGGAACTGGTGCTTTT GATATCTGGGGCCAAGGGACAATGGTCACCGTCTCCTCA | |
| MBN001 LCDR1 amino acid sequence | RASQSVSSSYLA | 19 |
| MBN001 LCDR2 amino acid sequence | GASSRAT | 20 |
| MBN001 LCDR3 amino acid sequence | QQYGSSPYT | 21 |
| MBN001 VL amino acid sequence | EIVLTQSPGTLSLSPGERATLSCRASQSVSSSYLAWYQQKPGQAPRLLIYGAS SRATGIPDRFSGSGSGTDFTLTISRLEPEDFAVYYCQQYGSSPYTFGQGTKLE IK | 22 |
| MBN001 VL nucleotide sequence | GAAATTGTATTGACGCAGTCTCCAGGGACCCTGTCTTTGTCTCCAGGGGAAAG AGCCACCCTCTCCTGCCGGGCCAGTCAGAGTGTCTCCAGCTCGTACTTAGCCT GGTACCAACAGAAACCTGGCCAGGCCCCCCGACTCCTCATCTATGGTGCCTCC TCAAGGGCCACTGGAATCCCAGACAGATTCAGTGGGAGTGGGTCTGGGACAGA CTTCACTCTCACCATCTCAAGACTGGAGCCTGAAGATTTTGCCGTATATTACT GTCAACAGTATGGGAGCTCACCGTACACTTTTGGCCAGGGGACCAAGCTGGAG ATCAAA | 23 |
| 6xHis-A3-B3 huCEACAM5 amino acid sequence | HHHHHHETVRFQGPKPSISSNNSKPVEDKDAVAFTCEPEAQNTTYLWWVNGQS LPVSPRLQLSNGNRTLTLFNVTRNDARAYVCGIQNSVSANRSDPVTLDVLYGP DTPIISPPDSSYLSGANLNLSCHSASNPSPQYSWRINGIPQQHTQVLFIAKIT PNNNGTYACFVSNLATGRNNSIVKSITVSASGTSPGLSA | 24 |
| Human CEACAM5 (aa 569-587) amino acid sequence | CGIQNSVSANRSDPVTL | 25 |
| Human CEACAM5 (aa 626-640) amino acid sequence | SWRINGIPQQHTQVL | 26 |
| Human CEACAM5 (aa 674-685) amino acid sequence | VSASGTSPGLSA | 27 |
| Human CEACAM5 (aa 618-641) amino acid sequence | ASNPSPQYSWRINGIPQQHTQVLF | 28 |
| Human CEACAM5 (590-605) amino acid sequence | LYGPDTPIISPPDSSY | 29 |
| hIgG1.3f amino acid sequence | ASTKGPSVFPLAPSSKSTSGGTAALGCLVKDYFPEPVTVSWNSGALTSGVHTF PAVLQSSGLYSLSSVVTVPSSSLGTQTYICNVNHKPSNTKVDKRVEPKSCDKT HTCPPCPAPEAEGAPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEALHNH YTQKSLSLSPG | 30 |
| Cleavable linker amino acid sequence | PVGVV | 31 |
| Human CEACAM5 | ASNPSPQY | 32 |

TABLE 10-continued

| Summary table of amino acid sequences and nucleic acid sequences | | |
|---|---|---|
| Description | Amino acid Sequence or nucleic acid sequence | SEQ ID NO. |
| (aa 618-625) amino acid sequence | | |
| Human CEACAM5 (aa 607-613) amino acid sequence | SGANLNL | 33 |
| Human CEACAM5 (aa 629-641) amino acid sequence | INGIPQQHTQVLF | 34 |
| MBP001 HCDR1 amino acid sequence | SHGMH | 35 |
| MBP001 HCDR2 amino acid sequence | FISYDGSYKSYVDSVKG | 36 |
| MBP001 HCDR3 amino acid sequence | GLTGTGAFDI | 37 |
| MBP001 VH amino acid sequence | QVQLVESGGGVVQPGRSLRLSCAASGIYFSSHGMHWVRQAPGKGLEWVTFISY DGSYKSYVDSVKGRFTISRDNSKNTLYLQMNSLRAEDTAVYYCATGLTGTGAF DIWGQGTMVTVSS | 38 |
| MBP001 VH nucleotide sequence | CAGGTGCAGCTGGTGGAGTCTGGGGGAGGCGTGGTCCAGCCTGGGAGGTCCCT GAGACTCTCCTGTGCAGCCTCTGGAATCTACTTCAGTAGCCATGGCATGCACT GGGTCCGCCAGGCTCCAGGCAAGGGGCTGGAGTGGGTGACATTTATATCATAT GATGGAAGTTATAAATCCTATGTCGACTCCGTGAAGGGCCGATTCACCATCTC CAGAGACAATTCCAAGAACACGCTGTATCTGCAAATGAACAGCCTGAGAGCTG AGGACACGGCTGTGTATTACTGTGCGACCGGATTAACTGGAACTGGTGCTTTT GATATCTGGGGCCAAGGGACAATGGTCACCGTCTCCTCA | 39 |
| MBP001 LCDR1 amino acid sequence | RASQSVSSSYLA | 40 |
| MBP001 LCDR2 amino acid sequence | GASSRAT | 41 |
| MBP001 LCDR3 amino acid sequence | QQYGSSPYT | 42 |
| MBP001 VL amino acid sequence | EIVLTQSPGTLSLSPGERATLSCRASQSVSSSYLAWYQQKPGQAPRLLIYGAS SRATGIPDRFSGSGSGTDFTLTISRLEPEDFAVYYCQQYGSSPYTFGQGTKLE IK | 43 |
| MBP001 VL nucleotide sequence | GAAATTGTATTGACGCAGTCTCCAGGGACCCTGTCTTTGTCTCCAGGGGAAAG AGCCACCCTCTCCTGCCGGGCCAGTCAGAGTGTCTCCAGCTCGTACTTAGCCT GGTACCAACAGAAACCTGGCCAGGCCCCCCGACTCCTCATCTATGGTGCCTCC TCAAGGGCCACTGGAATCCCAGACAGATTCAGTGGGAGTGGGTCTGGGACAGA CTTCACTCTCACCATCTCAAGACTGGAGCCTGAAGATTTTGCCGTATATTACT GTCAACAGTATGGGAGCTCACCGTACACTTTTGGCCAGGGGACCAAGCTGGAG ATCAAA | 44 |
| MBP001 HC amino acid sequence | QVQLVESGGGVVQPGRSLRLSCAASGIYFSSHGMHWVRQAPGKGLEWVTFISY DGSYKSYVDSVKGRFTISRDNSKNTLYLQMNSLRAEDTAVYYCATGLTGTGAF DIWGQGTMVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWING KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPG | 45 |
| MBP001 LC amino acid | EIVLTQSPGTLSLSPGERATLSCRASQSVSSSYLAWYQQKPGQAPRLLIYGAS SRATGIPDRFSGSGSGTDFTLTISRLEPEDFAVYYCQQYGSSPYTFGQGTKLE | 46 |

TABLE 10-continued

| Summary table of amino acid sequences and nucleic acid sequences | | |
|---|---|---|
| Description | Amino acid Sequence or nucleic acid sequence | SEQ ID NO. |
| sequence | IKRTVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKSFNR GEC | |
| MBP001 HC nucleotide sequence | CAGGTCCAGCTCGTGGAATCCGGAGGCGGAGTGGTGCAGCCGGGAAGATCACT GCGCCTGTCATGCGCAGCCTCGGGGATCTACTTTTCGTCCCACGGAATGCATT GGGTCCGCCAAGCTCCCGGAAAGGGTTTGGAATGGGTCACCTTCATTAGCTAC GACGGCTCCTACAAGTCGTACGTGGACTCCGTGAAGGGGAGGTTCACTATCTC CCGGGACAACAGCAAGAACACGCTGTACCTCCAAATGAACTCCCTTCGGGCCG AGGATACCGCCGTGTACTATTGTGCCACCGGTCTGACCGGCACTGGAGCGTTC GATATCTGGGGCCAGGGCACTATGGTCACCGTGTCCAGCGCTAGCACCAAGGG CCCATCGGTCTTCCCCCTGGCACCCTCCTCCAAGAGCACCTCTGGGGGCACAG CGGCCCTGGGCTGCCTGGTCAAGGACTACTTCCCCGAACCGGTGACGGTGTCG TGGAACTCAGGCGCCCTGACCAGCGGCGTGCACACCTTCCCGGCTGTCCTACA GTCCTCAGGACTCTACTCCCTCAGCAGCGTGGTGACCGTGCCCTCCAGCAGCT TGGGCACCCAGACCTACATCTGCAACGTGAATCACAAGCCCAGCAACACCAAG GTGGACAAGAGAGTTGAGCCCAAATCTTGTGACAAAACTCACACATGCCCACC GTGCCCAGCACCTGAACTCCTGGGGGGACCGTCAGTCTTCCTCTTCCCCCCAA AACCCAAGGACACCCTCATGATCTCCCGGACCCCTGAGGTCACATGCGTGGTG GTGGACGTGAGCCACGAAGACCCTGAGGTCAAGTTCAACTGGTACGTGGACGG CGTGGAGGTGCATAATGCCAAGACAAAGCCGCGGGAGGAGCAGTACAACAGCA CGTACCGTGTGGTCAGCGTCCTCACCGTCCTGCACCAGGACTGGCTGAATGGC AAGGAGTACAAGTGCAAGGTCTCCAACAAAGCCCTCCCAGCCCCCATCGAGAA AACCATCTCCAAAGCCAAAGGGCAGCCCCGAGAACCACAGGTGTACACCCTGC CCCCATCCCGGGAGGAGATGACCAAGAACCAGGTCAGCCTGACCTGCCTGGTC AAAGGCTTCTATCCCAGCGACATCGCCGTGGAGTGGGAGAGCAATGGGCAGCC GGAGAACAACTACAAGACCACGCCTCCCGTGCTGGACTCCGACGGCTCCTTCT TCCTCTATAGCAAGCTCACCGTGGACAAGAGCAGGTGGCAGCAGGGGAACGTC TTCTCATGCTCCGTGATGCATGAGGCTCTGCACAACCACTACACGCAGAAGTC ACTCTCCCTGTCCCCGGGT | 47 |
| MBP001 LC nucleotide sequence | GAAATTGTATTGACGCAGTCTCCAGGGACCCTGTCTTTGTCTCCAGGGGAAAG AGCCACCCTCTCCTGCCGGGCCAGTCAGAGTGTCTCCAGCTCGTACTTAGCCT GGTACCAACAGAAACCTGGCCAGGCCCCCCGACTCCTCATCTATGGTGCCTCC TCAAGGGCCACTGGAATCCCAGACAGATTCAGTGGGAGTGGGTCTGGGACAGA CTTCACTCTCACCATCTCAAGACTGGAGCCTGAAGATTTTGCCGTATATTACT GTCAACAGTATGGGAGCTCACCGTACACTTTTGGCCAGGGGACCAAGCTGGAG ATCAAACGTACGGTGGCTGCACCATCTGTCTTCATCTTCCCGCCATCTGATGA GCAGTTGAAATCTGGAACTGCCTCTGTTGTGTGCCTGCTGAATAACTTCTATC CCAGAGAGGCCAAAGTACAGTGGAAGGTGGATAACGCCCTCCAATCGGGTAAC TCCCAGGAGAGTGTCACAGAGCAGGACAGCAAGGACAGCACCTACAGCCTCAG CAGCACCCTGACGCTGAGCAAAGCAGACTACGAGAAACACAAAGTCTACGCCT GCGAAGTCACCCATCAGGGCCTGAGCTCGCCCGTCACAAAGAGCTTCAACAGG GGAGAGTGT | 48 |
| MBP002 VH amino acid sequence | QVQLVESGGGVVQPGRSLRLSCAASGITFSSHGMHWVRQAPGKGLEWVTFISY DGSYKSYVDSVKGRFTISRDNSKNTLYLQMNSLRAEDTAVYYCATGLTGTNAL DIWGQGTMVTVSS | 49 |
| MBP002 VL amino acid sequence | EIVLTQSPGTLSLSPGERATLSCRASQSVSSSYLAWYQQKPGQAPRLLIYYAS SRATGIPDRFSGSGSGTDFTLTISRLEPEDFAVYYCQQYGRSPYTFGQGTKLE IK | 50 |
| MBP003 VH amino acid sequence | QVQLVESGGGVVQPGRSLRLSCAASGITFSSHGMHWVRQAPGKGLEWVTFISY DGSYKSYVDSVKGRFTISRDNSKNTLYLQMNSLRAEDTAVYYCATGLTGTGAF DIWGQGTMVTVSS | 51 |
| MBP003 VL amino acid sequence | EIVLTQSPGTLSLSPGERATLSCRASQSVSSSYLAWYQQKPGQAPRLLIYGAS SRATGIPDRFSGSGSGTDFTLTISRLEPEDFAVYYCQQYGRSPYTFGQGTKLE IK | 52 |
| MBP002 VH nucleotide sequence | CAGGTCCAACTGGTGGAAAGCGGCGGTGGAGTGGTGCAGCCTGGACGGTCCCT GAGACTCTCATGTGCCGCCAGCGGAATCACCTTTTCGTCCCATGGCATGCACT GGGTCCGCCAAGCACCGGGAAAGGGGCTGGAATGGGTCACCTTCATTTCCTAC GATGGCTCGTACAAGTCCTACGTGGACTCAGTGAAAGGGAGGTTCACGATCTC CCGCGACAACTCGAAGAACACCCTGTACTTGCAAATGAACAGCCTGCGGGCTG AGGATACTGCCGTGTACTATTGCGCCACCGGACTTACCGGAACTAATGCGCTC GACATCTGGGGCCAGGGTACCATGGTCACTGTGTCCTCC | 53 |
| MBP002 VL nucleotide sequence | GAAATTGTATTGACGCAGTCTCCAGGGACCCTGTCTTTGTCTCCAGGGGAAAG AGCCACCCTCTCCTGCCGGGCCAGTCAGAGTGTCTCCAGCTCGTACTTAGCCT GGTACCAACAGAAACCTGGCCAGGCCCCCCGACTCCTCATCTATTACGCCTCC TCAAGGGCCACTGGAATCCCAGACAGATTCAGTGGGAGTGGGTCTGGGACAGA CTTCACTCTCACCATCTCAAGACTGGAGCCTGAAGATTTTGCCGTATATTACT GTCAACAGTATGGGCGTTCACCGTACACTTTTGGCCAGGGGACCAAGCTGGAG ATCAAA | 54 |

TABLE 10-continued

Summary table of amino acid sequences and nucleic acid sequences

| Description | Amino acid Sequence or nucleic acid sequence | SEQ ID NO. |
|---|---|---|
| MBP003 VH nucleotide sequence | CAAGTGCAGTTGGTGGAAAGCGGAGGCGGAGTGGTGCAGCCCGGAAGAAGCCT GCGCCTTTCTTGTGCCGCTAGCGGTATCACGTTCTCCTCACATGGGATGCACT GGGTCCGCCAAGCACCGGGAAAGGGCCTGGAATGGGTCACCTTCATCTCGTAC GACGGTTCATATAAGTCGTACGTGGATTCCGTGAAAGGGGGGTTCACTATTTC CCGGGACAACTCCAAGAACACCCTCTACCTCCAAATGAACTCCCTGAGGGCCG AGGATACCGCCGTGTACTACTGCGCGACCGGACTGACCGGAACTGGCGCCTTT GACATCTGGGGCCAGGGCACTATGGTCACCGTGTCGTCC | 55 |
| MBP003 VL nucleotide sequence | GAAATTGTATTGACGCAGTCTCCAGGGACCCTGTCTTTGTCTCCAGGGGAAAG AGCCACCCTCTCCTGCCGGGCCAGTCAGAGTGTCTCCAGCTCGTACTTAGCCT GGTACCAACAGAAACCTGGCCAGGCCCCCCGACTCCTCATCTATGGTGCCTCC TCAAGGGCCACTGGAATCCCAGACAGATTCAGTGGGAGTGGGTCTGGGACAGA CTTCACTCTCACCATCTCAAGACTGGAGCCTGAAGATTTTGCCGTATATTACT GTCAACAGTATGGGCGTTCACCGTACACTTTTGGCCAGGGGACCAAGCTGGAG ATCAAA | 56 |
| aa 571-587 of SEQ ID NO: 24 | YVCGIQNSVSANRSDPVTL | 57 |
| aa 626-640 of SEQ ID NO: 24 | SWRINGIPQQHTQVL | 58 |
| aa 590-605 of SEQ ID NO: 24 | DVLYGPDTPIISPPDSSY | 59 |
| (aa 674-685 of SEQ ID NO: 24) | ITVSASGTSPGLSA | 60 |
| MBN001 Mutational Scan HCDR1 amino acid sequence | GITFSSH | 61 |
| MBN001 Mutational Scan HCDR2 amino acid sequence | TFISYDGSYKSYVDSVKG | 62 |
| MBN001 Mutational Scan HCDR3 amino acid sequence | TGLTGTGAFDI | 63 |
| MBN001 Mutational Scan LCDR1 amino acid sequence | RASQSVSSSYLA | 64 |
| MBN001 Mutational Scan LCDR2 amino acid sequence | GASSRAT | 65 |
| MBN001 Mutational Scan LCDR3 amino acid sequence | QQYGSSPY | 66 |
| MBP004 VH amino acid sequence | QVQLVESGGGVVQPGRSLRLSCAASGITFSSHGMHWVRQAPGKGLEWVTFISY DGSYKSYVDSVKGRFTISRDNSKNTLYLQMNSLRAEDTAVYYCATGLTGTGAF DIWGQGTMVTVSS | 67 |
| MBP004 VL amino acid sequence | EIVLTQSPGTLSLSPGERATLSCRASQSVSSSYLAWYQQKPGQAPRLLIYGAS SRATGIPDRFSGSGSGTDFTLTISRLEPEDFAVYYCQQYGRSPYTFGQGTKLE IK | 68 |

TABLE 10-continued

Summary table of amino acid sequences and nucleic acid sequences

| Description | Amino acid Sequence or nucleic acid sequence | SEQ ID NO. |
|---|---|---|
| MBP005 VH amino acid sequence | QVQLVESGGGVVQPGRSLRLSCAASGIYFSSHGMHWVRQAPGKGLEWVTFISY DGSYKSYVDSVKGRFTISRDNSKNTLYLQMNSLRAEDTAVYYCATGLTGTGAF DIWGQGTMVTVSS | 69 |
| MBP005 VL amino acid sequence | EIVLTQSPGTLSLSPGERATLSCRASQSVSSSYLAWYQQKPGQAPRLLIYGAS SRATGIPDRFSGSGSGTDFTLTISRLEPEDFAVYYCQQYGSSPYTFGQGTKLE IK | 70 |
| MBP006 VH amino acid sequence | QVQLVESGGGVVQPGRSLRLSCAASGITFSSHGMHWVRQAPGKGLEWVTFISY DGSYISYVDSVKGRFTISRDNSKNTLYLQMNSLRAEDTAVYYCATGLTGTGAN DIWGQGTMVTVSS | 71 |
| MBP006 VL amino acid sequence | EIVLTQSPGTLSLSPGERATLSCRASQSVSSSYLAWYQQKPGQAPRLLIYGAS SRATGIPDRFSGSGSGTDFTLTISRLEPEDFAVYYCQQYKSSPYTFGQGTKLE IK | 72 |
| MBP007 VH amino acid sequence | QVQLVESGGGVVQPGRSLRLSCAASGIYFSSHGMHWVRQAPGKGLEWVTFISY DGSYKSYVDSVKGRFTISRDNSKNTLYLQMNSLRAEDTAVYYCATGLTGTGAN DIWGQGTMVTVSS | 73 |
| MBP007 VL amino acid sequence | EIVLTQSPGTLSLSPGERATLSCRASQSVSSSYLAWYQQKPGQAPRLLIYGAS SRATGIPDRFSGSGSGTDFTLTISRLEPEDFAVYYCQQNKPSPYTFGQGTKLE IK | 74 |
| MBP008 VH amino acid sequence | QVQLVESGGGVVQPGRSLRLSCAASGITFSSHGMHWVRQAPGKGLEWVTFISY DGSYKSYVDSVKGRFTISRDNSKNTLYLQMNSLRAEDTAVYYCATGLTGTNAL DIWGQGTMVTVSS | 75 |
| MBP008 VL amino acid sequence | EIVLTQSPGTLSLSPGERATLSCRASQSVSSSYLAWYQQKPGQAPRLLIYYAS SRATGIPDRFSGSGSGTDFTLTISRLEPEDFAVYYCQQYGRSPYTFGQGTKLE IK | 76 |
| MBP009 VH amino acid sequence | QVQLVESGGGVVQPGRSLRLSCAASGIYFSSHGMHWVRQAPGKGLEWVTFISY DGSYKSYVDSVKGRFTISRDNSKNTLYLQMNSLRAEDTAVYYCATGLTGTGAF DIWGQGTMVTVSS | 77 |
| MBP009 VL amino acid sequence | EIVLTQSPGTLSLSPGERATLSCRASQSVSSIYLAWYQQKPGQAPRLLIYYAS SRATGIPDRFSGSGSGTDFTLTISRLEPEDFAVYYCQQYGSSPYTFGQGTKLE IK | 78 |
| MBP010 VH amino acid sequence | QVQLVESGGGVVQPGRSLRLSCAASGITFSSHGMHWVRQAPGKGLEWVTFISY DSSYKSYVDSVKGRFTISRDNSKNTLYLQMNSLRAEDTAVYYCATGLTGTGAF DIWGQGTMVTVSS | 79 |
| MBP010 VL amino acid sequence | EIVLTQSPGTLSLSPGERATLSCRASQSVSSSYLAWYQQKPGQAPRLLIYGAS SRATGIPDRFSGSGSGTDFTLTISRLEPEDFAVYYCQQNKRSPYTFGQGTKLE IK | 80 |
| MBP011 VH amino acid sequence | QVQLVESGGGVVQPGRSLRLSCAASGITFSSHGMHWVRQAPGKGLEWVTFISY DGSIKSYVDSVKGRFTISRDNSKNTLYLQMNSLRAEDTAVYYCATGLTGTGAF DIWGQGTMVTVSS | 81 |
| MBP011 VL amino acid sequence | EIVLTQSPGTLSLSPGERATLSCRASQSVSSSYLAWYQQKPGQAPRLLIYGAS SRATGIPDRFSGSGSGTDFTLTISRLEPEDFAVYYCQQYKRSPYTFGQGTKLE IK | 82 |
| MBP012 VH amino acid sequence | QVQLVESGGGVVQPGRSLRLSCAASGITFSSHGMHWVRQAPGKGLEWVTFASY DGSYKQYVDSVKGRFTISRDNSKNTLYLQMNSLRAEDTAVYYCATGLTGTGAF DIWGQGTMVTVSS | 83 |
| MBP012 VL amino acid sequence | EIVLTQSPGTLSLSPGERATLSCRASQSVSSSYLAWYQQKPGQAPRLLIYGAS SRNTGIPDRFSGSGSGTDFTLTISRLEPEDFAVYYCQQYKRSPYTFGQGTKLE IK | 84 |
| MBP013 VH amino acid sequence | QVQLVESGGGVVQPGRSLRLSCAASGIYFSSHGMHWVRQAPGKGLEWVTFISY DGSIKSYVDSVKGRFTISRDNSKNTLYLQMNSLRAEDTAVYYCATGLTGTNAF DIWGQGTMVTVSS | 85 |
| MBP013 VL amino acid sequence | EIVLTQSPGTLSLSPGERATLSCRASQSVSSSYLAWYQQKPGQAPRLLIYYAS SRNTGIPDRFSGSGSGTDFTLTISRLEPEDFAVYYCQQYGSSPYTFGQGTKLE IK | 86 |
| MBP014 VH amino acid sequence | QVQLVESGGGVVQPGRSLRLSCAASGITFSSHGMHWVRQAPGKGLEWVTFISY DSSYKLYVDSVKGRFTISRDNSKNTLYLQMNSLRAEDTAVYYCATGLTGTGAF DIWGQGTMVTVSS | 87 |

TABLE 10-continued

| Summary table of amino acid sequences and nucleic acid sequences | | |
|---|---|---|
| Description | Amino acid Sequence or nucleic acid sequence | SEQ ID NO. |
| MBP014 VL amino acid sequence | EIVLTQSPGTLSLSPGERATLSCRASQSVSSSYLAWYQQKPGQAPRLLIYYAS SRATGIPDRFSGSGSGTDFTLTISRLEPEDFAVYYCHQYGSSPYTFGQGTKLE IK | 88 |
| MBP015 VH amino acid sequence | QVQLVESGGGVVQPGRSLRLSCAASGIYFSSHGMHWVRQAPGKGLEWVTFITY DGSYKSYVDSVKGRFTISRDNSKNTLYLQMNSLRAEDTAVYYCATGLTGTGAF DIWGQGTMVTVSS | 89 |
| MBP015 VL amino acid sequence | EIVLTQSPGTLSLSPGERATLSCRASQSVSSSYLAWYQQKPGQAPRLLIYYAS SRNTGIPDRFSGSGSGTDFTLTISRLEPEDFAVYYCQQYGSSPYTFGQGTKLE IK | 90 |
| MBP016 VH amino acid sequence | QVQLVESGGGVVQPGRSLRLSCAASGITFSSHGMHWVRQAPGKGLEWVTFSSY DGSYKSYVDSVKGRFTISRDNSKNTLYLQMNSLRAEDTAVYYCATGLTGTNAF DIWGQGTMVTVSS | 91 |
| MBP016 VL amino acid sequence | EIVLTQSPGTLSLSPGERATLSCRASQSVSSSYLAWYQQKPGQAPRLLIYGAS SRNTGIPDRFSGSGSGTDFTLTISRLEPEDFAVYYCQQYKSSPYTFGQGTKLE IK | 92 |
| MBP017 VH amino acid sequence | QVQLVESGGGVVQPGRSLRLSCAASGITFSSHGMHWVRQAPGKGLEWVTFISY DGSYKSYVDSVKGRFTISRDNSKNTLYLQMNSLRAEDTAVYYCATGLIGTGAN DIWGQGTMVTVSS | 93 |
| MBP017 VL amino acid sequence | EIVLTQSPGTLSLSPGERATLSCRASQSVSSSYLAWYQQKPGQAPRLLIYYAS SRATGIPDRFSGSGSGTDFTLTISRLEPEDFAVYYCQQYGSSPYTFGQGTKLE IK | 94 |

Example 7: Mutational Scan and Optimization of Anti-CEACAM5 mAb MBN001

Figure 5A:
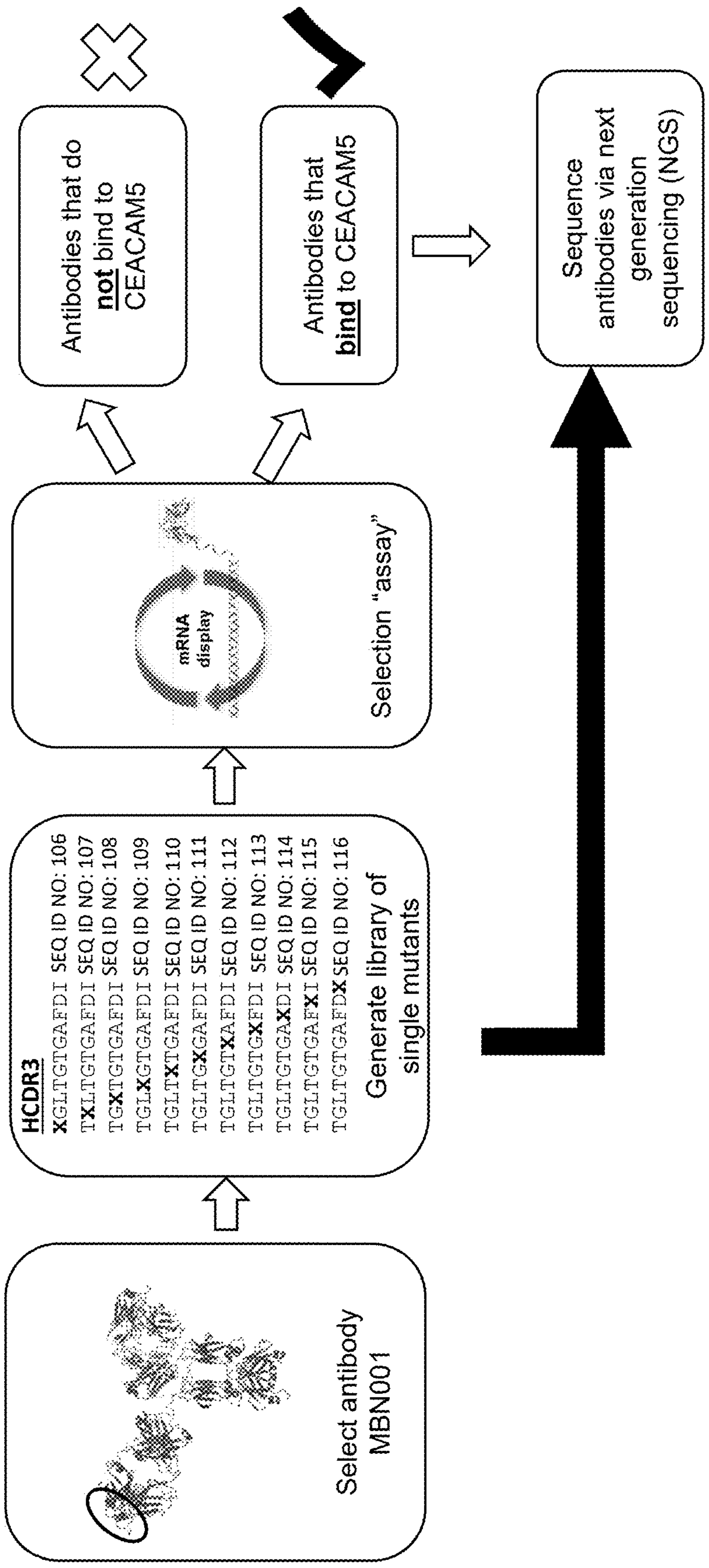

Mutational scanning was performed to identify variants of MBN001 with improved affinity for human and/or cynomolgus CEACAM5, as described in FIG. 5A. A single chain variable fragment (scFv) library was created that allows for single amino acid substitutions in the CDRs using NNK oligos. For each CDR, multiple oligos were designed that incorporated an NNK codon at each position (N=A, C, T, G and K=G, T) to allow for the encoding of all 20 amino acids plus a stop codon at each position. The Kabat definition was used for all CDRs, except for HCDR1, where the AbM definition was used. In some cases, CDR residues were omitted from the scan or additional non-germline Vernier zone amino acids were included in the scan. In particular, Vernier zone residues in the VH at positions 49 and 94 were included in the library design. Positions 33-35 in HCDR1 as well as position 97 in LCDR3 were omitted from the scan. Additionally, the following framework residues in the VH were reverted to germline in the library design: T7S, S40A, A68T, P84A. The diversified positions (MBN001 mutational scan for the analysis of CDR positions) are detailed in FIG. 5B.

The library was expressed in an mRNA display system (Xu et. al. (2002) *Chemistry & Biology* 9: 933-942; Roberts and Szostak (1997) Proc. Natl. Acad. Sci 94: 12297-12302) and taken through a single round of selection against human and cynomolgus CEACAM5. Briefly, the DNA library was subjected to transcription and translation in a manner that fuses the scFv protein to the encoding mRNA via a puromycin linkage. The scFv-mRNA fusions were exposed to biotinylated human CEACAM5 and biotinylated cynomolgus CEACAM5 in separate selections. scFvs that bound the targets were captured by streptavidin beads, eluted, and amplified by PCR. The captured antibodies were sequenced by NGS. The frequency of each sequence in the post-selection population was divided by the frequency of each selection in the starting population to calculate an enrichment ratio. This enrichment ratio was normalized to the enrichment ratio of the parent antibody sequence to generate a normalized enrichment ratio:

$$\text{Normalized enrichment ratio} = \frac{(\text{frequency after selection})/(\text{frequency in starting library})}{(\text{frequency of parent antibody after selection})/(\text{frequency of parent antibody in starting library})}$$

Using these normalized enrichment ratios (ERs), heat maps were generated to assess the effect of every single amino acid substitution upon the binding to human and cynomolgus CEACAM5. The error in the method was approximately 2-fold, and so ER values from 0.5 to 2 were considered to be neutral, while values over 2 were considered to be favorable, and values under 0.5 were considered to be unfavorable. This analysis provided a rich set of information about the effect of single amino acid substitutions, as is shown in FIG. 5C (MBN001 HCDR1 Human CEACAM5), FIG. 5D (MBN001 HCDR1 Cynomolgus CEACAM5), FIG. 5E (MBN001 HCDR2 Human CEACAM5), FIG. 5F (MBN001 HCDR2 Cynomolgus CEACAM5), FIG. 5G (MBN001 HCDR3 Human CEACAM5), FIG. 5H (MBN001 HCDR3 Cynomolgus CEACAM5), FIG. 5I (MBN001 LCDR1 Human CEACAM5), FIG. 5J (MBN001 LCDR1 Cynomolgus CEACAM5), FIG. 5K (MBN01 LCDR2 Human CEACAM5), FIG. 5L (MBN001 LCDR2 Cynomolgus CEACAM5), FIG. 5M (MBN001 LCDR3 Human CEACAM5), and FIG. 5N (MBN001 LCDR3 Cynomolgus CEACAM5), and as summarized in Table 11. Using the deep mutational scanning data, it is shown that many CDR positions (for example as shown for HCDR1-3 and LCDR1-3 in FIG. 5B) were tolerant to mutation, meaning that these substitutions can be made in the identified CDR position/amino acid sequence and maintain the desired of the antibody or antigen binding portion ability to bind human CEACAM5 and cynomolgus CEACAM5.

TABLE 11

Single site mutations in the CDRs of MBN001 that maintain or improve binding to human CEACAM5 and cynomolgus CEACAM5

| CDR Region | Position | Amino Acid substitutions that increase affinity to huCEACAM5 | Amino Acid substitutions that maintain binding to huCEACAM5 | Amino Acid substitutions that increase affinity to cyCEACAM5 | Amino Acid substitutions that maintain binding to cyCEACAM5 |
|---|---|---|---|---|---|
| HCDR1 | 26 | | G (parent), T, K, N, E, Q | | G (parent), S, T, K, H, Y, N, E |
| | 27 | | L, I (parent) | | L, I (parent) |
| | 28 | L, I, M, R, H, F, Y, D | G, A, C, S, T (parent), V, N, E, Q | C, L, I, M, H, F, Y, N | G, A, S, T (parent), V, R, W, D, E, Q |
| | 29 | | F (parent), Y | | F (parent), Y |
| | 30 | D | G, S (parent), Y, N, E | C, W | G, S (parent), T, V, L, R, D, E |
| | 31 | I, H, F, Y, W, D, E | C, S (parent), L, M, N, Q | H, F, Y, W, E | S (parent), T, V, L, I, M, K, R, N, D, Q |
| | 32 | | P, L, H (parent), Y, N | | P, L, H (parent), Y, N |
| | 33 | | Not scanned | | |
| | 34 | | Not scanned | | |
| | 35 | | Not scanned | | |
| HCDR2 | 49 (Vernier zone residue) | | G, A, C, S, T (parent), V, L, I, M, F, Y, N, D, E | | P, A, C, S, T (parent), V, L, I, M, K, H, F, Y, N, D, Q |
| | 50 | | C, M, F (parent), Y, E | | I, M, F (parent), Y, W |
| | 51 | A, S | G, T, V, L, I (parent), M, D, E | A, S | G, T, V, L, I (parent), M, F, D, E, Q |
| | 52 | T | S (parent), V | T | S (parent), V |
| | 52a | | Y (parent) | | H, Y (parent) |
| | 53 | | D (parent) | | D (parent), Q |
| | 54 | | G (parent), A, C, S, T, M, E, Q | S | G (parent), A, C, L, M, K, H, E, Q |
| | 55 | | S (parent), T | | S (parent), T |
| | 56 | I, M | L, Y (parent), W, Q | I, M | L, H, Y (parent), W |
| | 57 | P, V, L, I | A, C, S, T, M, K (parent), R, H, F, Y, W, N, D, E | V, L, I | P, A, C, S, T, M, K (parent), R, H, F, Y, W, N, E |
| | 58 | T, L, I, M, K, Q | G, A, C, S (parent), V, R, H, F, W, N | T, L, I, M, K, Q | P, G, A, C, S (parent), V, R, F, W, N |
| | 59 | | G, A, C, S, T, V, L, I, M, K, R, H, F, Y (parent), W, N, D, E, C | | G, A, C, T, V, L, I, M, K, R, H, F, Y (parent), W, N, Q |
| | 60 | | A, C, S, T, V (parent), L, I, M, F, Y, W, D, E | | P, A, C, S, T, V (parent), L, I, K, F, W, D, E, |
| | 61 | | P, G, A, C, S, T, V, L, I, M, K, R, F, Y, W, N, D (parent), E, Q | C | P, G, A, S, T, V, L, I, M, K, R, H, F, Y, W, N, D (parent), E, Q |
| | 62 | | P, G, A, C, S (parent), T, V, L, I, M, K, R, H, F, Y, W, N, D, E, Q | | P, G, A, C, S (parent), T, V, L, I, M, K, R, H, F, Y, W, D, Q |
| | 63 | T | G, A, C, S, V (parent), L, I, M, K, H, F, Y, W | T | P, G, A, C, S, V (parent), L, I, M, K, H, F, Y, W, N, D, E |
| | 64 | | K (parent), R, H, Y | | P, G, A, S, T, K (parent), R, H, Y, N |
| | 65 | W | P, G (parent), A, C, S, T, V, L, I, M, K, R, H, F, Y, N, D, E, Q | W | P, G (parent), A, C, S, T, V, L, I, M, K, R, H, F, Y, N, D, E, Q |
| HCDR3 | 94 (Vernier zone residue) | | T (parent) | | T (parent) |
| | 95 | | G (parent) | | G (parent) |
| | 96 | | C, L (parent) | C | L (parent), Q |
| | 97 | | T (parent) | | T (parent) |
| | 98 | | G (parent) | | G (parent) |

TABLE 11-continued

Single site mutations in the CDRs of MBN001 that maintain or improve binding to human CEACAM5 and cynomolgus CEACAM5

| CDR Region | Position | Amino Acid substitutions that increase affinity to huCEACAM5 | Amino Acid substitutions that maintain binding to huCEACAM5 | Amino Acid substitutions that increase affinity to cyCEACAM5 | Amino Acid substitutions that maintain binding to cyCEACAM5 |
|---|---|---|---|---|---|
| | 99 | | T (parent) | | T (parent) |
| | 100 | L, N | P, G (parent), C, V, I, D | N | P, G (parent), L, D |
| | 100a | | A (parent) | | A (parent), H |
| | 100b | S, V, L, M, K, H, Y, N | A, C, T, I, F (parent), W, D, Q | S, V, L, M, K, H, Y, N | A, C, T, I, F (parent), W, D, Q |
| | 101 | | D (parent) | | S, D (parent) |
| | 102 | | V, I (parent) | | V, I (parent), F, W |
| LCDR1 | 24 | | G, A, C, S, T, V, L, I, M, K, R (parent), H, F, Y, W, N, D, E, Q | | P, G, A, C, S, T, V, L, I, M, R (parent), F, Y, W, N, D, E, Q |
| | 25 | P, C | G, A (parent), S, T, V, L, I, M, F, N, D, Q | P, C, L, I, M | G, A (parent), S, T, V, H, F, Y, W, N, E |
| | 26 | | P, G, A, C, S (parent), T, V, L, I, M, K, R, H, F, Y, W, N, D, E, Q | | P, G, A, C, S (parent), T, V, L, I, M, K, R, F, Y, W, N, D, E, Q |
| | 27 | | P, G, A, C, S, T, V, L, I, M, K, R, H, F, Y, N, D, E, Q (parent) | | P, G, C, S, T, V, L, I, M, K, R, H, Y, W, N, E, Q (parent) |
| | 27a | | P, G, A, C, S (parent), T, V, L, I, M, K, R, H, F, Y, W, N, D, E, Q | Y, W | P, G, A, C, S (parent), T, V, L, I, M, R, H, F, N, Q |
| | 28 | P, C, M, F | S, T, V (parent), L, I, K, Y, D, Q | T, M, F | P, C, V (parent), L, I, K, Y |
| | 29 | | G, A, C, S (parent), L, H, Y, N, D, E, Q | G | P, C, S (parent), R, W, N, D, E |
| | 30 | | P, A, S (parent), V, I, D | P | A, S (parent), T, V, I, W |
| | 31 | P, V, I, W, Q | G, A, C, S (parent), T, L, M, K, R, H, F, Y, E | V, I, K, W | P, A, C, S (parent), T, L, M, R, H, Y |
| | 32 | P, G | A, S, T, V, I, M, H, F, Y (parent), W, N, D | | P, G, C, S, T, V, I, M, F, Y (parent), W, N, D, Q |
| | 33 | G, A, I | C, S, T, V, L (parent), M, K, R, F, Y, W, N, D, E, Q | I, M, Y, W | G, A, S, V, L (parent), K, R, F, N, E, Q |
| | 34 | | A (parent), C, S | | G, A (parent), C, S, T, M, Y |
| LCDR2 | 50 | A, S, M, F, Y, W | G (parent), C, T, V, R, H, N, Q | A, C, S, V, M, F, Y, W | G (parent), L, R, H |
| | 51 | P, G, C | A (parent), S, T, L, M, H, W, N, Q | P, G, C, H | A (parent), S, T, L, M, K, R, W, Q |
| | 52 | Y, Q | G, A, C, S (parent), T, V, L, I, K, R, F, W, N, D, E | F, Y, W, Q | A, C, S (parent), V, L, I, M, E |
| | 53 | F, Y, W | P, G, A, C, S (parent), T, V, M, H, N, Q | W | P, A, S (parent), T, H, F, Y, N, Q |
| | 54 | | P, A, C, T, V, L, I, M, K, R (parent), H, F, Y, W, N, E, Q | | P, C, T, L, I, M, K, R (parent), F, W, N, Q |
| | 55 | L, H, D | P, G, A (parent), S, M, Y, W, N, Q | L, M, F, Y, N, D | P, G, A (parent), S, T, H |
| | 56 | | P, C, S, T (parent), V, L, I, M, R, F, Y, W, N, D, Q | P, C, W, N | G, A, S, T (parent), L, I, K, R, H, F, Y |
| LCDR3 | 89 | S, M, H, F, Y, N, D | G, A, K, E, Q (parent) | S, H, D | P, G, A, M, K, F, Y, N, E, Q (parent) |
| | 90 | | Q (parent) | | Q (parent) |
| | 91 | S, T, N | G, A, C, V, F, Y (parent), D, Q | G, C, S, T, N, Q | A, H, Y (parent), D |
| | 92 | C, V, L, I, M, K, R, F, Y, W | G (parent), A, S, T, H, N, D, E, Q | L, I, M, K, R, Y, W, N | G (parent), A, C, S, T, V, F, Q |
| | 93 | P, V, L, I, M, R, H, F, Y, Q | A, C, S (parent), T, K, W, N | P, C, T, V, L, I, M, K, R, H, F, Y, W, N, Q | A, S (parent) |

TABLE 11-continued

Single site mutations in the CDRs of MBN001 that maintain or improve binding to human CEACAM5 and cynomolgus CEACAM5

| CDR Region | Position | Amino Acid substitutions that increase affinity to huCEACAM5 | Amino Acid substitutions that maintain binding to huCEACAM5 | Amino Acid substitutions that increase affinity to cyCEACAM5 | Amino Acid substitutions that maintain binding to cyCEACAM5 |
|---|---|---|---|---|---|
| | 94 | L, I, F, Y | P, G, A, C, S (parent), T, V, M, R, H, W, N, Q | C, L, I, M, F, Y, Q | G, A, S (parent), T, V, R, H, W |
| | 95 | V, M, K, R, H, Q | P (parent), A, C, T, L, I, F, Y, W, N, E | I, K | P (parent), A, C, T, V, L, M, R, H, F, W, N, E, Q |
| | 96 | S, T, V, I, M, H, W, N, D, Q | P, G, A, C, L, Y (parent), E | M, N, D, E | P, A, C, S, T, V, I, Y (parent), W, Q |
| | 97 | Not scanned | | | |

Example 8: Production and Analysis of Anti-CEACAM5 mAb Progeny of MBN001

This example describes the generation of progeny of anti-CEACAM5 antibody MBN001 and the characterization of the progeny antibodies. A subset of CDR amino acid substitutions that were predicted to improve MBN001 binding to human CEACAM5 or cynomolgus CEACAM5 based upon the deep mutational scanning data were selected for further analysis. Antibody genes with single amino acid substitutions and combinations of substitutions were synthesized in IgG expression vectors, transiently transfected into HEK cells, and purified via Protein A. In addition, the framework germline reversions described above were also incorporated into the sequences of the progeny. Purified IgG1.3 CEACAM5 mAb clones were characterized using the BIACORE® for high-throughput SPR-based monoclonal characterization.

The BIACORE® instrument was primed with 1×HBSP+ running buffer (Cytiva catalog no.BR100671). The CM5 chip (Cytiva catalog no. 29149604) was equilibrated to room temperature, and the BIACORE® instrument was re-primed. A human antibody Fc capture kit (Cytiva catalog no. 29234600) was utilized for this analysis. The human antibody Fc capture reagent was immobilized to both flow cells in all 8 flow channels of the CM5 chip via amine-coupling using the following conditions. Immobilization was performed at a temperature of 25° C. The anti-human Fc capture reagent was diluted to a concentration of 25 μg/mL in acetate pH5 buffer. The chip surface was activated by injecting a mixture of 1-ethyl-3-(-3-dimethylaminopropyl) carbodiimide hydrochloride (EDC) and N-hydroxy succinimide (NHS) for 420 seconds at a rate of 10 microliters per minute (uL/min). A concentration (25 ug/mL) of anti-human Fc capture reagent was then injected on the surface for 420 seconds at a rate of 10 uL/min. The remaining chip surface was blocked by injecting ethanolamine for 420 seconds at a rate of 10 uL/min. This process yielded immobilization levels at approximately 9000RU.

The SPR kinetics against full-length human and cyno CEACAM5 were set up as follows. The antibody capture was performed by diluting the antibodies to a concentration of 10 nM in HBSP+ buffer. The 10 nM mAbs were captured for 20 seconds at 5 uL/min to achieve capture levels of approximately 100RU. Analyte binding was performed by first making a titration series of full-length human and cyno CEACAM5 that were prepared (from 500 nM-0.23 nM) with three-fold dilutions in HBSP+ buffer. The association rate was 180 seconds at 30 uL/min. The dissociation rate was 600 seconds at 30 uL/min. Regeneration was performed using two injections of 3M magnesium chloride $MgCl_2$ for 30 seconds at 30 uL/min. A data fit was performed using a 1:1 binding model with global Rmax. Rmax reflects the maximal response when all ligand is occupied.

Figure 6B:
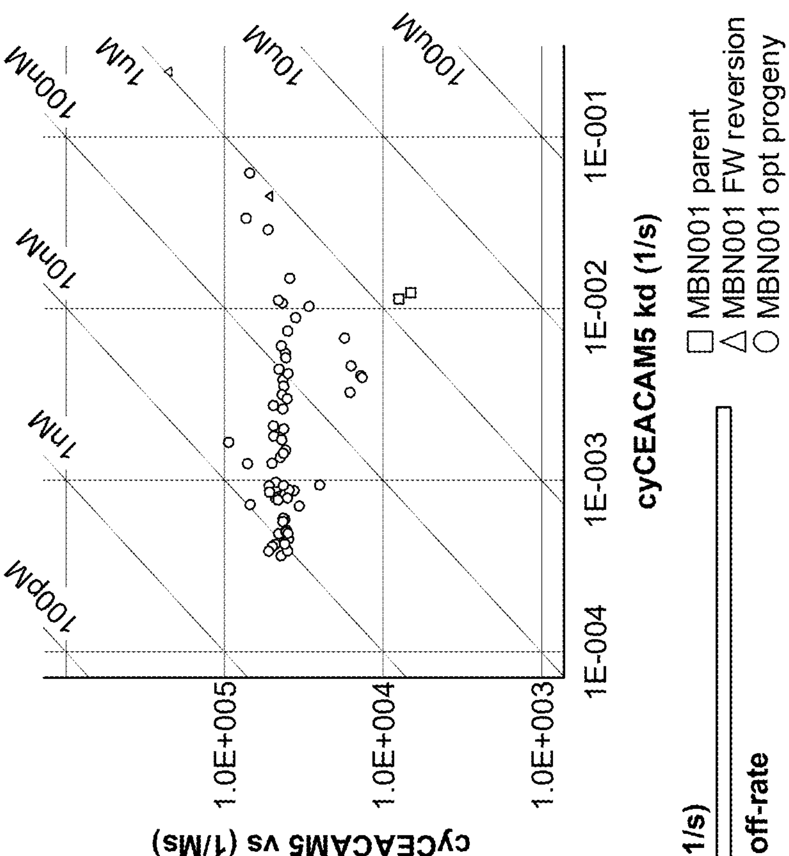
FIGS. 6A-6B are isoaffinity plots showing improvements to the on-rate and off-rate to human CEACAM5 (FIG. 6A) and cyno CEACAM5 (FIG. 6B) for parental antibody MBN001 compared to MBN001 optimized progeny.
Figure 6A:
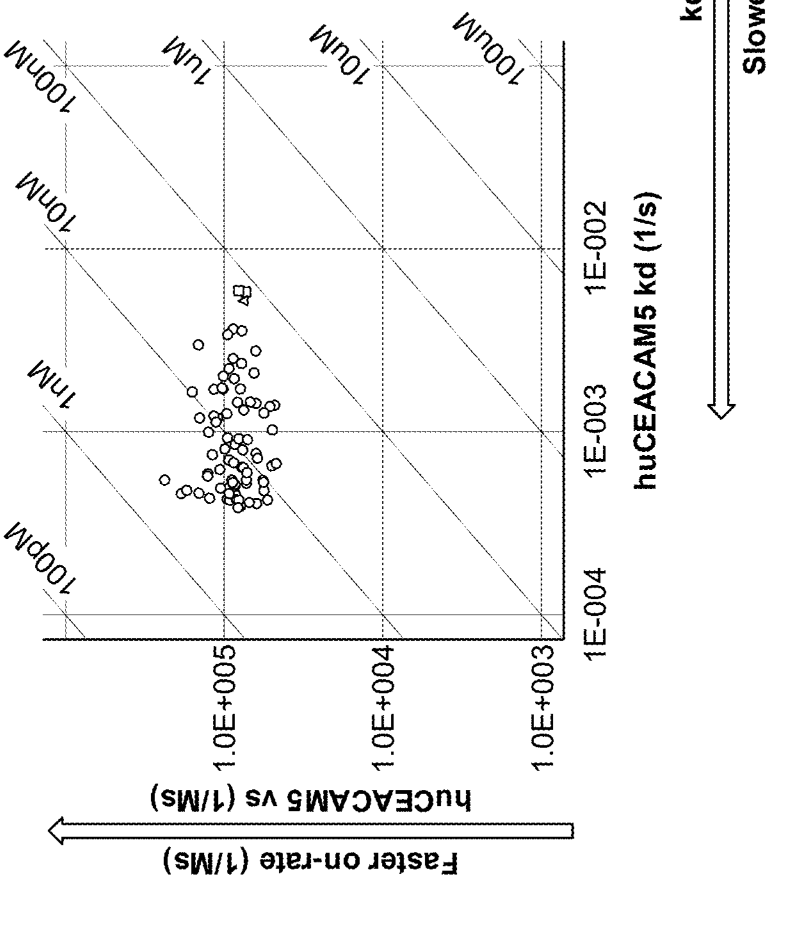
Figure 7A:
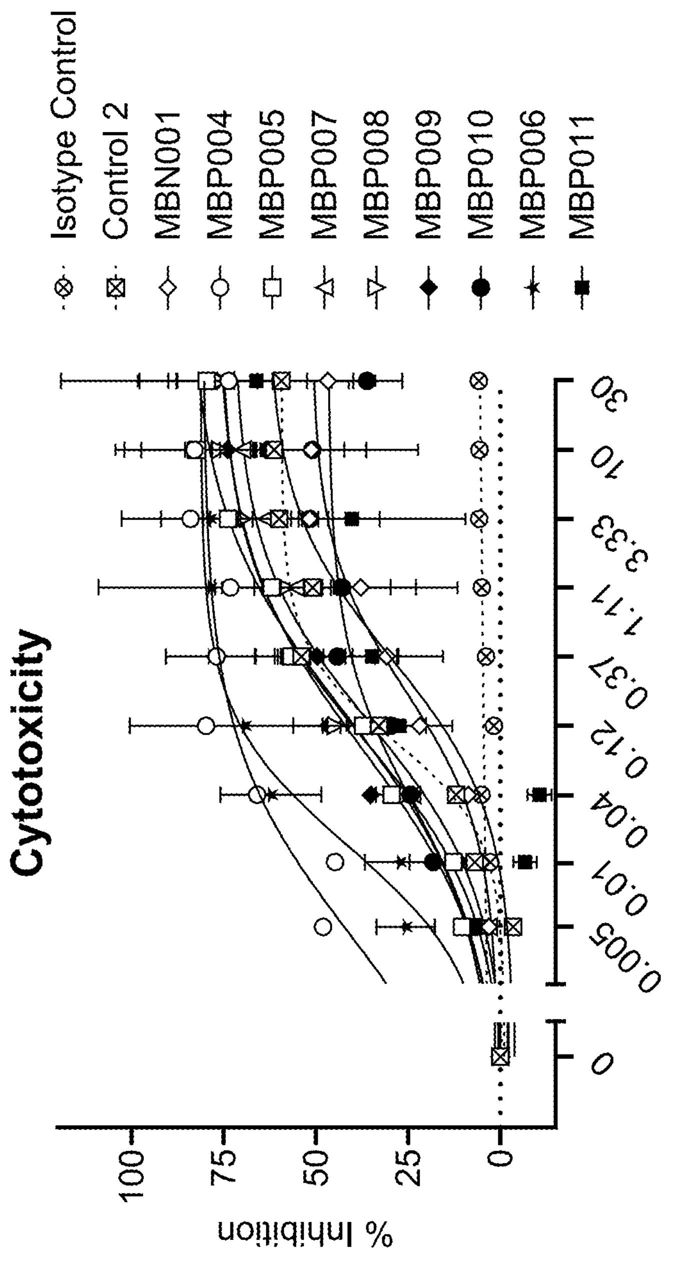
FIGS. 7A-7C are a set of graphs that shows percent inhibition of anti-CEACAM5 antibodies delivering cytotoxic agent MMAE conjugated to a VHH secondary antibody (FIG. 7A), internalization rates (FIG. 7B), and cytotoxicity levels of MBN001 antibody and selected progeny (MBP004, MBP005, MBP007, MBP008, MBP009, MBP010, MBP006, and MBP011) as a function of internalization (FIG. 7C) in MKN45 cells.
Figure 7B:
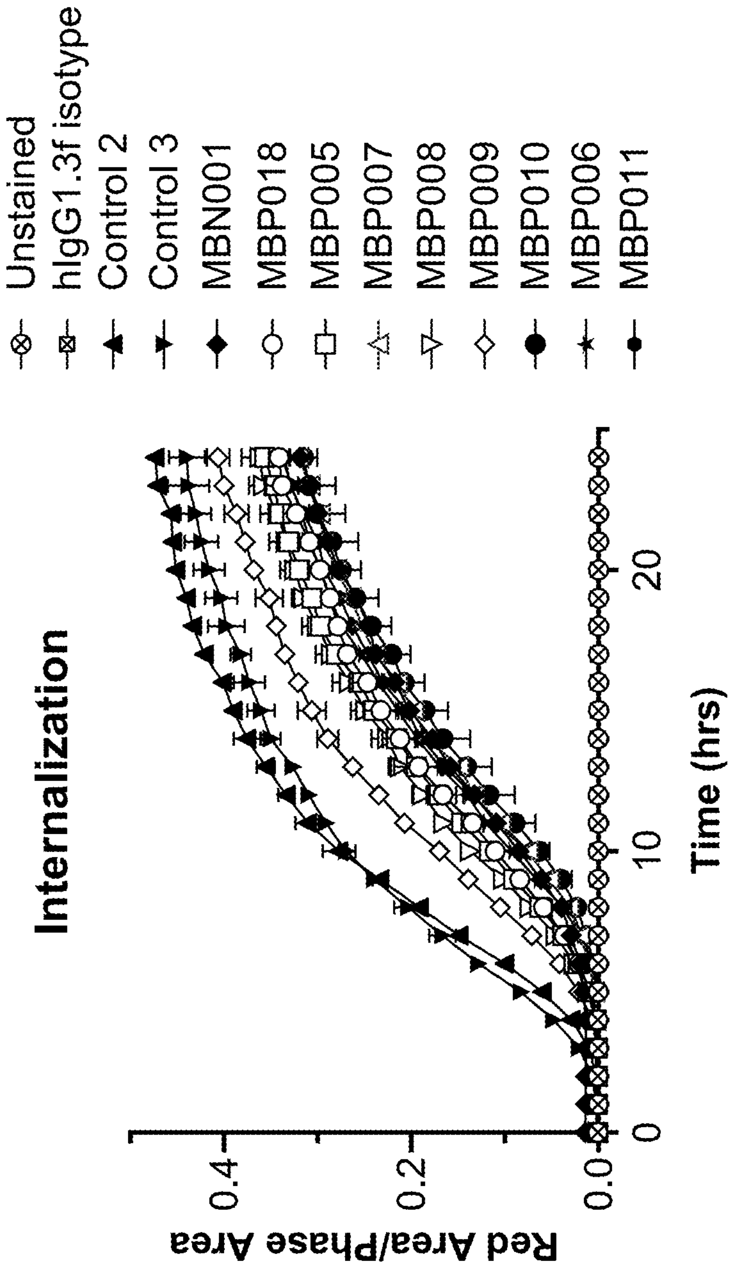
Figure 7C:
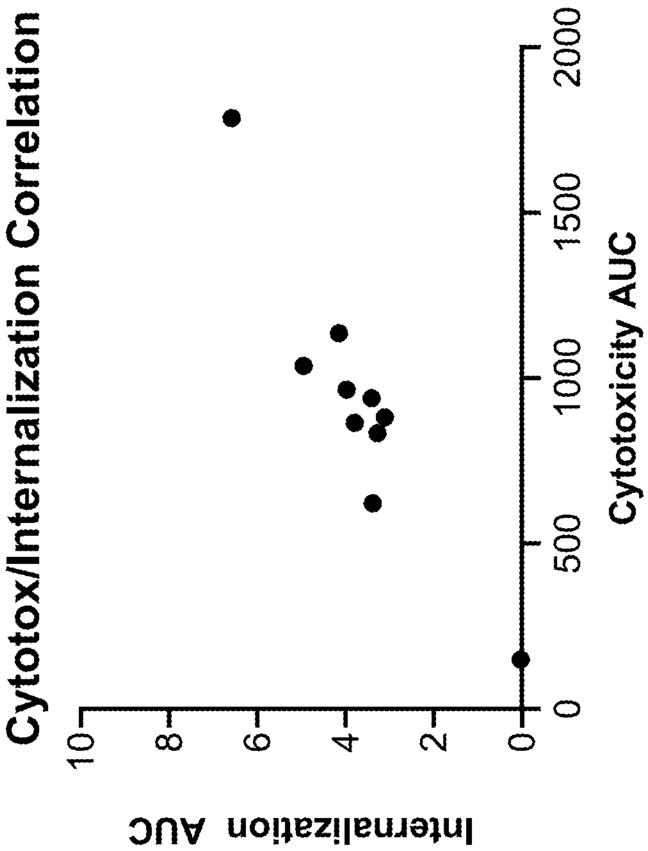

SPR data demonstrating improvements in huCEACAM5 and cynoCEACAM5 affinities for progeny antibodies are shown in the isoaffinity plots in FIG. 6A and FIG. 6B for the progeny antibodies with values reported below in Table 12A and Table 12B, which shows that each of the tested antibodies bind both human CEACAM5 and cyno CEACAM5. Data showed that these progeny selectively bound human CEACAM5 and did not bind CEACAM1, CEACAM6, CEACAM7, and CEACAM8. Note that these progeny were also made in a hIgG1 form 1 as opposed to the hIgG1.3f form described in this Example. Both the hIgG1 form and the hIgG1.3f form shared the same heavy chain variable region and the same light chain variable region, i.e., only the $CH_2$ regions of heavy chain were adapted, such that their binding characteristics would be expected to be similar. In fact, data show acceptable agreement (e.g., one-fold to two-fold similarity in human CEACAM5 and cyno CEACAM5 binding/SPR values) was observed between hIgG1 and hIgG1.3f versions of the progeny (data not shown). Data in FIG. 7A, FIG. 7B, and FIG. 7C confirm that the MBN001 progeny were effectively internalized into human CEACAM5 expressing cells and that these progeny could be used to effectively deliver cytotoxic agents and moieties. Data in FIG. 8A and FIG. 8B show absence of non-specific human CEACAM1 and human CEACAM6 cross-reactivity with MBN001 progeny mAbs MBP001, MBP003 and MBP002. FIGS. 9A-9D show that the FACS EC50 remained constant for each clone across cell lines and that the max MFI increases 10-fold from LS174T and BxPC3 to MKN45.

TABLE 12A

Binding data for hIgG1.3f progeny antibodies

| Ab identifier | Class | IgG1.3f Ab | Parent Ab | huCEACAM5 ka (1/Ms) | huCEACAM5 kd (1/s) | huCEACAM5 KD (M) | cyCEACAM5 ka (1/Ms) | cyCEACAM5 (1/s) | cyCEACAM5 KD (M) |
|---|---|---|---|---|---|---|---|---|---|
| MBN001 parent | IgG1 | | MBN001 | 7.36E+04 | 5.79E−03 | 7.86E−08 | 7.99E+03 | 1.14E−02 | 1.42E−06 |
| MBP004 | IgG1 | | MBN001 | 7.60E+04 | 1.31E−03 | 1.73E−08 | 4.41E+04 | 1.79E−03 | 4.06E−08 |
| MBP005 | IgG1 | | MBN001 | 1.17E+05 | 1.70E−03 | 1.46E−08 | 4.92E+04 | 1.79E−03 | 3.65E−08 |
| MBP006 | IgG1 | | MBN001 | 8.51E+04 | 5.13E−04 | 6.03E−09 | 4.86E+04 | 7.93E−04 | 1.63E−08 |
| MBP007 | IgG1 | | MBN001 | 7.96E+04 | 1.71E−03 | 2.15E−08 | 4.27E+04 | 9.24E−04 | 2.17E−08 |
| MBP008 | IgG1 | | MBN001 | 8.92E+04 | 5.27E−04 | 5.91E−09 | 4.03E+04 | 7.84E−04 | 1.95E−08 |
| MBP009 | IgG1 | | MBN001 | 1.72E+05 | 4.80E−04 | 2.78E−09 | 5.03E+04 | 4.09E−04 | 8.14E−09 |
| MBP010 | IgG1 | | MBN001 | 5.00E+04 | 1.02E−03 | 2.04E−08 | 3.40E+04 | 7.06E−04 | 2.08E−08 |
| MBP011 | IgG1 | | MBN001 | 4.71E+04 | 6.71E−04 | 1.42E−08 | 4.26E+04 | 8.23E−04 | 1.93E−08 |

TABLE 12B

Binding data for hIgG1 progeny antibodies

| Antibody identifier | Class | IgG1.3f antibody | Parent antibody | huCEACAM5 ka (1/Ms) | huCEACAM5 kd (1/s) | huCEACAM5 KD (M) | cyCEACAM5 ka (1/Ms) | cyCEACAM5 (1/s) | cyCEACAM5 KD (M) |
|---|---|---|---|---|---|---|---|---|---|
| MBP002 | IgG1 | MBP008 | MBN001 | 4.33E+04 | 2.28E−04 | 5.26E−09 | 3.78E+04 | 5.02E−04 | 1.33E−08 |
| MBP001 | IgG1 | MBP005 | MBN001 | 4.52E+04 | 1.17E−03 | 2.58E−08 | 3.31E+04 | 1.24E−03 | 3.74E−08 |
| MBP003 | IgG1 | MBP004 | MBN001 | 4.20E+04 | 9.82E−04 | 2.34E−08 | 2.64E+04 | 1.14E−03 | 4.31E−08 |

Example 9: Internalization Analysis of Recombinant IgG1.3 Progeny Antibodies

Internalization experiments were conducted for hIgG1.3 MBN001 progeny antibodies, listed in Table 13A below. Antibodies were evaluated for internalization using HCT-116-huCEACAM5, HCT-116-cyCEACAM5, and MKN45 cell lines.

Additional internalization experiments were conducted for hIgG1 antibodies MBP001, MBP002, and MBP003 using the MKN45 and Ls174T cell lines. The MKN45 or Ls174T cells were seeded at 10K cells/well (50 uL).

Cell lines were first analyzed for cell density and viability using a Vi-cell viability machine. The cell lines were diluted to 0.2E6 vc/mL in growth media, and a volume (50 uL) of each was dispensed to a flat-bottom 96-well plate to achieve cell counts of 10K cells/well. Ls174T media included MEM with 10% HI-FBS and 1% pen/strep. MKN45 media included RPMI (ATCC modification) with 10% HI-FBS and 1% pen/strep. HCT-116 media included McCoy's 5a with 10% HI-FBS, 1% pen/strep, and 6 μg/mL Blasticidin. Cells were allowed to adhere to wells of the 96-well plate (Corning Cat. No. 3595) at 37° C./5% $CO_2$ for approximately 4 hours.

Each test mAb and control mAb was labeled by first pre-mixing the respective antibody with a pHrodo red (Fab conjugated to pH-sensitive; Thermo cat #Z25612) secondary reagent at a 3:1 dye:mAb molar ratio. A series of dilutions were prepared at 2× target concentration in growth media. The final mAb target concentration was 25 nM. A volume (50 uL) of labeled mAb samples were added to the plated cells to achieve a target mAb concentration (25 nM).

Coated plates contacted with the labeled mAbs were incubated at 37° C. for 30 minutes. Each plate was then read using an Incucyte apparatus, which collected images from the red and phase channels [10× objective; 3 images/well] for a 24-hour duration, with reads of plates every 30 minutes. The data are shown in Table 13A and Table 13B.

Data show that the anti-CEACAM5 progeny antibodies—were internalized by the HCT-CEA cell line and MKN45 cell lines.

TABLE 13A

Internalization data for hIgG1.3 progeny antibodies

| antibody identifier | MKN45 24 hr red/phase AUC (internalization) | HCT116-huCEACAM5 red/phase AUC (internalization) | HCT116-cyCEACAM5 red/phase AUC (internalization) |
|---|---|---|---|
| MBP004 | 3.79 | 1.14 | 2.50 |
| MBP005 | 3.98 | 1.18 | 2.11 |
| MBP006 | 3.55 | 1.14 | 2.40 |
| MBP007 | 3.28 | 1.05 | 1.80 |
| MBP008 | 4.15 | 1.13 | 2.54 |
| MBP009 | 4.95 | 1.36 | 2.57 |
| MBP010 | 3.11 | 1.00 | 2.55 |
| MBP011 | 3.41 | 1.07 | 2.35 |

TABLE 13B

Internationalization data for hIgG1 progeny antibodies

| antibody identifier | Ls174T 24 hr red/phase AUC (internalization) | MKN45 24 hr red/phase AUC (internalization) |
|---|---|---|
| MBP001 | 0.69 | 2.42 |
| MBP002 | 0.72 | 2.58 |
| MBP003 | 0.67 | 2.62 |

MBN001 and certain progeny (e.g., MBP004 and MBP019) were analyzed for internalization to cynoCEACAM-5 expressing cells. It was observed that MBN001 and the progeny were efficiently internalized. Internalization of negative control mAbs was not observed.

Example 10—Conjugation Reaction with Compound A' and Anti-CEACAM5 mAbs to Yield DAR8 ADCs This example describes the conjugation of MBN001, and progeny (e.g., MBP001, MBP002, MBP003,) antibodies to Compound A'. Table 14 lists materials used for the conjugation method.

TABLE 14

| Reagents and consumables | | |
|---|---|---|
| Description | Manufacturer | Catalog number |
| Zeba Spin desalting columns 7 kDa MWCO | Thermo Fisher Scientific | 89893 |
| Amicon Ultra - 1 5 PLTK Ultracel-PL centrifugal filters Regenerated Cellulose (30 kDa MWCO) | Merck Millipore | UFC903024 |
| TCEP HCl, 0.5M, pH 7.0 | Sigma-Aldrich | 646547 |

tion was thawed. A fresh 10 mM TCEP working solution was prepared by combining 20 μl of 0.5 M TECP-HCl pH 7.0 with 980 μl of P5 conjugation buffer. Both reagents were vortexed prior to use.

The calculated amount of TCEP working solution was added to the solution of the MBP001 mAb and mixed by gentle swirling. The calculated amount of Compound A' stock was added immediately afterwards. The mixture was then incubated overnight at 23° C. in amber 50 ml tubes and spun at a speed of 300 rpm.

Conjugation efficiency was evaluated by LC-MS analysis. The conjugate samples were diluted to 1 mg/mL in 100 mM Tris pH 7.5. 20 μl of sample was reduced by adding 2 μl of 0.5M dithiothreitol (DTT) or TCEP. The samples were analyzed by LC-MS using an Agilent 1290 Infinity UPLC system coupled to a 6530 Accurate-Mass Q-TOF. The analytical column (Waters Inc., BEH C4 column, 1.7 um, 2.1 mm×50 mm) was equilibrated at 60° C. The mobile phase consisted of 0.1% formic acid in water (phase A) and 0.1% formic acid in acetonitrile (phase B). The system was operated at a flow rate of 200 l/min. The gradient condition (Compound A')

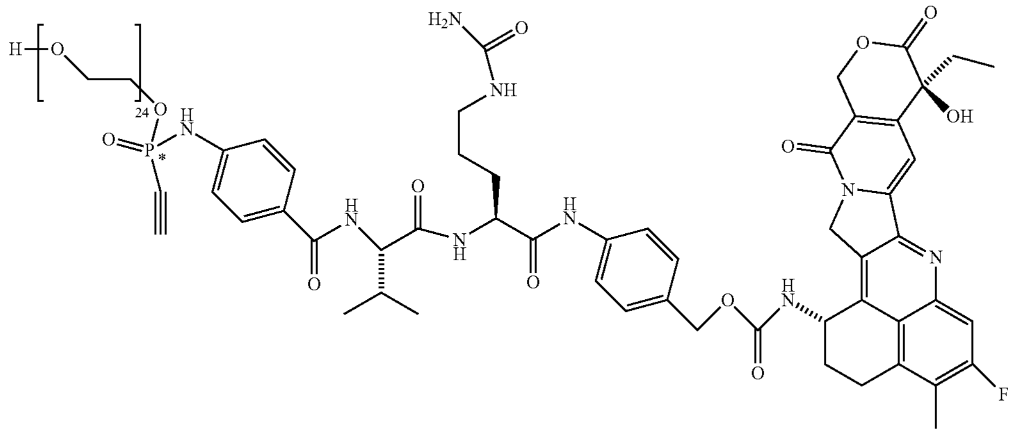

Firstly, each mAb was buffer-exchanged into P5 conjugation buffer (50 mM Tris, 100 mM NaCl, 1 mM EDTA, pH 8.3 at 25° C.) and adjusted to a concentration of 10 mg/ml. Next, Zeba Spin desalting columns were utilized. The columns were equilibrated with P5 conjugation buffer according to the manufacturers' instructions. Recovery-yields were usually >95%.

For the mAb stock solution with a concentration below 10 mg/ml, concentration and buffer exchange (diafiltration) were performed using protein concentrator spin columns (Amicon Ultra) according to the manufacturers' instructions. The spin columns are rinsed with P5 conjugation buffer prior to application of the mAb.

After buffer exchange, the mAb concentration was measured with a nanophotometer. P5 conjugation buffer was utilized as the blank. Finally, the mAb concentration was adjusted to 10 mg/ml with P5 conjugation buffer.

Next the mAb was transferred into amber plasticware. The conjugation reaction was performed protected from light. Conjugation with Compound A' was performed with a molar ratio of 7 eq. TCEP and 10 eq. of Compound A' per 1 equivalent of MBP001 mAb. Typically, a 40 mM Compound A' stock in DMSO and a 10 mM TCEP working solution were used. The 40 mM linker-payload stock soluwas as follows: 0-2 min., held at 27% B; 2-9 min., slow ramp from 27-37% B; 9-9.5 min., linear ramp from 37-90% B; 9.5-12.3 min., held at 90% B. The MS settings were as follows: Polarity=Positive, Capillary Voltage=4.2 kV, Sample Cone=40 V, Source Offset=15 V, Source Temperature=140° C., Desolvation Temperature=325° C. The data acquisition range was 900-3200 m/z. Deconvolution was done using Agilent MassHunter Walkup. If any unconjugated mAb was still present, another 1.4 equivalents of TCEP and 2 equivalents of Compound A' were added followed by incubation for 2-4 hours. The process yielded DAR8 ADCs.

Example 11: Cytotoxicity Analysis of Progeny Antibodies

This example assessed the cytotoxicity of CEACAM5 targeting mAbs of MBN001 progeny mAbs conjugated to Compound A', as described above. Cytotoxicity was measured by IC50 and AUC value of cellular growth inhibition across CEACAM5-expressing cell lines Ls174T and MKN45 cell lines. Data were used (along with binding and internalization data) to select mAbs for in-vivo efficacy testing.

The Ls174T cells and MKN45 cells were harvested using a trypsin/EDTA (0.25%) solution (Gibco Cat #25200-056). The media was removed and the cells were washed with 1×PBS (Ca+ and Mg free; Gibco Cat #14190-144). The cells were detached using the trypsin/EDTA solution. The trypsin/EDTA solution was neutralized with complete media. Cells were spun down at a speed of 1400 rpm for five minutes. The supernatant was removed and the cells were suspended in complete media corresponding to each cell line.

Cells were then counted and the cell concentration was adjusted to $1.0\times10^6$ cells/mL. Specific cells were diluted to the following concentrations: Ls174T: $0.125\times10^6$ cells/mL and MKN45: $0.1\times10^6$ cells/mL. A volume (20 μL) of the different cell suspensions were added to each well of a plate (PerkinElmer catalog no. 6007480). Plates were incubated for 20-24 hours. Dilutions of test reagents (e.g., antibody MBP001, MBP002 and MBP003 conjugated to Compound A') were prepared and the dilutions (20 μL) were added to the plates and allowed to incubate for 120 hrs. at 37° C.

Cell viability was determined using a Cell TiterGlo (CTG) 2.0 cell viability assay (Promega catalog no. G9242). The CTG reagents were removed from the refrigerator and allowed to equilibrate to room temperature. The assay plates were removed from the incubator and allowed to acclimate to room temperature. White backing adhesive was applied to the plate bottoms. A volume (40 μL) of CTG solution was added to each assay well and then mix on an orbital shaker for 2 minutes at a speed of 500 rpm. The assay plates were placed in the dark for 20 minutes. The plate covers were then removed and the luminescence was analyzed on an Envision plate reader. Data are shown in Table 15. Data show that the tested antibodies bound to the CEACAM5 on the different CEACAM5-expressing cells lines over 96 hours, such that the cytotoxic payloads were delivered to the cells for effective cytotoxic killing.

TABLE 15

Cytotoxicity data for progeny antibodies

| antibody identifier | MKN45 5-day cytotoxicity (IC50) | MKN45 5-day cytotoxicity (AUC) | Ls174T 5-day cytotoxicity (IC50) | Ls174T 5-day cytotoxicity (AUC) |
|---|---|---|---|---|
| MBP001 | 1.321 | 23852 | 2.031 | 18252 |
| MBP002 | 1.194 | 24071 | 1.594 | 18858 |
| MBP003 | 1.314 | 24378 | 2.208 | 18522 |
| MBP004 | 0.0041 | 2381 | 1.027 | 865 |
| MBP005 | 0.15 | 2348 | 10.97 | 964 |
| MBP006 | 0.018 | 2439 | 2.831 | 902 |
| MBP007 | 0.127 | 2074 | 24.9 | 834 |
| MBP008 | 0.968 | 2203 | 2.6 | 1136.00 |
| MBP009 | 0.08 | 2195 | 2.385 | 1037.00 |
| MBP010 | 0.035 | 1363 | 2.548 | 909.90 |
| MBP011 | 0.36 | 1770 | 4.468 | 938.90 |

Example 12: Analysis of Cytotoxic and ADCC Activity of Anti-CEACAM5 ADCs

This Example analyzed the cytotoxic activity of anti-CEACAM5 ADCs ADCP001A, ADCP001B and ADCP001C (i.e., progeny mAbs MBP003, MBP001 and MBP002, respectively, conjugated to Compound A') across CEACAM5-expressing cell lines LS174T, BxPC3 and MKN45. FIG. 10A, FIG. 10B, and FIG. 10C show % growth inhibition (as % cell viability) for selected antibody-conjugate-treated cells at the indicated antibody concentrations in: Ls174T (FIG. 10A), a low CEACAM5 expressing cell line; BxPC-3, a medium CEACAM5 expressing cell line (FIG. 10B) and, MKN45, a higher CEACAM5 expressing cell line (FIG. 10C). Data show that the progeny ADCs described herein demonstrated comparable or even improved cellular growth inhibition IC50 values compared to the parental ADCN001 (MBN001 conjugated to Compound A ADC; see FIG. 10D).

ADCC activity was also analyzed with anti-human lead CEACAM5 mAbs in a Jurkat-NFAT-FcγRIIIa (Promega) cell assay (catalog number G9901) using BxPC3 cells and MKN45 cells as target cells. See FIG. 11A and FIG. 11B. BxPC3 (CEACAM medium-expressing cell line) and MKN45 (CEACAM5 high-expressing cell line) cells were incubated with different concentrations of CEACAM5 mAbs (IgG1 or inactive IgG1.3f). Jurkat-FcγRIIIa effector cells were then co-incubated with targets cells for six hours. NFAT activation, reflecting the induced ADCC response, was assessed by determining luciferase activity. Data show that mAb progeny of MBP003, MBP001 and MBP002 had limited ADCC activity.

Example 13. Bystander Kill Analysis of Progeny Anti-CEACAM5 mAb ADCs

Depending on the linker design, membrane permeable cytotoxic drugs conjugated in an ADC that are released inside target positive cells can pass through the cell membrane and kill other cells that are in close proximity, including neighboring cancer cells that lack antigen expression (bystander effect). This Example performed assays to analyze the bystander kill characteristics of the anti-CEACAM5 ADCs.

Briefly, 8000 CEACAM5 antigen expressing MKN45 cells (antigen positive cells; Ag+) and 2000 HCT-116 cells that do not express CEACAM5 (antigen negative cells, Ag−) were plated in 96 well plate to determine ADC bystander killing using Incucyte for enumeration of live Ag− (green) or Ag+ (red) cells as a function following treatment with different doses of anti-CEACAM5 mAb+ Compound A' ADCs ADCP001A, ADCP001B and ADCP001C (N=3 was used for each treatment). Control cells were untreated. Dose-dependent percent cellular inhibition for Ag+ or Ag− cells was calculated at 72 hours and 120 hours by normalizing to untreated control wells. See FIG. 12A, FIG. 12B, FIG. 12C, and FIG. 12D. Each of the tested ADCs (comprising either MBP001, MBP002, or MBP003 conjugated to Compound A') were found to have the ability to release and kill bystander cells with the exatecan payload.

Example 14. Testing the In Vivo Anti-Tumor Efficacy of the Anti-CEACAM5 ADCs

This Example analyzed the in vivo anti-tumor efficacy of anti-CEACAM5 ADCs in the cell line-derived xenograft models (MKN45, BxPC3, and Ls174T). 2×106 MKN45 or 5×106 BxPC3, or 1×106 Ls174T cells were inoculated subcutaneously into the right flank of four to six weeks old immunodeficient female Athymic Nude mice (CRL 490, Charles River) or NSG mice (NOD.Cg-Prkdcscid Il2rgtm1Wjl/SzJ, stock 005557, Jackson Laboratory). Animals with tumor volume between 150 mm3-250 mm3 were randomized into treatment groups with mean tumor volume of 180 mm3 (N=7). Tumor bearing animals were treated with a single intravenous injection of buffer control (Phosphate-buffered saline (PBS)) or with ADCs. Tumor length (L) and width (W) were measured with calipers and tumor volumes were calculated using the formulation L*(W^2)/2.

Anti-CEACAM5 ADCN001 (MBN001 conjugated to Compound A') was evaluated for in vivo potency across MKN45, Ls174T and BxPC3 models. Results for tumor growth of the MKN45, BxPC3, and Ls174T models treated with 3 mg/kg of ADCN001 are provided in FIG. 15A, FIG. 15B, and FIG. 15C, and tumor growth of BxPC3 and Ls174T models treated with 10 mg/kg of ADCN001 are provided in FIG. 15D and FIG. 15E respectively. Data show that ADCN001 (MBN001 conjugated to Compound A') had anti-tumor effect in these models. FIGS. 17A-17D are a set of graphs showing efficacy of ADCV001 (MBV001, wild-type hIgG1 version of MBN001, conjugated to Compound A') in CDX models (MKN45 and BxPC3) after a single intravenous injection with either 3 mg/kg or 10 mg/kg of the ADC. Results for tumor growth of the MKN45 model and BxPC3 model treated with 3 mg/kg of ADCV001 are provided in FIG. 17A and FIG. 17B, and with 10 mg/kg of MBV001 are provided at FIG. 17C and FIG. 17D, respectively. Data shows that the ADCN001 (ADC in the wild-type IgG format of MBN001 conjugated with Compound A') was also effective in MKN45 and BxPC3 models.

Progenies of the anti-CEACAM5 mAb MBN001 (i.e., MBP001, MBP002 and MBP003) were also conjugated with Compound A' and tested for in vivo efficacy in MKN45 and BxPC3 models. Results for tumor growth upon treatment of 3 mg/kg of ADCs are provided in FIG. 18A and FIG. 18B, and upon treatment of 10 mg/kg of ADCs are provided in FIG. 18C and FIG. 18D respectively. These ADCs ADCP001A, ADCP001B and ADCP001C demonstrated robust anti-tumor activity in MKN45 and BxPC3 models. Plasma exposures of total ADCs were comparable among these three ADCs. Free payload plasma exposure of these ADCs was below the limit of quantification (data not shown).

In all the aforementioned in vivo efficacy studies, no significant effect on body weight was observed (data not shown). Thus, it appears that treatment of these anti-CEACAM5+ Compound A' ADCs was well tolerated through the course of treatment.

Example 15. Analysis of the Pharmacodynamic Markers of DDR Pathway in Tumors from Mice Treated with mAbs MBN001 Conjugated to Compound A'

This Examples analyzed the DNA damage response pathways elicited by treatment of cancer cells with ADCN001 (MBN001 conjugated to Compound A' as produced in Example 10). MKN45 tumors in mice (n=3) were treated with different amounts (1 mpk or 10 mpk) of the ADC. Expression of DNA damage response markers pKAP (1TF1b)(ser 824), pCHK1, yH2AX and apoptosis marker c-caspase 3 with loading control GAPDH were evaluated in tumor samples harvested from animals at 6, 24 or 168 hours post a single intravenous injection of the ADCN001. DNA damage markers pKAP1, pCHK1 and gH2AX were induced within 24 hours and sustained to 168 hours post-dosing with apoptosis marker cleaved c-caspase 3 induction at 168 hours post-dosing (FIG. 16A). Data was quantified and normalized to GAPDH control (FIG. 16B).

Example 16. HDX Epitope Mapping of Anti-CEACAM5 mAb MBN001

This Example analyzed the binding epitopes of human hCEACAM5 upon interaction with anti-CEACAM5 mAb MBN001 Hydrogen Deuterium Exchange mass spectrometry (HDX-MS) probes protein conformation and conformational dynamics in solution by monitoring the rate and extent of deuterium exchange of backbone amide hydrogen atoms [Huang et al. 2014, Analytical and Bioanalytical Chemistry, 406, 6541-6558; Wei, et al., 2014, Drug Discovery Today, 19, 95-102]. The level of hydrogen to deuterium exchange depends on the solvent accessibility of backbone amide hydrogen atoms, protein hydrogen bonding, time and pH. HDX-MS provides a read out for both hydrogen bonding and solvent accessibility. The mass increase of the protein upon HDX can be precisely measured by MS. Comparing the rates of exchange between the bound and unbound states in HDX experiments can provide valuable insights into the conformational dynamics, binding, specificity, and stability of proteins. Regions of the protein that exhibit slower rate of hydrogen exchange in bound vs unbound state (protection) are indicative of potential binding sites, or structural stabilization. In the context of an antigen/antibody interactions, the regions of the antigen where hydrogen exchange slows in the presence of the antibody are identified as potential epitopes. Protein regions that show faster hydrogen exchange in bound vs. unbound state of the protein (de-protection) signify structural destabilization. Hydrogen exchange rates are also sensitive to allosteric effects which can complicate the interpretation of the results.

Methods

For purposes of designing peptide constructs involving subdomains of CEACAM5, a full atom three-dimensional model of CEACAM5 was constructed using MOE software (Molecular Operating Environment (MOE) 2022.02 Chemical Computing Group ULC, 910-1010 Sherbrooke St. W., Montreal, QC H3A 2R7, Canada, 2023.) using the Ca coordinates from solution scattering data (Boehm, M. K. and Perkins, S. J. *FEBS Lett* 475, 11-16, (2000), PDB code 1E07). A ribbon representation of the 3D model of human CEACAM5 along with the separate structural domains is shown in FIG. 13A. The separate domains in the protein sequence corresponding to the 3D model are shown in FIG. 13B. The seven shaded areas in FIG. 13B correspond to the different structural domains in FIG. 13A.

Prior to epitope mapping experiments, non-deuterated experiments were carried out to generate a list of common peptides for recombinant hCEACAM5-A3-B3 construct (SEQ ID NO: 24), and protein complexes of hCEACAM5-A3-B3 construct and Fab of mAb MBN001 at 15 μM, 1:1 molar ratio. In the HDX-MS experiment, a volume (5 μL) of each sample was diluted into 55 μL of $D_2O$ buffer (10 mM phosphate buffer, $D_2O$, pH 7.0) to start the labeling reactions. The reactions were carried out for different periods of time: 20 sec, 1 min, 10 min and 60 min. By the end of each labeling reaction period, the reaction was quenched by adding quenching buffer (100 mM phosphate buffer with 4 M GdnCl and 0.4 M TCEP, pH 2.5, 1:1, v/v) and 50 μL of quenched sample was injected into a Waters HDX-MS system for analysis. The deuterium uptake levels of common peptic peptides were monitored in the absence/presence of Fab. Differences in hydrogen exchange rates between bound and free antigen were identified subtracting the mean deuteration value of each peptide in the bound antigen from the mean deuteration of the same peptide in the free antigen state. Changes considered significant if exceeded three times the propagated pooled standard uncertainly.

Results

The hCEACAM5-A3-B3 construct was chosen for HDX experiments based on epitope binning data indicating binding of MBN001 to A3-B3 region of hCEACAM5. For the purpose of this report, the N-terminal residue numbering on the antigen starts at 488 to align hCEACAM5-A3-B3 construct numbering with the canonical sequence of hCEACAM5 (UniProt entry: P06731). The hCEACAM5 protein is a complex glycoprotein. Seven predicted N-linked glycosylation sites are present in the truncated hCEACAM5-A3-B3 construct used for this analysis. The complexity and heterogeneity of hCEACAM5 posed a significant challenge for obtaining full sequence coverage. After method optimization, a sequence coverage of 60.1%, and 3.45 redundancy were achieved for hCEACAM5-A3-B3 construct with HDX-MS platform (FIG. 13C).

In the presence of MBN001, a significant reduction in the rate of hydrogen exchange on hCEACAM5 in the peptide regions covering residues 588 to 606, and residues 668 to 685 was observed when compared to unbound hCEACAM5 antigen (FIG. 13D)

Further interpretation of HDX differences requires consideration of additional factors related to the HDX process [Bai et al., 1993 Proteins. 17(1):75-86]. First, proline residues do not possess an amide hydrogen and thus do not report on the HDX process. Next, following proteolysis, the N-terminal residue of each peptide is transformed from an amide to an amine. Amines undergo rapid deuterium loss during analysis. In addition, the first amide residue of each peptide (i.e., the second residue) also undergoes rapid deuterium loss due to the influence of the N-terminal amine. Finally, overlapping regions can be used to narrow down the results.

Peptide region 590-606 is covered by multiple overlapping peptides, all showing strong protection. Thus, suggesting high confidence that the area engages in binding. The amino acids with significant protection are further narrowed down to:

(SEQ ID NO: 103)

DVL$^{590}$Y$^{591}$G$^{592}$PD$^{594}$T$^{595}$PI$^{597}$I$^{598}$S$^{599}$PPD$^{602}$S$^{603}$S$^{604}$Y$^{605}$L$^{606}$.

The area was considered the primary epitope by HDX-MS.

The peptide region 668-685 was covered by a single peptide. After exclusion of the first two N-terminal amino acids and Proline residue at position 681, the protected region remains long, covering 15 amino acids, namely:

(SEQ ID NO: 104)

IVK$^{670}$SITVSASGTSPGLSA$^{685}$

No data was available for the following regions on hCEACAM5: 501-522, 546-574, 612-615, and 642-662, therefore no conclusions were made about these residues.

The overall HDX effects of MBN001 binding on hCEACAM5 are illustrated on FIG. 13E.

Conclusions

HDX-MS identified following residues and peptide regions as potential epitopes on hCEACAM5(A3B3) upon binding with MBN001:

(SEQ ID NO: 117)

L$^{590}$, Y$^{591}$, G$^{592}$, D$^{594}$, T$^{595}$, I$^{597}$, I$^{598}$, S$^{599}$, D$^{602}$, S$^{603}$, S$^{604}$, Y$^{605}$, L$^{606}$, K$^{607}$SITVSASGTSPGLSA$^{685}$

Example 17. Cryo-EM Analysis of Bin 1 mAb MBP001

This Example describes the cryo-EM analysis performed for bin 1 mab MBP001. The CEACAM5 construct is approximately 20 KDa in size and the Fab of MBP001 was approximately 50 KDa in size. Particles significantly smaller than ~120 kDa are harder to pick and align using cryo-EM analysis. Accordingly, an anti-CEACAM5 bin2 mAb (of approximately 50 KDa) was also generated and mixed along with the CEACAM5 construct and the MBP001 Fab, in order to produce a complex structure of approximately 120 kDa. This combined structure made the cryo-EM analysis much easier to perform and confirmed that bin 1 binder MBP001 bound a different epitope than a bin 2 mAb. Below is a description of the different steps and methods that were performed.

Design of Human CEACAM5 A3-B3

CEACAM5, like other members of the CEA-related cell adhesion molecule (CEACAM) family of the immunoglobulin (Ig) gene superfamily, is a heavily glycosylated multi-domain protein whose domain boundaries have been manually assigned in Uniprot using PROSITE annotation rules (ID #P06731; Uniprot: the Universal Protein Knowledgebase in 2023; The UniProt Consortium (2023) *Nucleic Acids Research* 51, D523-D531.

However, for purposes of designing peptide constructs involving subdomains of CEACAM5, a full atom three-dimensional model of CEACAM5 was constructed using MOE software (Molecular Operating Environment (MOE) 2022.02 Chemical Computing Group ULC, 910-1010 Sherbrooke St. W., Montreal, QC H3A 2R7, Canada, 2023.) using the Ca coordinates from solution scattering data (Boehm, M. K. and Perkins, S. J. *FEBS Lett* 475, 11-16, (2000), PDB code 1E07). A ribbon representation of the 3D model of human CEACAM5 along with the separate structural domains is shown in FIG. 13A. The separate domains in the protein sequence corresponding to the 3D model are shown in FIG. 13B.

Designing the A3-B3 construct for purposes of screening antibodies further required the attachment of purification tags and a cleavage tag. For purification, a Histidine tag (amino sequence HHHHHH; SEQ ID NO: 95) and for protease cleavage the tobacco vein mottling virus (TVMV) tag (sequence ETVRFQG (SEQ ID NO: 102); Nallamsetty, *Protein Expr. Purif* 38, 108-15, 2004) were selected. These were attached at the N-terminal end of the A3-B3 construct, the N-terminal rather than the C-terminal being chosen for this purpose because we were interested in finding antibody-binding epitopes nearer to the C-terminus (i.e., B3 domain) in order to selectively bind the unshed rather than the shed or soluble form of CEACAM5 (shedding occurs near the C-terminus). The final construct is shown as SEQ ID No: 24.

Expression and Purification of hCEACAM5 A3-B3 Reagent

A human CEACAM5 A3-B3 domain protein (C-terminal region, 198 amino acid protein construct) shown below was constructed.

(SEQ ID NO: 96)

HHHHHHETVRFQGPKPSISSNNSKPVEDKDAVAFTCEPEAQNTTYLWWVN

GQSLPVSPRLQLSNGNRTLTLFNVTRNDARAYVCGIQNSVSANRSDPVTL

DVLYGPDTPIISPPDSSYLSGANLNLSCHSASNPSPQYSWRINGIPQQHT

QVLFIAKITPNNNGTYACFVSNLATGRNNSIVKSITVSASGTSPGLSA

The human CEACAM5 A3-B3 domain protein was expressed by transient transfection of Expi293F™ GnTI-Cells (Thermo Fisher) with DNA encoding A3-B3 protein using ExpiFectamine™ 293 Transfection Kit (Thermo Fisher). After 24 hours, transfected cells were fed with enhancers provided in the kit and grown at 37° C., 8% $CO_2$ and 150 RPM for total 4 days. Supernatant was harvested by centrifugation and using 0.22 um filtration (Corning).

Clarified medium of A3-B3 was purified from 5 ml Histrap excel column (Cytiva) and eluted with 250 mM imidazole-phosphate buffer. The eluate from the Histrap column was further purified with a preparative HiLoad Superdex 200 16/60 (Cytiva) to isolate A3-B3 monomer from aggregated material. Monomeric preparative size exclusion chromatography (SEC) fractions were pooled and filtered through a 0.22 m syringe filter (Pall) as the sample for CryoEM structure determination. Sample concentration was determined by A280 using a calculated molar extinction coefficient of 25,690 $M^{-1}$ $cm^{1}$. To assay the quality, the sample was checked by LC-MS, analytical SEC and SDS-PAGE.

Expression and Purification of Anti-CEACAM5 Fabs

Each Fab heavy chain (HC) generated shared the identical variable region (VH) and constant region (CH1) with its parental mAb. Two amino acids, GG, were added to the C-terminus of Fab HC. Fab Light chain (LC) remained the same as the parental mAb LC. DNA of Fab HC and LC was synthesized for expression.

```
Fab of MBP001:
Light Chain:
                                        (SEQ ID NO 46)
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPYTFG

QGTKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Heavy Chain:
                                       (SEQ ID NO: 100)
QVQLVESGGGVVQPGRSLRLSCAASGIYFSSHGMHWVRQAPGKGLEWVTF

ISYDGSYKSYVDSVKGRFTISRDNSKNTLYLQMNSLRAEDTAVYYCATGL

TGTGAFDIWGQGTMVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCGG

(comprising the VH of SEQ ID NO: 45)

Fab of bin 2 mAb:
Light Chain:
                                        (SEQ ID NO: 97)
DIQLTQSPSFLSASVGDRVTITCRASQGISTYLAWYQQKPGKAPKFLIYA

EKTLQSGVPSRFSGSGSGTEFTLTISSLQPEDFATYYCQQLASYPFTFGP

GTKVDIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Heavy Chain:
                                        (SEQ ID NO: 98)
QVQLQESGPGLVKPSGTLSLTCAVSGGSISSSDWWSWVRQPPGKGLEWIG

EIYHQGSTNYNPSLKSRVTISVDKSKNQFSLKLSSVTAADTAVYYCARAS

SSGYYGHDVWGQGTTVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKSCGG
```

The Fab of MBP001 and the Fab of the bin2 mAb were expressed in Expi293 cells (Thermo Fisher) by transient transfection with the Fab heavy chain (HC) and Fab light chain (LC) DNA using the same method described above for CEACAM5.

Each clarified medium of Fab was purified from 5 ml Hitrap Mabselect (Protein L) VL column (Cytiva) and eluted with glycine pH 3 buffer neutralized with Tris pH 8. To remove the free light chain, the Mabselect eluate was added over a 5 ml CaptureSelect CH1 XL column (Thermo Fisher) and eluted with glycine pH 3 solution. Finally, neutralized CH1 eluate was run over a HiLoad Superdex 75 16/60 (Cytiva) column to obtain highly monomeric Fab samples for Cryo EM. To assay the quality, the purified Fab samples were checked by LC-MS, analytical SEC and SDS-PAGE.

Complexing of +CEACAM5 A3-B3+MBP001 Fab+Fab of bin 2 mAb

Purified CEACAM5 was complexed with both MBP001 Fab and the Fab of the bin2 mAb using a ~1:1:1 molar ratio. Specifically, 1 mg of CEACAM5 (263 μl) was mixed with 2 mg of the MBP001 Fab (344 μl) and with 2 mg of the Fab of the bin2 mAb (384 μl) and incubated on ice for approximately 2.5 hours. After the incubation period, 50 μl of complexing reaction solution was passed through a Bio-Spin 30 Size-exclusion chromatography column (30 kDa MWCO, BioRad) to remove any contaminants and Apo-CEACAM5. Prior to use, Bio-Spin 30 columns were equilibrated with 1×PBS, and samples were applied according to the manufacturer's protocol. The final concentration of complexing reaction solution after passing through the Bio-Spin 30 column was 5.1 mg/ml, which was then used for preparation of cryoEM grids.

CryoEM Grid Preparation and data collection of CEACAM5+Fabs complex

Prior to applying to cryoEM grids, 9 μl of CEACAM5+Fabs complexing reaction solution was combined with 1 μl of 0.1% lauryl maltose neopentyl glycol (LMNG) to yield a final concentration of 0.01% LMNG. The presence of LMNG reduced sample interactions with the air-water-interface allowing for a reduction in particle degradation and an increase in observable particle orientations on grids (D'Imprima, et al. *eLife*. 8:e42747, 2019). After adding LMNG, 3.2 μl of sample was applied to plasma cleaned (22 secs at 20 mA) Quantifoil 1.2/1.3 Au 300 mesh grids and subsequently blotted and plunge frozen using an FEI Vitrobot machine (Thermofisher) following standard operating procedures. Grids were blotted for 5 secs with a blot force of 0 prior to plunge freezing. A total of 12 grids were made from the CEACAM5+Fabs complexing reaction and used for CryoEM screening and data collection. Data were collected using a G4 Titan Krios machine equipped with a Falcon 4i direct election detector and with EPU data acquisition software (Thermofisher). Movies s (9538 number of movies; 242 frames per stack in EER mode) were collected at 300 keV, using a 75,000× magnification (1.05 Å/pixel), and a total dose of 40 e/$Å^2$. A defocus range of −0.8 to −2.2 μm was used during data collection with 2 acquisition areas per hole.

Determination of the Structure by CryoEM of the CEACAM5 A3-B3 Domains Bound to Two Fabs During data collection, cryoEM movies were processed using cryoSPARC Live (Punjani et al., *Nat. Methods* 14, 290-296, 2017) using a standard workflow which included patch motion correction, patch CTF correction, blob auto-picking, and followed by initial particle curation using 2D classification. Templates generated from three selected classes from the initial 2D averages were used for a refined particle picking strategy with particles subsequently curated using a single round of 2D classification. Following template picking, 2D classes containing the best selected particles (24 classes) were used for ab initio reconstruction with an output of four 3D classes (Punjani et al., *Nat. Methods* 14, 290-296, 2017). The largest 3D class containing 415,405 particles was subjected to homogeneous refinement, which yielded a Gold Standard Fourier Shell Correlation (GSFSC) of 3.14 Å. This was followed by non-uniform refinement (Punjani et al. *Nat. Methods* 17, 1214-1221, 2020), which improved the resolution to yield a GSFSC of 3.08 Å. The resulting half maps were subjected to post-processing with DeepEMhancer (Sanchez-Garcia et al. *Commun. Biol.* 4, 874, 2021) and local resolution of the final map was calculated with cryoSPARC. The final refined map resulting from post-processing was used for initial model building in Chimera (Pettersen et al., *J. Comput. Chem.* 25, 1605-1612, 2004). Generic Fvs, CL:CH1 domain dimers and the B3 domain of CEACAM5 derived from an AlphaFold model (Jumper et al., *Nature* 596, 583-589, 2021) were manually fitted to the density and then model positions refined in Chimera. Further model building was performed using COOT (Emsley & Cowtan, *Acta Crystallogr Sect. D* 60, 2126-2132, 2004; Emsley et al., *Acta Crystallogr Sect. D* 66, 486-501, 2010). Real-space refinement was performed using PHENIX (Liebschner, et al., *Acta Crystallogr. Sect. D* 75, 861-877, 2019).

While much of the model building was straightforward at several places in the B3 domain a residue register shift was observed compared to the AlphaFold model. Following placement of the B3 domain, the A3 domain was fitted. The final model included:

1. CEACAM5 residues 505-529, 532-574, 579-676 and N-acetylglucosamine residues attached to Asn 508, Asn 529, Asn 553, Asn 560, Asn 612, Asn 650, and Asn 665.
2. The Fab of MBP001: light chain: 1-212 (Kabat numbering including residue 27A); heavy chain: 1-128 and 136-228 (Kabat numbering including residues 52A, 82A, 82B, 82C, 100A, and 100B)
3. The Fab of the bin 2 mAb: light chain: 1-55 and 59-213 (Kabat numbering=sequential numbering); heavy chain: 1-229 (Kabat numbering including 35A, 82A, 82B, 82C, 100A, 100B, and 100C).

FIG. 14A is a final cryoEM map of the Fab of bin 2 mAb, CEACAM5 and the MBP001 Fab showing local resolution. The local resolution in the vicinity of the binding sites for the two Fabs to the B3 domain of CEACAM5 is 3 Å or better.

FIG. 14B is a ribbon diagram of the final model. Light chains of the two Fabs are in light gray. Heavy chains of the two Fabs are in dark gray, and CEACAM5 is in black. Arrow shaped ribbons indicate β-strands and dashes indicate uninterpreted regions, which include CEACAM5 A3 domain residues 530-531 and 575-578, MBP001 heavy chain residues 129-135, and Fab of Bin 2 mAb heavy chain residues 130-135 and light chain residues 56-58 (adjacent to CDR-L2).

In the lists below, in contact residues (Sheriff et al. *J. Mol. Biol.* 197, 273-296, 1987; Sheriff, *Immunomethods* 3, 191-196, 1993) is a narrower definition of the epitope. Buried residues (Connolly, *J. Appl. Crystallogr.* 16, 548-558, 1983) is a broader definition of the epitope.

Epitope of MBP001 on the surface of CEACAM5 domain B3:

In contact residues:

Ile 597, Ile 598, Asn 630, Phe 656, Gly 663, Arg 664, Asn 665, Asn 666, Ser 667, Val 669, Lys 670, NAG 865 (attached to Asn 665)

Buried CEACAM5 residues with contacting residues underlined:

Glu 514, Asp 515, Arg 563, Gly 592, Pro 593, Asp 594, Thr 595, Pro 596, Ile 597, Ile 598, Pro 601, Ser 603, Ala 618, Arg 628, Asn 630, Gly 631, Thr 652, Ala 654, Phe 656, Val 657, Ser 658, Gly 663, Arg 664, Asn 665, Asn 666, Ser 667, Ile 668, Val 669, Lys 670, Ser 671, NAG 760 (attached to Asn 560), NAG 865 (attached to Asn 665)

Paratope of CEACAM5 domain B3 on the surface of MBP001.

In contact residues (Kabat Numbering):

MBP001 VL: Ser 31

MBP001 VH: Tyr 28, Ser 31, His 32, Tyr 52A, Asp 53, Gly 54, Ser 55, Thr 97, Gly 98

Buried residues (Kabat Numbering) with in-contact residues underlined:

MBP001 VL: Ser 31, Tyr 32, Tyr 49, Ser 53, Thr 56, Tyr 91, Glu 92, Ser 93 MBP001 VH: Tyr 28, Ser 30, Ser 31, His 32, Gly 33, Phe 50, Ser 52, Tyr 52A, Asp 53, Gly 54,

Ser 55, Tyr 56, Lys 57, Asp 61, Lys 64, Leu 96, Thr 97, Gly 98, Thr 99, Gly 100

FIG. 14C is a distinct binding analysis from FIG. 14B that shows contacting residues (epitopes and paratopes) defined as residues whose heavy atoms (CEACAM5/MBP001) lie within 4.5A of each other. In the figure they are colored in black, whereas in the sequences they are bolded. The sequences encompassing CDRs in MBP001 are underlined.

Paratope In contact residues (Kabat numbering) to go with FIG. 14C:

```
6xHis-A3-B3 huCEACAMS (MBP001 epitope residues
bolded)
                                      (SEQ ID NO: 24)
HHHHHHDTBVRFQGPKPSISSNNSKPVEDKDAVAFTCEPAQNTTYLWWVN

GQSLPVSPRLQLSNGNRTLTLFNVTRNDARAYVCGIQNSVSANRSDPVTL

DVLYGPDTPIISPPDSSYLSGANLNLSCHSASNPSPQYSWRINGIPQQHT

QVLFIAKITPNNNGTYACFVSNLATGRNNSIVKSITVSASGTSPGLSA
```

(bold in SEQ ID NO: 24: PDTPIISPP in line 3; F and GRNNSIVKS in line 4)

```
MBP001 VL (paratope residues bolded; CDRs
underlined)
                                      (SEQ ID NO: 46)
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPYTFG

QGTKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

```
MBP001 VH (paratope residues bolded; CRDs
underlined)
                                      (SEQ ID NO: 100)
QVQLVESGGGVVQPGRSLRLSCAASGIYFSSHGMHWVRQAPGKGLEWVTF

ISYDGSYKSYVDSVKGRFTISRDNSKNTLYLQMNSLRAEDTAVYYCATGL

TGTGAFDIWGQGTMVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCGG
```

In contact residues (Kabat Numbering):

MBP001 VL: Ser 31, Tyr 49, Ser 53, Gly 92

MBP001 VH: Tyr 28, Ser 31, His 32, Phe 50, Ser 52, Tyr 52A, Asp 53, Ser 55, Tyr 56, Leu 96, Thr 97, Gly 98, Thr 99

Example 18. Testing the In Vivo Anti-Tumor Efficacy of the ADCV001 as Compared to M9140

This Example analyzed the in vivo anti-tumor efficacy of ADCV001 (ADC in the wild-type IgG format of MBN001 conjugated with Compound A') and M9140, an anti-CEACAM5 ADC with a ß-glucuronide linker and an exatecan payload described in WO2022/048883 (e.g., Example 4), in a MKN45 cell line-derived xenograft models. An number of MKN45 cells ($2\times10^6$) were inoculated subcutaneously into the right flank of four to six weeks old immunodeficient female Athymic Nude mice (CRL 490, Charles River). Animals with tumor volume between 150 $mm^3$~220 $mm^3$ were randomized into treatment groups with mean tumor volume of 180 $mm^3$ (N=7). Tumor bearing animals were treated with a single intravenous injection of buffer control (Phosphate-buffered saline (PB S)) or with ADCs. Tumor length (L) and width (W) were measured with calipers and tumor volumes were calculated using the formulation L*(W^2)/2.

Results for tumor growth of the MKN45 model mice treated with ADCV001 or M9140 are provided in FIG. 19A, FIG. 19B, and FIG. 19C. Data show that had anti-tumor effect in these models. Results for tumor growth of the MKN45 model treated with 3 mg/kg of ADCV001 or 3 mg/kg of M9140 are provided in FIG. 19A. Data for mice treated with 10 mg/kg of ADCV001 or 10 mg/kg M9140 are provided at FIG. 19B and FIG. 19C. Data shows that the ADCV001 treatment was more effective in inhibiting tumor growth and reducing the tumor size in MKN45 models compared to treatment with M9140 at both 3 mg/kg and 10 mg/kg.

Example 19. PD Analysis of ADCV001 as Compared to M9140

This Example analyzed the DNA damage response pathway elicited by treatment of tumors with either ADCV001 (MBN001 conjugated to Compound A' as produced in Example 10) or M9140. Animals with MKN45 tumors were treated with 3 mg/kg of the ADCs (n=4). Expression of DNA damage response markers pKAP(1TF1b)(ser 824) and pCHK1 with loading control GAPDH were evaluated in tumor samples harvested from animals at 6, 48, 72, 240, and 336 hours post a single intravenous injection of ADCV001 and M9140. DNA damage markers pKAP1 and pCHK1 were induced 48 hours and sustained up to 336 hours post-dosing of ADCV001 whereas these markers were induced at 6 hours and sustained up to 72 hours post-dosing of M9140 (FIG. 20). Data show that ADCV001 achieved more sustained DNA damage pharmacodynamics and more anti-tumor activity than M9140.

Those skilled in the art will recognize or be able to ascertain using no more than routine experimentation, many equivalents of the specific aspects disclosed herein. Such equivalents are intended to be encompassed by the following claims.

What is claimed:

1. An antibody drug conjugate (ADC) having the formula (II):

(II)

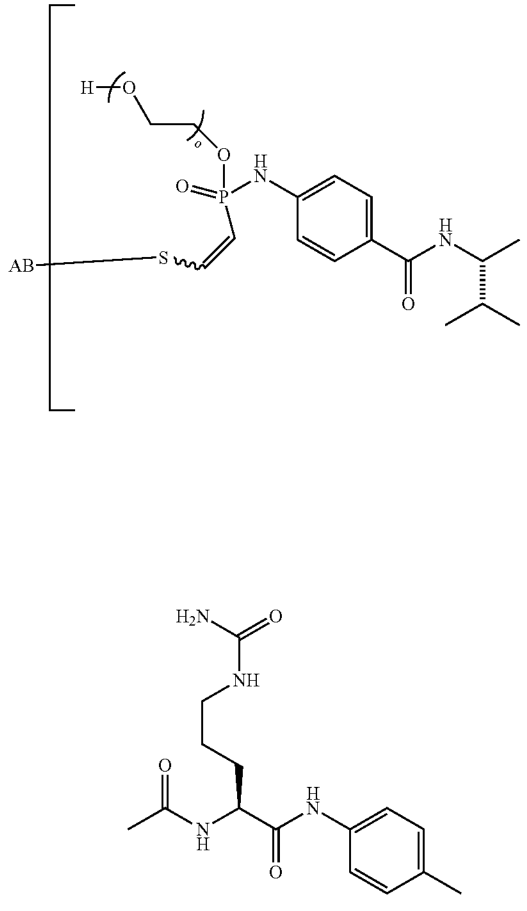

-continued

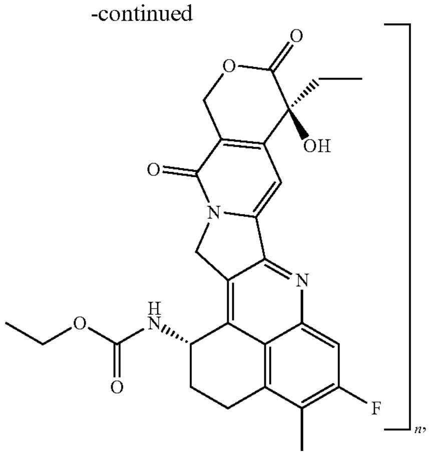

or a pharmaceutically acceptable salt, a stereoisomer or a solvate thereof, wherein:

~~~~ indicates that the configuration of the double bond is E or Z;

o is an integer ranging from 10 to 30;

n ranges from 1 to 20; and

AB is an anti-CEACAM5 antibody or an antigen binding portion thereof, which specifically binds to a carcinoembryonic antigen-related cell adhesion molecule-5 (CEACAM5), comprising:

(a) a heavy chain variable region (VH) which comprises complementarity determining region (CDR) 1, CDR2, and CDR3 regions comprising the amino acid sequences set forth in SEQ ID NOs: 14, 15, and 16, respectively, and (b) a light chain variable region (VL) which comprises CDR1, CDR2, and CDR3 regions comprising the amino acid sequences set forth in SEQ ID NOs: 19, 20, and 21, respectively.

**2**. The ADC of claim **1**, wherein the VH comprises the amino acid sequence set forth in SEO ID NO: 17, SEQ ID NO: 38, SEQ ID NO: 49, SEQ ID NO: 51, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, or SEQ ID NO: 93.
~~~~

3. The ADC of claim 2, wherein the VL comprises the amino acid sequence set forth in SEO ID NO: 22, SEQ ID NO: 43, SEQ ID NO: 50, SEQ ID NO: 52, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, or SEQ ID NO: 94.

4. The ADC of claim 1, wherein the VH and the VL comprise the amino acid sequence set forth in SEQ ID NO: 17 and the amino acid sequence set forth in SEQ ID NO: 22, respectively.

5. The ADC of claim 1, wherein the VH and the VL comprises:

(a) the amino acid sequence set forth in SEQ ID NO: 38 and the amino acid sequence set forth in SEQ ID NO: 43, respectively;

(b) the amino acid sequence set forth in SEQ ID NO: 49 and the amino acid sequence set forth in SEQ ID NO: 50, respectively;

(c) the amino acid sequence set forth in SEQ ID NO: 51 and the amino acid sequence set forth in SEQ ID NO: 52, respectively;

(d) the amino acid sequence set forth in SEQ ID NO: 67 and the amino acid sequence set forth in SEQ ID NO: 68, respectively;

(e) the amino acid sequence set forth in SEQ ID NO: 69 and the amino acid sequence set forth in SEQ ID NO: 70, respectively;

(f) the amino acid sequence set forth in SEQ ID NO: 71 and the amino acid sequence set forth in SEQ ID NO: 72, respectively;

(g) the amino acid sequence set forth in SEQ ID NO: 73 and the amino acid sequence set forth in SEQ ID NO: 74, respectively;

(h) the amino acid sequence set forth in SEQ ID NO: 75 and the amino acid sequence set forth in SEQ ID NO: 76, respectively;

(i) the amino acid sequence set forth in SEQ ID NO: 77 and the amino acid sequence set forth in SEQ ID NO: 78, respectively;

(j) the amino acid sequence set forth in SEQ ID NO: 79 and the amino acid sequence set forth in SEQ ID NO: 80, respectively;

(k) the amino acid sequence set forth in SEQ ID NO: 81 and the amino acid sequence set forth in SEQ ID NO: 82, respectively;

(l) the amino acid sequence set forth in SEQ ID NO: 83 and the amino acid sequence set forth in SEQ ID NO: 84, respectively;

(m) the amino acid sequence set forth in SEQ ID NO: 85 and the amino acid sequence set forth in SEQ ID NO: 86, respectively;

(n) the amino acid sequence set forth in SEQ ID NO: 87 and the amino acid sequence set forth in SEQ ID NO: 88, respectively;

(o) the amino acid sequence set forth in SEQ ID NO: 89 and the amino acid sequence set forth in SEQ ID NO: 90, respectively;

(p) the amino acid sequence set forth in SEQ ID NO: 91 and the amino acid sequence set forth in SEQ ID NO: 92, respectively; or (q) the amino acid sequence set forth in SEQ ID NO: 93 and the amino acid sequence set forth in SEQ ID NO: 94, respectively.

6. The ADC of claim 1, wherein o is 22, 23, 24, 25, or 26.

7. The ADC of claim 1, wherein n ranges from 6 to 8.

8. An antibody drug conjugate (ADC) having the formula (II):

(II)

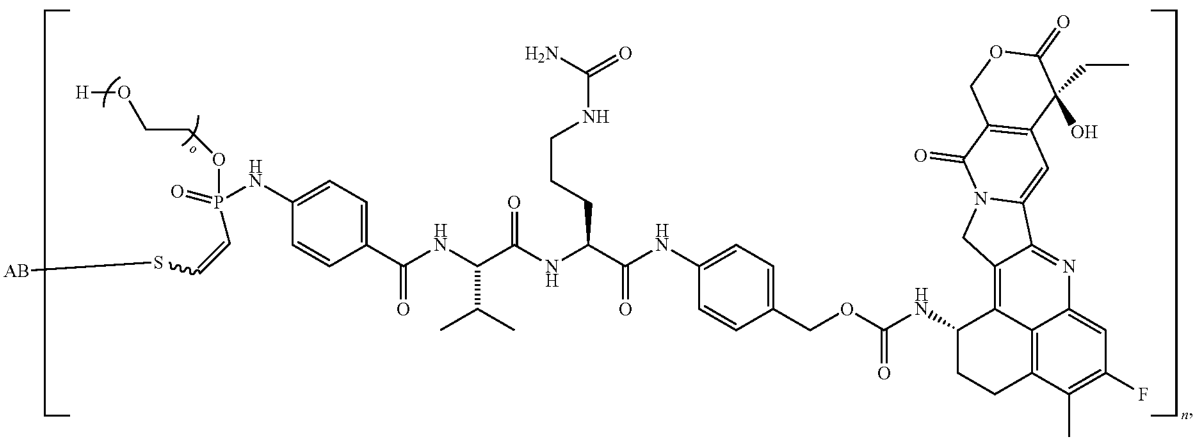

or a pharmaceutically acceptable salt, a stereoisomer, or a solvate thereof, wherein ~~~ indicates that the configuration of the double bond is E or Z; n is 8; o is an integer of 24; and AB is an anti-CEACAM5 antibody or antigen binding portion thereof comprising a heavy chain variable region (VH) and a light chain variable region (VL) which comprise the amino acid sequence set forth in SEQ ID NO: 38 and the amino acid sequence set forth in SEQ ID NO: 43, respectively.

9. The ADC of claim 1, wherein the anti-CEACAM5 antibody comprises a heavy chain and a light chain comprising the amino acid sequence set forth in SEQ ID NO: 45 and the amino acid sequence set forth in SEQ ID NO: 46, respectively.

10. The ADC of claim 1, wherein the anti-CEACAM5 antibody comprises an IgG1 constant region, an IgG2 constant region, an IgG3 constant region, an IgG4 constant region, or a variant thereof.

11. A pharmaceutical composition comprising the ADC of claim 1, and a pharmaceutically acceptable carrier.

12. A kit comprising the ADC of claim 1, and instructions for use.

13. A method of producing the ADC of claim 1 comprising conjugating a thiol-containing compound of AB-$(SH)_n$ with Compound A:

(Compound A)

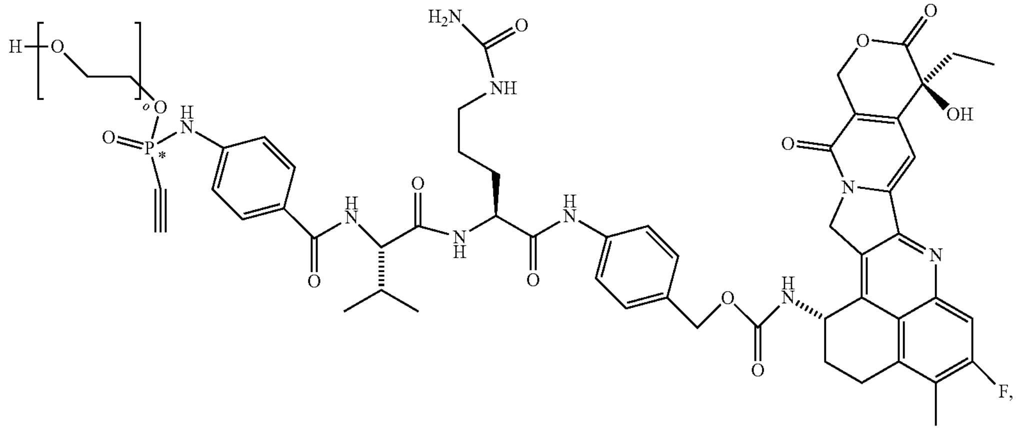

wherein AB is the anti-CEACAM5 antibody or antigen binding portion thereof, and n ranges from 1 to 20.

14. A method of treating a cancer that expresses CEACAM5 in a subject in need thereof comprising administering to the subject a therapeutically effective amount of the ADC of claim 1.

15. The method of claim 14, wherein the cancer comprises colorectal cancer, breast cancer, lung cancer including non-small cell lung cancer, ovarian cancer, pancreatic cancer, bladder cancer, uterine/cervical cancer, prostate cancer, testicular cancer, esophageal cancer, gastric cancer, gastrointestinal cancer, colon cancer, kidney cancer, head and neck cancer, stomach cancer, germ cell cancer, bone cancer, liver cancer, thyroid cancer, skin cancer, neoplasm of the central nervous system, lymphoma, leukemia, myeloma, sarcoma, or myelodysplastic syndromes.

16. An antibody drug conjugate (ADC) having the formula (II):

wherein ~~~ indicates that the configuration of the double bond is E or Z; n is 8; o is 24; AB is an anti-CEACAM5 antibody comprising a heavy chain and a light chain which comprises the amino acid sequence set forth in SEQ ID NO: 45 and the amino acid sequence set forth in SEQ ID NO: 46, respectively.

17. The ADC of claim 8, wherein the anti-CEACAM5 antibody consists of two heavy chains and two light chains wherein each heavy chain comprises the amino acid sequence set forth in SEQ ID NO: 45 and wherein each light chain comprises the amino acid sequence set forth in SEQ ID NO: 46, respectively.

18. A pharmaceutical composition comprising the ADC of claim 16, and a pharmaceutically acceptable carrier.

19. A method of producing the ADC of claim 16 comprising conjugating a thiol-containing compound of AB-$(SH)_n$ with Compound A':

(II)

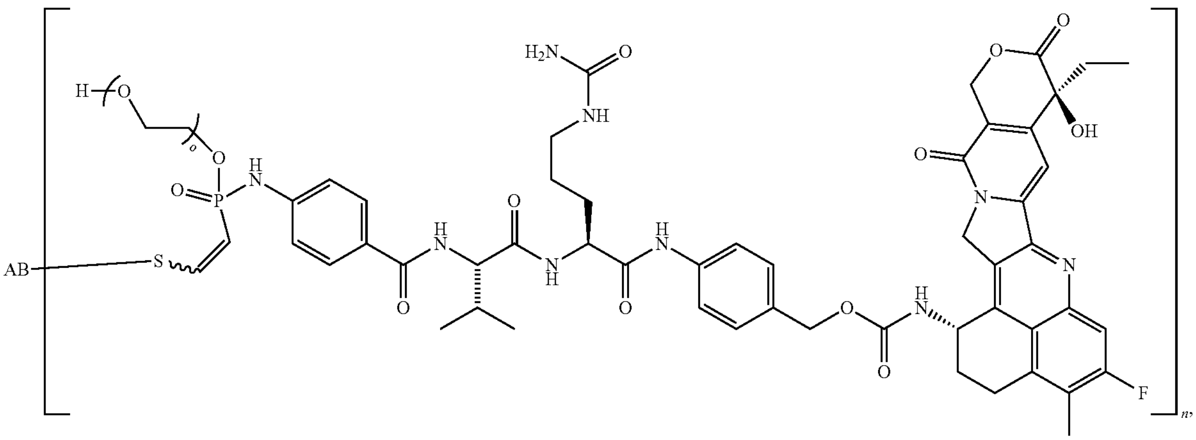

(Compound A')

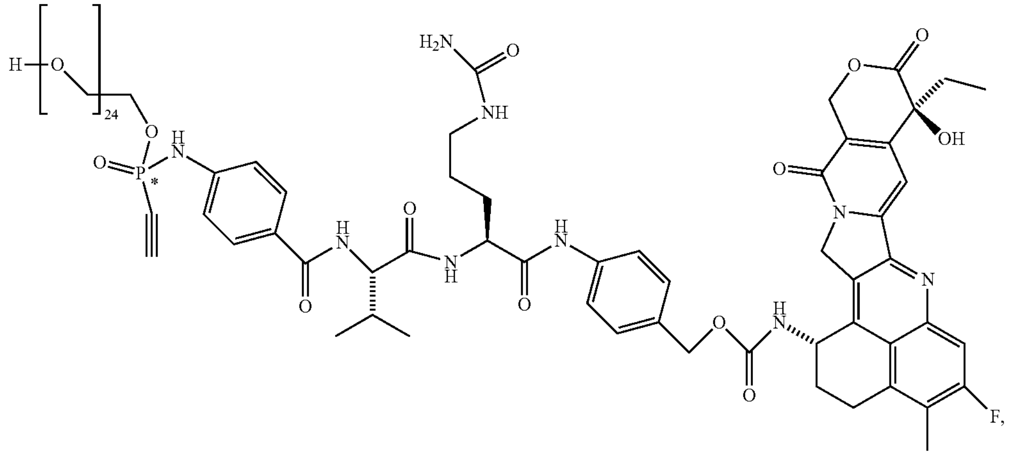

wherein AB is the anti-CEACAM5 antibody or antigen binding portion thereof, and n is 8.

20. A method of treating a cancer that expresses CEACAM5 in a subject in need thereof comprising administering to the subject a therapeutically effective amount of the ADC of claim 16.

21. The method of claim 20, wherein the cancer comprises: colorectal cancer, breast cancer, lung cancer, ovarian cancer, pancreatic cancer, bladder cancer, uterine/cervical cancer, prostate cancer, testicular cancer, esophageal cancer, gastric cancer, gastrointestinal cancer, colon cancer, kidney cancer, head and neck cancer, stomach cancer, germ cell cancer, bone cancer, liver cancer, thyroid cancer, skin cancer, neoplasm of the central nervous system, lymphoma, leukemia, myeloma, sarcoma, and or myelodysplastic syndromes.

22. The method of claim 21, wherein the cancer is colorectal cancer.

23. The method of claim 21, wherein the lung cancer is non-small cell lung cancer.

* * * * *